US012735686B2

(12) United States Patent
Yang et al.

(10) Patent No.: US 12,735,686 B2
(45) Date of Patent: Sep. 15, 2026

(54) ENZYMATIC DEGRADATION OF POLYETHYLENE TEREPHTHALATE

(71) Applicant: BioMetis Technology, Inc., Redwood City, CA (US)

(72) Inventors: Jie Yang, Foster City, CA (US); Xiyun Zhang, San Ramon, CA (US); Khin Oo, Daly City, CA (US); Goutami Banerjee, Daly City, CA (US)

(73) Assignee: BioMetis Technology, Inc., Redwood City, CA (US)

( * ) Notice: Subject to any disclaimer, the term of this patent is extended or adjusted under 35 U.S.C. 154(b) by 119 days.

(21) Appl. No.: 18/682,722

(22) PCT Filed: Aug. 11, 2022

(86) PCT No.: PCT/US2022/074866

§ 371 (c)(1),
(2) Date: Feb. 9, 2024

(87) PCT Pub. No.: WO2023/019222

PCT Pub. Date: Feb. 16, 2023

(65) Prior Publication Data

US 2025/0368971 A1 Dec. 4, 2025

Related U.S. Application Data

(60) Provisional application No. 63/232,122, filed on Aug. 11, 2021.

(51) Int. Cl.

| | |
|---|---|
| ***C12N 9/18*** | (2006.01) |
| ***A62D 3/02*** | (2007.01) |
| ***B29B 17/04*** | (2006.01) |
| ***C08G 63/02*** | (2006.01) |
| ***C12N 9/16*** | (2006.01) |
| ***C12N 15/52*** | (2006.01) |
| ***C12P 7/40*** | (2006.01) |

(52) U.S. Cl.

CPC . *C12N 9/18* (2013.01); *C12P 7/40* (2013.01)

(58) Field of Classification Search

CPC ... C12N 9/18; C12N 9/16; C12N 9/00; C12N 15/52; C12P 7/40; B29B 17/04; A62D 3/02; C08G 63/02

See application file for complete search history.

(56) References Cited

U.S. PATENT DOCUMENTS 11,680,252 B2 * 6/2023 Chen .............. C12Y 301/01074 435/197

FOREIGN PATENT DOCUMENTS

| | | |
|---|---|---|
| WO | 2019/168811 A1 | 9/2019 |
| WO | 2020/021118 A1 | 1/2020 |
| WO | 2021/145822 A1 | 7/2021 |

OTHER PUBLICATIONS

International Search Report issued in corresponding International Patent Application No. PCT/US2022/074866 dated Dec. 15, 2022.

Written Opinion issued in corresponding International Patent Application No. PCT/US2022/074866 dated Dec. 15, 2022.

* cited by examiner

*Primary Examiner* — Maryam Monshipouri

(74) *Attorney, Agent, or Firm* — Morgan, Lewis & Bockius LLP

(57) ABSTRACT

The present disclosure provides variant enzymes for use in the enzymatic degradation of polyethylene terephthalate (PET).

11 Claims, 51 Drawing Sheets

Specification includes a Sequence Listing.

Figure 1

```
  1 snpyqrgpnp trsalttdgp fsvatysvsr lsvsgfgggv iyyptgttlt fggiamspgy
 61 tadasslawl grrlashgfv vivintnsrl dfpdsrasql saalnylrts spsavrarld
121 anrlavaghs mgggatlris eqiptlkagv pltpwhtdkt fntpvpqliv gaeadtvapv
181 sqhaipfyqn lpsttpkvyv eldnathfap nspnaaisvy tiswmklwvd ndtryrqflc
241 nvndpalsdf rsnnrhcq
```

Figure 2A

```
                1                                                      50
    SEQ_ID_NO_1 ---------- ---------- ---------- ---------- ----------
    SEQ_ID_NO_4 H--------- ---------- ---------- ---------- ----------
    SEQ_ID_NO_6 ---------- ---------- ---------- ---------- ----------
         Q47RJ7 ---------- -MPPHAARPG PAQNRRGRAM AVITPRRERS SLLS------
       CBY05529 ---------- -MPPHAARPG PAQNRRGCAM AVMTPRRERS SLLS------
       PZN61876 ---------- ---------- ---------M AVMTPRRERS SLLS------
       AAZ54921 ---------- ---------- ---------M AVMTPRRERS SLLS------
       BAK48590 ---------- ---------- ---------M SVTTPRR-ET SLLS------
     A0A147KJY8 ---------- ---------- ---------M SVTTPRR-RT PLLS------
   WP_083947829 ---------- ---------- ---------- ---------- -MLS------
     A0A4R6UW92 ---------- ---------- MNMTNSTLDQ PTESPAKSAS PLSRG-----
     A0A5Q2RDB8 ---------- ---------- ---------M KGKPHMTTTA RRRQ------
       ACU97777 ---------- ---------- ----MRIRRQ AGTGARASMA RAIG------
     A0A561WKJ0 ---------- ---------- ---------M SVLHQT---- ----------
         G0FYZ7 ---------- ---------- ---------M SALTSQPTSS GSSEKIPRLR
     A0A0N0A0T6 ---------- ---------- ---------- ---------- ---MPNEVYS
     A0A1W2C2B9 ---------- ---------- ---MRTWSPW LQGRGRSSPC S--LPNEVYS
     A0A2T0T7X1 ---------- ---------- ---------M LPGRFPSRRF G--VYNDVQL
     A0A5Q0HE30 ---------- ---------- ---------- ---------- ----------
     A0A1Q4WZS7 ---------- ---------- ---------- ---------- ----------
     A0A4R4NB20 -MTGDFADAR GPAACADCAR PGAGPRLRPV PGSRLPAPPP EQERTDVRSL
     A0A1D8SZ57 ---------- ---------- ---------M QRNPRTRT-- -------RAT
         Q9L2J6 ---------- ---------- ---------M QQNPHTHAAP GAARPVLRGV
     A0A089Z882 ---------- ---------- ---------M QQQHRTDSAT P------RRR
     A0A1H9JKT6 ---------- ---------- ---------M EPQQHDTTPG TATR--HRGA
     A0A1Y5XYT9 ---------- ---------- ---------M RRGVRILTGL TIAP------
         R4SZ25 ---------- ---------- ---------M RSTTRILCGL ----------
     A0A1Q8CLB3 ---------- ---------- ---------M RRTLRTLCGL A---------
         U5W5F9 ---------- ---------- ---------M QSPTIPARLR AR--------
       AAE13316 ---------- ---------- ---------- ---------- ----------
```

Figure 2B

```
               51                                                   100
 SEQ_ID_NO_1   ---------- ---------- ---------- ---------- ---SNPYQRG
 SEQ_ID_NO_4   ----HHHHHS SGLVPR---- ---------- ---------G SHMSNPYQRG
 SEQ_ID_NO_6   ---------- ---------- ---------- ---------- --QTNPYARG
       Q47RJ7  -RALRFTAAA ATALVTAVSL ---------- -------AAP AHAANPYERG
     CBY05529  -RALQVTAAA ATALVTAVSL ---------- -------AAP AHAANPYERG
     PZN61876  -RALQVTAAA ATALVTAVSL ---------- -------AAP AHAANPYERG
     AAZ54921  -RALQVTAAA ATALVTAVSL ---------- -------AAP AHAANPYERG
     BAK48590  -RALRATAAA ATAVVATVAL ---------- -------AAP AQAANPYERG
   A0A147KJY8  -RVLRTAAVA ATAAASVLAL ---------- -------SAP AQAANPYERG
 WP_083947829  -QVTAVVAAA A----AAVTL ---------- -------SAP ALAANPYERG
   A0A4R6UW92  VRTAIRTAVA AALVAGGVGI ---------- -------ASP AYAANPYERG
   A0A5Q2RDB8  -TFVAIIAML LASLALSPGA ---------- -------DAQ AS--NPYQRG
     ACU97777  -VMTTALAVL VGAVGGVAGA ---------- -------EVS TAQDNPYERG
   A0A561WKJ0  -WRSALATTL IAAIVTLLG- ---------- -----APA-- -RAANPYERG
       G0FYZ7  GWRAKAAGVV LAALALTTG- ---------- -----VAAPA PAAANPYERG
   A0A0N0A0T6  -AVQLRTLIP LALTLVLVTG ---------- -------TAA QAADNPYERG
   A0A1W2C2B9  -AVQLRTLIP IALSMVLLGG ---------- -------TVA QAADNPYERG
   A0A2T0T7X1  RSVFTTVTLV AALVGGAIGA ---------- -------SPA IAAENPYERG
   A0A5Q0HE30  ---------- ---MALALAA ---------- -------PQA TAAETEYRRG
   A0A1Q4WZS7  -----MPALI PALALSLVGV ---------- -------TPA TGAEEEFRRG
   A0A4R4NB20  PSRAAKTLLA TALAAGALAV PQ-------- ----ALSQAA QAADNPYERG
   A0A1D8SZ57  RR--RFAGVT AAVAAVLA-- ---LSTLTGP --------GA QAADNPYERG
       Q9L2J6  RR--RLAAVT AAVAAVLV-- ---LGTLTGP --------GA QAADNPYERG
   A0A089Z882  RRTGRLTGLA AATAAVIG-- ---LSTLSGT --------GA HAADNPYERG
   A0A1H9JKT6  PR--RLTKLG VALAMVLGGV GVALPTAQAT QDSGAAPAAV QAAENPYERG
   A0A1Y5XYT9  ----VIGAVV AAGVPATALG AVVTGTPTTA IG-----AVE LSAENPYERG
       R4SZ25  ------ATVA ALTVAPTAY- ---------- ---------- -AAENPYERG
   A0A1Q8CLB3  -----LAGSV LAGTASTAS- ---------- ---------- -AQENPYERG
       U5W5F9  -RLFVTAAAT LTLVAGSLTG ---------- ------ATAA QAAENPYERG
     AAE13316  ------MKFF TTILST---- ---------- --------AS LVAALPAAVD
```

Figure 2C

```
              101                                                    150
  SEQ_ID_NO_1  PNPTRSALTT -DGPFSVATY SVSRLSVSGF GGGVIYYPTG TTL-TFGGIA
  SEQ_ID_NO_4  PNPTRSALTA -DGPFSVATY TVSRLSVSGF GGGVIYYPTG TSL-TFGGIA
  SEQ_ID_NO_6  PNPTAASLEA SAGPFTVRSF TVSRP--SGY GAGTVYYPTN AGG-TVGAIA
       Q47RJ7  PNPTDALLEA RSGPFSVSEE RASRFGADGF GGGTIYYPR- ENN-TYGAVA
     CBY05529  PNPTDALLEA RSGPFSVSEE NVSRLGASGF GGGTIYYPR- ENN-TYGAVA
     PZN61876  PNPTDALLEA RSGPFSVSEE NVSRLSASGF GGGTIYYPR- ENN-TYGAVA
     AAZ54921  PNPTDALLEA SSGPFSVSEE NVSRLSASGF GGGTIYYPR- ENN-TYGAVA
     BAK48590  PNPTESMLEA RSGPFSVSEE RASRFGADGF GGGTIYYPR- ENN-TYGAIA
   A0A147KJY8  PNPTQALLEA RSGPFSVSSE RAWRLGSDGF GGGTIYYPR- ENN-TYGAVA
 WP_083947829  PDPTQASLEA SRGPFPVSEE RVSSP-VSGF GGGTIYYPQ- ENN-TYGAVA
   A0A4R6UW92  PDPTDSSVEA LRGPYSVDDT SVSSL-VSGF GGGTVYYPTG TNE-TFGAVV
   A0A5Q2RDB8  PNPTQSSIEA LRGPYSTTTT SVSSF-VSGF GGGTIYYPTG TNE-TFGGVV
     ACU97777  PDPTEDSIEA IRGPFSVATE RVSSF-ASGF GGGTIYYPRE TDEGTFGAVA
   A0A561WKJ0  PAPTTASIEA TRGPFAIAQL TVARSSVSGF GGGTVYYPTD TSAGTFGAVA
       G0FYZ7  PDPTTASIEA TSGSFATSTV TVSRLAVSGF GGGTIYYPTT TTAGTFGALS
   A0A0N0A0T6  PAPTVSSIEA LRGPFAVSET SVSSL-VGGF GGGTIYYPTS TTSGTFGAVA
   A0A1W2C2B9  PAPTNSSIEA SRGSFAVSET SVSSL-VSGF GGGTIYYPTS TSAGTFGAVA
   A0A2T0T7X1  PAPTNSSIEA SRGSFAVSET SVSSLSVTGF GGGTIYYPTS TSAGTFGAIA
   A0A5Q0HE30  PAPTNSSIEA LRGPFAVSET SVSSLLVTGF GGGTIYYPTS TAEGTFGAVA
   A0A1Q4WZS7  PAPTNSSIEA SRGPFATSST TVSSLSVTGF GGGTIYYPTS TAEGTFGAIA
   A0A4R4NB20  PAPTQSSIEA LRGPFATSQT SVSSLSVSGF GGGTIYYPTS TAAGTFGAVA
   A0A1D8SZ57  PAPTESSIEA SRGSYSVADT RVSSLAVTGF GGGTIYYPTS TADGTFGAVV
       Q9L2J6  PAPTESSIEA LRGPYSVADT SVSSLAVTGF GGGTIYYPTS TSDGTFGAVV
   A0A089Z882  PAPTQSSIEA LRGPYAVSQT SVSSLAVTGF GGGTIYYPTS TADGTFGAVA
   A0A1H9JKT6  PDPTERSIEA ARGPYSVSET RVSSLSVTGF GGGTIYYPTT TSDGTFGAVA
   A0A1Y5XYT9  PDPTESSIEA SRGPFSVSQT TVSRLSATGF GGGTIYYPTS TSEGTFGALA
       R4SZ25  PDPTESSIEA SRGSFAVSQT SVSSLAVTGF GGGTIYYPTS TAQGTFGAVA
   A0A1Q8CLB3  PDPTENSIEA TRGPFAVSQT SVSSLVVTGF GGGTIYYPTS TAEGTFGAVA
       U5W5F9  PAPTSAVLDA SRGPFATSQQ SVSSLSVSGF GGGVIYYPTS TSAGTFGGIA
     AAE13316  SNHTPAAPEL VARQLGAIEN GLESGSANAC PDAILIFARG STEPGNMGIT
```

Figure 2D

```
             151                                                200
 SEQ_ID_NO_1  MSPGYTADAS SLAWLGRRLA SHGFVVIVIN TNSRLDFPDS RASQLSAAL-
 SEQ_ID_NO_4  MSPGYTADAS SLAWLGRRLA SHGFVVLVIN TNSRFDYPDS RASQLSAAL-
 SEQ_ID_NO_6  IVPGYTARQS SIKWWGPRLA SHGFVVITID TNSTLDQPSS RSSQQMAALR
      Q47RJ7  ISPGYTGTQA SVAWLGERIA SHGFVVITID TNTTLDQPDS RARQLNAAL-
    CBY05529  ISPGYTGTQA SVAWLGKRIA SHGFVVITID TITTLDQPDS RARQLNAAL-
    PZN61876  ISPGYTGTEA SIAWLGERIA SHGFVVITID TITTLDQPDS RAEQLNAAL-
    AAZ54921  ISPGYTGTEA SIAWLGERIA SHGFVVITID TITTLDQPDS RAEQLNAAL-
    BAK48590  ISPGYTGTQS SIAWLGERIA SHGFVVIAID TNTTLDQPDS RARQLNAAL-
  A0A147KJY8  ISPGYTGTQA SVAWLGERIA SHGFVVITID TNTTLDQPDS RARQLDAAL-
WP_083947829  ISPGYTATQS SVAWLGERIA SHGFVVITID TNTTLDQPDS RADQLEAAL-
  A0A4R6UW92  IAPGYTASSS SMSWMGERLA SQGFVIFTID TNTRYDQPDS RGDQISAAL-
  A0A5Q2RDB8  VAPGFTASQS SMSWLGHRLA SQGFVVFTID TNGRFDQPGS RADQLLAAA-
    ACU97777  VAPGFTASQG SMSWYGERVA SQGFIVFTID TNTRLDQPGQ RGRQLLAAL-
  A0A561WKJ0  ISPGFTASQS SVSWLGPRIA SQGFVVITID TLSVYDQPDA RGTQLLAAL-
      G0FYZ7  IAPGFTATQS SIAWLGPRLA SQGFVVFTID TLTTSDQPDS RGRQLLASL-
  A0A0N0A0T6  VSPGYTGTQS SISWLGPRLA SQGFVVFTID TNTIYDQPDS RASQLLAAL-
  A0A1W2C2B9  ISPGYTGTQS TISWLGPRLA SQGFVIFTID TNSRYDQPDS RASQLLAAL-
  A0A2T0T7X1  VSPGYTGTQS SISWLGPRIA SQGFVVFTID TITTLDQPDS RASQLLAAL-
  A0A5Q0HE30  ISPGYTGTQS SISWLGPRLA SQGFVVFTID TNTTLDQPDS RADQLLAAL-
  A0A1Q4WZS7  VSPGYTASQS SMAWLGPRIA SQGFVVFTID TNSRYDQPDS RASQLLSAL-
  A0A4R4NB20  VAPGFTADQS SMAWLGPRLA SQGFVIFTID TNTRLDQPDS RARQLNAAL-
  A0A1D8SZ57  ISPGYTAYQS SIAWLGPRLA SQGFVVFTID TNTTLDQPDS RGRQLLAAL-
      Q9L2J6  IAPGFTAYQS SIAWLGPRLA SQGFVVFTID TNTTLDQPDS RGRQLLAAL-
  A0A089Z882  ISPGFTAYES SIAWLGPRLA SQGFVVFTID TNTTMDQPAS RGDQLLAAL-
  A0A1H9JKT6  VSPGYTADQS SMAWYGPRLA SQGFVVFTID TNTRYDQPDS RGDQLLAAL-
  A0A1Y5XYT9  ISPGFTATQS SISWMGPRLA SQGFVVITID TLSTLDQPDS RGDQLRAAL-
      R4SZ25  ISPGFTATQS SIAWIGPRLA SQGFVVFTID TNTIYDQPDS RGDQLLAAL-
  A0A1Q8CLB3  VSPGFTATQS SIAWIGPRLA SQGFVVITID TLTVLDQPDS RGDQLLAAL-
      U5W5F9  ISPGYTASWS SISWLGPRIA SHGFVVIGIE TNSVFDQPSS RGNQLLAAL-
    AAE13316  VGPALANG-- --------LE SHIRNIWIQG VGGPYDAALA TN--------
```

Figure 2E

```
             201                                                  250
SEQ_ID_NO_1  --NYLRTSSP SAVRARLDAN RLAVAGHSMG GGATLRISEQ IPTLKAGVPL
SEQ_ID_NO_4  --NYLRTSSP SAVRARLDAN RLAVAGHSMG GGGTLRIAEQ NPSLKAAVPL
SEQ_ID_NO_6  QVASLNGTSS SPIYGKVDTA RMGVMGWSMG GGGSLISAAN NPSLKAAAPQ
     Q47RJ7  --DYMINDAS SAVRSRIDSS RLAVMGHSMG GGGTLRLASQ RPDLKAAIPL
   CBY05529  --DYMINDAS SAVRSRIDSS RLAVMGHSMG GGGSLRLASQ RPDLKAAIPL
   PZN61876  --NHMINRAS STVRSRIDSS RLAVMGHSMG GGGSLRLASQ RPDLKAAIPL
   AAZ54921  --NHMINRAS STVRSRIDSS RLAVMGHSMG GGGTLRLASQ RPDLKAAIPL
   BAK48590  --DYMLTDAS SAVRNRIDAS RLAVMGHSMG GGGTLRLASQ RPDLKAAIPL
 A0A147KJY8  --DHMLNDAS SAVRSRIDRN RLAVMGHSMG GGGTLRLASQ RPDLKAAIPL
WP_083947829 --DHMVDGAS STVRSRIDRN RLAVMGHSMG GGGTLRLASR RPDLKAAIPL
 A0A4R6UW92  --DYLVEDST SAVRNRIDPD RLAAMGHSMG GGGTLAVAAD RPELKAAIPL
 A0A5Q2RDB8  --DYLADDSS SAVQARLDDS RMAVMGHSMG GGGSIEASSD RSSLKASIPL
   ACU97777  --DYLVERSD RKVRERLDPN RLAVMGHSMG GGGSLEATVM RPSLKASIPL
 A0A561WKJ0  --DYLTGSSA --VRTRIDAT RLGVMGHSMG GGGSLAASRT RPALQAAVPL
     G0FYZ7  --DYLTQQSS --VRSRIDST RLGVVGHSMG GGGTLEAARS RPTLQAAVPL
 A0A0N0A0T6  --DYLTQQSS --VRSRIDAT RLGVMGHSMG GGGTLRAASQ RPTLQAAIPL
 A0A1W2C2B9  --DYLTQQSS --VRTRIDSS RLGVMGHSMG GGGTLRAASQ RPSLQAAIPL
 A0A2T0T7X1  --DYLTQRSA --VRARIDAT RLGVMGHSMG GGGTLRAAAN RPALQAAIPL
 A0A5Q0HE30  --DYLTQRSS --VRTRIDNT RLGVMGHSMG GGGTLRAAEQ RPSLQAAIPL
 A0A1Q4WZS7  --DYLTQRSS --VRSRIDAS RLGVMGHSMG GGGTLRAAEQ RPALQAAIPL
 A0A4R4NB20  --DYLTQRSS --VRSRIDAS RLGVMGHSMG GGGTLEIAED RPQLQAAIPL
 A0A1D8SZ57  --DYLTGRSS --VRERIDSS RLGVMGHSMG GGGSLEAAKS RPSLQAAIPL
     Q9L2J6  --DYLTGRSS --VRGRIDSG RLGVMGHSMG GGGTLEAAKS RPSLQAAIPL
 A0A089Z882  --DYLTQRSS --VRGRVDAT RLGVMGHSMG GGGSLEAAKD RPSLQAAIPL
 A0A1H9JKT6  --DYLTQRSS --VRGRIDSG RLAVMGHSMG GGGSLEAAKD RPSLKAAIPL
 A0A1Y5XYT9  --TYLTQRST --VRTRIDAS RLAVAGHSMG GGGSLEAAAD QPTLQAAIPI
     R4SZ25  --DYLTQRST --VRSRIDTS RLAVAGHSMG GGGSLEAAQD RPSLQAAVPL
 A0A1Q8CLB3  --DYLTQRSS --VRGRIDAS RLAVSGHSMG GGGSLEATET RPSLQASVPL
     U5W5F9  --DYLTTRSS --VRTRVDAS RLAVAGHSMG GGGSLEAAKD RPSLQAAVPL
   AAE13316  ---FLPRGTS ---QANIDEG KRLFALANQK CPNTPVVAGG YSQGAALIAA
```

Figure 2F

```
              251                                                300
 SEQ_ID_NO_1  TPWHTDKTFN -TPVPQLIVG AEADTVAPVS QHAIPFYQNL PSTTPKVYVE
 SEQ_ID_NO_4  TPWHTDKTFN -TSVPVLIVG AEADTVAPVS QHAIPFYQNL PSTTPKVYVE
 SEQ_ID_NO_6  APWDSSTNFS SVTVPTLIFA CENDSIAPVN SSALPIYDSM SRN-AKQFLE
      Q47RJ7  TPWHLNKNWS SVRVPTLIIG ADLDTIAPVL THARPFYNSL PTSISKAYLE
    CBY05529  TPWHLNKNWS SVRVPTLIIG ADLDTIAPVL THARPFYNSL PTSISKAYLE
    PZN61876  TPWHLNKNWS SVTVPTLIIG ADLDTIAPVA THAKPFYNSL PSSISKAYLE
    AAZ54921  TPWHLNKNWS SVTVPTLIIG ADLDTIAPVA THAKPFYNSL PSSISKAYLE
    BAK48590  TPWHLNKSWR DITVPTLIIG AEYDTIASVT LHSKPFYNSI PSPTDKAYLE
  A0A147KJY8  TPWHLNKSWS NVQVPTLIIG ADLDTIAPVL THAEPFYNSI PTSTRKAYLE
WP_083947829  TPWHLNKSWS NVQVPTLIIG AENDTVAPVA LHAEPSYTSI PTSTRKAYLE
  A0A4R6UW92  TPWHLDKTWS EVDVPTMIIG AENDTVASVS SHSIPFYNSL SGAPDKVYLE
  A0A5Q2RDB8  TPWHTRKTWS SVQVPTLVVG AENDSVASTS SHAIPLYNGL PSSLDKAYLE
    ACU97777  TPWNLDKTWG QVQVPTFIIG AELDTIASVR THAKPFYESL PSSLPKAYME
  A0A561WKJ0  APWHTTKSWS TDRVPTLIIG AESDTVAPVA SHAEPFYTSL PSTLDKAYLE
      G0FYZ7  TAWDLTKNWS TLQVPTLVVG AQSDTVAPVA SHSIPFYTSL PSTLDRAYLE
  A0A0N0A0T6  TAWHTTKNWS SVRVPTLVVG AEDDSIAPVA THSEPFYTTL PSTLDKAYLE
  A0A1W2C2B9  TGWHTTKNWS SVRVPTLVVG AENDSVASVS SHSEPFYTSL PSTLDKAYLE
  A0A2T0T7X1  TGWHTDKTWG DVRVPTLVVG ADGDTIAPVA THSKPFYNSL PSSLDRAYLE
  A0A5Q0HE30  TGWHTDKTWG SVRVPTLVIG ADGDTIAPVS SHSEPFYTTL PSTLDKAYLE
  A0A1Q4WZS7  TGWHTDKTWG SVRVPTLVVG AENDSVASVS SHSIPFYNSL PSTLDKAYLE
  A0A4R4NB20  TPWDLQKNFS DVRVPTMIIG AEADTIAPVA THSKPFYTSI PASSEKAYLE
  A0A1D8SZ57  TPWNLDKTWP EVSTPTLVVG ADGDTIAPVA SHAEPFYSSL PSATDRAYLE
      Q9L2J6  TPWNLDKSWP EVSTPTLVVG ADGDTIAPVA SHAEPFYSGL PSSTDRAYLE
  A0A089Z882  TPWNLDKTWS EVRTPTLIFG ADGDTIAPVS SHAEPFYQNL PSSLDKAYLE
  A0A1H9JKT6  TPWNLDKTWR EITVPTFIVG ADGDSIASVR SHAEPFYESL PSSTDRAYME
  A0A1Y5XYT9  AAWNTQKTWS TLRVPTFVIG GESDSVAPVA SHSIPFYTSI PASAEKAYME
      R4SZ25  APWNTQKSWS SLRVPTFIIG GESDSVAPVA SHSIPFYTSI PATAEKAYME
  A0A1Q8CLB3  APWNADKTWS SVRTPTFIIG GESDSVASVS SHSIPFYQSI PAASEKAYME
      U5W5F9  APWNTTKTWS GLQVPTLIIG GESDTVAPVS SHSIPFYNSI PSSAEKAYLE
    AAE13316  AVSELSGAVK EQVKGVALFG YTQN---LQN RGGIPNY--- PRERTKVFCN
```

Figure 2G

```
               301                                                    350
SEQ_ID_NO_1    LDNATHFAPN SPNAA---IS VYTISWMKLW VDNDTRYRQF LCN----VND
SEQ_ID_NO_4    LDNASHFAPN SNNAA---IS VYTISWMKLW VDNDTRYRQF LCN----VND
SEQ_ID_NO_6    INGGSHSCAN SGNSNQALIG KKGVAWMKRF MDNDTRYSTF ACENPNSTRV
Q47RJ7         LDGATHFAPN IPNKI---IG KYSVAWLKRF VDNDTRYTQF LCPGPRDGLF
CBY05529       LDGATHFAPN IPNKI---IG KYSVAWLKRF VDNDTRYTQF LCPGPRDGLF
PZN61876       LDGATHFAPN IPNKI---IG KYSVAWLKRF VDNDTRYTQF LCPGPRDGLF
AAZ54921       LDGATHFAPN IPNKI---IG KYSVAWLKRF VDNDTRYTQF LCPGPRDGLF
BAK48590       LDGASHFAPN ITNKT---IG MYSVAWLKRF VDEDTRYTQF LCPGPRTGLL
A0A147KJY8     LDGATHFAPN ITNST---IG MYSVAWLKRF VDEDTRYTQF LCPGPRTGLF
WP_083947829   LNGASHFAPS VANAT---IG MYGVAWLKRF VDEDTRYTRF LCPGPRTGLF
A0A4R6UW92     LDGASHFAPN LSNTT---IA KYSISWLKRF VDEDTRYSQF LCPGPSTGLG
A0A5Q2RDB8     LDGASHFAPN SNNTT---IA AYSISWLKRF VDNDTRYDQF LCG-PNHTAD
ACU97777       LDGATHFAPN IPNTT---IA KYVISWLKRF VDEDTRYSQF LC--PN-PTD
A0A561WKJ0     LNNASHSAPT SANVT---VA KYSISWLKRF IDNDTRYEQF LC--PAPSGS
G0FYZ7         LRGASHFAPN SPNTT---IA KYTLSWLKRF IDNDTRYEQF LC--PIPSTS
A0A0N0A0T6     LNNATHFAPN SNNTT---IA KYSISWLKRF IDNDTRYEQF LC--PAPGRS
A0A1W2C2B9     LNNASHFAPN SPNTT---IA KYSISWLKRF IDNDTRYEQF LC--PAPGRS
A0A2T0T7X1     LRGATHFTPN SSNTT---IA KYSISWLKRF IDNDTRYEQF LC--PTPSSS
A0A5Q0HE30     LNGATHFTPN TSNTT---IA KYSISWLKRF IDNDTRYEQF LC--PAPRG-
A0A1Q4WZS7     LNGASHFAPN SSNTT---IA KYSIAWLKRF IDNDTRYEQF LC--PSPANS
A0A4R4NB20     LNGASHFAPN IANTT---IA KYSISWLKRY IDNDTRYDQF LC--PGPSRD
A0A1D8SZ57     LNNATHFSPN TSNTT---IA KYSISWLKRF IDNDTRYEQF LC--PLPRPS
Q9L2J6         LNNATHFSPN TSNTT---IA KYSISWLKRF IDDDTRYEQF LC--PLPRPS
A0A089Z882     LNNATHFTPN SNDTT---IA KYSISWLKRF IDNDTRYEQF LC--PLPRPS
A0A1H9JKT6     LNNATHFTPN TSNTE---IA KYSISWLKRF VDNDTRYEQF LC--PLPRPS
A0A1Y5XYT9     LDNASHFFPQ TPNTT---MA KYMISWLKRF VDNDTRYEQF LC--PAPN-D
R4SZ25         LDNASHFFPN TANTT---MA KYTISWLKRF VDNDTRYEQF LC--PAPD-D
A0A1Q8CLB3     LDGASHFFPN TPNTT---MA KYLISWMKRF VDNDTRYEQF LC--PPPN-D
U5W5F9         LNNASHFFPQ STNTP---TG RQAVAWLKRF VDNDTRYDQF IC--PGPS-S
AAE13316       VGDAVCTG-- --------TL IITPAHLSYT IEARGEAARF LR--------
```

Figure 2H

```
              351                                          400
 SEQ_ID_NO_1  PALSDFRSNN RHCQ------ ---------- ---------- ----------
 SEQ_ID_NO_4  PALSDFRTNN RHCQ------ ---------- ---------- ----------
 SEQ_ID_NO_6  SDFRTANCSL EHHHHHH--- ---------- ---------- ----------
      Q47RJ7  GEVEEYRSTC PF-------- ---------- ---------- ----------
    CBY05529  GEVEEYRSTC PF-------- ---------- ---------- ----------
    PZN61876  GEVEEYRSTC PF-------- ---------- ---------- ----------
    AAZ54921  GEVEEYRSTC PF-------- ---------- ---------- ----------
    BAK48590  SDVEEYRSTC PF-------- ---------- ---------- ----------
  A0A147KJY8  SDVEEYRSTC PF-------- ---------- ---------- ----------
WP_083947829  SDVEEYRSTC PF-------- ---------- ---------- ----------
  A0A4R6UW92  SDVSDYRNTC PV-------- ---------- ---------- ----------
  A0A5Q2RDB8  RDISDYRSTC PYSPVDPGDP GDPGTPGGEC VRTHTRNHVD AGRATNVWGT
    ACU97777  RAIEEYRSTC PY-------- ---------- ---------- ----------
  A0A561WKJ0  -AIQEYRDTC PHS------- ---------- ---------- ----------
      G0FYZ7  LSISDYRGNC PHNG------ ---------- ---------- ----------
  A0A0N0A0T6  TLIEEYRDTC PHS------- ---------- ---------- ----------
  A0A1W2C2B9  TLIEEYRDTC PHS------- ---------- ---------- ----------
  A0A2T0T7X1  LLIAEFRGNC PHSS------ ---------- ---------- ----------
  A0A5Q0HE30  AAIQEYRDTC PHST------ ---------- ---------- ----------
  A0A1Q4WZS7  SLISDYRDTC PHGV------ ---------- ---------- ----------
  A0A4R4NB20  LNISEYRDTC PNS------- ---------- ---------- ----------
  A0A1D8SZ57  LTIEEYRGNC PHGS------ ---------- ---------- ----------
      Q9L2J6  LTIEEYRGNC PHGS------ ---------- ---------- ----------
  A0A089Z882  LTIEEYRGNC PHTS------ ---------- ---------- ----------
  A0A1H9JKT6  LAIEEFRGNC PH-------- ---------- ---------- ----------
  A0A1Y5XYT9  REISDYRDTC PHS------- ---------- ---------- ----------
      R4SZ25  RAISDYRDTC PHA------- ---------- ---------- ----------
  A0A1Q8CLB3  SDIEEYRHTC PHV------- ---------- ---------- ----------
      U5W5F9  SSISDYRNSC PLT------- ---------- ---------- ----------
    AAE13316  ---DRIRA-- ---------- ---------- ---------- ----------
```

Figure 2I

```
             401                                435
SEQ_ID_NO_1  ---------- ---------- ---------- -----
SEQ_ID_NO_4  ---------- ---------- ---------- -----
SEQ_ID_NO_6  ---------- ---------- ---------- -----
     Q47RJ7  ---------- ---------- ---------- -----
   CBY05529  ---------- ---------- ---------- -----
   PZN61876  ---------- ---------- ---------- -----
   AAZ54921  ---------- ---------- ---------- -----
   BAK48590  ---------- ---------- ---------- -----
 A0A147KJY8  ---------- ---------- ---------- -----
WP_083947829 ---------- ---------- ---------- -----
 A0A4R6UW92  ---------- ---------- ---------- -----
 A0A5Q2RDB8  AYAVGSGDNL GSHSYFNYVS LQSISGGWTE VSSCP
   ACU97777  ---------- ---------- ---------- -----
 A0A561WKJ0  ---------- ---------- ---------- -----
     G0FYZ7  ---------- ---------- ---------- -----
 A0A0N0A0T6  ---------- ---------- ---------- -----
 A0A1W2C2B9  ---------- ---------- ---------- -----
 A0A2T0T7X1  ---------- ---------- ---------- -----
 A0A5Q0HE30  ---------- ---------- ---------- -----
 A0A1Q4WZS7  ---------- ---------- ---------- -----
 A0A4R4NB20  ---------- ---------- ---------- -----
 A0A1D8SZ57  ---------- ---------- ---------- -----
     Q9L2J6  ---------- ---------- ---------- -----
 A0A089Z882  ---------- ---------- ---------- -----
 A0A1H9JKT6  ---------- ---------- ---------- -----
 A0A1Y5XYT9  ---------- ---------- ---------- -----
     R4SZ25  ---------- ---------- ---------- -----
 A0A1Q8CLB3  ---------- ---------- ---------- -----
     U5W5F9  ---------- ---------- ---------- -----
   AAE13316  ---------- ---------- ---------- -----
```

Figure 3

| | %Sequence Identity w.r.t. SEQ ID NO:1 |
|---|---|
| SEQ ID NO:4 | 94 |
| SEQ ID NO:6 | 42 |
| Q47RJ7 | 55 |
| CBY05529 | 56 |
| PZN61876 | 56 |
| AAZ54921 | 56 |
| BAK48590 | 56 |
| A0A147KJY8 | 55 |
| WP_083947829 | 54 |
| A0A4R6UW92 | 56 |
| A0A5Q2RDB8 | 58 |
| ACU97777 | 55 |
| A0A561WKJ0 | 55 |
| G0FYZ7 | 55 |
| A0A0N0A0T6 | 57 |
| A0A1W2C2B9 | 57 |
| A0A2T0T7X1 | 56 |
| A0A5Q0HE30 | 56 |
| A0A1Q4WZS7 | 58 |
| A0A4R4NB20 | 56 |
| A0A1D8SZ57 | 54 |
| Q9L2J6 | 54 |
| A0A089Z882 | 55 |
| A0A1H9JKT6 | 56 |
| A0A1Y5XYT9 | 55 |
| R4SZ25 | 55 |
| A0A1Q8CLB3 | 55 |
| U5W5F9 | 57 |
| AAE13316.1 | 13 |

| Colony Tracking Number | Improvement of Total Activity w.r.t. G1P: PF at pH8.0, 65°C, 72hr | Improvement of Thermostability w.r.t. G1P: PF at 86°C, 3hr followed by pH8.0, 65°C, 72hr | AA Mutations w.r.t G1P |
|---|---|---|---|
| ICL00002082 | 1.09 | 1.60 | T136A |
| ICL00002119 | 1.38 | 1.73 | L90Y |
| ICL00002250 | 1.32 | 1.34 | D158L |
| ICL00002407 | 1.09 | 1.35 | F92G |
| ICL00002455 | 1.86 | 2.04 | A127S |
| ICL00002587 | 1.67 | 1.50 | F92L |
| ICL00002892 | 1.10 | 1.59 | D158E |
| ICL00002957 | 1.20 | 2.00 | D158I |
| ICL00003148 | 1.17 | 4.79 | S212F |
| ICL00003268 | 2.23 | 2.96 | N211F |
| ICL00003464 | 1.69 | 7.47 | N211M |
| ICL00003521 | 2.11 | 3.17 | N211V |
| ICL00003619 | 1.79 | 3.87 | S212L |
| ICL00004007 | 1.34 | 1.66 | S212M |
| ICL00004572 | 1.08 | 2.00 | T136V |
| ICL00004599 | 2.52 | 3.03 | S181R |
| ICL00004620 | 1.04 | 5.11 | N211L |
| ICL00004701 | 2.79 | 3.51 | S181C |
| ICL00004746 | 2.54 | 1.81 | R251K |
| ICL00004960 | 1.30 | 10.50 | D203R |
| ICL00005328 | 1.21 | 1.47 | T17A/S27T/I82L/S252T |
| ICL00005456 | 1.35 | 1.10 | T17A/S27T/T48S/I82L |
| ICL00005564 | 3.91 | 3.24 | S27T/T48S/I82L/F92Y/S252T |
| ICL00005612 | 1.19 | 1.53 | T17A/S27T/T48S |
| ICL00005678 | 1.50 | 1.35 | T17A/S27T |
| ICL00005703 | 1.99 | 4.82 | T17A/S27T/T48S/I82L/L90F/F92Y/S252T |
| ICL00005893 | 1.41 | 1.32 | D18R/V40T/I139A/D203N |
| ICL00006174 | 1.55 | 2.69 | D18R |
| ICL00007723 | 1.32 | 1.59 | S32K |
| ICL00007799 | 1.71 | 1.07 | T48S |
| ICL00007884 | 1.22 | 1.56 | T25V |
| ICL00007898 | 1.20 | 1.18 | V23T |
| ICL00007932 | 1.02 | 1.45 | S27W |
| ICL00007957 | 1.01 | 1.06 | S22I/Y26K |
| ICL00008145 | 1.52 | 1.13 | V23L |

Figure 7B

| Colony Tracking Number | Improvement of Total Activity w.r.t. G1P: PF at pH8.0, 65°C, 72hr | Improvement of Thermostability w.r.t. G1P: PF at 86°C, 3hr followed by pH8.0, 65°C, 72hr | AA Mutations w.r.t G1P |
|---|---|---|---|
| ICL00008196 | 1.23 | 1.70 | S27F |
| ICL00008216 | 1.17 | 1.41 | A24V |
| ICL00008219 | 1.12 | 1.31 | Y26L |
| ICL00008225 | 1.21 | 1.48 | S22V |
| ICL00008265 | 1.46 | 1.57 | S13R |
| ICL00008348 | 1.16 | 1.37 | S22K |
| ICL00008461 | 1.09 | 1.30 | A14K |
| ICL00008475 | 1.06 | 1.17 | S32Q |
| ICL00008588 | 1.21 | 1.26 | N9S |
| ICL00008962 | 1.07 | 1.09 | P20T |
| ICL00008996 | 1.18 | 1.15 | N2R |
| ICL00009048 | 1.19 | 1.37 | S1A |
| ICL00009065 | 1.03 | 1.24 | N9E |
| ICL00009097 | 1.80 | 3.36 | S27L **(G2P)** |
| ICL00009224 | 1.13 | 1.30 | Y26T |
| ICL00010754 | 1.35 | 1.01 | N204S |
| ICL00010780 | 1.25 | 1.10 | S193K |
| ICL00010882 | 1.33 | 1.44 | V219L |
| ICL00010896 | 1.19 | 1.23 | S193N |
| ICL00010936 | 1.01 | 1.23 | N204K |
| ICL00010943 | 1.19 | 1.48 | S193P |
| ICL00011142 | 1.20 | 3.14 | R255L |
| ICL00011148 | 1.03 | 1.38 | N231S |
| ICL00011374 | 1.14 | 1.29 | S193H |
| ICL00011392 | 1.17 | 1.12 | R255V |
| ICL00011544 | 1.07 | 1.29 | A246D |
| ICL00011557 | 1.14 | 1.39 | R255M |
| ICL00011716 | 1.17 | 1.63 | Q189L |
| ICL00011873 | 1.09 | 1.73 | S193E |
| ICL00012205 | 1.07 | 1.03 | S98N |
| ICL00012227 | 1.63 | 1.23 | S113K |
| ICL00012261 | 1.06 | 1.41 | T160V |
| ICL00012306 | 1.01 | 1.20 | N162R |
| ICL00012320 | 1.15 | 2.86 | N87I |
| ICL00012326 | 1.12 | 1.90 | N122E |

Figure 7C

| Colony Tracking Number | Improvement of Total Activity w.r.t. G1P: PF at pH8.0, 65°C, 72hr | Improvement of Thermostability w.r.t. G1P: PF at 86°C, 3hr followed by pH8.0, 65°C, 72hr | AA Mutations w.r.t G1P |
|---|---|---|---|
| ICL00012345 | 1.06 | 2.64 | N87L |
| ICL00012356 | 1.13 | 1.18 | S101K |
| ICL00012359 | 1.29 | 1.31 | S101A |
| ICL00012402 | 1.30 | 1.17 | Q142L |
| ICL00012403 | 1.23 | 1.21 | A114K |
| ICL00012416 | 1.14 | 1.11 | S101F/T136A |
| ICL00012464 | 1.19 | 1.24 | S110R |
| ICL00012482 | 1.10 | 1.02 | S98V |
| ICL00012493 | 1.14 | 1.80 | T160K |
| ICL00012514 | 1.03 | 1.38 | R108K |
| ICL00012584 | 1.27 | 1.39 | S98L |
| ICL00012627 | 1.49 | 1.30 | R108T |
| ICL00012633 | 1.14 | 1.34 | N87V |
| ICL00012656 | 1.04 | 1.30 | S113Q |
| ICL00012658 | 1.31 | 1.02 | T109L |
| ICL00012662 | 1.15 | 1.33 | R108H |
| ICL00012671 | 1.03 | 1.65 | S101H |
| ICL00012729 | 1.09 | 1.45 | N87H |
| ICL00012758 | 1.09 | 1.66 | N87M |
| ICL00012801 | 1.01 | 1.16 | T109K |
| ICL00012844 | 1.02 | 1.43 | R108E |
| ICL00012857 | 1.06 | 1.26 | S113A |
| ICL00012942 | 1.15 | 1.53 | S98A |
| ICL00012974 | 1.11 | 1.09 | N122A |
| ICL00013044 | 1.01 | 1.02 | S101W |
| ICL00013060 | 1.20 | 1.28 | N122S |
| ICL00013096 | 1.76 | 2.67 | N87F |
| ICL00013100 | 1.23 | 2.22 | Q142W |
| ICL00013155 | 1.01 | 1.47 | T160R |
| ICL00013169 | 1.19 | 1.46 | S98T |
| ICL00013185 | 1.10 | 1.04 | S110G |
| ICL00013203 | 1.05 | 1.06 | S101N |
| ICL00013205 | 1.60 | 1.17 | N122P |
| ICL00013208 | 1.03 | 1.19 | N87R |
| ICL00013211 | 1.07 | 1.65 | S101Q |

Figure 7D

| Colony Tracking Number | Improvement of Total Activity w.r.t. G1P: PF at pH8.0, 65°C, 72hr | Improvement of Thermostability w.r.t. G1P: PF at 86°C, 3hr followed by pH8.0, 65°C, 72hr | AA Mutations w.r.t G1P |
|---|---|---|---|
| ICL00013218 | 1.05 | 1.32 | S113R |
| ICL00013227 | 1.35 | 1.06 | R108C |
| ICL00013243 | 1.43 | 2.00 | N87Y |
| ICL00013247 | 1.37 | 1.27 | R108Q |
| ICL00013314 | 1.19 | 1.40 | R108S |
| ICL00013329 | 1.05 | 1.03 | R108P |
| ICL00013378 | 1.12 | 1.06 | N122H |
| ICL00013380 | 1.25 | 1.08 | A114V |
| ICL00013386 | 1.18 | 1.67 | S98E |
| ICL00013398 | 1.03 | 1.24 | S113N |
| ICL00013405 | 1.33 | 1.41 | I82F |
| ICL00013444 | 1.02 | 1.28 | S98M |
| ICL00014454 | 1.20 | 1.05 | T17L |
| ICL00014577 | 1.86 | 1.20 | Y60H |
| ICL00014581 | 1.17 | 1.54 | S252T |
| ICL00014863 | 1.05 | 1.08 | T17C |
| ICL00014900 | 1.18 | 1.07 | T17G |
| ICL00014910 | 1.29 | 1.26 | T17S |
| ICL00014948 | 1.42 | 1.12 | V229I |

Figure 8A

| Colony Tracking Number | Improvement of Thermostability w.r.t. G1P: PF at 86°C, 3hr followed by pH8.0, 65°C, 72hr | AA Mutations w.r.t G1P |
|---|---|---|
| ICL00003326 | 1.45 | S181A |
| ICL00003543 | 1.45 | T206G |
| ICL00003873 | 4.05 | N211I |
| ICL00004073 | 1.89 | D203V |
| ICL00004246 | 1.25 | D158K |
| ICL00004507 | 2.03 | A174K |
| ICL00004604 | 3.85 | A174R |
| ICL00004797 | 5.11 | E173R |
| ICL00005377 | 1.51 | T17A/S27T/I82L |
| ICL00008040 | 1.07 | S1M |
| ICL00008384 | 1.23 | T25F |
| ICL00008521 | 1.08 | S32M |
| ICL00008535 | 1.18 | Y26K |
| ICL00008555 | 1.39 | S34R |
| ICL00008628 | 1.18 | S22R |
| ICL00008912 | 1.17 | T25Q |
| ICL00008957 | 1.08 | T25R |
| ICL00008972 | 1.39 | T48N |
| ICL00011040 | 1.63 | R236C |
| ICL00011072 | 1.83 | A216P |
| ICL00011100 | 1.21 | V219K |
| ICL00011261 | 1.14 | N231L |
| ICL00011269 | 1.30 | N231Q |
| ICL00011336 | 1.02 | V219R |
| ICL00011353 | 1.02 | F250Y |
| ICL00011377 | 1.44 | Q189I |
| ICL00011563 | 1.15 | I222L |
| ICL00011570 | 1.02 | V219I |
| ICL00012235 | 1.49 | T160Q |
| ICL00012311 | 1.70 | N87K |
| ICL00012329 | 1.30 | I82M |
| ICL00012335 | 1.32 | S98Q/A209V |
| ICL00012728 | 1.05 | K147N |
| ICL00012740 | 1.77 | S101R |
| ICL00012777 | 1.01 | S101D |
| ICL00013327 | 1.11 | R108V |

Figure 8B

| Colony Tracking Number | Improvement of Thermostability w.r.t. G1P: PF at 86°C, 3hr followed by pH8.0, 65°C, 72hr | AA Mutations w.r.t G1P |
|---|---|---|
| ICL00013334 | 1.01 | T160S |
| ICL00013955 | 1.03 | T17A |
| ICL00014745 | 1.09 | T17K/A125S |
| ICL00014884 | 1.36 | T17Q |

Figure 9A

| Colony Tracking Number | Improvement of Total Activity w.r.t. G1P: PF at pH8.0, 65°C, 72hr | AA Mutations w.r.t G1P |
|---|---|---|
| ICL00002273 | 1.68 | F92V |
| ICL00002384 | 1.83 | F92I |
| ICL00002394 | 1.31 | R138L |
| ICL00002395 | 2.29 | S57V |
| ICL00002398 | 2.10 | M56I |
| ICL00002408 | 1.41 | T136M |
| ICL00002426 | 1.77 | S57M |
| ICL00002451 | 1.71 | M56L |
| ICL00002454 | 1.47 | A127V |
| ICL00002458 | 1.26 | S88K |
| ICL00002463 | 1.17 | T153L |
| ICL00002464 | 1.39 | L70M |
| ICL00002490 | 1.19 | T157A |
| ICL00002492 | 1.05 | G149V |
| ICL00002511 | 1.34 | L90K |
| ICL00002572 | 1.74 | F92K |
| ICL00002575 | 1.50 | V150L |
| ICL00002726 | 1.48 | F92N |
| ICL00002830 | 1.35 | A97F |
| ICL00002907 | 1.18 | A55V |
| ICL00002926 | 1.16 | T136S |
| ICL00003056 | 1.08 | A102V/T136M |
| ICL00003247 | 1.19 | T206P |
| ICL00003278 | 1.21 | P179Q |
| ICL00003410 | 2.43 | F208L |
| ICL00003475 | 1.29 | V170L |
| ICL00003638 | 2.11 | T206R |
| ICL00003718 | 1.62 | T206L |
| ICL00003752 | 2.12 | T206K |
| ICL00004309 | 1.03 | A55L |
| ICL00004349 | 1.64 | F208T |
| ICL00004360 | 1.17 | F208G |
| ICL00004409 | 1.23 | T157G |
| ICL00004439 | 1.24 | S57I |
| ICL00004440 | 1.04 | G149S |
| ICL00004447 | 1.47 | F92Q |

Figure 9B

| Colony Tracking Number | Improvement of Total Activity w.r.t. G1P: PF at pH8.0, 65°C, 72hr | AA Mutations w.r.t G1P |
|---|---|---|
| ICL00004493 | 1.02 | I139T |
| ICL00004570 | 1.10 | G149C |
| ICL00004663 | 1.13 | R251I |
| ICL00004687 | 2.28 | R251V |
| ICL00004709 | 1.10 | F161W |
| ICL00004829 | 1.20 | Q182T |
| ICL00004900 | 2.36 | I217S |
| ICL00004929 | 1.06 | F208R |
| ICL00004936 | 1.64 | I185L |
| ICL00004989 | 1.14 | I185Y |
| ICL00005005 | 1.31 | P213R |
| ICL00005066 | 1.15 | D249T |
| ICL00005133 | 1.61 | T17A/S27T/T48S/I82L/L90F/Q167V/P213N/S252T |
| ICL00005159 | 1.88 | T17A/S27T/L90F/F92Y/P213N |
| ICL00005170 | 1.43 | T17A/S27T/T48S/A135G/Q167V/P213N |
| ICL00005175 | 1.46 | T17A/S27T/L90F/A135G/S140A/Q167V/P213N/S252T |
| ICL00005183 | 1.13 | T17A/T48S/P213N |
| ICL00005218 | 1.46 | T17A/S27T/I82L/L90F/F92Y/Q167V |
| ICL00005240 | 3.46 | T17A/T48S/I82L/F92Y/Q167V/S252T |
| ICL00005248 | 1.49 | S27T/T48S/I82L/S140A/I143N/G149A |
| ICL00005327 | 1.14 | T17A/S27T/I82L/T145S/G149A/P213N |
| ICL00005347 | 1.02 | T17A/S27T/T48S/I82L/P213N/S252T |
| ICL00005408 | 1.07 | T17A/Q167V |
| ICL00005428 | 3.20 | T17A/I82L/F92Y/P213N |
| ICL00005493 | 2.02 | T17A/T48S/I82L/L90F/A135G/S140A/Q167V |
| ICL00005494 | 1.45 | S27T/I82L/P213N |
| ICL00005495 | 1.74 | T17A/S27T/I82L/P213N |
| ICL00005508 | 2.19 | T17A/I82L/L90F/F92Y/Q167V |
| ICL00005512 | 1.08 | T17A/T48S/I82L |
| ICL00005528 | 5.36 | T17A/S27T/T48S/L90F/F92Y |
| ICL00005536 | 1.55 | T17A/S27T/T48S/I82L/L90F/Q167V |
| ICL00005568 | 1.65 | T17A/I82L/L90F/F92Y/A135G/S140A/I143N/G149A/Q167V |
| ICL00005577 | 2.43 | T17A/S27T/L90F/F92Y/A135G/Q167V/S252T |
| ICL00005594 | 1.04 | T17A/S27T/T48S/P213N |
| ICL00005609 | 1.70 | T17A/S27T/T48S/I82L/L90F/P213N/S252T |

Figure 9C

| Colony Tracking Number | Improvement of Total Activity w.r.t. G1P: PF at pH8.0, 65°C, 72hr | AA Mutations w.r.t G1P |
|---|---|---|
| ICL00005649 | 1.35 | T17A/S27T/T48S/I82L/L90F/F92Y/S140A/T145S/P213N |
| ICL00005661 | 1.42 | T17A/S27T/I82L/P213N/S252T |
| ICL00005697 | 1.83 | S27T/T48S/I82L/L90F/A135G/S140A/I143N/T145S/P213N |
| ICL00005699 | 1.34 | T17A/S27T/T48S/I82L/L90F/F92Y/S140A/T145S |
| ICL00005719 | 1.18 | T17A/S27T/T48S/A135G/S140A |
| ICL00005720 | 1.06 | T17A/S27T/I82L/G149A/Q167V/P213N |
| ICL00005732 | 1.25 | T17A/I82L/S140A/I143N/Q167V/P213N/S252T |
| ICL00005743 | 1.38 | T17A/S27T/T48S/T145S/Q167V |
| ICL00005745 | 2.06 | T17A/S27T/T48S/I82L/L90F/F92Y/Q167V/S252T |
| ICL00005778 | 1.90 | I82F/R108T/L119I/V150I/F161W/Q167T/T194S/D203N |
| ICL00005815 | 4.18 | N9A/D18R/M56I/N85D/L119I/N254R |
| ICL00006031 | 1.13 | R108T/L119I/K147Q/F161W/A184S/D203N |
| ICL00006249 | 1.51 | T16E/D18R/M56I/K147Q/Q167T/A184S/D203N |
| ICL00006285 | 1.60 | T16E/D18R/R108T/K147Q/Q167T/A184S/N190S/T194S |
| ICL00006354 | 2.63 | Q5E/S22A/R72P/H77Q/F92Q |
| ICL00006389 | 1.21 | T16E/D18R/S22A/V40T/A97G/S101L/L119I/A127M/Q167 T/D203N |
| ICL00006409 | 2.23 | D18R/M56I/R72P/H77Q/F92Q/A127M/V150I/A184S/D203 N/N254R |
| ICL00006438 | 1.08 | T16E/D18R/Y26T/S88T/S101L/H156N/V200L |
| ICL00006466 | 1.48 | T16E/D18R/S22A/M56I/N85D/L119I/A184S |
| ICL00006472 | 2.11 | T16E/D18R/V40T/S88T/L119I/A127M/V150I/D203N |
| ICL00006482 | 1.30 | M56I/S88T/R108T/N190S/L227R |
| ICL00006522 | 3.10 | N9A/S22A/G46S/M56I/R72P/F92Q/L119I/T221S/M225L |
| ICL00006530 | 2.26 | A14S/L15I/S22A/F92Q/I143R/Q167T/V219K |
| ICL00006562 | 3.09 | D18R/M56I/I139A/L227R/W228F |
| ICL00006566 | 2.95 | S22A/I54V/R72P/F92Q/V150I/V200L |
| ICL00006581 | 1.09 | S22A/G46S/S101L/F161W/D203N/R236E |
| ICL00006661 | 1.90 | T16E/D18R/G53A/I54V/R72P/L119I/A127M/Q167T/V200 L |
| ICL00006710 | 3.67 | D18R/I54V/I82F/R108T/V150I/N253Y/N254R |
| ICL00006743 | 2.42 | T16E/D18R/M56I/N85D/S88T/R108T/F161W/Q167T |
| ICL00006771 | 1.71 | G53A/R108T/Q167T/A184S/T194S/N243P |
| ICL00006790 | 1.90 | N9A/S22A/Q167T |
| ICL00006811 | 2.84 | T16E/D18R/M56I/A127M/R138E/T194S/V200L/M225L |

Figure 9D

| Colony Tracking Number | Improvement of Total Activity w.r.t. G1P: PF at pH8.0, 65°C, 72hr | AA Mutations w.r.t G1P |
|---|---|---|
| ICL00006843 | 1.72 | S22A/A97G/V150I/D203N/M225L/R236E |
| ICL00006877 | 3.91 | D18R/I54V/M56I/R138E/I139A/T194S/D203N/V219K/F250I |
| ICL00006896 | 1.26 | D18R/V40T/I82F/S101L/N105D/L119I/H156N/F161W/N190S/T194S/D203N |
| ICL00006914 | 2.47 | N9A/V40T/L49G/I54V/R108T/V150I/D203N/T221S/M225L |
| ICL00006921 | 1.65 | D18R/I54V/I82F/N105D/A127M/A184S/S218A/V219K/M225L/N241P/N243P |
| ICL00006928 | 1.73 | L15I/D18R/R108T/R138E/I139A/F161W/A184S/N190S/D203N |
| ICL00006935 | 1.23 | S22A/L49G/M56I/V83T/S101L/R108T/L119I/A127M/T194S |
| ICL00006942 | 1.94 | M56I/I82F/R108T/I139A/F161W/T194S/D203N/N241P |
| ICL00006978 | 1.34 | I143R/Q167T/V198A/W228F |
| ICL00006980 | 1.07 | S22A/A24S/G46S/V150I/Q167T |
| ICL00006984 | 2.13 | S88T/R108T/V150I/A184S/D203N/T221S/M225L/N243P |
| ICL00007007 | 1.65 | Q5E/N9A/M56I/F92Q/R108T/L119I/Q167T/N253Y |
| ICL00007084 | 2.24 | T16E/D18R/V40T/M56I/I82F/R108T/L119I/F161W/L227R/Q258P |
| ICL00007113 | 1.70 | D18R/V40T/M56I/R108T/R138E/H156N |
| ICL00007179 | 1.57 | D18R/M56I/R138E/I139A/N190S/D203N/M225L |
| ICL00007298 | 1.37 | T16E/D18R/M56I/V150I/S218A/V219K |
| ICL00007465 | 1.48 | T16E/D18R/S88T/R108T/W228F |
| ICL00007504 | 1.56 | D18R/N85D/R108T/L119I/N190S/T194S |
| ICL00007604 | 1.35 | D18R/G46S/M56I/R108T/A127M/R138E/I139A/N190S/L227R/W228F/R236E |
| ICL00007658 | 1.83 | D18R/I139A/F161W/W228F |
| ICL00007805 | 1.15 | G46L |
| ICL00007887 | 1.29 | S1G |
| ICL00007890 | 2.02 | S32Y/A62T |
| ICL00008057 | 1.08 | S13L |
| ICL00008180 | 1.21 | N9S/T25H |
| ICL00008192 | 1.35 | R30K |
| ICL00008296 | 1.12 | T25A |
| ICL00008309 | 1.25 | V33T |
| ICL00008359 | 1.26 | V33Q |
| ICL00008376 | 1.82 | V33G |
| ICL00008393 | 1.15 | A68F |

Figure 9E

| Colony Tracking Number | Improvement of Total Activity w.r.t. G1P: PF at pH8.0, 65°C, 72hr | AA Mutations w.r.t G1P |
|---|---|---|
| ICL00008636 | 1.09 | S27H |
| ICL00008936 | 1.28 | S22P |
| ICL00009061 | 1.21 | S1R |
| ICL00010801 | 2.21 | V177A/A216L |
| ICL00010809 | 1.01 | R255E |
| ICL00010811 | 1.01 | S193V |
| ICL00010827 | 1.02 | A246K |
| ICL00010831 | 1.01 | R236K |
| ICL00010885 | 1.14 | R255Y |
| ICL00010888 | 1.07 | N204A |
| ICL00010945 | 1.17 | S193F |
| ICL00010950 | 1.10 | A246T |
| ICL00010970 | 1.25 | N204R |
| ICL00010981 | 1.24 | T194S |
| ICL00011066 | 1.08 | V219F |
| ICL00011150 | 1.54 | N204A/Q237R |
| ICL00011156 | 1.09 | A216V |
| ICL00011159 | 1.06 | T194G |
| ICL00011246 | 1.06 | R255W |
| ICL00011384 | 1.09 | R236Q |
| ICL00011413 | 1.58 | R255S |
| ICL00011509 | 1.09 | S193T |
| ICL00011585 | 1.02 | R255G |
| ICL00011635 | 1.08 | A216S |
| ICL00011679 | 1.34 | S223A |
| ICL00011733 | 1.40 | Q189V |
| ICL00011827 | 2.22 | A246S |
| ICL00011919 | 1.04 | V242T |
| ICL00012070 | 1.47 | S223C |
| ICL00012171 | 1.31 | A117N |
| ICL00012175 | 1.20 | N122R |
| ICL00012281 | 1.10 | R108N |
| ICL00012342 | 1.15 | S101V |
| ICL00012400 | 1.81 | N162E |
| ICL00012534 | 1.35 | T109F |
| ICL00012591 | 1.03 | T109R |

Figure 9F

| Colony Tracking Number | Improvement of Total Activity w.r.t. G1P: PF at pH8.0, 65°C, 72hr | AA Mutations w.r.t G1P |
|---|---|---|
| ICL00012596 | 1.14 | A117Q |
| ICL00012912 | 1.21 | K147F |
| ICL00012929 | 1.22 | A117G |
| ICL00012941 | 1.02 | S110H |
| ICL00012945 | 1.22 | L74W |
| ICL00013009 | 1.25 | S113Y |
| ICL00013089 | 1.30 | A117S |
| ICL00013150 | 1.33 | S98D |
| ICL00013160 | 1.12 | K147G |
| ICL00013170 | 1.09 | P164S |
| ICL00013172 | 1.24 | N162H |
| ICL00013228 | 1.26 | S113T |
| ICL00013231 | 1.28 | S101M |
| ICL00013248 | 1.03 | T109N |
| ICL00013251 | 1.30 | A121S |
| ICL00013266 | 1.06 | A114S |
| ICL00013343 | 1.08 | A114L |
| ICL00013423 | 1.12 | N87W |
| ICL00013433 | 1.08 | S113P |
| ICL00013476 | 1.56 | N162P |
| ICL00013866 | 1.01 | V229C |
| ICL00013929 | 1.16 | A125S |
| ICL00014084 | 1.95 | Y60A |
| ICL00014177 | 1.30 | Y60I |
| ICL00014360 | 2.06 | T163S |
| ICL00014465 | 1.21 | T17H |
| ICL00014486 | 1.04 | L119M |
| ICL00014565 | 1.01 | R12K |
| ICL00014609 | 2.12 | T195F |
| ICL00014700 | 1.16 | F21W |

Figure 9G

| Colony Tracking Number | Improvement of Total Activity w.r.t. G1P: PF at pH8.0, 65°C, 72hr | AA Mutations w.r.t G1P |
|---|---|---|
| ICL00024094 | 1.56 | L90F/F92G/D158L/A174R/D203V |
| ICL00024108 | 1.69 | V23L/A24V/S32K/N87F/F92Y/A125S/T136A |
| ICL00024121 | 2.61 | P20T/L90Y/F92L/S101M/D158E/A174K/I222L |
| ICL00024155 | 1.32 | D18R/S32K/Y60H/L90F |
| ICL00024157 | 2.22 | P20T/F21W/A24V/L90Y/F92L/T109K/A125S/T136A |
| ICL00024167 | 1.91 | Y60H/S101A/A114K/A117Q/D203R/I222L |
| ICL00024241 | 1.41 | S32Q/F92G/S101Q/A114K/Q142W/D158I/D203R/I222L |
| ICL00024247 | 1.26 | T17G/L90F/F92L/T109R/A114K/D158E/D203V/I222L |
| ICL00024297 | 1.49 | R12K/S32K/F92L/T136A/D158E/A174R |
| ICL00024334 | 2.11 | L90F/F92G/T109K/A125S/A174K |
| ICL00024335 | 1.96 | S32K/L90F/F92L/T109K/A114K/Q142W |
| ICL00024354 | 1.20 | V23T/S32Q/N87I/L90F/F92Y/S101N/A114V/Q142W/A174 R/D203R/I222L/V229I |
| ICL00024372 | 2.46 | S32Q/F92G/A114V/D203V |
| ICL00024388 | 2.67 | R12K/S32K/L90Y/F92L/T136A/A174K/D203V/I222L |
| ICL00024391 | 3.17 | R12K/A14K/V23T/L90Y/F92G/S101A/D203R |
| ICL00024401 | 2.75 | T17G/S32M/L90Y/F92Y/D203R/A216P |
| ICL00024406 | 1.70 | S32Q/F92L/A114V/A125S |
| ICL00024416 | 2.18 | P20T/F21W/S32M/L90Y/F92G/A114K/A125S/T136V/D15 8E/A174K/D203V/I222L |
| ICL00024437 | 1.34 | R12K/F21W/S32K/F92L/T109K/A125S/T136V/D158E/D20 3R |
| ICL00024448 | 3.00 | T17Q/L90Y/F92L/A174K/D203V/I222L |
| ICL00024524 | 1.43 | F21W/F92L/S101A/A117Q/D203R |
| ICL00024546 | 1.26 | T17A/S32M/Y60H/Q142L/D203V/I222L |
| ICL00024565 | 2.14 | R12K/Y60H/L90F/S101R/A114V/A117N/D158E |
| ICL00024581 | 1.77 | T17S/D18R/L90Y/F92G/A114V/A117Q/D203R |
| ICL00024595 | 1.58 | L90Y/F92L/S101A/S110R/A125S/Q142W/A174R/A216P |
| ICL00024600 | 1.07 | S32M/S110R/A125S/D158E |
| ICL00024625 | 2.14 | R12K/V23L/A24V/F92G/T136V/D203R |
| ICL00024627 | 3.74 | A24V/S32Q/F92L/T136V |
| ICL00024632 | 3.27 | S32K/L90Y/F92G/A114K/D203V |
| ICL00024661 | 1.68 | S32M/L90F/F92G/A114V/A117N/A125S/A174K/D203R |
| ICL00024669 | 1.20 | R12K/T17A/V23L/A24V/L90F/F92G/S101N/A125S/Q142 W/D158I/D203R |
| ICL00024670 | 1.23 | P20T/F21W/Y60I/S101A/T109K/A174K |
| ICL00024675 | 1.41 | T17C/L90Y/F92L/S101N/T109L/S110R/A125S/A174K/D2 03R |

Figure 9H

| Colony Tracking Number | Improvement of Total Activity w.r.t. G1P: PF at pH8.0, 65°C, 72hr | AA Mutations w.r.t G1P |
|---|---|---|
| ICL00024684 | 2.91 | T17Q/L90F/F92G/S101M/A117Q/T136A/D158I/A174R |
| ICL00024718 | 3.31 | V23L/L90F/F92G/A125S/D203V/I222L |
| ICL00024772 | 3.93 | T17C/L90Y/F92L/A125S/T136V/D158E/A174K |
| ICL00024785 | 1.32 | V23L/S32Q/Y60I/A117Q/T136A/A174K/V229C |
| ICL00024799 | 3.23 | V23T/L90F/F92Y/D203V |
| ICL00024813 | 2.12 | R12K/A24V/Y60H/A174R |
| ICL00024825 | 1.10 | T17G/P20T/Y60I/F92G/D203V |
| ICL00024839 | 2.67 | L90Y/F92L/S110R/A125S/D158E/D203V |
| ICL00024847 | 2.79 | T17Q/L90Y/F92L/T109L/T136A/D158E/A174R/D203V/V229C |
| ICL00024914 | 2.33 | R12K/V23T/A24V/S32Q/F92G/D158L/A174R/D203R |
| ICL00024925 | 2.71 | S32M/N87Y/L90F/F92G/A174K/D203V |
| ICL00024934 | 1.41 | T17S/V23L/S32Q/L90F/F92L/A114K/A117N/A125S/T136V/D158E/D203V/V229I |
| ICL00024942 | 2.77 | P20T/F21W/S32M/L90Y/F92G/T109L/S110R |
| ICL00024943 | 2.49 | A14K/S32M/L90Y/S101R/A114V/T136A/A216P |
| ICL00024962 | 2.43 | P20T/F21W/L90Y/F92G/A125S/A174K/V229I |
| ICL00024966 | 1.60 | V23L/S32K/L90F/F92L/S101R/T109R/T136V/I222L |
| ICL00025010 | 2.36 | A24V/F92L/Q142L/A216P |
| ICL00025986 | 2.67 | F92G/A125S/T136A/D158E/A216P |
| ICL00026026 | 1.62 | N87R/F92G/A117N/D203V/A216P |
| ICL00026034 | 1.10 | R12K/A14K/F92G/S110R/A117N/A125S/A174R/D203R |
| ICL00026058 | 2.38 | S32Q/N87F/L90F/F92G/S101M/A114V/A117Q/D203V |
| ICL00026071 | 1.79 | T17Q/A24V/N87M/F92G/A114K/A117N/D158E/D203R/I222L |
| ICL00026072 | 1.95 | N2R/S32Q/L90F/F92G/Q142L/D203V |
| ICL00026095 | 1.55 | A14K/S32Q/L90F/F92G/A114K/A117N/A174R/D203V/A216P/I222L |
| ICL00026110 | 1.08 | R12K/P20T/D158E/D203R/I222L |
| ICL00026111 | 1.82 | N2R/A14K/T17A/L90F/F92G/S101H/A174R/D203V |
| ICL00026144 | 3.04 | T17G/A24V/L90F/F92G/Q142W |
| ICL00026159 | 3.27 | S32K/L90Y/F92Y/S101A |
| ICL00026164 | 3.13 | V23T/N87I/F92G/A125S/T136A/D158L/D203R |

Figure 9I

| Colony Tracking Number | Improvement of Total Activity w.r.t. G1P: PF at pH8.0, 65°C, 72hr | AA Mutations w.r.t G1P |
|---|---|---|
| ICL00026166 | 1.15 | T17S/N87L/V229I |
| ICL00026190 | 1.83 | A24T/L90F/F92L/A125S/T136A/D203V |
| ICL00026191 | 2.53 | R12K/A14K/F92G/T109R/T136A/Q142L/D158E/A174K/D203R/I222L |
| ICL00026196 | 2.15 | A24V/S32Q/Y60A/T136A |
| ICL00026232 | 1.32 | D18R/S32Q/N87H/L90Y/F92G/S101K/Q142L/D158I/A174R |
| ICL00026236 | 2.64 | T17A/F21W/S32K/N87F/L90F/F92Y/S101Q/T136A/D203R |
| ICL00026238 | 2.36 | A24V/L90F/F92G/A114V/A117N/T136V/Q142L/D203V/V229C |
| ICL00026256 | 2.62 | T17Q/L90Y/F92G/S101N/T109L/S110R/T136V/Q142L/D203V/A216P |
| ICL00026306 | 3.43 | S32Q/L90Y/F92L/T109K/A125S/T136V |
| ICL00026310 | 1.87 | Y60H/N87K/A114K/A117Q/D158E/A174K/A216P |
| ICL00026327 | 1.54 | P20T/L90Y/T109K/T136A/D158I/D203R |
| ICL00026342 | 2.37 | T17L/Y60A/D203V |
| ICL00026344 | 2.55 | N2R/S32Q/L90Y/F92Y/T109K/D203V |
| ICL00026349 | 1.35 | T17H/A24V/S32Q/L90Y/F92L/S101H/A114K/D158I/A174R/D203V |
| ICL00026353 | 1.30 | N2R/S32M/F92Y/T109K/S110R/I222L |
| ICL00026354 | 1.44 | P20T/F92Y/S101K/A125S/D158E/D203R |
| ICL00026368 | 1.56 | R12K/A14K/P20T/F21W/S32M/F92L |
| ICL00026393 | 1.42 | R12K/A14K/V23T/A24V/L90F/F92L/S101W/T136A/D203V |
| ICL00026466 | 2.15 | T17L/S32K/F92L/T109L/A114V/T136V/D158L/R236H |
| ICL00026476 | 2.25 | P20T/F21W/S32Q/N87F/F92L/D158E/D203V |
| ICL00026496 | 2.81 | F21W/L90F/F92G/S101A/A114V/A125S/T136V/Q142L/D203V/A216P |
| ICL00026534 | 1.94 | P20T/F21W/S32K/F92G/A125S/V229I |
| ICL00026535 | 2.53 | V23T/A24V/L90Y/F92G/A125S/T136V/D203V |
| ICL00026552 | 1.99 | P20T/S32K/L90Y/F92G/S101N/T109L/S110R/A125S/A174K/D203R/A216P |
| ICL00026561 | 1.57 | V23L/L90F/F92L/T136A/D203R/I222L |
| ICL00026618 | 3.01 | R12K/A14K/A24V/N87L/L90Y/A125S/T136V/A216P |
| ICL00026643 | 1.55 | P20T/F21W/L90Y/A125S |
| ICL00026671 | 1.44 | N2R/L90Y/A114K/A117Q/D203V/V229I |
| ICL00026673 | 1.56 | F21W/S32K/L90Y/A125S/D158E/A216P/V229I |

Figure 9J

| Colony Tracking Number | Improvement of Total Activity w.r.t. G2P: PF at pH8.0, 65°C, 72hr | AA Mutations w.r.t G1P |
|---|---|---|
| ICL00015105 | 1.35 | S27L/T136V |
| ICL00015156 | 1.03 | S27L/P8T/T17Q/F21W/S101A/T136V/Q142L |
| ICL00015324 | 1.02 | S27L/N2R/T17L |
| ICL00015579 | 1.11 | S27L/V23T/A24V/T136A/Q142W |
| ICL00015633 | 1.11 | S27L/F21W/T136V |
| ICL00015643 | 1.31 | S27L/T17Q/T109K/A114K/T136V/V229I |
| ICL00015653 | 1.19 | S27L/T17Q |
| ICL00015773 | 1.42 | S27L/T136V/I222L/V229C |
| ICL00015796 | 1.36 | S27L/T17A/A114V/A117N/T136A |
| ICL00015830 | 1.07 | S27L/N2R/T136A |
| ICL00015846 | 1.02 | S27L/N2R/T17A |
| ICL00015853 | 1.16 | S27L/T17C/S101A/T136V |
| ICL00015873 | 1.04 | S27L/P20T/T136A |
| ICL00015972 | 1.12 | S27L/T136V/Q142W/V229I |
| ICL00016002 | 1.05 | S27L/T109K/T136V/I222L/V229I |
| ICL00016095 | 1.01 | S27L/T17L/S101H/A117N/Q142L/I222L/V229I |
| ICL00016114 | 1.22 | S27L/S101Q/T109L/A117N/T136A/Q142L |
| ICL00016342 | 1.03 | S27L/T109K/S110R/S193N/S252T/R255M |
| ICL00016399 | 1.19 | S27L/S22R/Y26K/R236Q |
| ICL00016411 | 1.67 | S27L/L90F/F92L/S98E/S113Y/A114K/T136A/D158E/S181R/T206G/S212M/V219I |
| ICL00016478 | 1.55 | S27L/N9S/S22P/T48N/L90Y/F92G/T109K/S110R/T136A/Q189V/N211F/R236Q |
| ICL00016797 | 1.02 | S27L/T17A/Y26L/T48N/I82M/S101D/R236Q |
| ICL00016852 | 1.24 | S27L/Y26T/S101D/D158E/V219I/S252T |
| ICL00016862 | 1.36 | S27L/S13R/S98E/T136V/S181R/T206G/V229I/N231S |
| ICL00016937 | 1.36 | S27L/F21W/F92L/S98N/S193P/I222L |
| ICL00017036 | 1.46 | S27L/S1G/Y26K/L90Y/S113Y/A114V/T136A/Q189V/N204R/N211L/R236Q |
| ICL00017369 | 2.59 | S27L/S22K/I82L/L90Y/F92G/R108S/A117N/D158E/S193N |
| ICL00017517 | 1.33 | S27L/S1G/N9S/T48S/L90Y/S98T/S101A/S113N/A114K/L119M/S193N/T206G/S252T |
| ICL00017595 | 1.12 | S27L/N9E/R12K/S22P/V23L/T160R/D203R/I222L |
| ICL00017708 | 1.12 | S27L/N9E/R12K/S22P/V23T/T48S/S98E/R108S/T160S/Q189V/T206G/S212L/V229I |

Figure 9K

| Colony Tracking Number | Improvement of Total Activity w.r.t. G2P: PF at pH8.0, 65°C, 72hr | AA Mutations w.r.t G1P |
|---|---|---|
| ICL00017714 | 1.45 | S27L/S1A/N2R/N9S/T48N/L90F/F92L/D203V/S223A |
| ICL00017757 | 2.78 | S27L/N9E/R12K/V23T/I82M/L90Y/F92L/T136V/N204K/N231S/R255M |
| ICL00017873 | 1.49 | S27L/S1G/N9S/S22V/I82F/L90Y/F92L/A117N/L119M/Q142L/T206G/S212L/S223A |
| ICL00017905 | 1.55 | S27L/N9S/Y60H/R108C/S193P/V219L |
| ICL00017934 | 1.47 | S27L/N9E/S22K/S32M/L90F/F92G/R108T/L119M/Q189V/I222L/S223A/R236Q |
| ICL00017976 | 1.39 | S27L/T17Q/F92G/S98N/Q142L/Q189L/R236C |
| ICL00018033 | 1.50 | S27L/N9E/R12K/Q142W/T160Q/T206G/S212M |
| ICL00018093 | 1.39 | S27L/Y26T/S113N/A114V/T136A/D158E/D203R/N211F/R236Q/S252T/R255M |
| ICL00018101 | 2.45 | S27L/S1A/T17H/S22V/L90Y/F92G/S98E/A114V/T136A |
| ICL00018188 | 1.97 | S27L/N9E/T48S/I82M/L90Y/F92L/N122A/A127S/T160S/A174R/T206G/S212L/R255M |
| ICL00018404 | 1.57 | S27L/N9S/S22P/V23L/L90Y/F92G/A125S/T160S/N204R/I222L/S223A/R236Q |
| ICL00018431 | 1.14 | S27L/N9E/S22P/T48S/L90Y/F92L/T109R/E173R/A174K/D203V/S223A |
| ICL00018459 | 1.25 | S27L/R12K/Y26K/T48N/I82L/L90F/A125S/N211I/A216P |
| ICL00018572 | 1.39 | S27L/N9S/R12K/F92Y/T109K/S110R/T160K/Q189L/S223A/S252T/R255M |
| ICL00018576 | 1.01 | S27L/S1A/N2R/N9E/R12K/S32K/N87F/R108T/N211I/V219K/R255M |
| ICL00018627 | 1.05 | S27L/L90F/F92G/N122A/T136A/T160V/E173R/D203R/S252T |
| ICL00018644 | 2.41 | S27L/L90Y/F92G/S98T/T109L/D158I/S193K/V219K/R236Q/S252T |
| ICL00018837 | 1.15 | S27L/N9E/R12K/T48N/L90F/S98L/R108Q/A117Q/T136A/T206G/S212F/V219I/V229I/R255L |
| ICL00018957 | 1.19 | S27L/S1A/S22V/N87K/R108K/N122E/D158E/S193P/V219I/R255M |
| ICL00019051 | 1.05 | S27L/F21W/Y26T/S34R/R108H/L119M/N211M/R236C/S252T |
| ICL00019281 | 2.22 | S27L/S1A/N9E/R12K/V23T/T48S/N87H/S101Q/Q189L/N211M/V219I/R236Q/R255M |
| ICL00019296 | 1.99 | S27L/N9S/T25Q/L90Y/S101D/T136A/Q142L/Q189L/R236Q |
| ICL00019312 | 2.68 | S27L/A14K/I82F/F92G/S98E/R108C/A117N/L119M/Q189V/T206G/I222L/S223A |

Figure 9L

| Colony Tracking Number | Improvement of Total Activity w.r.t. G2P: PF at pH8.0, 65°C, 72hr | AA Mutations w.r.t G1P |
|---|---|---|
| ICL00019341 | 2.33 | S27L/T17C/Y26T/N87V/R108C/N122E/T136V/S193P/S252T/R255M |
| ICL00019489 | 2.81 | S27L/L90Y/F92G/T109L/N122S/R255M |
| ICL00019574 | 1.37 | S27L/R12K/L90Y/T160V/A174R/R236Q |
| ICL00019589 | 1.04 | S27L/N9E/R12K/T48N/L90Y/F92G/S98T/S113R/N122R/A127S/T136A/A174K/N204K/S212L |
| ICL00019618 | 1.61 | S27L/V23T/L90Y/F92G/S98E/T109L/A125S/T160V/A174K/S181C/S193K/T206G/S212M/R255M |
| ICL00019634 | 1.03 | S27L/A24V/F92G/S101D/A114V/A117N/A125S/T136V/D203R |
| ICL00019661 | 1.12 | S27L/R12K/S32Q/S101Q |
| ICL00019736 | 1.70 | S27L/L90F/F92G/T136V/A174R/D203R |
| ICL00019743 | 1.27 | S27L/P20T/S32K/L90Y/D203V |
| ICL00019873 | 1.19 | S27L/N2R/A14K/T17S/L90Y/T109K/T136V/A216P |
| ICL00019890 | 1.19 | S27L/N2R/V23T/A24V/S32M/L90Y/F92G |
| ICL00020004 | 1.65 | S27L/A14K/L90Y/F92L/S101D/A117N/D158I/D203R |
| ICL00020035 | 1.37 | S27L/F21W/N87H/A114V/A117N/T136V |
| ICL00020130 | 1.19 | S27L/N2R/V23T/A24V/N87M/F92L/S101K/A125S/T136A |
| ICL00020240 | 1.24 | S27L/L90Y/F92L/S101N/T109R/S110R/Q142W |
| ICL00020265 | 1.45 | S27L/S32M/F92G/A216P |
| ICL00020456 | 1.46 | S27L/F21W/L90Y/F92L/A114K/A117N/T136A/D203V |
| ICL00020806 | 1.09 | S27L/N2R/V23T/S32M/N87M/F92L/T136A |
| ICL00020830 | 1.93 | S27L/R12K/L90F/F92G/S101A/D203V |
| ICL00020832 | 1.82 | S27L/A24V/L90F/F92G |
| ICL00020874 | 1.36 | S27L/R12K/F92L/S101A/A125S/T136A/D203R |
| ICL00021047 | 1.18 | S27L/R12K/V23L/L90F/F92L/A114K/T136A/D158E/D203V/I222L |
| ICL00021082 | 1.68 | S27L/L90F/F92G |
| ICL00021198 | 1.17 | S27L/T17L/L90F/F92G/A125S/A174R/D203V |
| ICL00022077 | 1.37 | S27L/N2R/N87K/A114K/A117Q/T136V/D203V |
| ICL00022293 | 1.11 | S27L/N2R/A114K/T136V/D203V |
| ICL00022297 | 1.32 | S27L/N2R/T17A/T136V/A216P |
| ICL00022389 | 1.33 | S27L/N2R/R12K/N87F/T136V/D158E/A174R |
| ICL00022421 | 1.38 | S27L/D203R |
| ICL00022429 | 1.38 | S27L/R12K/T17Q/T136V/D203V/A216P |

Figure 9M

| Colony Tracking Number | Improvement of Total Activity w.r.t. G2P: PF at pH8.0, 65°C, 72hr | AA Mutations w.r.t G1P |
|---|---|---|
| ICL00022507 | 1.69 | S27L/N87F/T109L/Q142L |
| ICL00022559 | 1.02 | S27L/N2R/T17Q/A24V/A114K/A117Q/T136A/D158E/A174K/D203V/I222L |
| ICL00022567 | 1.07 | S27L/N2R/P20T/F21W/N87M/T109R/A117N/A125S/T136V/D203V/I222L |
| ICL00022638 | 1.44 | S27L/V23T/A24V/T136A/D158E/A174K/D203V/I222L |
| ICL00022671 | 1.03 | S27L/R12K/V23L/A114K/T136A/D158I/D203V/I222L |
| ICL00022776 | 1.77 | S27L/N87Y/T136V/D158E/D203V |
| ICL00022809 | 1.08 | S27L/T109K/S110R/D203R |
| ICL00022817 | 1.06 | S27L/N2R/T17L/A125S/T136A/D158E |
| ICL00022909 | 1.13 | S27L/A24V/D158E/A174K/A216P |
| ICL00022974 | 1.06 | S27L/T17G/V23L/N87L/A117Q/A125S/T136V/D158E/V229C |
| ICL00022977 | 2.32 | S27L/V23L/N87L/T109R/A114K/A117N/A125S/T136V/Q142L |
| ICL00023114 | 1.63 | S27L/N87Y/S101A/A114V/A117Q/T136V/A174K/A216P/I222L |
| ICL00023130 | 1.21 | S27L/R12K/T109R/Q142L |
| ICL00023421 | 1.09 | S27L/D203V |
| ICL00023612 | 1.48 | S27L/T17G/N87F/S101A/D203V |
| ICL00023655 | 1.06 | S27L/T17L/N87M/Q142L/D203V |
| ICL00023715 | 1.05 | S27L/N2R/R12K/S101D/A117N/T136A/D203V |
| ICL00023819 | 1.23 | S27L/R12K/P20T/F21W/A114K/Q142W/D203R |
| ICL00023836 | 1.01 | S27L/N2R/T17G/T109L/S110R/A114K/A117Q/T136V/Q142L/D203R |
| ICL00023911 | 1.06 | S27L/N2R |
| ICL00026699 | 1.58 | S27L/S32K/L90F/F92G/S101M/A114V/A117N/A125S/T136A/D158E/D203V |
| ICL00026739 | 1.83 | S27L/R12K/T17A/F21W/S32Q/Y60H/D203R |
| ICL00026757 | 2.05 | S27L/R12K/F92L/S110R/T136V/I222L |
| ICL00026766 | 2.38 | S27L/A14K/V23T/A24V/L90Y/F92G/A114V/A117Q/Q142L/A174R/I222L |
| ICL00026785 | 1.37 | S27L/F21W/S32Q/L90Y/S101D/T109K/A125S/T136A/A174K |
| ICL00026858 | 2.42 | S27L/V23T/L90Y/F92G/T136A/D203V/A216P |
| ICL00026885 | 3.31 | S27L/T17S/L90Y/F92G/A117N/T136A/D158L |
| ICL00026903 | 1.12 | S27L/A14K/V23L/A24V/F92L/Q142W/D203V |
| ICL00026906 | 2.14 | S27L/T17L/L90F/F92G/S101K/A174K |

Figure 9N

| Colony Tracking Number | Improvement of Total Activity w.r.t. G2P: PF at pH8.0, 65°C, 72hr | AA Mutations w.r.t G1P |
|---|---|---|
| ICL00026952 | 1.01 | S27L/L90F/F92L/A125S/T136V/A174K/D203V/A216P/I222L |
| ICL00026975 | 1.69 | S27L/R12K/P20T/S32M/L90F/F92G/S101M/A114V/D203V |
| ICL00027010 | 1.35 | S27L/T17A/S32Q/L90F/F92L/T136V/Q142W/A174K/D203R |
| ICL00027020 | 1.34 | S27L/R12K/S32M/L90F/F92G/S101W/A114V/D158I/I222L |
| ICL00027052 | 2.34 | S27L/P20T/S32M/L90Y/F92L/A114V/A117N/I222L |
| ICL00027066 | 2.07 | S27L/T17C/L90Y/F92G/T136A/A174K/D203V |
| ICL00027067 | 1.30 | S27L/S32Q/N87Y/F92G/T109K/A114K/A117N/T136V/D203V/V229C |
| ICL00027073 | 1.83 | S27L/F21W/L90F/F92G/T136V/A174R |
| ICL00027087 | 1.05 | S27L/P20T/N87Y/T136A/D203V/I222L |
| ICL00027091 | 2.27 | S27L/A24V/L90Y/F92L/D158I/A174K/D203R/I222L |
| ICL00027102 | 1.56 | S27L/F21W/S32Q/L90Y/S110R/A114K/T136V/D203R/A216P/V229I |
| ICL00027186 | 2.19 | S27L/N87H/F92G/D203R |
| ICL00027190 | 1.15 | S27L/R12K/S32K/Y60A/A125S/T136V/D158L |
| ICL00027212 | 1.45 | S27L/V23T/A24V/S32Q/L90F/F92L/T136A |
| ICL00027275 | 1.25 | S27L/F92L/A114V/D158E/D203R |
| ICL00027329 | 1.73 | S27L/S32Q/L90Y/D203V/V229I |
| ICL00027330 | 1.07 | S27L/V23T/S32Q/Y60H/T109K/T136V/A216P/I222L |
| ICL00027332 | 1.05 | S27L/A14K/A24V/L90F/F92G/T109K/T136V/D158L/A174R/D203V/I222L/V229I |
| ICL00027420 | 1.48 | S27L/R12K/N87F/A174K |
| ICL00027421 | 1.46 | S27L/P20T/S32Q/Y60H/T109K/A114V/T136A/A174K |
| ICL00027432 | 1.04 | S27L/V23T/A24V/Y60A/A125S/A174R/A216P |
| ICL00027436 | 1.84 | S27L/F92Y/D158L/I222L |
| ICL00027502 | 1.54 | S27L/V23L/A24V/L90Y/F92G/D203V/I222L |
| ICL00027545 | 1.24 | S27L/V23T/A24V/S32Q/L90F/F92G/S101H/T136A/A174K/D203V/V229C |
| ICL00027572 | 1.12 | S27L/S32K/N87H/A125S |
| ICL00027600 | 1.61 | S27L/P20T/F21W/F92G/A114V |
| ICL00027601 | 1.83 | S27L/T17L/V23L/A24V/L90Y/F92L/A117N/T136V/L137M/Q142L |
| ICL00027603 | 1.74 | S27L/P20T/L90Y/D203R |
| ICL00027613 | 1.13 | S27L/S110R/Q142L/D158I/D203R/V229I |
| ICL00027615 | 1.01 | S27L/P20T/S32Q/L90F/F92L/T109K/S110R/A125S/D203V |

Figure 9O

| Colony Tracking Number | Improvement of Total Activity w.r.t. G2P: PF at pH8.0, 65°C, 72hr | AA Mutations w.r.t G1P |
|---|---|---|
| ICL00027619 | 1.87 | S27L/V23T/A24V/L90F/F92G/D158E/D203R |
| ICL00028399 | 1.49 | S27L/F92G/T136A/A174R/D203V/V229C |
| ICL00028473 | 1.26 | S27L/P20T/L90Y/F92G/T109R/S110R/A125S/D203R |
| ICL00028524 | 1.61 | S27L/A14K/L90Y/F92L/D158L/A174R/D203V |
| ICL00028530 | 1.25 | S27L/F21W/S32Q/L90Y/F92G/T109L/S110R/A117N/D158I/A174K/D203V |
| ICL00028665 | 1.33 | S27L/R12K/A114K/A117N/D158E/D203V |
| ICL00028670 | 1.05 | S27L/T17S/N87H/T109R/A114K/A117N/T136V/Q142W/D203V |
| ICL00028711 | 1.06 | S27L/N2R/N87Y |
| ICL00028716 | 1.03 | S27L/T17S/V23T/A24V/S32Q/Y60H/N87K/T136A/D203R |
| ICL00028725 | 1.49 | S27L/P20T/F92Y/T109K/D158E/D203V |
| ICL00028798 | 1.18 | S27L/S32K/N87M/F92L/S101M/T109L/S110R/D203V |
| ICL00028833 | 2.82 | S27L/L90Y/F92G/T136A/D158E/D203V/A216P/V229I |
| ICL00028865 | 1.71 | S27L/A14K/S32M/F92L/A125S |
| ICL00028868 | 2.86 | S27L/L90Y/F92G/T136V/D158L/D203V |
| ICL00028895 | 2.18 | S27L/A24V/L90Y/F92G/S101A/T109L/S110R/A117Q/A174R/D203R |
| ICL00028917 | 1.93 | S27L/P20T/S101D/A114V/T136V/Q142W/D158E/D203R/A216P |
| ICL00028920 | 1.34 | S27L/N87Y/F92G/S101Q/A114K/A117N/T136A/D158L/D203R/A216P |
| ICL00028962 | 1.64 | S27L/V23T/A24V/N87Y/L90Y/F92L/S101D/T109R/A174K/D203R/A216P |
| ICL00028982 | 1.05 | S27L/N2R/P20T/F21W/L90F/F92Y |
| ICL00029054 | 1.54 | S27L/L90Y/F92G/D158I/D203V/V229C |
| ICL00029064 | 2.00 | S27L/S32Q/F92G/Q142W/I222L |
| ICL00029068 | 1.12 | S27L/N2R/R12K/S32M/N87Q/L90F/F92L/I222L |
| ICL00029092 | 1.40 | S27L/R12K/S32K/F92L/A114V/A117Q/T136A/D158E/A216P |
| ICL00029093 | 3.13 | S27L/L90Y/F92G |
| ICL00029107 | 1.32 | S27L/R12K/F21W/S32M/F92G/T136V/Q142L/D203R |
| ICL00029140 | 2.12 | S27L/R12K/A14K/L90Y/F92L/A125S/A174K |
| ICL00029141 | 1.02 | S27L/A24V/A114V/A117Q/T136V/D203V |
| ICL00029149 | 2.97 | S27L/R12K/T17Q/V23L/S32M/L90Y/F92G/S101D/T136V/I222L |
| ICL00029167 | 1.09 | S27L/V23T/A24V/S32Q/F92L/S101N/T109L/S110R/D203R |
| ICL00029172 | 1.38 | S27L/P20T/Y60H/N87K/T136A/A174R/D203V |

Figure 9P

| Colony Tracking Number | Improvement of Total Activity w.r.t. G2P: PF at pH8.0, 65°C, 72hr | AA Mutations w.r.t G1P |
|---|---|---|
| ICL00029173 | 1.48 | S27L/P20T/F21W/L90Y/F92L/T136A/A174R/D203V/V229C |
| ICL00029174 | 1.49 | S27L/T17G/F21W/S32K/L90F/F92G/A125S/T136A/A174K |
| ICL00029199 | 1.31 | S27L/T17G/N87Y/T136A/D203V/A216P |
| ICL00029219 | 1.42 | S27L/F21W/L90F/F92G/S101D/A117N/T136A/A174K/D203V |
| ICL00029303 | 1.16 | S27L/R12K/A14K/A24V/L90Y/D203V |
| ICL00029304 | 1.19 | S27L/N2R/L90F/F92G/S101M/Q142L/D158L |
| ICL00029361 | 1.08 | S27L/N2R/T17C/A24V/N87K/A174K/A216P |
| ICL00029375 | 1.14 | S27L/N87M/Q142L/I222L |
| ICL00031774 | 1.16 | S27L/F92L/S98T/R108C/A117Q/A127S/Q142L/Q189V/A216P/R236Q |
| ICL00031820 | 1.45 | S27L/S22K/F92L/R108H/A127S/T136A/N211I |
| ICL00031919 | 1.80 | S27L/F21W/T48S/L90Y/F92L/T109L/A127S/T136V/N204K/S223A |
| ICL00031936 | 1.45 | S27L/T17L/L90Y/F92L/S98M/A174K/D203V/N211M/S212L/S223A |
| ICL00031945 | 1.56 | S27L/N87K/S98M/N211M |
| ICL00032000 | 1.29 | S27L/N9E/S22P/L90Y/N204K |
| ICL00032160 | 1.78 | S27L/S32M/T48S/F92G/A127S/Q142W |
| ICL00032187 | 1.24 | S27L/T17S/S22K/L90F/F92L/D158E/D203V/V219I/S252T |
| ICL00032196 | 1.28 | S27L/L90F/F92L/A127S/D203V |
| ICL00032208 | 1.52 | S27L/T25F/L90Y/F92G/N204R/S223A/N231S/R236C |
| ICL00032229 | 1.34 | S27L/F21W/S22V/T48S/L90F/F92L |
| ICL00032231 | 2.39 | S27L/S1A/S98T/S113K/A114V/L119M/A127S/Q142W/S193K/V219K/S252T/R255L |
| ICL00032241 | 2.17 | S27L/A24V/I82L/L90F/F92G/T109L/L119M/A127S/E173R/N204K |
| ICL00032282 | 1.03 | S27L/T17C/Y60H/L90F/A127S/E173R/A174R/N204K |
| ICL00032284 | 1.53 | S27L/L90F/F92L/Q142W/D203V/S223A |
| ICL00032351 | 1.64 | S27L/P20Q/L90Y/Q142L/S223A |
| ICL00032357 | 1.35 | S27L/N9S/Y60A/A216P/R236Q/R255M |
| ICL00032378 | 2.34 | S27L/F92G/R108C/S110R/A117Q/T136A/N211M |
| ICL00032380 | 1.17 | S27L/S22P/Y60H/S98A/S113K/A114K/T136V/Q189L/S193H |
| ICL00032410 | 1.58 | S27L/V23L/S98A/Q142L/N211M |
| ICL00032471 | 1.39 | S27L/V23L/Y26L/L31M/T48S/F92G/A174R/N204K/S252T |

Figure 9Q

| Colony Tracking Number | Improvement of Total Activity w.r.t. G2P: PF at pH8.0, 65°C, 72hr | AA Mutations w.r.t G1P |
|---|---|---|
| ICL00032491 | 1.34 | S27L/S13R/A14K/Y26T/T136A/S181R/N211M/S212M |
| ICL00032493 | 2.62 | S27L/F21W/I82F/L90Y/F92G/A127S/N211M |
| ICL00032565 | 2.08 | S27L/P20T/Y60H/S98L/T136A/R255L |
| ICL00032569 | 1.08 | S27L/P20T/S34R/N87M/D158E/S252T |
| ICL00032570 | 1.82 | S27L/T25A/L90F/F92G/Q189L/S193P/V229I |
| ICL00032573 | 1.08 | S27L/V219L/I222L |
| ICL00032659 | 1.02 | S27L/N9E/T48S/L90F/F92L/S98N/R108H/S110R/S113Y/N211V/S212L/S252T |
| ICL00032721 | 1.71 | S27L/L90F/F92Y/S113R/V219I/R255L |
| ICL00032725 | 1.53 | S27L/F21W/S22K/T48S/F92G/T109R/A127S |
| ICL00032765 | 1.86 | S27L/S1G/A14K/P20T/S32K/T48S/L90Y/F92L/T109L/T160R/V219L/I222L/S252T/R255L |
| ICL00032814 | 1.71 | S27L/L90F/F92G/D158E/T160R/S193N/N204K/S223A |
| ICL00032848 | 1.73 | S27L/A14K/Y26T/F92L/Q142L/S212L |
| ICL00032855 | 1.78 | S27L/S22R/L90Y/F92G/V126I/A127S/A174K/N204K |
| ICL00032968 | 1.37 | S27L/P20T/T25A/L90F/F92L/A117N/L119M/S252T/R255L |
| ICL00033027 | 1.58 | S27L/T17A/A24V/T48S/L90F/F92G/T109R/A127S/T160K/D203R/S223A |
| ICL00033067 | 1.07 | S27L/F21W/T48S/T109L/A127S/V219I/R255L |
| ICL00033176 | 1.10 | S27L/A14K/S22P/T48S/L90F/F92L/T109L/A127S/Q142L/A174R/N204K/S223A |
| ICL00033197 | 1.01 | S27L/T136A/S212M/N231S |
| ICL00033301 | 1.57 | S27L/F21W/L90F/F92G/A127S/S223A |
| ICL00033317 | 2.06 | S27L/T48S/L90Y/F92L/R108S/S110R/A127S/T136V/E173R/S223A |
| ICL00033533 | 1.86 | S27L/T48S/F92G/S98E/Q142L/Q189V/S193P/N204R/S223A |
| ICL00033548 | 1.30 | S27L/T17S/L90F/F92Y/S101K/A127S/T136V/N204R/N211I/V229I/N231S |
| ICL00033559 | 2.40 | S27L/N9E/F21W/T48S/L90Y/F92L/T109R/N204K/R236Q |
| ICL00033571 | 1.20 | S27L/N9E/S22R/T48S/F92L/S101N/A127S/E173R/N204R |
| ICL00033575 | 1.24 | S27L/S22K/N87F/A117Q/S181C/N204K/N211M/V229I/N231S/R236Q |
| ICL00033591 | 1.54 | S27L/N9S/T48S/L90F/F92G/S101N/A127S/N204K/A216P/S252T/R255M |
| ICL00033593 | 1.70 | S27L/I82L/S193H/N211M/S212F/S223A |
| ICL00033594 | 2.02 | S27L/A14K/P20T/T48S/L90F/F92G/S98N/R108C/T136A/N204K/N211L/S212L/R236Q/S252T |

Figure 9R

| Colony Tracking Number | Improvement of Total Activity w.r.t. G2P: PF at pH8.0, 65°C, 72hr | AA Mutations w.r.t G1P |
|---|---|---|
| ICL00033653 | 1.71 | S27L/S13R/T17L/T25Q/L90F/F92G/R108C/A127S/T160R/I222L/R255L |
| ICL00033677 | 2.53 | S27L/T48S/L90Y/F92G/T109L/S193N |
| ICL00033696 | 2.36 | S27L/S22V/T48S/L90Y/F92L/S98E/A127S/T136A/N204K/A216P/S223A |
| ICL00033714 | 1.65 | S27L/V23L/N87H/F92L/R108C/S110R/N122A/T160S/Q189L/S193P/N204K/S223A/R255L |
| ICL00033737 | 1.36 | S27L/F92G/A127S/A174R/S223A/V229I/N231S/R236C |
| ICL00033740 | 1.61 | S27L/S1G/L90Y/A127S/E173R/S223A |
| ICL00033846 | 2.10 | S27L/F92Y/S98N/Q142W |
| ICL00033909 | 1.48 | S27L/P20T/S32M/S34R/T48S/L90Y/F92L/R108K/A127S/Q142W/A174R/N204K/V219I/S252T |
| ICL00034025 | 2.25 | S27L/F92G/A127S/Q189V/S193N/S223A |
| ICL00034065 | 1.08 | S27L/S34R/F92G/S110R/D158L/D203V/R255M |
| ICL00034182 | 2.12 | S27L/N9E/F21W/T48S/F92G/T109L/A127S/R236C |
| ICL00034192 | 1.71 | S27L/S1A/S22P/T48S/L90Y/F92G/A127S/E173R/A174R/N204K/S223A |
| ICL00034240 | 1.01 | S27L/S22K/T48S/T160S/N204K |
| ICL00034243 | 1.33 | S27L/F21W/T48S/L90Y/F92G/S98V/R108C/A127S/N211L/S212M/N231S/R236C |
| ICL00034264 | 1.05 | S27L/V23L/A24V/A114K/T136A/I222L/V229I |
| ICL00034622 | 1.39 | S27L/P20T/S101H/T109R/A114V/T136A/Q142L/I222L/V229I |
| ICL00035440 | 1.21 | S27L/V23L/S101H/T109K/A114K/A117N/T136V/Q142L/I222L/V229I |
| ICL00035481 | 1.09 | S27L/T17L/F21W/S101H/T109R/A114V/T136A/Q142L/I222L/V229I |
| ICL00035505 | 1.40 | S27L/T17S/T136V/Q142L/I222L/V229C |
| ICL00035526 | 1.36 | S27L/T17C/S22P/T48S/L90F/F92G/A127S/A174R/P192A/S193H/N204K/S223A/V229I/N231S/R236Q/R255L |
| ICL00035531 | 1.22 | S27L/N9E/T48N/N87H/F92L/A174K/Q189L/S193K/N204R/V219I |
| ICL00035551 | 1.40 | S27L/A14K/V23L/Y26L/L90F/F92G/S98E/S113K/A114K/T136A/V229I/N231S |
| ICL00035558 | 2.51 | S27L/L90Y/F92L/S101D/A117N/Q142L/S193N |
| ICL00035590 | 1.01 | S27L/S22K/T25A/L90Y/Q142L/E173R/N204K/S223A |
| ICL00035602 | 1.07 | S27L/P20T/L90Y/T109L/A127S/A174K/V229C |
| ICL00035610 | 1.97 | S27L/S22V/L90Y/F92L/A117Q/R236C/R255L |
| ICL00035710 | 2.23 | S27L/V23L/A24G/Y26T/I82F/L90Y/F92G/R108H/T136A/D158L/T160K/D203V |

Figure 9S

| Colony Tracking Number | Improvement of Total Activity w.r.t. G2P: PF at pH8.0, 65°C, 72hr | AA Mutations w.r.t G1P |
|---|---|---|
| ICL00035724 | 1.52 | S27L/A14K/S22K/F92G/A127S/N204K/V229I |
| ICL00035770 | 1.19 | S27L/S22V/L90F/F92G/A127S/A174R/A216P/R236C |
| ICL00035778 | 1.61 | S27L/V23L/Y60A/S98T/T109L/A127S/T136V/T160Q/N204K/S223A/R255L |
| ICL00035819 | 1.71 | S27L/S13R/L90Y/S98L/T160V/Q189L/S193P/A216P/S252T/N253S/R255L |
| ICL00035823 | 1.62 | S27L/S22R/I82M/F92L/T109L/A127S/Q142W/Q189L/S223A |
| ICL00035834 | 2.14 | S27L/S1G/Y60A/L90F/F92L/N122E/T136A/N204K/S223A/N231S |
| ICL00035839 | 2.20 | S27L/S32K/F92G/S98L/R108Q/S110R/R255L |
| ICL00035855 | 2.09 | S27L/L90Y/F92G/L119M/A127S/A174R/S252T |
| ICL00035862 | 1.19 | S27L/L90F/S110R/S181R/N211F |
| ICL00035934 | 1.37 | S27L/A14K/S22P/Y60H/S110R/N122S/D158I/N204K/S223A/R255M |
| ICL00036094 | 1.05 | S27L/F92L/S98V/T109L/N122A/E173R/R255L |
| ICL00036169 | 1.53 | S27L/S22R/N87L/F92G/R236C |
| ICL00036178 | 1.34 | S27L/S32M/S34R/I82L/F92G/N204K/S223A |
| ICL00036235 | 1.55 | S27L/A24V/T25Q/Y60I/A127S/A174K/N204K/V219I/S223A/S252T/R255M |
| ICL00036239 | 2.11 | S27L/S98V/T136A/N211F |
| ICL00036276 | 1.70 | S27L/N9S/L90F/F92L/A127S/N204R/S212M |
| ICL00036287 | 1.02 | S27L/S22R/T48S/F92G/R108H/S110R/A127S/E173R/N204K/S223A/R236Q |
| ICL00036293 | 2.84 | S27L/A14K/L90Y/F92G/A127S |
| ICL00036332 | 1.09 | S27L/A14K/T48S/F92G/E173R/N204R/S223A/N231S |
| ICL00036349 | 1.76 | S27L/L90Y/T109R/S113N/V219L/I222L |
| ICL00036373 | 2.09 | S27L/N9S/T48S/L90Y/T136A/T206G/S223A |
| ICL00036387 | 1.63 | S27L/S22K/T48N/L90F/F92G/N204K/S223A/V229C/N231S |
| ICL00036443 | 1.34 | S27L/S22P/T48S/L90F/F92G/A127S/A174R/N204R/S223A |
| ICL00036446 | 1.03 | S27L/S1G/P20T/S32K/S34R/T48S/N87F/S98A/A127S/T136A |
| ICL00036453 | 1.24 | S27L/F21W/S22R/S98E/Q142L/T160V/S223A/S252T/R255L |
| ICL00036454 | 1.84 | S27L/P20T/T48S/F92Y/R108K/S110R/A127S/V219L/S223A/V229I/R236Q |
| ICL00036455 | 2.54 | S27L/Y26T/L90Y/F92L/A127S/V219L/S252T/R255L |
| ICL00036510 | 1.05 | S27L/N9S/F21W/T48S/F92L/A127S/D203V/S212F |

Figure 9T

| Colony Tracking Number | Improvement of Total Activity w.r.t. G2P: PF at pH8.0, 65°C, 72hr | AA Mutations w.r.t G1P |
|---|---|---|
| ICL00036526 | 1.19 | S27L/F21W/Y60H/S98E/L119M/D158E/R236Q |
| ICL00036577 | 1.39 | S27L/F21W/S22R/L90F/F92L/N122S/Q142W/R236Q |
| ICL00036610 | 2.07 | S27L/F21W/T48S/L90F/F92G/T109K |
| ICL00036629 | 2.11 | S27L/L90Y/F92L/T109R/A127S/E173R/N204K/S223A |
| ICL00036782 | 2.58 | S27L/N9S/F21W/T48S/L90Y/F92G/A127S/N204K/V219I/R255M |
| ICL00036790 | 1.82 | S27L/N9E/I82F/L90Y/F92L/S95N/T109L/A127S/A174R/S223A |
| ICL00036809 | 1.30 | S27L/L90F/F92L/S98L/N204K/A216P |
| ICL00036837 | 1.62 | S27L/A24V/T48S/A117Q/N211M/S212M/S223A |
| ICL00036848 | 2.43 | S27L/L90Y/F92G/T109L/A127S/N204R/S223A |
| ICL00036911 | 1.01 | S27L/N2R/S32Q/N87K/A125S/V219L |
| ICL00037006 | 1.78 | S27L/S22P/T48S/L90F/F92L/S193N/V219L/S223A |
| ICL00037042 | 1.91 | S27L/T25Q/L119M/N211M/R236Q |
| ICL00037061 | 2.58 | S27L/L90Y/F92G/N122S/A127S/E173R/A216P/R236Q |
| ICL00037075 | 1.85 | S27L/P20T/S32K/L90F/F92G/N122E/D158E/T160S/Q189L/S223A/S252T |
| ICL00037121 | 1.93 | S27L/N9S/F21W/T48S/N87H/L90F/F92L/S113N/V229C |
| ICL00037148 | 1.96 | S27L/T25Q/I82L/L90F/F92G/S98L/S113R/A114V/T136A/S181R |
| ICL00037152 | 3.42 | S27L/P20T/R108Q/S110R/D203V/N211I |
| ICL00037185 | 1.89 | S27L/S1G/N2R/P20T/Y26T/S32M/T48S/L90Y/F92L/A127S/N204R/V219L |
| ICL00037200 | 2.01 | S27L/A14K/P20T/T48N/L90F/F92G/A117Q/A127S |
| ICL00037224 | 1.51 | S27L/N9S/T48N/L90Y/F92L/S98M/T109K/A127S/N204R/N211I/S212L/V219I |
| ICL00037313 | 1.21 | S27L/F21W/S22R/T48S/L90F/F92L/R108Q/A174K/N204K/S212F/S223A |
| ICL00037319 | 1.35 | S27L/S22R/Y60H/S98T/T136V/S193K/R236Q |
| ICL00037336 | 2.70 | S27L/S22K/Y26K/N87Y/L90Y/F92G/T109R/A127S/S252T/R255L |
| ICL00037337 | 1.58 | S27L/L90F/F92L/T109L |
| ICL00037371 | 1.49 | S27L/F21W/F92L/N204K/S252T/R255L |
| ICL00037378 | 2.44 | S27L/V23L/L90Y/F92G/A127S/S193K/N204R/V219I/R236C/R255L |
| ICL00037436 | 2.29 | S27L/F21W/L90Y/F92G/A114V/N122S/A127S/N204K/S223A/S252T |
| ICL00037450 | 1.92 | S27L/P20T/Y60A/T109L/Q189L/S212L |
| ICL00037473 | 3.18 | S27L/S22V/T48S/L90Y/F92G/N204K |

Figure 9U

| Colony Tracking Number | Improvement of Total Activity w.r.t. G2P: PF at pH8.0, 65°C, 72hr | AA Mutations w.r.t G1P |
|---|---|---|
| ICL00037489 | 1.66 | S27L/S22V/S32K/T48S/I82F/F92G/A127S/N204K/S223A |
| ICL00037554 | 2.16 | S27L/A55L |
| ICL00037558 | 1.20 | S27L/A97V |
| ICL00037611 | 1.02 | S27L/F250L |
| ICL00037629 | 1.05 | S27L/T109G |
| ICL00037651 | 1.02 | S27L/G38D |
| ICL00037677 | 1.13 | S27L/A97S |
| ICL00037847 | 1.26 | S27L/A55V/A216T |
| ICL00037864 | 1.11 | S27L/P20D |
| ICL00037901 | 1.27 | S27L/A55V |
| ICL00037943 | 1.03 | S27L/T109Y |
| ICL00037946 | 1.11 | S27L/V165I |
| ICL00037948 | 1.12 | S27L/A184G |
| ICL00037955 | 1.28 | S27L/A97E |
| ICL00037961 | 1.10 | S27L/A184S |
| ICL00037963 | 1.15 | S27L/A97F |
| ICL00037988 | 1.40 | S27L/A97T |
| ICL00038033 | 1.13 | S27L/K197Y |
| ICL00038067 | 1.39 | S27L/A55I |
| ICL00038071 | 1.06 | S27L/A97P |
| ICL00038085 | 1.14 | S27L/A55M |
| ICL00038089 | 1.01 | S27L/P20E |
| ICL00038124 | 1.12 | S27L/A117L |
| ICL00038135 | 1.11 | S27L/T109L |
| ICL00038140 | 1.08 | S27L/K197T |
| ICL00038189 | 1.09 | S27L/T136S |
| ICL00038207 | 1.45 | S27L/A97L |
| ICL00038219 | 1.13 | S27L/T109A |
| ICL00038277 | 1.15 | S27L/P20I |
| ICL00038296 | 1.05 | S27L/L191V |
| ICL00038299 | 1.08 | S27L/A184C |
| ICL00038304 | 1.09 | S27L/A97Q |
| ICL00038308 | 1.03 | S27L/F250V |
| ICL00038341 | 1.13 | S27L/K197V |
| ICL00038353 | 1.05 | S27L/A117S |
| ICL00038364 | 1.08 | S27L/K197R |

Figure 9V

| Colony Tracking Number | Improvement of Total Activity w.r.t. G2P: PF at pH8.0, 65°C, 72hr | AA Mutations w.r.t G1P |
|---|---|---|
| ICL00038379 | 1.06 | S27L/T109K |
| ICL00038424 | 1.23 | S27L/A55C |
| ICL00038486 | 1.51 | S27L/N2S/V177A |
| ICL00038559 | 1.33 | S27L/Q142D |
| ICL00038580 | 1.31 | S27L/G149C |
| ICL00038591 | 1.15 | S27L/F21Y |
| ICL00038623 | 1.26 | S27L/G149A |
| ICL00038726 | 1.21 | S27L/P164E |
| ICL00038757 | 1.16 | S27L/Y26C |
| ICL00038766 | 1.04 | S27L/T17N |
| ICL00038783 | 1.32 | S27L/S57M |
| ICL00038791 | 1.01 | S27L/D249I |
| ICL00038792 | 1.01 | S27L/T17S |
| ICL00038834 | 1.06 | S27L/P164T |
| ICL00038837 | 1.09 | S27L/Q142L |
| ICL00038861 | 1.32 | S27L/D249N |
| ICL00038862 | 1.06 | S27L/I185R |
| ICL00038865 | 1.27 | S27L/V83L |
| ICL00038866 | 1.32 | S27L/G149S |
| ICL00038869 | 1.02 | S27L/A24D |
| ICL00038901 | 1.24 | S27L/R251V |
| ICL00038914 | 1.02 | S27L/V83I |
| ICL00038944 | 1.05 | S27L/S110N |
| ICL00039000 | 1.10 | S27L/T17M |
| ICL00039034 | 1.14 | S27L/F161W |
| ICL00039051 | 1.09 | S27L/G46E |
| ICL00039053 | 1.02 | S27L/D249T |
| ICL00039063 | 1.06 | S27L/T17I |
| ICL00039064 | 1.61 | S27L/S57C |
| ICL00039113 | 1.30 | S27L/S57T |
| ICL00039173 | 1.67 | S27L/S57L |
| ICL00039195 | 1.07 | S27L/Q167T |
| ICL00039260 | 1.76 | S27L/S57E |
| ICL00039288 | 1.10 | S27L/T17K |
| ICL00039321 | 1.45 | S27L/G149N |
| ICL00039344 | 1.06 | S27L/Q142E |

Figure 9W

| Colony Tracking Number | Improvement of Total Activity: PF at pH8.0, 65°C, 72hr | AA Mutations w.r.t G1P |
|---|---|---|
| ICL00039414 | 1.38 | S27L/S57F |
| ICL00039500 | 1.17 | S27L/T17A |
| ICL00039501 | 1.13 | S27L/P164H |
| ICL00039564 | 1.47 | S27L/T17R |
| ICL00039573 | 1.22 | S27L/G149T |
| ICL00039613 | 1.12 | S27L/R251T |
| ICL00039624 | 1.07 | S27L/S101Y |
| ICL00039636 | 1.56 | S27L/S57V |
| ICL00039637 | 1.13 | S27L/A24T |
| ICL00039669 | 1.14 | S27L/I185E |
| ICL00039701 | 1.35 | S27L/G46N |
| ICL00039711 | 1.02 | S27L/P164N |
| ICL00039733 | 1.83 | S27L/P164S |
| ICL00039734 | 1.28 | S27L/Q167V |
| ICL00039757 | 1.37 | S27L/F161V |
| ICL00039766 | 1.61 | S27L/S57I |
| ICL00039771 | 1.53 | S27L/G149D |
| ICL00039784 | 1.12 | S27L/Q167I |
| ICL00039794 | 1.05 | S27L/I185Q |
| ICL00043486 | 1.01 | S27L/A114V/A117N/T136A/I222L/V229I |
| ICL00043848 | 1.54 | S27L/A24V/V229C |
| ICL00044168 | 1.11 | S27L/F21W |
| ICL00043551 | 1.07 | S27L/F21W/A114V/T136A/I222L/V229I |
| ICL00044152 | 1.37 | S27L/F21W/A24V |
| ICL00044069 | 1.39 | S27L/F21W/A24V/A114V/A117Q/Q142W/I222L/V229C |
| ICL00043633 | 1.36 | S27L/F21W/I222L/V229C |
| ICL00043952 | 1.43 | S27L/F21W/I222L/V229I |
| ICL00043637 | 1.34 | S27L/F21W/Q142L/I222L/V229C |
| ICL00044295 | 1.27 | S27L/F21W/S101M/I222L/V229C |
| ICL00043472 | 1.26 | S27L/F21W/T109K/S110R/T136A/V229I |
| ICL00044315 | 1.10 | S27L/F21W/T109R/A117N/T136V/I222L/V229I |
| ICL00044330 | 1.57 | S27L/F21W/T109R/A117N/T136V/Q142W/I222L/V229C |
| ICL00043752 | 1.25 | S27L/F21W/T136A |

Figure 9X

| Colony Tracking Number | Improvement of Total Activity: PF at pH8.0, 65°C, 72hr | AA Mutations w.r.t G1P |
|---|---|---|
| ICL00043749 | 1.34 | S27L/I222L/V229I |
| ICL00044510 | 1.39 | S27L/P20T/A117Q/I222L/V229C |
| ICL00044441 | 1.02 | S27L/P20T/A24V/S101Q/T109R/A117Q/I222L/V229I |
| ICL00044350 | 1.34 | S27L/P20T/F21W/I222L/V229C |
| ICL00044428 | 1.30 | S27L/P20T/F21W/Q142W/I222L/V229C |
| ICL00044371 | 1.43 | S27L/P20T/F21W/Q142W/I222L/V229I |
| ICL00043526 | 1.62 | S27L/P20T/F21W/T109K/A117N/I222L/V229C |
| ICL00043688 | 1.50 | S27L/P20T/F21W/T109L/T136A/Q142W/I222L/V229C |
| ICL00043610 | 1.62 | S27L/P20T/F21W/T109R/A117Q/T136V/Q142L/I222L/V229I |
| ICL00043813 | 1.25 | S27L/P20T/F21W/T136A/Q142L/I222L/V229I |
| ICL00043577 | 1.39 | S27L/P20T/F21W/V229I |
| ICL00044052 | 1.21 | S27L/P20T/I222L/V229C |
| ICL00043941 | 1.18 | S27L/P20T/S101H/A114V/A117N/I222L/V229I |
| ICL00044090 | 1.34 | S27L/P20T/S101M/A114V/A117N/Q142W/I222L/V229C |
| ICL00043686 | 1.64 | S27L/P20T/S101M/I222L/V229I |
| ICL00044408 | 1.55 | S27L/P20T/T109K/A114K/Q142W/I222L/V229C |
| ICL00043842 | 1.26 | S27L/P20T/T109L/S110R/A117N/I222L/V229I |
| ICL00043764 | 1.28 | S27L/P20T/T109R/A114K/A117Q/T136V/I222L/V229C |
| ICL00043458 | 1.17 | S27L/P20T/V23T/A24V/I222L/V229I |
| ICL00043499 | 1.48 | S27L/P20T/V23T/A24V/T109L/S110R/I222L/V229I |
| ICL00043924 | 1.35 | S27L/S101M/A114V/A117Q/T136A |
| ICL00043528 | 1.36 | S27L/S101M/T136A/I222L/V229I |
| ICL00044207 | 1.30 | S27L/S101N/A117Q/I222L |
| ICL00043491 | 1.35 | S27L/S101Q/Q142L/I222L/V229I |
| ICL00043684 | 1.70 | S27L/S101W/A114V/T136V/V229C |
| ICL00044177 | 1.22 | S27L/T109K/A117N/T136V/I222L/V229C |
| ICL00043973 | 1.05 | S27L/T109R/A117N/I222L/V229C |
| ICL00043940 | 1.42 | S27L/T109R/I222L/V229I |
| ICL00043944 | 1.23 | S27L/T136V/Q142W/I222L/V229I |
| ICL00043759 | 1.61 | S27L/T17A/A24V/S101D/S110R/T136A |
| ICL00043639 | 1.25 | S27L/T17A/F21W/S101Q/I222L/V229C |
| ICL00043731 | 1.29 | S27L/T17A/F21W/T109R/S110R/I222L/V229I |
| ICL00044539 | 1.13 | S27L/T17A/P20T/S101Q/T109K/S110R/T136A/I222L/V229C |
| ICL00043846 | 1.43 | S27L/T17A/V23L/S101M/T109K/S110R/A114V/A117Q/T136V/V229I |

Figure 9Y

| Colony Tracking Number | Improvement of Total Activity: PF at pH8.0, 65°C, 72hr | AA Mutations w.r.t G1P |
|---|---|---|
| ICL00043721 | 1.19 | S27L/T17A/V23T/A24V/T136A |
| ICL00044006 | 1.29 | S27L/T17C/A114K/A117N/T136V/I222L/V229I |
| ICL00043926 | 1.26 | S27L/T17C/T109K/A117N/T136A/I222L/V229I |
| ICL00043983 | 1.25 | S27L/T17G/F21W/A117N/I222L/V229I |
| ICL00044547 | 1.39 | S27L/T17G/P20T/F21W/A117Q/I222L/V229C |
| ICL00043831 | 1.04 | S27L/T17G/V23T/A24V/T109L/A117Q/T136A/I222L/V229I |
| ICL00043487 | 1.34 | S27L/T17H/F21W/T136V/Q142W/I222L/V229I |
| ICL00043844 | 1.83 | S27L/T17H/S101Q/T136V/Q142L/V229C |
| ICL00044382 | 1.24 | S27L/T17L/S101M/T109K/S110R/A117Q/I222L/V229C |
| ICL00043812 | 1.25 | S27L/T17L/T109L/S110R/A117Q/I222L/V229I |
| ICL00043849 | 1.34 | S27L/T17Q/A24V/S101W/T136A |
| ICL00044328 | 1.60 | S27L/T17Q/Q142L/I222L/V229I |
| ICL00044164 | 1.56 | S27L/T17Q/S101D/T136A/I222L/V229I |
| ICL00044355 | 1.24 | S27L/T17Q/T136A/I222L/V229C |
| ICL00044226 | 1.31 | S27L/T17Q/T136A/I222L/V229I |
| ICL00043568 | 1.39 | S27L/T17Q/V23T/A24V/I222L/V229I |
| ICL00044481 | 1.25 | S27L/T17S/F21W/Q142L |
| ICL00043742 | 1.20 | S27L/T17S/S101N/T109K/A117N/T136V/Q142L/I222L/V229C |
| ICL00044186 | 1.31 | S27L/T17S/V229I |
| ICL00043608 | 1.24 | S27L/V229I |
| ICL00044340 | 1.12 | S27L/V23L/A114V/A117N/T136A/I222L/V229I |
| ICL00044232 | 1.26 | S27L/V23L/A117Q |
| ICL00043536 | 1.06 | S27L/V23L/A24V/S101K/A117N/I222L/V229C |
| ICL00043839 | 1.28 | S27L/V23L/A24V/T136A/Q142W/I222L/V229I |
| ICL00043592 | 1.29 | S27L/V23L/I222L/V229C |
| ICL00043955 | 1.14 | S27L/V23L/T136A/I222L/V229I |
| ICL00043772 | 2.02 | S27L/V23T/A24V/I222L/V229C |
| ICL00044326 | 1.15 | S27L/V23T/A24V/T109K/A114K/A117Q/T136A/I222L/V229C |
| ICL00044127 | 1.40 | S27L/V23T/Q142L/I222L/V229C |
| ICL00043537 | 1.33 | S27L/V23T/T109L/A114V/T136A/Q142L/I222L/V229C |
| ICL00040026 | 1.27 | S27L/A117Y |
| ICL00040387 | 1.38 | S27L/A24D/K197L |
| ICL00040146 | 1.48 | S27L/A24D/L191F/R251Q |
| ICL00040453 | 1.42 | S27L/A24D/S110K |

Figure 9Z

| Colony Tracking Number | Improvement of Total Activity: PF at pH8.0, 65°C, 72hr | AA Mutations w.r.t G1P |
|---|---|---|
| ICL00041680 | 1.57 | S27L/A24D/T109L/K197L |
| ICL00040241 | 1.50 | S27L/A24D/T136S/F250V |
| ICL00040069 | 1.78 | S27L/A24H/G46E |
| ICL00040102 | 1.07 | S27L/A24H/R251V |
| ICL00040329 | 1.13 | S27L/A24N |
| ICL00041935 | 1.26 | S27L/A24N/P164S/K197V/R251T |
| ICL00041682 | 1.26 | S27L/A55V/V83L/A117T |
| ICL00040423 | 1.04 | S27L/F21Y/A184S |
| ICL00041467 | 1.06 | S27L/F21Y/A55T/T109A/A184S |
| ICL00040495 | 1.14 | S27L/F21Y/G46E/A117T/T136S/G149C/R251Q |
| ICL00040518 | 1.16 | S27L/F250L/R251Q |
| ICL00040336 | 1.34 | S27L/G46E/A55I/Q142E |
| ICL00041273 | 1.14 | S27L/G46N/I139T/Q142E/P164T/I185A/V229L/F250V |
| ICL00041071 | 1.11 | S27L/G46R/T109K/T136S/D249T |
| ICL00040224 | 1.07 | S27L/I139T/Q142E/I169V |
| ICL00042190 | 1.24 | S27L/K197R/R251E |
| ICL00042046 | 1.11 | S27L/N2E/G46N/A55V/I185Y/D249I |
| ICL00040842 | 1.27 | S27L/N2E/G46S/V83L/T136S/A172T/V229C/D249N |
| ICL00041002 | 1.51 | S27L/N2E/I169L/F250L/R251Q |
| ICL00041977 | 1.54 | S27L/N2E/P20E/F250V/R251L |
| ICL00040909 | 1.30 | S27L/N2E/P20I/T109L/L191V/K197L/V229C |
| ICL00039972 | 1.19 | S27L/N2E/R251L |
| ICL00040106 | 1.22 | S27L/N2F |
| ICL00041835 | 1.39 | S27L/N2F/D249N/F250L |
| ICL00041533 | 1.23 | S27L/N2F/G46E |
| ICL00040002 | 1.54 | S27L/N2F/P20E |
| ICL00042252 | 1.04 | S27L/N2F/P20E/S110D/A184S/L191V/R251V |
| ICL00040887 | 1.23 | S27L/N2F/P20I/F21Y/R251Q |
| ICL00041364 | 1.34 | S27L/N2F/R251Q |
| ICL00041574 | 1.10 | S27L/N2F/S101C/A117F/P164S |
| ICL00041845 | 1.08 | S27L/N2F/S101Y/Q142L/G149T/Q167I/I169C/V229L |
| ICL00040388 | 1.29 | S27L/N2L |
| ICL00042100 | 1.32 | S27L/N2L/A172T |
| ICL00039916 | 1.33 | S27L/N2L/A24H/A55C/V229L |
| ICL00040800 | 1.23 | S27L/N2L/A24T |
| ICL00041736 | 1.31 | S27L/N2L/G46E/T109K/F161V |

Figure 9AA

| Colony Tracking Number | Improvement of Total Activity: PF at pH8.0, 65°C, 72hr | AA Mutations w.r.t G1P |
|---|---|---|
| ICL00040487 | 1.33 | S27L/N2L/P20E/F21Y/V229L |
| ICL00040442 | 1.01 | S27L/N2L/T17I/T136S/P164H/D249M |
| ICL00041938 | 1.27 | S27L/N2L/T17N/S57C/S110D/A117L/P164N/I185G/V229L/R251T |
| ICL00041080 | 1.67 | S27L/N2S/A24D/S101Y/P164E/V165I/I185E |
| ICL00040174 | 1.52 | S27L/N2S/A24N/G46E/A55L/Q142D/V229C/R251L |
| ICL00040463 | 1.08 | S27L/N2S/A55V/I185Q/R251E |
| ICL00040566 | 1.35 | S27L/N2S/P20D/A97C/A117F/F250L/R251E |
| ICL00040090 | 1.20 | S27L/N2S/V83L/A184S |
| ICL00040060 | 1.14 | S27L/P164T/V165I/R251E |
| ICL00040865 | 1.20 | S27L/P20D/A55T/A117Y/K197R |
| ICL00041737 | 1.05 | S27L/P20D/F21Y/A55T/F250L/R251V |
| ICL00039868 | 1.32 | S27L/P20D/F21Y/F250V |
| ICL00042042 | 1.54 | S27L/P20D/F21Y/G46N/S110K/T163I/Q167V |
| ICL00041640 | 1.73 | S27L/P20D/G46N/A55C/S110N/T163I/A184S |
| ICL00040630 | 1.27 | S27L/P20D/G46S/A55I/K197T |
| ICL00042201 | 1.20 | S27L/P20D/S57E/S101C |
| ICL00040296 | 1.42 | S27L/P20E/A24D/D249S/F250V |
| ICL00042171 | 1.25 | S27L/P20E/F21Y/G46E/V83L/A97Q |
| ICL00041696 | 1.01 | S27L/P20E/F21Y/I139T/P164H/K197T/R251E |
| ICL00041182 | 1.43 | S27L/P20E/F21Y/K197T |
| ICL00040186 | 1.19 | S27L/P20E/F21Y/S110D/A117S |
| ICL00040431 | 1.17 | S27L/P20E/F21Y/S57T/P164N/A184C/V229C |
| ICL00040166 | 1.24 | S27L/P20I/F21Y/A117F/I185G/D249N |
| ICL00041084 | 1.10 | S27L/Q142H/I185S/R251A |
| ICL00040993 | 1.03 | S27L/S110D/A184S/K197T |
| ICL00042211 | 1.07 | S27L/S110K/A117Y/P164R |
| ICL00040629 | 1.12 | S27L/S57C/R251E |
| ICL00040501 | 1.03 | S27L/T136S/D249T |
| ICL00041708 | 1.35 | S27L/T163I |
| ICL00041406 | 1.38 | S27L/T17H/S110K |
| ICL00042123 | 1.21 | S27L/T17I/A24D/S57I |
| ICL00040258 | 1.68 | S27L/T17N/A117S/V229L/R251A |
| ICL00039911 | 1.24 | S27L/T17S/R251T |
| ICL00040420 | 1.17 | S27L/V83L/A97S/A184C/D249S |
| ICL00041699 | 1.11 | S27L/V83L/F250V/R251E |

Figure 10A

| Position | Parent | Variant | Position | Parent | Variant |
|---|---|---|---|---|---|
| 27 | S | L, F, H, T, W | 68 | A | F |
| 1 | S | A, G, M, R | 70 | L | M |
| 2 | N | E, F, L, R, S | 72 | R | P |
| 5 | Q | E | 74 | L | W |
| 9 | N | A, E, S | 77 | H | Q |
| 12 | R | K | 82 | I | F, L, M |
| 13 | S | L, R | 83 | V | I, L, T |
| 14 | A | K, S | 85 | N | D |
| 15 | L | I | 87 | N | F, H, I, K, L, M, Q, R, V, W, Y |
| 16 | T | E | 88 | S | K, T |
| 17 | T | A, C, G, H, I, K, L, M, N, Q, R, S | 90 | L | F, K, Y |
| 18 | D | R | 92 | F | G, I, K, L, N, Q, V, Y |
| 20 | P | D, E, I, Q, T | 97 | A | C, E, F, G, L, P, Q, S, T, V |
| 21 | F | W, Y | 98 | S | A, D, E, L, M, N, Q, T, V |
| 22 | S | A, I, K, P, R, V | 101 | S | A, C, D, F, H, K, L, M, N, Q, R, V, W, Y |
| 23 | V | L, T | 102 | A | V |
| 24 | A | D, G, H, N, S, T, V | 105 | N | D |
| 25 | T | A, F, H, Q, R, V | 108 | R | C, E, H, K, N, P, Q, S, T, V |
| 26 | Y | C, K, L, T | 109 | T | A, F, G, K, L, N, R, Y |
| 30 | R | K | 110 | S | D, G, H, K, N, R |
| 32 | S | K, M, Q, Y | 113 | S | A, K, N, P, Q, R, T, Y |
| 33 | V | G, Q, T | 114 | A | K, L, S, V |
| 34 | S | R | 117 | A | F, G, L, N, Q, S, T, Y |
| 40 | V | T | 119 | L | I, M |
| 46 | G | E, L, N, R, S | 121 | A | S |
| 48 | T | N, S | 122 | N | A, E, H, P, R, S |
| 49 | L | G | 125 | A | S |
| 53 | G | A | 127 | A | M, S, V |
| 54 | I | V | 135 | A | G |
| 55 | A | C, I, L, M, T, V | 136 | T | A, M, S, V |
| 56 | M | I, L | 138 | R | E, L |
| 57 | S | C, E, F, I, L, M, T, V | 139 | I | A, T |
| 60 | Y | A, H, I | 140 | S | A |
| 62 | A | T | 142 | Q | D, E, H, L, W |

Figure 10B

| Position | Parent | Variant | Position | Parent | Variant |
|---|---|---|---|---|---|
| 143 | I | N, R | 206 | T | G, K, L, P, R |
| 145 | T | S | 208 | F | G, L, R, T |
| 147 | K | F, G, N, Q | 209 | A | V |
| 149 | G | A, C, D, N, S, T, V | 211 | N | F, I, L, M, V |
| 150 | V | I, L | 212 | S | F, L, M |
| 153 | T | L | 213 | P | N, R |
| 156 | H | N | 216 | A | L, P, S, T, V |
| 157 | T | A, G | 217 | I | S |
| 158 | D | E, I, K, L | 218 | S | A |
| 160 | T | K, Q, R, S, V | 219 | V | F, I, K, L, R |
| 161 | F | V, W | 221 | T | S |
| 162 | N | E, H, P, R | 222 | I | L |
| 163 | T | I, S | 223 | S | A, C |
| 164 | P | E, H, N, R, S, T | 225 | M | L |
| 167 | Q | I, T, V | 227 | L | R |
| 170 | V | L | 228 | W | F |
| 173 | E | R | 229 | V | C, I, L |
| 174 | A | K, R | 231 | N | L, Q, S |
| 177 | V | A | 236 | R | C, E, H, K, Q |
| 179 | P | Q | 237 | Q | R |
| 181 | S | A, C, R | 241 | N | P |
| 182 | Q | T | 242 | V | T |
| 184 | A | C, G, S | 243 | N | P |
| 185 | I | A, E, G, L, Q, R, S, Y | 246 | A | D, K, S, T |
| 189 | Q | I, L, V | 249 | D | I, M, N, S, T |
| 190 | N | S | 250 | F | I, L, V, Y |
| 193 | S | E, F, H, K, N, P, T, V | 251 | R | A, E, I, K, L, Q, T, V |
| 194 | T | G, S | 252 | S | T |
| 195 | T | F | 253 | N | S, Y |
| 198 | V | A | 254 | N | R |
| 200 | V | L | 255 | R | E, G, L, M, S, V, W, Y |
| 203 | D | N, R, V | 258 | Q | P |
| 204 | N | A, K, R, S | | | |
| 8 | P | T | 165 | V | I |
| 31 | L | M | 169 | I | C, L, V |
| 38 | G | D | 172 | A | T |
| 95 | S | N | 191 | L | F, V |
| 126 | V | I | 192 | P | A |
| 137 | L | M | 197 | K | L, R, T, V, Y |

Figure 11A

>SEQ ID NO:1 (wild type Bhr-PETase, G1P)
SNPYQRGPNPTRSALTTDGPFSVATYSVSRLSVSGFGGGVIYYPTGTTLTFGGIAMSPGYTADASS
LAWLGRRLASHGFVVIVINTNSRLDFPDSRASQLSAALNYLRTSSPSAVRARLDANRLAVAGHSMG
GGATLRISEQIPTLKAGVPLTPWHTDKTFNTPVPQLIVGAEADTVAPVSQHAIPFYQNLPSTTPKV
YVELDNATHFAPNSPNAAISVYTISWMKLWVDNDTRYRQFLCNVNDPALSDFRSNNRHCQ >SEQ ID NO:2 (N.A. encoding wild type Bhr-PETase, codon optimized)
TCTAACCCATACCAGAGGGGACCTAACCCTACTAGGAGTGCCTTGACCACCGATGGTCCTTTCAGT
GTCGCCACCTACTCTGTCTCTAGGTTGTCTGTCTCTGGTTTCGGAGGTGGAGTCATCTACTACCCA
ACCGGAACCACCCTTACCTTCGGAGGTATCGCCATGTCTCCCGGATACACTGCCGATGCTTCTAGT
CTTGCTTGGTTGGGTAGGAGGCTTGCTAGTCACGGATTCGTCGTCATCGTCATCAACACCAACAGT
AGGTTGGACTTTCCAGACAGTAGGGCCTCTCAGCTTTCTGCCGCCCTTAACTACCTTAGGACCTCT
TCTCCAAGTGCCGTTAGAGCTAGGTTGGACGCTAATAGATTGGCTGTCGCTGGACACTCTATGGGT
GGAGGTGCCACTTTGAGGATCAGTGAGCAGATCCCTACCCTTAAAGCCGGTGTTCCTTTGACCCCT
TGGCACACTGACAAGACCTTCAACACTCCAGTCCCACAGTTGATTGTCGGAGCCGAAGCCGATACT
GTTGCTCCAGTTTCTCAGCACGCCATCCCATTCTACCAGAACCTTCCTAGTACCACCCCAAAGGTC
TACGTCGAGTTGGATAACGCCACCCACTTCGCTCCAAACTCTCCAAACGCTGCCATCAGTGTTTAC
ACCATTTCTTGGATGAAGTTGTGGGTCGACAACGACACTAGATATAGACAGTTCCTTTGCAACGTC
AACGACCCAGCTTTGTCTGACTTTAGAAGTAACAATAGACATTGTCAG >SEQ ID NO:3 (N.A. encoding wild type Bhr-PETase, codon optimized)
AGTAACCCATACCAGCGCGGTCCGAATCCGACCCGTAGTGCGCTGACGACCGATGGTCCGTTTAGC
GTGGCCACCTACAGCGTGAGCCGTCTGAGTGTTAGCGGCTTTGGCGGCGGTGTTATCTACTACCCG
ACGGGCACCACGCTGACCTTTGGTGGCATCGCCATGAGTCCGGGCTACACCGCGGACGCCAGTAGT
CTGGCGTGGCTCGGTCGTCGTCTGGCGAGCCATGGCTTCGTGGTGATCGTGATCAACACCAACAGC
CGCCTCGACTTTCCAGATAGTCGTGCCAGTCAGCTGAGCGCCGCGCTGAATTATCTGCGTACCAGT
AGCCCAAGCGCGGTTCGTGCCCGTCTGGATGCCAATCGCCTCGCCGTTGCCGGTCATAGTATGGGC
GGTGGTGCCACGCTGCGTATCAGCGAACAGATTCCGACGCTGAAAGCGGGCGTGCCACTGACCCCA
TGGCACACGGACAAGACGTTTAACACCCCGGTTCCGCAGCTCATTGTGGGTGCCGAAGCCGACACC
GTTGCCCCAGTTAGCCAGCACGCGATCCCGTTTTACCAGAATCTGCCAAGCACCACGCCGAAAGTT
TACGTGGAACTCGACAACGCGACCCACTTTGCGCCGAACAGTCCGAACGCCGCCATCAGCGTGTAC
ACCATCAGCTGGATGAAACTCTGGGTGGACAACGATACCCGCTACCGCCAGTTTCTGTGCAACGTT
AATGATCCGGCGCTGAGCGACTTCCGCAGCAATAACCGCCATTGCCAG

Figure 11B

>SEQ ID NO:4 (wild type Lcc-PETase)
HHHHHHSSGLVPRGSHMSNPYQRGPNPTRSALTADGPFSVATYTVSRLSVSGFGGGVIYYPTGTSL
TFGGIAMSPGYTADASSLAWLGRRLASHGFVVLVINTNSRFDYPDSRASQLSAALNYLRTSSPSAV
RARLDANRLAVAGHSMGGGGTLRIAEQNPSLKAAVPLTPWHTDKTFNTSVPVLIVGAEADTVAPVS
QHAIPFYQNLPSTTPKVYVELDNASHFAPNSNNAAISVYTISWMKLWVDNDTRYRQFLCNVNDPAL
SDFRTNNRHCQ >SEQ ID NO: 5 (N.A. encoding wild type Lcc-PETase)
CATCATCATCATCATCACAGCAGCGGCCTGGTGCCGCGCGGCAGCCATATGAGTAACCCATACCAG
CGCGGTCCGAATCCGACCCGTAGTGCGCTGACGGCCGATGGTCCGTTTAGCGTGGCCACCTACACC
GTGAGCCGTCTGAGTGTTAGCGGCTTTGGCGGCGGTGTTATCTACTACCCGACGGGCACCAGTCTG
ACCTTTGGTGGCATCGCCATGAGTCCGGGCTACACCGCGGACGCCAGTAGTCTGGCGTGGCTCGGT
CGTCGTCTGGCGAGCCATGGCTTCGTGGTGCTGGTGATCAACACCAACAGCCGCTTCGACTATCCA
GATAGTCGTGCCAGTCAGCTGAGCGCCGCGCTGAATTATCTGCGTACCAGTAGCCCAAGCGCGGTT
CGTGCCCGTCTGGATGCCAATCGCCTCGCCGTTGCCGGTCATAGTATGGGCGGTGGTGGTACGCTG
CGTATCGCCGAACAGAATCCGAGTCTGAAAGCGGCCGTGCCACTGACCCCATGGCACACGGACAAG
ACGTTTAACACCAGCGTTCCGGTGCTCATTGTGGGTGCCGAAGCCGACACCGTTGCCCCAGTTAGC
CAGCACGCGATCCCGTTTTACCAGAATCTGCCAAGCACCACGCCGAAAGTTTACGTGGAACTCGAC
AACGCGAGCCACTTTGCGCCGAACAGTAATAACGCCGCCATCAGCGTGTACACCATCAGCTGGATG
AAACTCTGGGTGGACAACGATACCCGCTACCGCCAGTTTCTGTGCAACGTTAATGATCCGGCGCTG
AGCGACTTCCGCACCAATAACCGCCATTGCCAG >SEQ ID NO:6 (wild type Is-PETase)
QTNPYARGPNPTAASLEASAGPFTVRSFTVSRPSGYGAGTVYYPTNAGGTVGAIAIVPGYTARQSS
IKWWGPRLASHGFVVITIDTNSTLDQPSSRSSQQMAALRQVASLNGTSSSPIYGKVDTARMGVMGW
SMGGGGSLISAANNPSLKAAAPQAPWDSSTNFSSVTVPTLIFACENDSIAPVNSSALPIYDSMSRN
AKQFLEINGGSHSCANSGNSNQALIGKKGVAWMKRFMDNDTRYSTFACENPNSTRVSDFRTANCSL
EHHHHHH >SEQ ID NO:7 ((N.A. encoding wild type Is-PETase)
CAGACGAATCCATACGCCCGCGGTCCAAATCCAACCGCGGCGAGTCTGGAAGCCAGTGCGGGCCCA
TTCACCGTTCGCAGCTTTACCGTTAGTCGTCCAAGCGGTTACGGTGCCGGCACCGTGTACTACCCG
ACGAATGCGGGTGGTACCGTGGGTGCGATCGCCATCGTTCCGGGCTATACCGCGCGCCAGAGTAGC
ATCAAATGGTGGGGTCCACGTCTGGCGAGTCATGGCTTCGTGGTGATCACGATCGACACCAATAGC
ACCCTCGATCAGCCAAGCAGCCGCAGCAGTCAACAGATGGCGGCGCTGCGCCAAGTTGCCAGTCTG
AACGGCACGAGTAGCAGCCCGATTTACGGTAAAGTGGACACCGCGCGTATGGGCGTGATGGGCTGG
AGCATGGGTGGTGGTGGCAGTCTGATCAGTGCCGCCAACAATCCAAGCCTCAAAGCGGCGGCGCCA
CAAGCGCCATGGGATAGCAGCACGAACTTTAGCAGCGTGACCGTGCCAACGCTGATCTTCGCGTGC
GAAAACGACAGCATCGCCCCGGTGAATAGCAGTGCGCTGCCGATCTATGACAGCATGAGTCGCAAC
GCCAAGCAGTTTCTGGAGATCAACGGTGGCAGCCATAGCTGCGCGAACAGCGGCAACAGCAATCAA
GCCCTCATCGGTAAAAAGGGCGTGGCGTGGATGAAGCGCTTTATGGACAACGACACCCGCTACAGC
ACCTTCGCGTGCGAGAATCCGAACAGTACCCGCGTGAGCGATTTCCGCACCGCCAATTGCAGCCTC
GAGCACCACCACCACCACCAC

SEQUENCE LISTING

```
Sequence total quantity: 34
SEQ ID NO: 1            moltype = AA  length = 258
FEATURE                 Location/Qualifiers
source                  1..258
                        mol_type = protein
                        organism = unidentified
SEQUENCE: 1
SNPYQRGPNP TRSALTTDGP FSVATYSVSR LSVSGFGGGV IYYPTGTTLT FGGIAMSPGY  60
TADASSLAWL GRRLASHGFV VIVINTNSRL DFPDSRASQL SAALNYLRTS SPSAVRARLD  120
ANRLAVAGHS MGGGATLRIS EQIPTLKAGV PLTPWHTDKT FNTPVPQLIV GAEADTVAPV  180
```

```
SQHAIPFYQN LPSTTPKVYV ELDNATHFAP NSPNAAISVY TISWMKLWVD NDTRYRQFLC  240
NVNDPALSDF RSNNRHCQ                                                258

SEQ ID NO: 2            moltype = DNA  length = 774
FEATURE                 Location/Qualifiers
source                  1..774
                        mol_type = unassigned DNA
                        organism = unidentified
SEQUENCE: 2
tctaacccat accagagggg acctaaccct actaggagtg ccttgaccac cgatggtcct  60
ttcagtgtcg ccacctactc tgtctctagg ttgtctgtct ctggtttcgg aggtggagtc  120
atctactacc caaccggaac caccccttacc ttcggaggta tcgccatgtc tcccggatac  180
actgccgatg cttctagtct tgcttggttg ggtaggaggc ttgctagtca cggattcgtc  240
gtcatcgtca tcaacaccaa cagtaggttg gactttccag acagtagggc ctctcagctt  300
tctgccgccc ttaactacct taggacctct tctccaagtg ccgttagagc taggttggac  360
gctaatagat tggctgtcgc tggacactct atgggtggag gtgccacttt gaggatcagt  420
gagcagatcc ctacccttaa agccggtgtt cctttgaccc cttggcacac tgacaagacc  480
ttcaacactc cagtcccaca gttgattgtc ggagccgaag ccgatactgt tgctccagtt  540
tctcagcacg ccatcccatt ctaccagaac cttcctagta ccaccccaaa ggtctacgtc  600
gagttggata acgccaccca cttcgctcca aactctccaa acgctgccat cagtgtttac  660
accatttctt ggatgaagtt gtgggtcgac aacgacacta gatatagaca gttcctttgc  720
aacgtcaacg acccagcttt gtctgacttt agaagtaaca atagacattg tcag         774

SEQ ID NO: 3            moltype = DNA  length = 774
FEATURE                 Location/Qualifiers
source                  1..774
                        mol_type = unassigned DNA
                        organism = unidentified
SEQUENCE: 3
agtaacccat accagcgcgg tccgaatccg acccgtagtg cgctgacgac cgatggtccg  60
tttagcgtgg ccacctacag cgtgagccgt ctgagtgtta gcggctttgg cggcggtgtt  120
atctactacc cgacgggcac cacgctgacc tttggtggca tcgccatgag tccgggctac  180
accgcggacg ccagtagtct ggcgtggctc ggtcgtcgtc tggcgagcca tggcttcgtg  240
gtgatcgtga tcaacaccaa cagccgcctc gactttccag atagtcgtgc cagtcagctg  300
agcgccgcgc tgaattatct gcgtaccagt agcccaagcg cggttcgtgc ccgtctggat  360
gccaatcgcc tcgccgttgc cggtcatagt atgggcggtg gtgccacgct gcgtatcagc  420
gaacagattc cgacgctgaa agcgggcgtg ccactgaccc catggcacac ggacaagacg  480
tttaacaccc cggttccgca gctcattgtg ggtgccgaag ccgacaccgt tgccccagtt  540
agccagcacg cgatcccgtt ttaccagaat ctgccaagca ccacgccgaa agtttacgtg  600
gaactcgaca acgcgaccca ctttgcgccg aacagtccga acgccgccat cagcgtgtac  660
accatcagct ggatgaaact ctgggtggac aacgataccc gctaccgcca gtttctgtgc  720
aacgttaatg atccggcgct gagcgacttc cgcagcaata accgccattg ccag         774

SEQ ID NO: 4            moltype = AA  length = 275
FEATURE                 Location/Qualifiers
source                  1..275
                        mol_type = protein
                        organism = unidentified
SEQUENCE: 4
HHHHHHSSGL VPRGSHMSNP YQRGPNPTRS ALTADGPFSV ATYTVSRLSV SGFGGGVIYY  60
PTGTSLTFGG IAMSPGYTAD ASSLAWLGRR LASHGFVVLV INTNSRFDYP DSRASQLSAA  120
LNYLRTSSPS AVRARLDANR LAVAGHSMGG GGTLRIAEQN PSLKAAVPLT PWHTDKTFNT  180
SVPVLIVGAE ADTVAPVSQH AIPFYQNLPS TTPKVYVELD NASHFAPNSN NAAISVYTIS  240
WMKLWVDNDT RYRQFLCNVN DPALSDFRTN NRHCQ                             275

SEQ ID NO: 5            moltype = DNA  length = 825
FEATURE                 Location/Qualifiers
source                  1..825
                        mol_type = unassigned DNA
                        organism = unidentified
SEQUENCE: 5
catcatcatc atcatcacag cagcggcctg gtgccgcgcg gcagccatat gagtaaccca  60
taccagcgcg gtccgaatcc gacccgtagt gcgctgacgg ccgatggtcc gtttagcgtg  120
gccacctaca ccgtgagccg tctgagtgtt agcggctttg gcggcggtgt tatctactac  180
ccgacgggca ccagtctgac ctttggtggc atcgccatga gtccgggcta caccgcggac  240
gccagtagtc tggcgtggct cggtcgtcgt ctggcgagcc atggcttcgt ggtgctggtg  300
atcaacacca acagccgctt cgactatcca gatagtcgtg ccagtcagct gagcgccgcg  360
ctgaattatc tgcgtaccag tagcccaagc gcggttcgtg cccgtctgga tgccaatcgc  420
ctcgccgttg ccggtcatag tatgggcggt ggtggtacgc tgcgtatcgc cgaacagaat  480
ccgagtctga aagcggccgt gccactgacc ccatggcaca cggacaagac gtttaacacc  540
agcgttccgg tgctcattgt gggtgccgaa gccgacaccg ttgccccagt tagccagcac  600
gcgatcccgt tttaccagaa tctgccaagc accacgccga aagtttacgt ggaactcgac  660
aacgcgagcc actttgcgcc gaacagtaat aacgccgcca tcagcgtgta caccatcagc  720
tggatgaaac tctgggtgga caacgatacc cgctaccgcc agtttctgtg caacgttaat  780
gatccggcgc tgagcgactt ccgcaccaat aaccgccatt gccag                   825

SEQ ID NO: 6            moltype = AA  length = 271
FEATURE                 Location/Qualifiers
source                  1..271
```

```
                        mol_type = protein
                        organism = unidentified
SEQUENCE: 6
QTNPYARGPN PTAASLEASA GPFTVRSFTV SRPSGYGAGT VYYPTNAGGT VGAIAIVPGY  60
TARQSSIKWW GPRLASHGFV VITIDTNSTL DQPSSRSSQQ MAALRQVASL NGTSSSPIYG  120
KVDTARMGVM GWSMGGGGSL ISAANNPSLK AAAPQAPWDS STNFSSVTVP TLIFACENDS  180
IAPVNSSALP IYDSMSRNAK QFLEINGGSH SCANSGNSNQ ALIGKKGVAW MKRFMDNDTR  240
YSTFACENPN STRVSDFRTA NCSLEHHHHH H                                 271

SEQ ID NO: 7            moltype = DNA  length = 813
FEATURE                 Location/Qualifiers
source                  1..813
                        mol_type = unassigned DNA
                        organism = unidentified
SEQUENCE: 7
cagacgaatc catacgcccg cggtccaaat ccaaccgcgg cgagtctgga agccagtgcg  60
ggcccattca ccgttcgcag ctttaccgtt agtcgtccaa gcggttacgg tgccggcacc  120
gtgtactacc cgacgaatgc gggtggtacc gtgggtgcga tcgccatcgt tccgggctat  180
accgcgcgcc agagtagcat caaatggtgg ggtccacgtc tggcgagtca tggcttcgtg  240
gtgatcacga tcgacaccaa tagcaccctc gatcagccaa gcagccgcag cagtcaacag  300
atggcggcgc tgcgccaagt tgccagtctg aacggcacga gtagcagccc gatttacggt  360
aaagtggaca ccgcgcgtat gggcgtgatg ggctggagca tgggtggtgg tggcagtctg  420
atcagtgccg ccaacaatcc aagcctcaaa gcggcggcgc cacaagcgcc atgggatagc  480
agcacgaact ttagcagcgt gaccgtgcca acgctgatct tcgcgtgcga aaacgacagc  540
atcgccccgg tgaatagcag tgcgctgccg atctatgaca gcatgagtcg caacgccaag  600
cagtttctgg agatcaacgg tggcagccat agctgcgcga acagcggcaa cagcaatcaa  660
gccctcatcg gtaaaaaggg cgtggcgtgg atgaagcgct ttatggacaa cgacacccgc  720
tacagcacct tcgcgtgcga gaatccgaac agtacccgcg tgagcgattt ccgcaccgcc  780
aattgcagcc tcgagcacca ccaccaccac cac                               813

SEQ ID NO: 8            moltype = AA  length = 319
FEATURE                 Location/Qualifiers
source                  1..319
                        mol_type = protein
                        organism = Thermobifida fusca
SEQUENCE: 8
MPPHAARPGP AQNRRGRAMA VITPRRERSS LLSRALRFTA AAATALVTAV SLAAPAHAAN  60
PYERGPNPTD ALLEARSGPF SVSEERASRF GADGFGGGTI YYPRENNTYG AVAISPGYTG  120
TQASVAWLGE RIASHGFVVI TIDTNTTLDQ PDSRARQLNA ALDYMINDAS SAVRSRIDSS  180
RLAVMGHSMG GGGTLRLASQ RPDLKAAIPL TPWHLNKNWS SVRVPTLIIG ADLDTIAPVL  240
THARPFYNSL PTSISKAYLE LDGATHFAPN IPNKIIGKYS VAWLKRFVDN DTRYTQFLCP  300
GPRDGLFGEV EEYRSTCPF                                               319

SEQ ID NO: 9            moltype = AA  length = 319
FEATURE                 Location/Qualifiers
source                  1..319
                        mol_type = protein
                        organism = Thermobifida fusca
SEQUENCE: 9
MPPHAARPGP AQNRRGCAMA VMTPRRERSS LLSRALQVTA AAATALVTAV SLAAPAHAAN  60
PYERGPNPTD ALLEARSGPF SVSEENVSRL GASGFGGGTI YYPRENNTYG AVAISPGYTG  120
TQASVAWLGK RIASHGFVVI TIDTITTLDQ PDSRARQLNA ALDYMINDAS SAVRSRIDSS  180
RLAVMGHSMG GGGSLRLASQ RPDLKAAIPL TPWHLNKNWS SVRVPTLIIG ADLDTIAPVL  240
THARPFYNSL PTSISKAYLE LDGATHFAPN IPNKIIGKYS VAWLKRFVDN DTRYTQFLCP  300
GPRDGLFGEV EEYRSTCPF                                               319

SEQ ID NO: 10           moltype = AA  length = 301
FEATURE                 Location/Qualifiers
source                  1..301
                        mol_type = protein
                        organism = Thermobifida fusca
SEQUENCE: 10
MAVMTPRRER SSLLSRALQV TAAAATALVT AVSLAAPAHA ANPYERGPNP TDALLEARSG  60
PFSVSEENVS RLSASGFGGG TIYYPRENNT YGAVAISPGY TGTEASIAWL GERIASHGFV  120
VITIDTITTL DQPDSRAEQL NAALNHMINR ASSTVRSRID SSRLAVMGHS MGGGGSLRLA  180
SQRPDLKAAI PLTPWHLNKN WSSVTVPTLI IGADLDTIAP VATHAKPFYN SLPSSISKAY  240
LELDGATHFA PNIPNKIIGK YSVAWLKRFV DNDTRYTQFL CPGPRDGLFG EVEEYRSTCP  300
F                                                                  301

SEQ ID NO: 11           moltype = AA  length = 301
FEATURE                 Location/Qualifiers
source                  1..301
                        mol_type = protein
                        organism = Thermobifida fusca
SEQUENCE: 11
MAVMTPRRER SSLLSRALQV TAAAATALVT AVSLAAPAHA ANPYERGPNP TDALLEASSG  60
PFSVSEENVS RLSASGFGGG TIYYPRENNT YGAVAISPGY TGTEASIAWL GERIASHGFV  120
VITIDTITTL DQPDSRAEQL NAALNHMINR ASSTVRSRID SSRLAVMGHS MGGGGTLRLA  180
SQRPDLKAAI PLTPWHLNKN WSSVTVPTLI IGADLDTIAP VATHAKPFYN SLPSSISKAY  240
```

```
LELDGATHFA PNIPNKIIGK YSVAWLKRFV DNDTRYTQFL CPGPRDGLFG EVEEYRSTCP  300
F                                                                   301

SEQ ID NO: 12          moltype = AA  length = 300
FEATURE                Location/Qualifiers
source                 1..300
                       mol_type = protein
                       organism = Thermobifida alba
SEQUENCE: 12
MSVTTPRRET SLLSRALRAT AAAATAVVAT VALAAPAQAA NPYERGPNPT ESMLEARSGP  60
FSVSEERASR FGADGFGGGT IYYPRENNTY GAIAISPGYT GTQSSIAWLG ERIASHGFVV  120
IAIDTNTTLD QPDSRARQLN AALDYMLTDA SSAVRNRIDA SRLAVMGHSM GGGGTLRLAS  180
QRPDLKAAIP LTPWHLNKSW RDITVPTLII GAEYDTIASV TLHSKPFYNS IPSPTDKAYL  240
ELDGASHFAP NITNKTIGMY SVAWLKRFVD EDTRYTQFLC PGPRTGLLSD VEEYRSTCPF  300

SEQ ID NO: 13          moltype = AA  length = 300
FEATURE                Location/Qualifiers
source                 1..300
                       mol_type = protein
                       organism = Thermobifida cellulosilytica
SEQUENCE: 13
MSVTTPRRRT PLLSRVLRTA AVAATAAASV LALSAPAQAA NPYERGPNPT QALLEARSGP  60
FSVSSERAWR LGSDGFGGGT IYYPRENNTY GAVAISPGYT GTQASVAWLG ERIASHGFVV  120
ITIDTNTTLD QPDSRARQLD AALDHMLNDA SSAVRSRIDR NRLAVMGHSM GGGGTLRLAS  180
QRPDLKAAIP LTPWHLNKSW SNVQVPTLII GADLDTIAPV LTHAEPFYNS IPTSTRKAYL  240
ELDGATHFAP NITNSTIGMY SVAWLKRFVD EDTRYTQFLC PGPRTGLFSD VEEYRSTCPF  300

SEQ ID NO: 14          moltype = AA  length = 284
FEATURE                Location/Qualifiers
source                 1..284
                       mol_type = protein
                       organism = Thermobifida cellulosilytica
SEQUENCE: 14
MLSQVTAVVA AAAAAVTLSA PALAANPYER GPDPTQASLE ASRGPFPVSE ERVSSPVSGF  60
GGGTIYYPQE NNTYGAVAIS PGYTATQSSV AWLGERIASH GFVVITIDTN TTLDQPDSRA  120
DQLEAALDHM VDGASSTVRS RIDRNRLAVM GHSMGGGGTL RLASRRPDLK AAIPLTPWHL  180
NKSWSNVQVP TLIIGAENDT VAPVALHAEP SYTSIPTSTR KAYLELNGAS HFAPSVANAT  240
IGMYGVAWLK RFVDEDTRYT RFLCPGPRTG LFSDVEEYRS TCPF                    284

SEQ ID NO: 15          moltype = AA  length = 312
FEATURE                Location/Qualifiers
source                 1..312
                       mol_type = protein
                       organism = Actinorugispora endophytica
SEQUENCE: 15
MNMTNSTLDQ PTESPAKSAS PLSRGVRTAI RTAVAAALVA GGVGIASPAY AANPYERGPD  60
PTDSSVEALR GPYSVDDTSV SSLVSGFGGG TVYYPTGTNE TFGAVVIAPG YTASSSSMSW  120
MGERLASQGF VIFTIDTNTR YDQPDSRGDQ ISAALDYLVE DSTSAVRNRI DPDRLAAMGH  180
SMGGGGTLAV AADRPELKAA IPLTPWHLDK TWSEVDVPTM IIGAENDTVA SVSSHSIPFY  240
NSLSGAPDKV YLELDGASHF APNLSNTTIA KYSISWLKRF VDEDTRYSQF LCPGPSTGLG  300
SDVSDYRNTC PV                                                       312

SEQ ID NO: 16          moltype = AA  length = 371
FEATURE                Location/Qualifiers
source                 1..371
                       mol_type = protein
                       organism = Actinomarinicola tropica
SEQUENCE: 16
MKGKPHMTTT ARRRQTFVAI IAMLLASLAL SPGADAQASN PYQRGPNPTQ SSIEALRGPY  60
STTTTSVSSF VSGFGGGTIY YPTGTNETFG GVVVAPGFTA SQSSMSWLGH RLASQGFVVF  120
TIDTNGRFDQ PGSRADQLLA AADYLADDSS SAVQARLDDS RMAVMGHSMG GGGSIEASSD  180
RSSLKASIPL TPWHTRKTWS SVQVPTLVVG AENDSVASTS SHAIPLYNGL PSSLDKAYLE  240
LDGASHFAPN SNNTTIAAYS ISWLKRFVDN DTRYDQFLCG PNHTADRDIS DYRSTCPYSP  300
VDPGDPGDPG TPGGECVRTH TRNHVDAGRA TNVWGTAYAV GSGDNLGSHS YFNYVSLQSI  360
SGGWTEVSSC P                                                        371

SEQ ID NO: 17          moltype = AA  length = 304
FEATURE                Location/Qualifiers
source                 1..304
                       mol_type = protein
                       organism = Saccharomonospora viridis
SEQUENCE: 17
MRIRRQAGTG ARASMARAIG VMTTALAVLV GAVGGVAGAE VSTAQDNPYE RGPDPTEDSI  60
EAIRGPFSVA TERVSSFASG FGGGTIYYPR ETDEGTFGAV AVAPGFTASQ GSMSWYGERV  120
ASQGFIVFTI DTNTRLDQPG QRGRQLLAAL DYLVERSDRK VRERLDPNRL AVMGHSMGGG  180
GSLEATVMRP SLKASIPLTP WNLDKTWGQV QVPTFIIGAE LDTIASVRTH AKPFYESLPS  240
SLPKAYMELD GATHFAPNIP NTTIAKYVIS WLKRFVDEDT RYSQFLCPNP TDRAIEEYRS  300
TCPY                                                                304
```

```
SEQ ID NO: 18           moltype = AA  length = 289
FEATURE                 Location/Qualifiers
source                  1..289
                        mol_type = protein
                        organism = Actinoplanes teichomyceticus
SEQUENCE: 18
MSVLHQTWRS ALATTLIAAI VTLLGAPARA ANPYERGPAP TTASIEATRG PFAIAQLTVA  60
RSSVSGFGGG TVYYPTDTSA GTFGAVAISP GFTASQSSVS WLGPRIASQG FVVITIDTLS  120
VYDQPDARGT QLLAALDYLT GSSAVRTRID ATRLGVMGHS MGGGGSLAAS RTRPALQAAV  180
PLAPWHTTKS WSTDRVPTLI IGAESDTVAP VASHAEPFYT SLPSTLDKAY LELNNASHSA  240
PTSANVTVAK YSISWLKRFI DNDTRYEQFL CPAPSGSAIQ EYRDTCPHS             289

SEQ ID NO: 19           moltype = AA  length = 309
FEATURE                 Location/Qualifiers
source                  1..309
                        mol_type = protein
                        organism = Amycolatopsis mediterranei
SEQUENCE: 19
MSALTSQPTS SGSSEKIPRL RGWRAKAAGV VLAALALTTG VAAPAPAAAN PYERGPDPTT  60
ASIEATSGSF ATSTVTVSRL AVSGFGGGTI YYPTTTTAGT FGALSIAPGF TATQSSIAWL  120
GPRLASQGFV VFTIDTLTTS DQPDSRGRQL LASLDYLTQQ SSVRSRIDST RLGVVGHSMG  180
GGGTLEAARS RPTLQAAVPL TAWDLTKNWS TLQVPTLVVG AQSDTVAPVA SHSIPFYTSL  240
PSTLDRAYLE LRGASHFAPN SPNTTIAKYT LSWLKRFIDN DTRYEQFLCP IPSTSLSISD  300
YRGNCPHNG                                                          309

SEQ ID NO: 20           moltype = AA  length = 291
FEATURE                 Location/Qualifiers
source                  1..291
                        mol_type = protein
                        organism = Nocardia sp.
SEQUENCE: 20
MPNEVYSAVQ LRTLIPLALT LVLVTGTAAQ AADNPYERGP APTVSSIEAL RGPFAVSETS  60
VSSLVGGFGG GTIYYPTSTT SGTFGAVAVS PGYTGTQSSI SWLGPRLASQ GFVVFTIDTN  120
TIYDQPDSRA SQLLAALDYL TQQSSVRSRI DATRLGVMGH SMGGGGTLRA ASQRPTLQAA  180
IPLTAWHTTK NWSSVRVPTL VVGAEDDSIA PVATHSEPFY TTLPSTLDKA YLELNNATHF  240
APNSNNTTIA KYSISWLKRF IDNDTRYEQF LCPAPGRSTL IEEYRDTCPH S           291

SEQ ID NO: 21           moltype = AA  length = 309
FEATURE                 Location/Qualifiers
source                  1..309
                        mol_type = protein
                        organism = Lentzea albidocapillata
SEQUENCE: 21
MRTWSPWLQG RGRSSPCSLP NEVYSAVQLR TLIPIALSMV LLGGTVAQAA DNPYERGPAP  60
TNSSIEASRG SFAVSETSVS SLVSGFGGGT IYYPTSTSAG TFGAVAISPG YTGTQSTISW  120
LGPRLASQGF VIFTIDTNSR YDQPDSRASQ LLAALDYLTQ QSSVRTRIDS SRLGVMGHSM  180
GGGGTLRAAS QRPSLQAAIP LTGWHTTKNW SSVRVPTLVV GAENDSVASV SSHSEPFYTS  240
LPSTLDKAYL ELNNASHFAP NSPNTTIAKY SISWLKRFID NDTRYEQFLC PAPGRSTLIE  300
EYRDTCPHS                                                          309

SEQ ID NO: 22           moltype = AA  length = 306
FEATURE                 Location/Qualifiers
source                  1..306
                        mol_type = protein
                        organism = Umezawaea tangerina
SEQUENCE: 22
MLPGRFPSRR FGVYNDVQLR SVFTTVTLVA ALVGGAIGAS PAIAAENPYE RGPAPTNSSI  60
EASRGSFAVS ETSVSSLSVT GFGGGTIYYP TSTSAGTFGA IAVSPGYTGT QSSISWLGPR  120
IASQGFVVFT IDTITTLDQP DSRASQLLAA LDYLTQRSAV RARIDATRLG VMGHSMGGGG  180
TLRAAANRPA LQAAIPLTGW HTDKTWGDVR VPTLVVGADG DTIAPVATHS KPFYNSLPSS  240
LDRAYLELRG ATHFTPNSSN TTIAKYSISW LKRFIDNDTR YEQFLCPTPS SSLLIAEFRG  300
NCPHSS                                                             306

SEQ ID NO: 23           moltype = AA  length = 273
FEATURE                 Location/Qualifiers
source                  1..273
                        mol_type = protein
                        organism = Saccharothrix syringae
SEQUENCE: 23
MALALAAPQA TAAETEYRRG PAPTNSSIEA LRGPFAVSET SVSSLLVTGF GGGTIYYPTS  60
TAEGTFGAVA ISPGYTGTQS SISWLGPRLA SQGFVVFTID TNTTLDQPDS RADQLLAALD  120
YLTQRSSVRT RIDNTRLGVM GHSMGGGGTL RAAEQRPSLQ AAIPLTGWHT DKTWGSVRVP  180
TLVIGADGDT IAPVSSHSEP FYTTLPSTLD KAYLELNGAT HFTPNTSNTT IAKYSISWLK  240
RFIDNDTRYE QFLCPAPRGA AIQEYRDTCP HST                                273

SEQ ID NO: 24           moltype = AA  length = 282
FEATURE                 Location/Qualifiers
source                  1..282
                        mol_type = protein
```

```
                         organism = Saccharothrix sp.
SEQUENCE: 24
MPALIPALAL SLVGVTPATG AEEEFRRGPA PTNSSIEASR GPFATSSTTV SSLSVTGFGG  60
GTIYYPTSTA EGTFGAIAVS PGYTASQSSM AWLGPRIASQ GFVVFTIDTN SRYDQPDSRA  120
SQLLSALDYL TQRSSVRSRI DASRLGVMGH SMGGGGTLRA AEQRPALQAA IPLTGWHTDK  180
TWGSVRVPTL VVGAENDSVA SVSSHSIPFY NSLPSTLDKA YLELNGASHF APNSSNTTIA  240
KYSIAWLKRF IDNDTRYEQF LCPSPANSSL ISDYRDTCPH GV                    282

SEQ ID NO: 25            moltype = AA  length = 340
FEATURE                  Location/Qualifiers
source                   1..340
                         mol_type = protein
                         organism = Actinomadura bangladeshensis
SEQUENCE: 25
MTGDFADARG PAACADCARP GAGPRLRPVP GSRLPAPPPE QERTDVRSLP SRAAKTLLAT  60
ALAAGALAVP QALSQAAQAA DNPYERGPAP TQSSIEALRG PFATSQTSVS SLSVSGFGGG  120
TIYYPTSTAA GTFGAVAVAP GFTADQSSMA WLGPRLASQG FVIFTIDTNT RLDQPDSRAR  180
QLNAALDYLT QRSSVRSRID ASRLGVMGHS MGGGGTLEIA EDRPQLQAAI PLTPWDLQKN  240
FSDVRVPTMI IGAEADTIAP VATHSKPFYT SIPASSEKAY LELNGASHFA PNIANTTIAK  300
YSISWLKRYI DNDTRYDQFL CPGPSRDLNI SEYRDTCPNS                       340

SEQ ID NO: 26            moltype = AA  length = 301
FEATURE                  Location/Qualifiers
source                   1..301
                         mol_type = protein
                         organism = Streptomyces olivaceus
SEQUENCE: 26
MQRNPRTRTR ATRRRFAGVT AAVAAVLALS TLTGPGAQAA DNPYERGPAP TESSIEASRG  60
SYSVADTRVS SLAVTGFGGG TIYYPTSTAD GTFGAVVISP GYTAYQSSIA WLGPRLASQG  120
FVVFTIDTNT TLDQPDSRGR QLLAALDYLT GRSSVRERID SSRLGVMGHS MGGGGSLEAA  180
KSRPSLQAAI PLTPWNLDKT WPEVSTPTLV VGADGDTIAP VASHAEPFYS SLPSATDRAY  240
LELNNATHFS PNTSNTTIAK YSISWLKRFI DNDTRYEQFL CPLPRPSLTI EEYRGNCPHG  300
S                                                                 301

SEQ ID NO: 27            moltype = AA  length = 310
FEATURE                  Location/Qualifiers
source                   1..310
                         mol_type = protein
                         organism = Streptomyces coelicolor
SEQUENCE: 27
MQQNPHTHAA PGAARPVLRG VRRRLAAVTA AVAAVLVLGT LTGPGAQAAD NPYERGPAPT  60
ESSIEALRGP YSVADTSVSS LAVTGFGGGT IYYPTSTSDG TFGAVVIAPG FTAYQSSIAW  120
LGPRLASQGF VVFTIDTNTT LDQPDSRGRQ LLAALDYLTG RSSVRGRIDS GRLGVMGHSM  180
GGGGTLEAAK SRPSLQAAIP LTPWNLDKSW PEVSTPTLVV GADGDTIAPV ASHAEPFYSG  240
LPSSTDRAYL ELNNATHFSP NTSNTTIAKY SISWLKRFID DDTRYEQFLC PLPRPSLTIE  300
EYRGNCPHGS                                                        310

SEQ ID NO: 28            moltype = AA  length = 306
FEATURE                  Location/Qualifiers
source                   1..306
                         mol_type = protein
                         organism = Streptomyces glaucescens
SEQUENCE: 28
MQQQHRTDSA TPRRRRRTGR LTGLAAATAA VIGLSTLSGT GAHAADNPYE RGPAPTQSSI  60
EALRGPYAVS QTSVSSLAVT GFGGGTIYYP TSTADGTFGA VAISPGFTAY ESSIAWLGPR  120
LASQGFVVFT IDTNTTMDQP ASRGDQLLAA LDYLTQRSSV RGRVDATRLG VMGHSMGGGG  180
SLEAAKDRPS LQAAIPLTPW NLDKTWSEVR TPTLIFGADG DTIAPVSSHA EPFYQNLPSS  240
LDKAYLELNN ATHFTPNSND TTIAKYSISW LKRFIDNDTR YEQFLCPLPR PSLTIEEYRG  300
NCPHTS                                                            306

SEQ ID NO: 29            moltype = AA  length = 319
FEATURE                  Location/Qualifiers
source                   1..319
                         mol_type = protein
                         organism = Streptomyces radiopugnans
SEQUENCE: 29
MEPQQHDTTP GTATRHRGAP RRLTKLGVAL AMVLGGVGVA LPTAQATQDS GAAPAAVQAA  60
ENPYERGPDP TERSIEAARG PYSVSETRVS SLSVTGFGGG TIYYPTTTSD GTFGAVAVSP  120
GYTADQSSMA WYGPRLASQG FVVFTIDTNT RYDQPDSRGD QLLAALDYLT QRSSVRGRID  180
SGRLAVMGHS MGGGGSLEAA KDRPSLKAAI PLTPWNLDKT WREITVPTFI VGADGDSIAS  240
VRSHAEPFYE SLPSSTDRAY MELNNATHFT PNTSNTEIAK YSISWLKRFV DNDTRYEQFL  300
CPLPRPSLAI EEFRGNCPH                                              319

SEQ ID NO: 30            moltype = AA  length = 308
FEATURE                  Location/Qualifiers
source                   1..308
                         mol_type = protein
                         organism = Kibdelosporangium aridum
SEQUENCE: 30
```

-continued

```
MRRGVRILTG LTIAPVIGAV VAAGVPATAL GAVVTGTPTT AIGAVELSAE NPYERGPDPT  60
ESSIEASRGP FSVSQTTVSR LSATGFGGGT IYYPTSTSEG TFGALAISPG FTATQSSISW  120
MGPRLASQGF VVITIDTLST LDQPDSRGDQ LRAALTYLTQ RSTVRTRIDA SRLAVAGHSM  180
GGGGSLEAAA DQPTLQAAIP IAAWNTQKTW STLRVPTFVI GGESDSVAPV ASHSIPFYTS  240
IPASAEKAYM ELDNASHFFP QTPNTTMAKY MISWLKRFVD NDTRYEQFLC PAPNDREISD  300
YRDTCPHS                                                           308

SEQ ID NO: 31          moltype = AA  length = 285
FEATURE                Location/Qualifiers
source                 1..285
                       mol_type = protein
                       organism = Amycolatopsis keratiniphila
SEQUENCE: 31
MRSTTRILCG LATVAALTVA PTAYAAENPY ERGPDPTESS IEASRGSFAV SQTSVSSLAV  60
TGFGGGTIYY PTSTAQGTFG AVAISPGFTA TQSSIAWIGP RLASQGFVVF TIDTNTIYDQ  120
PDSRGDQLLA ALDYLTQRST VRSRIDTSRL AVAGHSMGGG GSLEAAQDRP SLQAAVPLAP  180
WNTQKSWSSL RVPTFIIGGE SDSVAPVASH SIPFYTSIPA TAEKAYMELD NASHFFPNTA  240
NTTMAKYTIS WLKRFVDNDT RYEQFLCPAP DDRAISDYRD TCPHA                  285

SEQ ID NO: 32          moltype = AA  length = 287
FEATURE                Location/Qualifiers
source                 1..287
                       mol_type = protein
                       organism = Actinophytocola xanthii
SEQUENCE: 32
MRRTLRTLCG LALAGSVLAG TASTASAQEN PYERGPDPTE NSIEATRGPF AVSQTSVSSL  60
VVTGFGGGTI YYPTSTAEGT FGAVAVSPGF TATQSSIAWI GPRLASQGFV VITIDTLTVL  120
DQPDSRGDQL LAALDYLTQR SSVRGRIDAS RLAVSGHSMG GGGSLEATET RPSLQASVPL  180
APWNADKTWS SVRTPTFIIG GESDSVASVS SHSIPFYQSI PAASEKAYME LDGASHFFPN  240
TPNTTMAKYL ISWMKRFVDN DTRYEQFLCP PPNDSDIEEY RHTCPHV                287

SEQ ID NO: 33          moltype = AA  length = 298
FEATURE                Location/Qualifiers
source                 1..298
                       mol_type = protein
                       organism = Actinoplanes friuliensis
SEQUENCE: 33
MQSPTIPARL RARRLFVTAA ATLTLVAGSL TGATAAQAAE NPYERGPAPT SAVLDASRGP  60
FATSQQSVSS LSVSGFGGGV IYYPTSTSAG TFGGIAISPG YTASWSSISW LGPRIASHGF  120
VVIGIETNSV FDQPSSRGNQ LLAALDYLTT RSSVRTRVDA SRLAVAGHSM GGGGSLEAAK  180
DRPSLQAAVP LAPWNTTKTW SGLQVPTLII GGESDTVAPV SSHSIPFYNS IPSSAEKAYL  240
ELNNASHFFP QSTNTPTGRQ AVAWLKRFVD NDTRYDQFIC PGPSSSSISD YRNSCPLT    298

SEQ ID NO: 34          moltype = AA  length = 229
FEATURE                Location/Qualifiers
source                 1..229
                       mol_type = protein
                       organism = unidentified
SEQUENCE: 34
MKFFTTILST ASLVAALPAA VDSNHTPAAP ELVARQLGAI ENGLESGSAN ACPDAILIFA  60
RGSTEPGNMG ITVGPALANG LESHIRNIWI QGVGGPYDAA LATNFLPRGT SQANIDEGKR  120
LFALANQKCP NTPVVAGGYS QGAALIAAAV SELSGAVKEQ VKGVALFGYT QNLQNRGGIP  180
NYPRERTKVF CNVGDAVCTG TLIITPAHLS YTIEARGEAA RFLRDRIRA              229
```

ENZYMATIC DEGRADATION OF POLYETHYLENE TEREPHTHALATE

SEQUENCE LISTING SUBMISSION VIA PATENT CENTER

The contents of the electronic sequence listing (sequence-listing.xml; Size: 42,232 bytes; and Date of Creation: Feb. 16, 2022) is herein incorporated by reference in its entirety.

BACKGROUND OF THE INVENTION

The use of polyethylene terephthalate (PET) is widespread and ubiquitous. As such, PET is a major source of environmental pollution globally. Physical recycling is possible but underused in many settings. Enzymatic degradation has been explored in the last decades but has proven challenging.

Provided herein are variant enzymes for use in the enzymatic degradation of PET.

BRIEF SUMMARY OF THE INVENTION

In one aspect, the present disclosure relates to a composition comprising a variant Bhr-PETase as compared to SEQ ID NO:1, wherein said variant comprises at least one amino acid substitution compared to SEQ ID NO: 1 at an amino acid position(s) selected from the group consisting of 27, 1, 2, 5, 9, 12, 13, 14, 15, 16, 17, 18, 20, 21, 22, 23, 24, 25, 26, 30, 32, 33, 34, 40, 46, 48, 49, 53, 54, 55, 56, 57, 60, 62, 68, 70, 72, 74, 77, 82, 83, 85, 87, 88, 90, 92, 97, 98, 101, 102, 105, 108, 109, 110, 113, 114, 117, 119, 121, 122, 125, 127, 135, 136, 138, 139, 140, 142, 143, 145, 147, 149, 150, 153, 156, 157, 158, 160, 161, 162, 163, 164, 167, 170, 173, 174, 177, 179, 181, 182, 184, 185, 189, 190, 193, 194, 195, 198, 200, 203, 204, 206, 208, 209, 211, 212, 213, 216, 217, 218, 219, 221, 222, 223, 225, 227, 228, 229, 231, 236, 237, 241, 242, 243, 246, 249, 250, 251, 252, 253, 254, 255, 258, 8, 31, 38, 95, 126, 137, 165, 169, 172, 191, 192 and 197, wherein said variant Bhr-PETase has at least 85% identity to SEQ ID NO:1 and has PETase activity. In another aspect, the present disclosure relates to a composition comprising a variant Bhr-PETase as compared to SEQ ID NO:1, wherein said variant comprises a amino acid substitution at position 27 and at least one further amino acid substitution compared to SEQ ID NO: 1 at an amino acid position(s) selected from the group consisting of 1, 2, 5, 9, 12, 13, 14, 15, 16, 17, 18, 20, 21, 22, 23, 24, 25, 26, 30, 32, 33, 34, 40, 46, 48, 49, 53, 54, 55, 56, 57, 60, 62, 68, 70, 72, 74, 77, 82, 83, 85, 87, 88, 90, 92, 97, 98, 101, 102, 105, 108, 109, 110, 113, 114, 117, 119, 121, 122, 125, 127, 135, 136, 138, 139, 140, 142, 143, 145, 147, 149, 150, 153, 156, 157, 158, 160, 161, 162, 163, 164, 167, 170, 173, 174, 177, 179, 181, 182, 184, 185, 189, 190, 193, 194, 195, 198, 200, 203, 204, 206, 208, 209, 211, 212, 213, 216, 217, 218, 219, 221, 222, 223, 225, 227, 228, 229, 231, 236, 237, 241, 242, 243, 246, 249, 250, 251, 252, 253, 254, 255, 258, 8, 31, 38, 95, 126, 137, 165, 169, 172, 191, 192 and 197, wherein said variant Bhr-PETase has at least 85% identity to SEQ ID NO:1 and has PETase activity. In another aspect, the present disclosure relates to a composition comprising a variant Bhr-PETase as compared to SEQ ID NO:1, wherein said variant comprises at least one amino acid substitution compared to SEQ ID NO: 1 at an amino acid position(s) selected from the group consisting of 27, 1, 2, 5, 9, 12, 13, 14, 15, 16, 17, 18, 20, 21, 22, 23, 24, 25, 26, 30, 32, 33, 34, 40, 46, 48, 49, 53, 54, 55, 56, 57, 60, 62, 68, 70, 72, 74, 77, 82, 83, 85, 87, 88, 90, 92, 97, 98, 101, 102, 105, 108, 109, 110, 113, 114, 117, 119, 121, 122, 125, 127, 135, 136, 138, 139, 140, 142, 143, 145, 147, 149, 150, 153, 156, 157, 158, 160, 161, 162, 163, 164, 167, 170, 173, 174, 177, 179, 181, 182, 184, 185, 189, 190, 193, 194, 195, 198, 200, 203, 204, 206, 208, 209, 211, 212, 213, 216, 217, 218, 219, 221, 222, 223, 225, 227, 228, 229, 231, 236, 237, 241, 242, 243, 246, 249, 250, 251, 252, 253, 254, 255, 258, 8, 31, 38, 95, 126, 137, 165, 169, 172, 191, 192 and 197, wherein said variant Bhr-PETase has at least 85% identity to SEQ ID NO:1 and has PETase activity equal to or greater than wild type Bhr-PETase, SEQ ID NO: 1. In some embodiments, said amino acid substitution above is at an amino acid position(s) selected from the group consisting of 27, 1, 2, 5, 9, 12, 13, 14, 15, 16, 17, 18, 20, 21, 22, 23, 24, 25, 26, 30, 32, 33, 34, 40, 46, 48, 49, 53, 54, 55, 56, 57, 60, 62, 68, 70, 72, 74, 77, 82, 83, 85, 87, 88, 90, 92, 97, 98, 101, 102, 105, 108, 109, 110, 113, 114, 117, 119, 121, 122, 125, 127, 135, 136, 138, 139, 140, 142, 143, 145, 147, 149, 150, 153, 156, 157, 158, 160, 161, 162, 163, 164, 167, 170, 173, 174, 177, 179, 181, 182, 184, 185, 189, 190, 193, 194, 195, 198, 200, 203, 204, 206, 208, 209, 211, 212, 213, 216, 217, 218, 219, 221, 222, 223, 225, 227, 228, 229, 231, 236, 237, 241, 242, 243, 246, 249, 250, 251, 252, 253, 254, 255 and 258. In some embodiments, said amino acid substitution above is at an amino acid position(s) selected from the group consisting of 27, 2, 17, 20, 21, 23, 24, 40, 46, 49, 55, 57, 77, 83, 97, 101, 102, 109, 110, 114, 117, 135, 136, 139, 140, 142, 143, 149, 161, 163, 164, 167, 184, 185, 195, 222, 227, 228, 229, 249, 250 and 251. In some embodiments, said amino acid substitution above is at an amino acid position(s) selected from the group consisting of 8, 126, 137, 165, 169, 172, 191, 192 and 197.

In some embodiments, said amino acid substitution is selected from the group consisting of S27L, S27F, S27H, S27T, S27W, S1A, S1G, S1M, S1R, N2E, N2F, N2L, N2R, N2S, Q5E, N9A, N9E, N9S, R12K, S13L, S13R, A14K, A14S, L15I, T16E, T17A, T17C, T17G, T17H, T17I, T17K, T17L, T17M, T17N, T17Q, T17R, T17S, D18R, P20D, P20E, P20I, P20Q, P20T, F21W, F21Y, S22A, S22I, S22K, S22P, S22R, S22V, V23L, V23T, A24D, A24G, A24H, A24N, A24S, A24T, A24V, T25A, T25F, T25H, T25Q, T25R, T25V, Y26C, Y26K, Y26L, Y26T, R30K, S32K, S32M, S32Q, S32Y, V33G, V33Q, V33T, S34R, V40T, G46E, G46L, G46N, G46R, G46S, T48N, T48S, L49G, G53A, I54V, A55C, A55I, A55L, A55M, A55T, A55V, M56I, M56L, S57C, S57E, S57F, S57I, S57L, S57M, S57T, S57V, Y60A, Y60H, Y60I, A62T, A68F, L70M, R72P, L74W, H77Q, I82F, I82L, I82M, V83I, V83L, V83T, N85D, N87F, N87H, N87I, N87K, N87L, N87M, N87Q, N87R, N87V, N87W, N87Y, S88K, S88T, L90F, L90K, L90Y, F92G, F92I, F92K, F92L, F92N, F92Q, F92V, F92Y, A97C, A97E, A97F, A97G, A97L, A97P, A97Q, A97S, A97T, A97V, S98A, S98D, S98E, S98L, S98M, S98N, S98Q, S98T, S98V, S101A, S101C, S101D, S101F, S101H, S101K, S101L, S101M, S101N, S101Q, S101R, S101V, S101W, S101Y, A102V, N105D, R108C, R108E, R108H, R108K, R108N, R108P, R108Q, R108S, R108T, R108V, T109A, T109F, T109G, T109K, T109L, T109N, T109R, T109Y, SHOD, S110G, S110H, S110K, S110N, S110R, S113A, S113K, S113N, S113P, S113Q, S113R, S113T, S113Y, A114K, A114L, A114S, A114V, A117F, A117G, A117L, A117N, A117Q, A117S, A117T, A117Y, L119I, L119M, A121S, N122A, N122E, N122H, N122P, N122R, N122S, A125S, A127M, A127S, A127V, A135G, T136A, T136M, T136S, T136V, R138E, R138L, I139A, I139T, S140A, Q142D, Q142E, Q142H, Q142L, Q142W, I143N, I143R, T145S, K147F, K147G, K147N, K147Q, G149A, G149C, G149D, G149N, G149S, G149T, G149V, V150I, V150L, T153L, H156N, T157A, T157G, D158E, D158I, D158K, D158L, T160K, T160Q, T160R, T160S, T160V, F161V, F161W, N162E, N162H, N162P, N162R, T163I, T163S, P164E, P164H, P164N, P164R, P164S, P164T, Q167I, Q167T, Q167V, V170L, E173R, A174K, A174R, V177A, P179Q, S181A, S181C, S181R, Q182T, A184C, A184G, A184S, I185A, I185E, I185G, I185L, I185Q, I185R, I185S, I185Y, Q189I, Q189L, Q189V, N190S, S193E, S193F, S193H, S193K, S193N, S193P, S193T, S193V, T194G, T194S, T195F, V198A, V200L, D203N, D203R, D203V, N204A, N204K, N204R, N204S, T206G, T206K, T206L, T206P, T206R, F208G, F208L, F208R, F208T, A209V, N211F, N211I, N211L, N211M, N211V, S212F, S212L, S212M, P213N, P213R, A216L, A216P, A216S, A216T, A216V, I217S, S218A, V219F, V219I, V219K, V219L, V219R, T22I S, I222L, S223A, S223C, M225L, L227R, W228F, V229C, V229I, V229L, N231L, N231Q, N231S, R236C, R236E, R236H, R236K, R236Q, Q237R, N241P, V242T, N243P, A246D, A246K, A246S, A246T, D249I, D249M, D249N, D249S, D249T, F250I, F250L, F250V, F250Y, R251A, R251E, R251I, R251K, R251L, R251Q, R251T, R251V, S252T, N253S, N253Y, N254R, R255E, R255G, R255L, R255M, R255S, R255V, R255W, R255Y, Q258P, P8T, L31M, G38D, S95N, V126I, L137M, V165I, I169C, I169L, I169V, A172T, L191F, L191V, P192A, K197L, K197R, K197T, K197V and K197Y. In some embodiments, said amino acid substitution is selected from the group consisting of S27L, S27F, S27H, S27T, S27W, S1A, S1G, S1M, S1R, N2R, Q5E, N9A, N9E, N9S, R12K, S13L, S13R, A14K, A14S, L15I, T16E, T17A, T17C, T17G, T17H, T17K, T17L, T17Q, T17S, D18R, P20T, F21W, S22A, S22I, S22K, S22P, S22R, S22V, V23L, V23T, A24S, A24V, T25A, T25F, T25H, T25Q, T25R, T25V, Y26K, Y26L, Y26T, R30K, S32K, S32M, S32Q, S32Y, V33G, V33Q, V33T, S34R, V40T, G46L, G46S, T48N, T48S, L49G, G53A, I54V, A55L, A55V, M56I, M56L, S57I, S57M, S57V, Y60A, Y60H, Y60I, A62T, A68F, L70M, R72P, L74W, H77Q, I82F, I82L, I82M, V83T, N85D, N87F, N87H, N87I, N87K, N87L, N87M, N87R, N87V, N87W, N87Y, S88K, S88T, L90F, L90K, L90Y, F92G, F92I, F92K, F92L, F92N, F92Q, F92V, F92Y, A97F, A97G, S98A, S98D, S98E, S98L, S98M, S98N, S98Q, S98T, S98V, S101A, S101D, S101F, S101H, S101K, S101L, S101M, S101N, S101Q, S101R, S101V, S101W, A102V, N105D, R108C, R108E, R108H, R108K, R108N, R108P, R108Q, R108S, R108T, R108V, T109F, T109K, T109L, T109N, T109R, S110G, S110H, S110R, S113A, S113K, S113N, S113P, S113Q, S113R, S113T, S113Y, A114K, A114L, A114S, A114V, A117G, A117N, A117Q, A117S, L119I, L119M, A121S, N122A, N122E, N122H, N122P, N122R, N122S, A125S, A127M, A127S, A127V, A135G, T136A, T136M, T136S, T136V, R138E, R138L, I139A, I139T, S140A, Q142L, Q142W, I143N, I143R, T145S, K147F, K147G, K147N, K147Q, G149A, G149C, G149S, G149V, V150I, V150L, T153L, H156N, T157A, T157G, D158E, D158I, D158K, D158L, T160K, T160Q, T160R, T160S, T160V, F161W, N162E, N162H, N162P, N162R, T163S, P164S, Q167T, Q167V, V170L, E173R, A174K, A174R, V177A, P179Q, S181A, S181C, S181R, Q182T, A184S, I185L, I185Y, Q189I, Q189L, Q189V, N190S, S193E, S193F, S193H, S193K, S193N, S193P, S193T, S193V, T194G, T194S, T195F, V198A, V200L, D203N, D203R, D203V, N204A, N204K, N204R, N204S, T206G, T206K, T206L, T206P, T206R, F208G, F208L, F208R, F208T, A209V, N211F, N211I, N211L, N211M, N211V, S212F, S212L, S212M, P213N, P213R, A216L, A216P, A216S, A216V, I217S, S218A, V219F, V219I, V219K, V219L, V219R, T221S, I222L, S223A, S223C, M225L, L227R, W228F, V229C, V229I, N231L, N231Q, N231S, R236C, R236E, R236K, R236Q, Q237R, N241P, V242T, N243P, A246D, A246K, A246S, A246T, D249T, F250I, F250Y, R251I, R251K, R251V, S252T, N253Y, N254R, R255E, R255G, R255L, R255M, R255S, R255V, R255W, R255Y and Q258P. In some embodiments, said amino acid substitution is selected from the group consisting of S27L, S27F, S27H, S27T, S27W, N2R, T17A, T17C, T17G, T17H, T17K, T17L, T17Q, T17S, P20T, F21W, V23L, V23T, A24S, A24V, V40T, G46L, G46S, L49G, A55L, A55V, S57I, S57M, S57V, H77Q, V83T, A97F, A97G, S101A, S101D, S101F, S101H, S101K, S101L, S101M, S101N, S101Q, S101R, S101V, S101W, A102V, T109F, T109K, T109L, T109N, T109R, S110G, S110H, S110R, A114K, A114L, A114S, A114V, A117G, A117N, A117Q, A117S, A135G, T136A, T136M, T136S, T136V, I139A, I139T, S140A, Q142L, Q142W, I143N, I143R, G149A, G149C, G149S, G149V, F161W, T163S, P164S, Q167T, Q167V, A184S, I185L, I185Y, T195F, I222L, L227R, W228F, V229C, V229I, D249T, F250I, F250Y, R251I, R251K and R251V. In some embodiments, said amino acid substitution is selected from the group consisting of N2E, N2F, N2L, N2S, P8T, T17I, T17M, T17N, T17R, P20D, P20E, P20I, P20Q, F21Y, A24D, A24G, A24H, A24N, A24T, Y26C, L31M, G38D, G46E, G46N, G46R, A55C, A55I, A55M, A55T, S57C, S57E, S57F, S57L, S57T, V83I, V83L, N87Q, S95N, A97C, A97E, A97L, A97P, A97Q, A97S, A97T, A97V, S101C, S101Y, T109A, T109G, T109Y, S110D, S110K, S110N, A117F, A117L, A117T, A117Y, V126I, L137M, Q142D, Q142E, Q142H, G149D, G149N, G149T, F161V, T163I, P164E, P164H, P164N, P164R, P164T, V165I, Q167I, I169C, I169L, I169V, A172T, A184C, A184G, I185A, I185E, I185G, I185Q, I185R, I185S, L191F, L191V, P192A, K197L, K197R, K197T, K197V, K197Y, A216T, V229L, R236H, D249I, D249M, D249N, D249S, F250L, F250V, R251A, R251E, R251L, R251Q, R251T and N253S.

In some embodiments, said variant Bhr-PETase enzyme has one or more amino acid substitutions at one of said positions, two of said positions, three of said positions, four of said positions, five of said positions, six of said positions, seven of said positions, eight of said positions, nine of said positions, ten of said positions, eleven of said positions, twelve of said positions, thirteen of said positions, fourteen of said positions, fifteen of said positions, sixteen of said positions, seventeen of said positions, eighteen of said positions, nineteen of said positions or twenty of said positions.

In some embodiments, said variant Bhr-PETase comprises a set of amino acid substitutions selected from the group consisting of A102V/T136M,
A14S/L15I/S22A/F92Q/1143R/Q167T/V219K,
D18R/G46S/M56I/R108T/A127M/R138E/1139A/N190S/L227R/W228F/R236E,
D18R/1139A/F161W/W228F,
D18R/154V/I82F/N105D/A127M/A184S/S218A/V219K/M225L/N241P/N243P,
D18R/154V/I82F/R108T/V150I/N253Y/N254R, -continued D18R/I54V/M56I/R138E/1139A/T194S/D203N/V219K/F250I, D18R/M56I/I139A/L227R/W228F, D18R/M56I/R138E/1139A/N190S/D203N/M225L, D18R/M56I/R72P/H77Q/F92Q/A127M/V150I/A184S/D203N/N254R, D18R/N85D/R108T/L119I/N190S/T194S, D18R/V40T/1139A/D203N, D18R/V40T/I82F/S101L/N105D/L119I/H156N/F161W/N190S/T194S/D203N, D18R/V40T/M56I/R108T/R138E/H156N, G53A/R108T/Q167T/A184S/T194S/N243P, I143R/Q167T/V198A/W228F, I82F/R108T/L119I/V150I/F161W/Q167T/T194S/D203N, L15I/D18R/R108T/R138E/1139A/F161W/A184S/N190S/D203N, M56I/I82F/R108T/1139A/F161W/T194S/D203N/N241P, M56I/S88T/R108T/N190S/L227R, N204A/Q237R, N9A/D18R/M56I/N85D/L119I/N254R, N9A/S22A/G46S/M56I/R72P/F92Q/L119I/T221S/M225L, N9A/S22A/Q167T, N9A/V40T/L49G/I54V/R108T/V150I/D203N/T221S/M225L, N9S/T25H, Q5E/N9A/M56I/F92Q/R108T/L119I/Q167T/N253Y, Q5E/S22A/R72P/H77Q/F92Q, R108T/L119I/K147Q/F161W/A184S/D203N, S101F/T136A, S22A/A24S/G46S/V150I/Q167T, S22A/A97G/V150I/D203N/M225L/R236E, S22A/G46S/S101L/F161W/D203N/R236E, S22A/I54V/R72P/F92Q/V150I/V200L, S22A/L49G/M56I/V83T/S101L/R108T/L119I/A127M/T194S, S22I/Y26K, S27T/I82L/P213N, S27T/T48S/I82L/F92Y/S252T, S27T/T48S/I82L/L90F/A135G/S140A/1143N/T145S/P213N, S27T/T48S/I82L/S140A/1143N/G149A, S32Y/A62T, S88T/R108T/V150I/A184S/D203N/T221S/M225L/N243P, S98Q/A209V, T16E/D18R/G53A/I54V/R72P/L119I/A127M/Q167T/V200L, T16E/D18R/M56I/A127M/R138E/T194S/V200L/M225L, T16E/D18R/M56I/K147Q/Q167T/A184S/D203N, T16E/D18R/M56I/N85D/S88T/R108T/F161W/Q167T, T16E/D18R/M56I/V150I/S218A/V219K, T16E/D18R/R108T/K147Q/Q167T/A184S/N190S/T194S, T16E/D18R/S22A/M56I/N85D/L119I/A184S, T16E/D18R/S22A/V40T/A97G/S101L/L119I/A127M/Q167T/D203N, T16E/D18R/S88T/R108T/W228F, T16E/D18R/V40T/M56I/I82F/R108T/L119I/F161W/L227R/Q258P, T16E/D18R/V40T/S88T/L119I/A127M/V150I/D203N, T16E/D18R/Y26T/S88T/S101L/H156N/V200L, T17A/I82L/F92Y/P213N, T17A/I82L/L90F/F92Y/A135G/S140A/1143N/G149A/Q167V, T17A/I82L/L90F/F92Y/Q167V, T17A/I82L/S140A/1143N/Q167V/P213N/S252T, T17A/Q167V, T17A/S27T, T17A/S27T/I82L, T17A/S27T/I82L/G149A/Q167V/P213N, T17A/S27T/I82L/L90F/F92Y/Q167V, T17A/S27T/I82L/P213N, T17A/S27T/I82L/P213N/S252T, T17A/S27T/I82L/S252T, T17A/S27T/I82L/T145S/G149A/P213N, T17A/S27T/L90F/A135G/S140A/Q167V/P213N/S252T, T17A/S27T/L90F/F92Y/A135G/Q167V/S252T, T17A/S27T/L90F/F92Y/P213N, T17A/S27T/T48S, T17A/S27T/T48S/A135G/Q167V/P213N, T17A/S27T/T48S/A135G/S140A, T17A/S27T/T48S/I82L, T17A/S27T/T48S/I82L/L90F/F92Y/Q167V/S252T, T17A/S27T/T48S/I82L/L90F/F92Y/S140A/T145S, T17A/S27T/T48S/I82L/L90F/F92Y/S140A/T145S/P213N, T17A/S27T/T48S/I82L/L90F/F92Y/S252T, T17A/S27T/T48S/I82L/L90F/P213N/S252T, T17A/S27T/T48S/I82L/L90F/Q167V, T17A/S27T/T48S/I82L/L90F/Q167V/P213N/S252T, T17A/S27T/T48S/I82L/P213N/S252T, T17A/S27T/T48S/L90F/F92Y, T17A/S27T/T48S/P213N, T17A/S27T/T48S/T145S/Q167V, T17A/T48S/I82L, T17A/T48S/I82L/F92Y/Q167V/S252T, T17A/T48S/I82L/L90F/A135G/S140A/Q167V, T17A/T48S/P213N, T17K/A125S, V177A/A216L, L90F/F92G/D158L/A174R/D203V, V23L/A24V/S32K/N87F/F92Y/A125S/T136A, P20T/L90Y/F92L/S101M/D158E/A174K/I222L, D18R/S32K/Y60H/L90F, P20T/F21W/A24V/L90Y/F92L/T109K/A125S/T136A, Y60H/S101A/A114K/A117Q/D203R/I222L, S32Q/F92G/S101Q/A114K/Q142W/D158I/D203R/I222L, T17G/L90F/F92L/T109R/A114K/D158E/D203V/I222L, R12K/S32K/F92L/T136A/D158E/A174R, L90F/F92G/T109K/A125S/A174K, S32K/L90F/F92L/T109K/A114K/Q142W, V23T/S32Q/N87I/L90F/F92Y/S101N/A114V/Q142W/A174R/D203R/I222L/V229I, S32Q/F92G/A114V/D203V, R12K/S32K/L90Y/F92L/T136A/A174K/D203V/I222L, R12K/A14K/V23T/L90Y/F92G/S101A/D203R, T17G/S32M/L90Y/F92Y/D203R/A216P, S32Q/F92L/A114V/A125S, P20T/F21W/S32M/L90Y/F92G/A114K/A125S/T136V/D158E/A174K/D203V/I222L, R12K/F21W/S32K/F92L/T109K/A125S/T136V/D158E/D203R, T17Q/L90Y/F92L/A174K/D203V/I222L, F21W/F92L/S101A/A117Q/D203R, T17A/S32M/Y60H/Q142L/D203V/I222L, R12K/Y60H/L90F/S101R/A114V/A117N/D158E, T17S/D18R/L90Y/F92G/A114V/A117Q/D203R, L90Y/F92L/S101A/S110R/A125S/Q142W/A174R/A216P, S32M/S110R/A125S/D158E, R12K/V23L/A24V/F92G/T136V/D203R, A24V/S32Q/F92L/T136V, S32K/L90Y/F92G/A114K/D203V, S32M/L90F/F92G/A114V/A117N/A125S/A174K/D203R, R12K/T17A/V23L/A24V/L90F/F92G/S101N/A125S/Q142W/D158I/D203R, P20T/F21W/Y60I/S101A/T109K/A174K, T17C/L90Y/F92L/S101N/T109L/S110R/A125S/A174K/D203R, T17Q/L90F/F92G/S101M/A117Q/T136A/D158I/A174R, V23L/L90F/F92G/A125S/D203V/I222L, T17C/L90Y/F92L/A125S/T136V/D158E/A174K, -continued V23L/S32Q/Y60I/A117Q/T136A/A174K/V229C, V23T/L90F/F92Y/D203V, R12K/A24V/Y60H/A174R, T17G/P20T/Y60I/F92G/D203V, L90Y/F92L/S110R/A125S/D158E/D203V, T17Q/L90Y/F92L/T109L/T136A/D158E/A174R/D203V/V229C, R12K/V23T/A24V/S32Q/F92G/D158L/A174R/D203R, S32M/N87Y/L90F/F92G/A174K/D203V, T17S/V23L/S32Q/L90F/F92L/A114K/A117N/A125S/T136V/D158E/D203V/V229I, P20T/F21W/S32M/L90Y/F92G/T109L/S110R, A14K/S32M/L90Y/S101R/A114V/T136A/A216P, P20T/F21W/L90Y/F92G/A125S/A174K/V229I, V23L/S32K/L90F/F92L/S101R/T109R/T136V/I222L, A24V/F92L/Q142L/A216P, F92G/A125S/T136A/D158E/A216P, N87R/F92G/A117N/D203V/A216P, R12K/A14K/F92G/S110R/A117N/A125S/A174R/D203R, S32Q/N87F/L90F/F92G/S101M/A114V/A117Q/D203V, T17Q/A24V/N87M/F92G/A114K/A117N/D158E/D203R/I222L, N2R/S32Q/L90F/F92G/Q142L/D203V, A14K/S32Q/L90F/F92G/A114K/A117N/A174R/D203V/A216P/I222L, R12K/P20T/D158E/D203R/I222L, N2R/A14K/T17A/L90F/F92G/S101H/A174R/D203V, T17G/A24V/L90F/F92G/Q142W, S32K/L90Y/F92Y/S101A, V23T/N87I/F92G/A125S/T136A/D158L/D203R, T17S/N87L/V229I, A24T/L90F/F92L/A125S/T136A/D203V, R12K/A14K/F92G/T109R/T136A/Q142L/D158E/A174K/D203R/I222L, A24V/S32Q/Y60A/T136A, D18R/S32Q/N87H/L90Y/F92G/S101K/Q142L/D158I/A174R, T17A/F21W/S32K/N87F/L90F/F92Y/S101Q/T136A/D203R, A24V/L90F/F92G/A114V/A117N/T136V/Q142L/D203V/V229C, T17Q/L90Y/F92G/S101N/T109L/S110R/T136V/Q142L/D203V/A216P, S32Q/L90Y/F92L/T109K/A125S/T136V, Y60H/N87K/A114K/A117Q/D158E/A174K/A216P, P20T/L90Y/T109K/T136A/D158I/D203R, T17L/Y60A/D203V, N2R/S32Q/L90Y/F92Y/T109K/D203V, T17H/A24V/S32Q/L90Y/F92L/S101H/A114K/D158I/A174R/D203V, N2R/S32M/F92Y/T109K/S110R/I222L, P20T/F92Y/S101K/A125S/D158E/D203R, R12K/A14K/P20T/F21W/S32M/F92L, R12K/A14K/V23T/A24V/L90F/F92L/S101W/T136A/D203V, T17L/S32K/F92L/T109L/A114V/T136V/D158L/R236H, P20T/F21W/S32Q/N87F/F92L/D158E/D203V, F21W/L90F/F92G/S101A/A114V/A125S/T136V/Q142L/D203V/A216P, P20T/F21W/S32K/F92G/A125S/V229I, V23T/A24V/L90Y/F92G/A125S/T136V/D203V, P20T/S32K/L90Y/F92G/S101N/T109L/S110R/A125S/A174K/D203R/A216P, V23L/L90F/F92L/T136A/D203R/I222L, R12K/A14K/A24V/N87L/L90Y/A125S/T136V/A216P, P20T/F21W/L90Y/A125S, N2R/L90Y/A114K/A117Q/D203V/V2291, F21W/S32K/L90Y/A125S/D158E/A216P/V229I, S27L/T136V, S27L/P8T/T17Q/F21W/S101A/T136V/Q142L, S27L/N2R/T17L, S27L/V23T/A24V/T136A/Q142W, S27L/F21W/T136V, S27L/T17Q/T109K/A114K/T136V/V229I, S27L/T17Q, S27L/T136V/I222L/V229C, S27L/T17A/A114V/A117N/T136A, S27L/Parent, S27L/N2R/T136A, S27L/N2R/T17A, S27L/T17C/S101A/T136V, S27L/P20T/T136A, S27L/T136V/Q142W/V229I, S27L/T109K/T136V/I222L/V2291, S27L/T17L/S101H/A117N/Q142L/I222L/V229I, S27L/S101Q/T109L/A117N/T136A/Q142L, S27L/T109K/S110R/S193N/S252T/R255M, S27L/S22R/Y26K/R236Q, S27L/L90F/F92L/S98E/S113Y/A114K/T136A/D158E/S181R/T206G/S212M/V219I, S27L/N9S/S22P/T48N/L90Y/F92G/T109K/S110R/T136A/Q189V/N211F/R236Q, S27L/T17A/Y26L/T48N/182M/S101D/R236Q, S27L/Y26T/S101D/D158E/V219I/S252T, S27L/S13R/S98E/T136V/S181R/T206G/V229I/N231S, S27L/F21W/F92L/S98N/S193P/I222L, S27L/S1G/Y26K/L90Y/S113Y/A114V/T136A/Q189V/N204R/N211L/R236Q, S27L/S22K/I82L/L90Y/F92G/R108S/A117N/D158E/S193N, S27L/S1G/N9S/T48S/L90Y/S98T/S101A/S113N/A114K/L119M/S193N/T206G/S252T, S27L/N9E/R12K/S22P/V23L/T160R/D203R/I222L, S27L/N9E/R12K/S22P/V23T/T48S/S98E/R108S/T160S/Q189V/T206G/S212L/V229I, S27L/S1A/N2R/N9S/T48N/L90F/F92L/D203V/S223A, S27L/N9E/R12K/V23T/182M/L90Y/F92L/T136V/N204K/N231S/R255M, S27L/S1G/N9S/S22V/I82F/L90Y/F92L/A117N/L119M/Q142L/T206G/S212L/S223A, S27L/N9S/Y60H/R108C/S193P/V219L, S27L/N9E/S22K/S32M/L90F/F92G/R108T/L119M/Q189V/I222L/S223A/R236Q, S27L/T17Q/F92G/S98N/Q142L/Q189L/R236C, S27L/N9E/R12K/Q142W/T160Q/T206G/S212M, S27L/Y26T/S113N/A114V/T136A/D158E/D203R/N211F/R236Q/S252T/R255M, S27L/S1A/T17H/S22V/L90Y/F92G/S98E/A114V/T136A, S27L/N9E/T48S/182M/L90Y/F92L/N122A/A127S/T160S/A174R/T206G/S212L/R255M, S27L/N9S/S22P/V23L/L90Y/F92G/A125S/T160S/N204R/I222L/S223A/R236Q, S27L/N9E/S22P/T48S/L90Y/F92L/T109R/E173R/A174K/D203V/S223A, S27L/R12K/Y26K/T48N/I82L/L90F/A125S/N211I/A216P, S27L/N9S/R12K/F92Y/T109K/S110R/T160K/Q189L/S223A/S252T/R255M, S27L/S1A/N2R/N9E/R12K/S32K/N87F/R108T/N211I/V219K/R255M, S27L/L90F/F92G/N122A/T136A/T160V/E173R/D203R/S252T, S27L/L90Y/F92G/S98T/T109L/D158I/S193K/V219K/R236Q/S252T, S27L/N9E/R12K/T48N/L90F/S98L/R108Q/A117Q/T136A/T206G/S212F/V219I/V229I/R255L, S27L/S1A/S22V/N87K/R108K/N122E/D158E/S193P/V219I/R255M, -continued S27L/F21W/Y26T/S34R/R108H/L119M/N211M/R236C/S252T, S27L/S1A/N9E/R12K/V23T/T48S/N87H/S101Q/Q189L/N211M/V219I/R236Q/R255M, S27L/N9S/T25Q/L90Y/S101D/T136A/Q142L/Q189L/R236Q, S27L/A14K/I82F/F92G/S98E/R108C/A117N/L119M/Q189V/T206G/I222L/S223A, S27L/T17C/Y26T/N87V/R108C/N122E/T136V/S193P/S252T/R255M, S27L/L90Y/F92G/T109L/N122S/R255M, S27L/R12K/L90Y/T160V/A174R/R236Q, S27L/N9E/R12K/T48N/L90Y/F92G/S98T/S113R/N122R/A127S/T136A/A174K/N204K/S212L, S27L/V23T/L90Y/F92G/S98E/T109L/A125S/T160V/A174K/S181C/S193K/T206G/S212M/R255M, S27L/A24V/F92G/S101D/A114V/A117N/A125S/T136V/D203R, S27L/R12K/S32Q/S101Q, S27L/L90F/F92G/T136V/A174R/D203R, S27L/P20T/S32K/L90Y/D203V, S27L/N2R/A14K/T17S/L90Y/T109K/T136V/A216P, S27L/N2R/V23T/A24V/S32M/L90Y/F92G, S27L/A14K/L90Y/F92L/S101D/A117N/D158I/D203R, S27L/F21W/N87H/A114V/A117N/T136V, S27L/N2R/V23T/A24V/N87M/F92L/S101K/A125S/T136A, S27L/L90Y/F92L/S101N/T109R/S110R/Q142W, S27L/S32M/F92G/A216P, S27L/F21W/L90Y/F92L/A114K/A117N/T136A/D203V, S27L/N2R/V23T/S32M/N87M/F92L/T136A, S27L/R12K/L90F/F92G/S101A/D203V, S27L/A24V/L90F/F92G, S27L/R12K/F92L/S101A/A125S/T136A/D203R, S27L/R12K/V23L/L90F/F92L/A114K/T136A/D158E/D203V/I222L, S27L/L90F/F92G, S27L/A14K/P20T/S32Q/L90Y/A125S/D203V, S27L/T17L/L90F/F92G/A125S/A174R/D203V, S27L/N2R/N87K/A114K/A117Q/T136V/D203V, S27L/N2R/A114K/T136V/D203V, S27L/N2R/T17A/T136V/A216P, S27L/N2R/R12K/N87F/T136V/D158E/A174R, S27L/D203R, S27L/R12K/T17Q/T136V/D203V/A216P, S27L/N87F/T109L/Q142L, S27L/N2R/T17Q/A24V/A114K/A117Q/T136A/D158E/A174K/D203V/I222L, S27L/N2R/P20T/F21W/N87M/T109R/A117N/A125S/T136V/D203V/I222L, S27L/V23T/A24V/T136A/D158E/A174K/D203V/I222L, S27L/R12K/V23L/A114K/T136A/D158I/D203V/I222L, S27L/N87Y/T136V/D158E/D203V, S27L/T109K/S110R/D203R, S27L/N2R/T17L/A125S/T136A/D158E, S27L/A24V/D158E/A174K/A216P, S27L/T17G/V23L/N87L/A117Q/A125S/T136V/D158E/V229C, S27L/V23L/N87L/T109R/A114K/A117N/A125S/T136V/Q142L, S27L/N87Y/S101A/A114V/A117Q/T136V/A174K/A216P/I222L, S27L/R12K/T109R/Q142L, S27L/D203V, S27L/T17G/N87F/S101A/D203V, S27L/T17L/N87M/Q142L/D203V, S27L/N2R/R12K/S101D/A117N/T136A/D203V, S27L/R12K/P20T/F21W/A114K/Q142W/D203R, S27L/N2R/T17G/T109L/S110R/A114K/A117Q/T136V/Q142L/D203R, S27L/N2R, S27L/S32K/L90F/F92G/S101M/A114V/A117N/A125S/T136A/D158E/D203V, S27L/R12K/T17A/F21W/S32Q/Y60H/D203R, S27L/R12K/F92L/S110R/T136V/I222L, S27L/A14K/V23T/A24V/L90Y/F92G/A114V/A117Q/Q142L/A174R/I222L, S27L/F21W/S32Q/L90Y/S101D/T109K/A125S/T136A/A174K, S27L/V23T/L90Y/F92G/T136A/D203V/A216P, S27L/T17S/L90Y/F92G/A117N/T136A/D158L, S27L/A14K/V23L/A24V/F92L/Q142W/D203V, S27L/T17L/L90F/F92G/S101K/A174K, S27L/L90F/F92L/A125S/T136V/A174K/D203V/A216P/I222L, S27L/R12K/P20T/S32M/L90F/F92G/S101M/A114V/D203V, S27L/T17A/S32Q/L90F/F92L/T136V/Q142W/A174K/D203R, S27L/R12K/S32M/L90F/F92G/S101W/A114V/D158I/I222L, S27L/P20T/S32M/L90Y/F92L/A114V/A117N/I222L, S27L/T17C/L90Y/F92G/T136A/A174K/D203V, S27L/S32Q/N87Y/F92G/T109K/A114K/A117N/T136V/D203V/V229C, S27L/F21W/L90F/F92G/T136V/A174R, S27L/P20T/N87Y/T136A/D203V/I222L, S27L/A24V/L90Y/F92L/D158I/A174K/D203R/I222L, S27L/F21W/S32Q/L90Y/S110R/A114K/T136V/D203R/A216P/V229I, S27L/N87H/F92G/D203R, S27L/R12K/S32K/Y60A/A125S/T136V/D158L, S27L/V23T/A24V/S32Q/L90F/F92L/T136A, S27L/F92L/A114V/D158E/D203R, S27L/S32Q/L90Y/D203V/V229I, S27L/V23T/S32Q/Y60H/T109K/T136V/A216P/I222L, S27L/A14K/A24V/L90F/F92G/T109K/T136V/D158L/A174R/D203V/I222L/V229I, S27L/R12K/N87F/A174K, S27L/P20T/S32Q/Y60H/T109K/A114V/T136A/A174K, S27L/V23T/A24V/Y60A/A125S/A174R/A216P, S27L/F92Y/D158L/I222L, S27L/V23L/A24V/L90Y/F92G/D203V/I222L, S27L/V23T/A24V/S32Q/L90F/F92G/S101H/T136A/A174K/D203V/V229C, S27L/S32K/N87H/A125S, S27L/P20T/F21W/F92G/A114V, S27L/T17L/V23L/A24V/L90Y/F92L/A117N/T136V/L137M/Q142L, S27L/P20T/L90Y/D203R, S27L/S110R/Q142L/D158I/D203R/V229I, S27L/P20T/S32Q/L90F/F92L/T109K/S110R/A125S/D203V, S27L/V23T/A24V/L90F/F92G/D158E/D203R, S27L/F92G/T136A/A174R/D203V/V229C, S27L/P20T/L90Y/F92G/T109R/S110R/A125S/D203R, S27L/A14K/L90Y/F92L/D158L/A174R/D203V, S27L/F21W/S32Q/L90Y/F92G/T109L/S110R/A117N/D158I/A174K/D203V, S27L/R12K/A114K/A117N/D158E/D203V, S27L/T17S/N87H/T109R/A114K/A117N/T136V/Q142W/D203V, S27L/N2R/N87Y, S27L/T17S/V23T/A24V/S32Q/Y60H/N87K/T136A/D203R, S27L/P20T/F92Y/T109K/D158E/D203V, S27L/S32K/N87M/F92L/S101M/T109L/S110R/D203V, S27L/L90Y/F92G/T136A/D158E/D203V/A216P/V229I, S27L/A14K/S32M/F92L/A125S, S27L/L90Y/F92G/T136V/D158L/D203V, S27L/A24V/L90Y/F92G/S101A/T109L/S110R/A117Q/A174R/D203R, -continued S27L/P20T/S101D/A114V/T136V/Q142W/D158E/D203R/A216P,
S27L/N87Y/F92G/S101Q/A114K/A117N/T136A/D158L/D203R/A216P,
S27L/V23T/A24V/N87Y/L90Y/F92L/S101D/T109R/A174K/D203R/A216P,
S27L/N2R/P20T/F21W/L90F/F92Y, S27L/L90Y/F92G/D158I/D203V/V229C,
S27L/S32Q/F92G/Q142W/I222L, S27L/N2R/R12K/S32M/N87Q/L90F/F92L/I222L,
S27L/R12K/S32K/F92L/A114V/A117Q/T136A/D158E/A216P, S27L/L90Y/F92G,
S27L/R12K/F21W/S32M/F92G/T136V/Q142L/D203R,
S27L/R12K/A14K/L90Y/F92L/A125S/A174K, S27L/A24V/A114V/A117Q/T136V/D203V,
S27L/R12K/T17Q/V23L/S32M/L90Y/F92G/S101D/T136V/I222L,
S27L/V23T/A24V/S32Q/F92L/S101N/T109L/S110R/D203R,
S27L/P20T/Y60H/N87K/T136A/A174R/D203V,
S27L/P20T/F21W/L90Y/F92L/T136A/A174R/D203V/V229C,
S27L/T17G/F21W/S32K/L90F/F92G/A125S/T136A/A174K,
S27L/T17G/N87Y/T136A/D203V/A216P,
S27L/F21W/L90F/F92G/S101D/A117N/T136A/A174K/D203V,
S27L/R12K/A14K/A24V/L90Y/D203V, S27L/N2R/L90F/F92G/S101M/Q142L/D158L,
S27L/N2R/T17C/A24V/N87K/A174K/A216P, S27L/N87M/Q142L/I222L,
S27L/F92L/S98T/R108C/A117Q/A127S/Q142L/Q189V/A216P/R236Q,
S27L/S22K/F92L/R108H/A127S/T136A/N211I,
S27L/F21W/T48S/L90Y/F92L/T109L/A127S/T136V/N204K/S223A,
S27L/T17L/L90Y/F92L/S98M/A174K/D203V/N211M/S212L/S223A,
S27L/N87K/S98M/N211M, S27L/N9E/S22P/L90Y/N204K,
S27L/S32M/T48S/F92G/A127S/Q142W,
S27L/T17S/S22K/L90F/F92L/D158E/D203V/V219I/S252T,
S27L/L90F/F92L/A127S/D203V, S27L/T25F/L90Y/F92G/N204R/S223A/N231S/R236C,
S27L/F21W/S22V/T48S/L90F/F92L,
S27L/S1A/S98T/S113K/A114V/L119M/A127S/Q142W/S193K/V219K/S252T/R255L,
S27L/A24V/I82L/L90F/F92G/T109L/L119M/A127S/E173R/N204K,
S27L/T17C/Y60H/L90F/A127S/E173R/A174R/N204K,
S27L/L90F/F92L/Q142W/D203V/S223A, S27L/P20Q/L90Y/Q142L/S223A,
S27L/N9S/Y60A/A216P/R236Q/R255M,
S27L/F92G/R108C/S110R/A117Q/T136A/N211M,
S27L/S22P/Y60H/S98A/S113K/A114K/T136V/Q189L/S193H,
S27L/V23L/S98A/Q142L/N211M,
S27L/V23L/Y26L/L31M/T48S/F92G/A174R/N204K/S252T,
S27L/S13R/A14K/Y26T/T136A/S181R/N211M/S212M,
S27L/F21W/I82F/L90Y/F92G/A127S/N211M, S27L/P20T/Y60H/S98L/T136A/R255L,
S27L/P20T/S34R/N87M/D158E/S252T, S27L/T25A/L90F/F92G/Q189L/S193P/V229I,
S27L/V219L/I222L,
S27L/N9E/T48S/L90F/F92L/S98N/R108H/S110R/S113Y/N211V/S212L/S252T,
S27L/L90F/F92Y/S113R/V219I/R255L, S27L/F21W/S22K/T48S/F92G/T109R/A127S,
S27L/S1G/A14K/P20T/S32K/T48S/L90Y/F92L/T109L/T160R/V219L/I222L/S252T/R255L,
S27L/L90F/F92G/D158E/T160R/S193N/N204K/S223A,
S27L/A14K/Y26T/F92L/Q142L/S212L,
S27L/S22R/L90Y/F92G/V126I/A127S/A174K/N204K,
S27L/P20T/T25A/L90F/F92L/A117N/L119M/S252T/R255L,
S27L/T17A/A24V/T48S/L90F/F92G/T109R/A127S/T160K/D203R/S223A,
S27L/F21W/T48S/T109L/A127S/V219I/R255L,
S27L/A14K/S22P/T48S/L90F/F92L/T109L/A127S/Q142L/A174R/N204K/S223A,
S27L/T136A/S212M/N231S, S27L/F21W/L90F/F92G/A127S/S223A,
S27L/T48S/L90Y/F92L/R108S/S110R/A127S/T136V/E173R/S223A,
S27L/T48S/F92G/S98E/Q142L/Q189V/S193P/N204R/S223A,
S27L/T17S/L90F/F92Y/S101K/A127S/T136V/N204R/N211I/V229I/N231S,
S27L/N9E/F21W/T48S/L90Y/F92L/T109R/N204K/R236Q,
S27L/N9E/S22R/T48S/F92L/S101N/A127S/E173R/N204R,
S27L/S22K/N87F/A117Q/S181C/N204K/N211M/V229I/N231S/R236Q,
S27L/N9S/T48S/L90F/F92G/S101N/A127S/N204K/A216P/S252T/R255M,
S27L/I82L/S193H/N211M/S212F/S223A,
S27L/A14K/P20T/T48S/L90F/F92G/S98N/R108C/T136A/N204K/N211L/S212L/R236Q/S252T,
S27L/S13R/T17L/T25Q/L90F/F92G/R108C/A127S/T160R/I222L/R255L,
S27L/T48S/L90Y/F92G/T109L/S193N,
S27L/S22V/T48S/L90Y/F92L/S98E/A127S/T136A/N204K/A216P/S223A,
S27L/V23L/N87H/F92L/R108C/S110R/N122A/T160S/Q189L/S193P/N204K/S223A/R255L,
S27L/F92G/A127S/A174R/S223A/V229I/N231S/R236C,
S27L/S1G/L90Y/A127S/E173R/S223A, S27L/F92Y/S98N/Q142W,
S27L/P20T/S32M/S34R/T48S/L90Y/F92L/R108K/A127S/Q142W/A174R/N204K/V219I/S252T,
S27L/F92G/A127S/Q189V/S193N/S223A,
S27L/S34R/F92G/S110R/D158L/D203V/R255M,
S27L/N9E/F21W/T48S/F92G/T109L/A127S/R236C,
S27L/S1A/S22P/T48S/L90Y/F92G/A127S/E173R/A174R/N204K/S223A,
S27L/S22K/T48S/T160S/N204K,
S27L/F21W/T48S/L90Y/F92G/S98V/R108C/A127S/N211L/S212M/N231S/R236C,
S27L/V23L/A24V/A114K/T136A/I222L/V229I,
S27L/P20T/S101H/T109R/A114V/T136A/Q142L/I222L/V229I,
S27L/V23L/S101H/T109K/A114K/A117N/T136V/Q142L/I222L/V229I,
S27L/T17L/F21W/S101H/T109R/A114V/T136A/Q142L/I222L/V229I,
S27L/T17S/T136V/Q142L/I222L/V229C,
S27L/T17C/S22P/T48S/L90F/F92G/A127S/A174R/P192A/S193H/N204K/S223A/V229I/N231S/R236Q/R255L, S27L/N9E/T48N/N87H/F92L/A174K/Q189L/S193K/N204R/V219I, -continued S27L/A14K/V23L/Y26L/L90F/F92G/S98E/S113K/A114K/T136A/V229I/N231S,
S27L/L90Y/F92L/S101D/A117N/Q142L/S193N,
S27L/S22K/T25A/L90Y/Q142L/E173R/N204K/S223A,
S27L/P20T/L90Y/T109L/A127S/A174K/V229C,
S27L/S22V/L90Y/F92L/A117Q/R236C/R255L,
S27L/V23L/A24G/Y26T/I82F/L90Y/F92G/R108H/T136A/D158L/T160K/D203V,
S27L/A14K/S22K/F92G/A127S/N204K/V229I,
S27L/S22V/L90F/F92G/A127S/A174R/A216P/R236C,
S27L/V23L/Y60A/S98T/T109L/A127S/T136V/T160Q/N204K/S223A/R255L,
S27L/S13R/L90Y/S98L/T160V/Q189L/S193P/A216P/S252T/N253S/R255L,
S27L/S22R/182M/F92L/T109L/A127S/Q142W/Q189L/S223A,
S27L/S1G/Y60A/L90F/F92L/N122E/T136A/N204K/S223A/N231S,
S27L/S32K/F92G/S98L/R108Q/S110R/R255L,
S27L/L90Y/F92G/L119M/A127S/A174R/S252T, S27L/L90F/S110R/S181R/N211F,
S27L/A14K/S22P/Y60H/S110R/N122S/D158I/N204K/S223A/R255M,
S27L/F92L/S98V/T109L/N122A/E173R/R255L, S27L/S22R/N87L/F92G/R236C,
S27L/S32M/S34R/I82L/F92G/N204K/S223A,
S27L/A24V/T25Q/Y60I/A127S/A174K/N204K/V219I/S223A/S252T/R255M,
S27L/S98V/T136A/N211F, S27L/N9S/L90F/F92L/A127S/N204R/S212M,
S27L/S22R/T48S/F92G/R108H/S110R/A127S/E173R/N204K/S223A/R236Q,
S27L/A14K/L90Y/F92G/A127S, S27L/A14K/T48S/F92G/E173R/N204R/S223A/N231S,
S27L/L90Y/T109R/S113N/V219L/I222L, S27L/N9S/T48S/L90Y/T136A/T206G/S223A,
S27L/S22K/T48N/L90F/F92G/N204K/S223A/V229C/N231S,
S27L/S22P/T48S/L90F/F92G/A127S/A174R/N204R/S223A,
S27L/S1G/P20T/S32K/S34R/T48S/N87F/S98A/A127S/T136A,
S27L/F21W/S22R/S98E/Q142L/T160V/S223A/S252T/R255L,
S27L/P20T/T48S/F92Y/R108K/S110R/A127S/V219L/S223A/V229I/R236Q,
S27L/Y26T/L90Y/F92L/A127S/V219L/S252T/R255L,
S27L/N9S/F21W/T48S/F92L/A127S/D203V/S212F,
S27L/F21W/Y60H/S98E/L119M/D158E/R236Q,
S27L/F21W/S22R/L90F/F92L/N122S/Q142W/R236Q,
S27L/F21W/T48S/L90F/F92G/T109K,
S27L/L90Y/F92L/T109R/A127S/E173R/N204K/S223A,
S27L/N9S/F21W/T48S/L90Y/F92G/A127S/N204K/V219I/R255M,
S27L/N9E/I82F/L90Y/F92L/S95N/T109L/A127S/A174R/S223A,
S27L/L90F/F92L/S98L/N204K/A216P, S27L/A24V/T48S/A117Q/N211M/S212M/S223A,
S27L/L90Y/F92G/T109L/A127S/N204R/S223A, S27L/N2R/S32Q/N87K/A125S/V219L,
S27L/S22P/T48S/L90F/F92L/S193N/V219L/S223A, S27L/T25Q/L119M/N211M/R236Q,
S27L/L90Y/F92G/N122S/A127S/E173R/A216P/R236Q,
S27L/P20T/S32K/L90F/F92G/N122E/D158E/T160S/Q189L/S223A/S252T,
S27L/N9S/F21W/T48S/N87H/L90F/F92L/S113N/V229C,
S27L/T25Q/I82L/L90F/F92G/S98L/S113R/A114V/T136A/S181R,
S27L/P20T/R108Q/S110R/D203V/N211I,
S27L/S1G/N2R/P20T/Y26T/S32M/T48S/L90Y/F92L/A127S/N204R/V219L,
S27L/A14K/P20T/T48N/L90F/F92G/A117Q/A127S,
S27L/N9S/T48N/L90Y/F92L/S98M/T109K/A127S/N204R/N211I/S212L/V219I,
S27L/F21W/S22R/T48S/L90F/F92L/R108Q/A174K/N204K/S212F/S223A,
S27L/S22R/Y60H/S98T/T136V/S193K/R236Q,
S27L/S22K/Y26K/N87Y/L90Y/F92G/T109R/A127S/S252T/R255L,
S27L/L90F/F92L/T109L, S27L/F21W/F92L/N204K/S252T/R255L,
S27L/V23L/L90Y/F92G/A127S/S193K/N204R/V219I/R236C/R255L,
S27L/F21W/L90Y/F92G/A114V/N122S/A127S/N204K/S223A/S252T,
S27L/P20T/Y60A/T109L/Q189L/S212L, S27L/S22V/T48S/L90Y/F92G/N204K,
S27L/S22V/S32K/T48S/I82F/F92G/A127S/N204K/S223A, S27L/A55L, S27L/A97V,
S27L/F250L, S27L/T109G, S27L/G38D, S27L/A97S, S27L/A55V/A216T, S27L/P20D,
S27L/A55V, S27L/T109Y, S27L/V165I, S27L/A184G, S27L/A97E, S27L/A184S,
S27L/A97F, S27L/A97T, S27L/K197Y, S27L/A55I, S27L/A97P, S27L/A55M, S27L/P20E,
S27L/A117L, S27L/T109L, S27L/K197T, S27L/T136S, S27L/A97L, S27L/T109A,
S27L/P201, S27L/L191V, S27L/A184C, S27L/A97Q, S27L/F250V, S27L/K197V,
S27L/A117S, S27L/K197R, S27L/T109K, S27L/A55C, S27L/N2S/V177A, S27L/Q142D,
S27L/G149C, S27L/F21Y, S27L/G149A, S27L/P164E, S27L/Y26C, S27L/T17N,
S27L/S57M, S27L/D2491, S27L/T17S, S27L/P164T, S27L/Q142L, S27L/D249N,
S27L/1185R, S27L/V83L, S27L/G149S, S27L/A24D, S27L/R251V, S27L/V83I,
S27L/S110N, S27L/T17M, S27L/F161W, S27L/G46E, S27L/D249T, S27L/T17I,
S27L/S57C, S27L/S57T, S27L/S57L, S27L/Q167T, S27L/S57E, S27L/T17K, S27L/G149N,
S27L/Q142E, S27L/S57F, S27L/T17A, S27L/P164H, S27L/T17R, S27L/G149T,
S27L/R251T, S27L/S101Y, S27L/S57V, S27L/A24T, S27L/1185E, S27L/G46N,
S27L/P164N, S27L/P164S, S27L/Q167V, S27L/F161V, S27L/S571, S27L/G149D
S27L/Q1671, S27L/1185Q, S27L/N2L/T17I/T136S/P164H/D249M,
S27L/P20E/F21Y/1139T/P164H/K197T/R251E, S27L/A114V/A117N/T136A/I222L/V229I,
S27L/P20T/A24V/S101Q/T109R/A117Q/I222L/V229I, S27L/S110D/A184S/K197T,
S27L/T136S/D249T, S27L/F21Y/A184S, S27L/N2F/P20E/S110D/A184S/L191V/R251V,
S27L/T17G/V23T/A24V/T109L/A117Q/T136A/I222L/V229I,
S27L/P20D/F21Y/A55T/F250L/R251V,S27L/T109R/A117N/I222L/V229C,
S27L/F21Y/A55T/T109A/A184S, S27L/V23L/A24V/S101K/A117N/I222L/V229C,
S27L/S110K/A117Y/P164R, S27L/1139T/Q142E/I169V, S27L/A24H/R251V,
S27L/F21W/A114V/T136A/I222L/V229I, S27L/N2S/A55V/1185Q/R251E,
S27L/N2F/S101Y/Q142L/G149T/Q167I/1169C/V229L, S27L/N2F/S101C/A117F/P164S,
S27L/Q142H/I185S/R251A, S27L/F21W/T109R/A117N/T136V/I222L/V229I, -continued S27L/G46R/T109K/T136S/D249T, S27L/N2E/G46N/A55V/1185Y/D249I,
S27L/V83L/F250V/R251E, S27L/F21W, S27L/S57C/R251E,
S27L/V23L/A114V/A117N/T136A/I222L/V229I, S27L/A24N,
S27L/T17A/P20T/S101Q/T109K/S110R/T136A/I222L/V229C, S27L/P164T/V165I/R251E,
S27L/F21Y/G46E/A117T/T136S/G149C/R251Q,
S27L/G46N/I139T/Q142E/P164T/1185A/V229L/F250V, S27L/V23L/T136A/I222L/V229I,
S27L/V23T/A24V/T109K/A114K/A117Q/T136A/I222L/V229C, S27L/F250L/R251Q,
S27L/P20E/F21Y/S57T/P164N/A184C/V229C, S27L/P20T/V23T/A24V/I222L/V229I,
S27L/V83L/A97S/A184C/D249S, S27L/P20T/S101H/A114V/A117N/I222L/V229I,
S27L/N2E/R251L, S27L/P20E/F21Y/S110D/A117S, S27L/T17A/V23T/A24V/T136A,
S27L/P20D/S57E/S101C, S27L/N2S/V83L/A184S,
S27L/T17S/S101N/T109K/A117N/T136V/Q142L/I222L/V229C,
S27L/P20D/A55T/A117Y/K197R, S27L/P20T/I222L/V229C, S27L/T171/A24D/S57I,
S27L/N2F, S27L/T109K/A117N/T136V/I222L/V229C, S27L/N2L/A24T,
S27L/N2F/P20I/F21Y/R251Q, S27L/N2F/G46E, S27L/T136V/Q142W/I222L/V229I,
S27L/K197R/R251E, S27L/T17S/R251T, S27L/P20I/F21Y/A117F/1185G/D249N,
S27L/T17L/S101M/T109K/S110R/A117Q/I222L/V229C,
S27L/T17Q/T136A/I222L/V229C, S27L/V2291, S27L/T17A/F21W/S101Q/I222L/V229C,
S27L/T17S/F21W/Q142L, S27L/T17L/T109L/S110R/A117Q/I222L/V229I,
S27L/F21W/T136A, S27L/P20E/F21Y/G46E/V83L/A97Q,
S27L/P20T/F21W/T136A/Q142L/I222L/V2291, S27L/T17G/F21W/A117N/I222L/V229I,
S27L/F21W/T109K/S110R/T136A/V229I, S27L/T17C/T109K/A117N/T136A/I222L/V229I,
S27L/P20T/T109L/S110R/A117N/I222L/V229I, S27L/A24N/P164S/K197V/R251T,
S27L/V23L/A117Q, S27L/A55V/V83L/A117T, S27L/P20D/G46S/A55I/K197T,
S27L/A117Y, S27L/F21W/S101M/I222L/V229C,
S27L/N2L/T17N/S57C/S110D/A117L/P164N/1185G/V229L/R251T,
S27L/N2E/G46S/V83L/T136S/A172T/V229C/D249N,
S27L/P20T/T109R/A114K/A117Q/T136V/I222L/V229C,
S27L/V23L/A24V/T136A/Q142W/I222L/V2291, S27L/N2L,
S27L/T17A/F21W/T109R/S110R/I222L/V229I,
S27L/T17C/A114K/A117N/T136V/I222L/V2291, S27L/V23L/I222L/V229C,
S27L/S101N/A117Q/I222L, S27L/N2E/P20I/T109L/L191V/K197L/V229C,
S27L/P20T/F21W/Q142W/I222L/V229C, S27L/N2L/G46E/T109K/F161V,
S27L/T17S/V2291, S27L/T17Q/T136A/I222L/V2291, S27L/N2L/A172T,
S27L/P20D/F21Y/F250V, S27L/N2L/A24H/A55C/V229L, S27L/N2L/P20E/F21Y/V229L,
S27L/V23T/T109L/A114V/T136A/Q142L/I222L/V229C, S27L/P20T/F21W/I222L/V229C,
S27L/T17H/F21W/T136V/Q142W/I222L/V2291, S27L/G46E/A55I/Q142E,
S27L/N2F/R251Q, S27L/F21W/Q142L/I222L/V229C, S27L/I222L/V229I,
S27L/P20T/S101M/A114V/A117N/Q142W/I222L/V229C,
S27L/T17Q/A24V/S101W/T136A, S27L/N2S/P20D/A97C/A117F/F250L/R251E,
S27L/S101M/A114V/A117Q/T136A, S27L/T163I, S27L/S101Q/Q142L/I222L/V229I,
S27L/F21W/I222L/V229C, S27L/S101M/T136A/I222L/V2291, S27L/F21W/A24V,
S27L/A24D/K197L, S27L/T17H/S110K, S27L/P20T/F21W/V229I,
S27L/T17G/P20T/F21W/A117Q/I222L/V229C,
S27L/F21W/A24V/A114V/A117Q/Q142W/I222L/V229C,
S27L/P20T/A117Q/I222L/V229C, S27L/T17Q/V23T/A24V/I222L/V229I,
S27L/N2F/D249N/F250L, S27L/V23T/Q142L/I222L/V229C,
S27L/P20E/A24D/D249S/F250V, S27L/A24D/S110K, S27L/T109R/I222L/V229I,
S27L/P20E/F21Y/K197T,
S27L/T17A/V23L/S101M/T109K/S110R/A114V/A117Q/T136V/V229I,
S27L/P20T/F21W/Q142W/I222L/V2291, S27L/F21W/I222L/V229I,
S27L/P20T/V23T/A24V/T109L/S110R/I222L/V229I, S27L/A24D/L191F/R251Q,
S27L/A24D/T136S/F250V, S27L/P20T/F21W/T109L/T136A/Q142W/I222L/V229C,
S27L/N2E/I169L/F250L/R251Q, S27L/N2S/A24N/G46E/A55L/Q142D/V229C/R251L,
S27L/N2E/P20E/F250V/R251L, S27L/N2F/P20E, S27L/A24V/V229C,
S27L/P20D/F21Y/G46N/S110K/T163I/Q167V,
S27L/P20T/T109K/A114K/Q142W/I222L/V229C, S27L/T17Q/S101D/T136A/I222L/V229I,
S27L/F21W/T109R/A117N/T136V/Q142W/I222L/V229C, S27L/A24D/T109L/K197L,
S27L/T17Q/Q142L/I222L/V229I, S27L/T17A/A24V/S101D/S110R/T136A,
S27L/P20T/F21W/T109R/A117Q/T136V/Q142L/I222L/V229I,
S27L/P20T/F21W/T109K/A117N/I222L/V229C, S27L/P20T/S101M/I222L/V229I,
S27L/N2S/A24D/S101Y/P164E/V165I/1185E, S27L/T17N/A117S/V229L/R251A,
S27L/S101W/A114V/T136V/V229C, S27L/P20D/G46N/A55C/S110N/T163I/A184S,
S27L/A24H/G46E, S27L/T17H/S101Q/T136V/Q142L/V229C and
S27L/V23T/A24V/I222L/V229C.

In some embodiments, said variant Bhr-PETase comprises a set of amino acid substitutions selected from the group consisting of A102V/T136M,
A14S/L15I/S22A/F92Q/I143R/Q167T/V219K,
D18R/G46S/M56I/R108T/A127M/R138E/I139A/N190S/L227R/W228F/R236E,
D18R/I139A/F161W/W228F,
D18R/I54V/I82F/N105D/A127M/A184S/S218A/V219K/M225L/N241P/N243P,
D18R/I54V/I82F/R108T/V150I/N253Y/N254R, -continued D18R/I54V/M56I/R138E/I139A/T194S/D203N/V219K/F250I, D18R/M56I/I139A/L227R/W228F, D18R/M56I/R138E/I139A/N190S/D203N/M225L, D18R/M56I/R72P/H77Q/F92Q/A127M/V150I/A184S/D203N/N254R, D18R/N85D/R108T/L119I/N190S/T194S, D18R/V40T/I139A/D203N, D18R/V40T/I82F/S101L/N105D/L119I/H156N/F161W/N190S/T194S/D203N, D18R/V40T/M56I/R108T/R138E/H156N, G53A/R108T/Q167T/A184S/T194S/N243P, I143R/Q167T/V198A/W228F, I82F/R108T/L119I/V150I/F161W/Q167T/T194S/D203N, L15I/D18R/R108T/R138E/I139A/F161W/A184S/N190S/D203N, M56I/I82F/R108T/I139A/F161W/T194S/D203N/N241P, M56I/S88T/R108T/N190S/L227R, N204A/Q237R, N9A/D18R/M56I/N85D/L119I/N254R, N9A/S22A/G46S/M56I/R72P/F92Q/L119I/T221S/M225L, N9A/S22A/Q167T, N9A/V40T/L49G/I54V/R108T/V150I/D203N/T221S/M225L, N9S/T25H, Q5E/N9A/M56I/F92Q/R108T/L119I/Q167T/N253Y, Q5E/S22A/R72P/H77Q/F92Q, R108T/L119I/K147Q/F161W/A184S/D203N, S101F/T136A, S22A/A24S/G46S/V150I/Q167T, S22A/A97G/V150I/D203N/M225L/R236E, S22A/G46S/S101L/F161W/D203N/R236E, S22A/I54V/R72P/F92Q/V150I/V200L, S22A/L49G/M56I/V83T/S101L/R108T/L119I/A127M/T194S, S22I/Y26K, S27T/I82L/P213N, S27T/T48S/I82L/F92Y/S252T, S27T/T48S/I82L/L90F/A135G/S140A/I143N/T145S/P213N, S27T/T48S/I82L/S140A/I143N/G149A, S32Y/A62T, S88T/R108T/V150I/A184S/D203N/T221S/M225L/N243P, S98Q/A209V, T16E/D18R/G53A/I54V/R72P/L119I/A127M/Q167T/V200L, T16E/D18R/M56I/A127M/R138E/T194S/V200L/M225L, T16E/D18R/M56I/K147Q/Q167T/A184S/D203N, T16E/D18R/M56I/N85D/S88T/R108T/F161W/Q167T, T16E/D18R/M56I/V150I/S218A/V219K, T16E/D18R/R108T/K147Q/Q167T/A184S/N190S/T194S, T16E/D18R/S22A/M56I/N85D/L119I/A184S, T16E/D18R/S22A/V40T/A97G/S101L/L119I/A127M/Q167T/D203N, T16E/D18R/S88T/R108T/W228F, T16E/D18R/V40T/M56I/I82F/R108T/L119I/F161W/L227R/Q258P, T16E/D18R/V40T/S88T/L119I/A127M/V150I/D203N, T16E/D18R/Y26T/S88T/S101L/H156N/V200L, T17A/I82L/F92Y/P213N, T17A/I82L/L90F/F92Y/A135G/S140A/I143N/G149A/Q167V, T17A/I82L/L90F/F92Y/Q167V, T17A/I82L/S140A/I143N/Q167V/P213N/S252T, T17A/Q167V, T17A/S27T, T17A/S27T/I82L, T17A/S27T/I82L/G149A/Q167V/P213N, T17A/S27T/I82L/L90F/F92Y/Q167V, T17A/S27T/I82L/P213N, T17A/S27T/I82L/P213N/S252T, T17A/S27T/I82L/S252T, T17A/S27T/I82L/T145S/G149A/P213N, T17A/S27T/L90F/A135G/S140A/Q167V/P213N/S252T, T17A/S27T/L90F/F92Y/A135G/Q167V/S252T, T17A/S27T/L90F/F92Y/P213N, T17A/S27T/T48S, T17A/S27T/T48S/A135G/Q167V/P213N, T17A/S27T/T48S/A135G/S140A, T17A/S27T/T48S/I82L, T17A/S27T/T48S/I82L/L90F/F92Y/Q167V/S252T, T17A/S27T/T48S/I82L/L90F/F92Y/S140A/T145S, T17A/S27T/T48S/I82L/L90F/F92Y/S140A/T145S/P213N, T17A/S27T/T48S/I82L/L90F/F92Y/S252T, T17A/S27T/T48S/I82L/L90F/P213N/S252T, T17A/S27T/T48S/I82L/L90F/Q167V, T17A/S27T/T48S/I82L/L90F/Q167V/P213N/S252T, T17A/S27T/T48S/I82L/P213N/S252T, T17A/S27T/T48S/L90F/F92Y, T17A/S27T/T48S/P213N, T17A/S27T/T48S/T145S/Q167V, T17A/T48S/I82L, T17A/T48S/I82L/F92Y/Q167V/S252T, T17A/T48S/I82L/L90F/A135G/S140A/Q167V, T17A/T48S/P213N, T17K/A125S and V177A/A216L.

In some embodiments, said variant Bhr-PETase comprises a set of amino acid substitutions selected from the group consisting of A102V/T136M, A14S/L15I/S22A/F92Q/I143R/Q167T/V219K, D18R/G46S/M56I/R108T/A127M/R138E/I139A/N190S/L227R/W228F/R236E, D18R/I139A/F161W/W228F, D18R/I54V/I82F/N105D/A127M/A184S/S218A/V219K/M225L/N241P/N243P, D18R/I54V/M56I/R138E/I139A/T194S/D203N/V219K/F250I, D18R/M56I/I139A/L227R/W228F, D18R/M56I/R138E/I139A/N190S/D203N/M225L, D18R/M56I/R72P/H77Q/F92Q/A127M/V150I/A184S/D203N/N254R, D18R/V40T/I139A/D203N, D18R/V40T/I82F/S101L/N105D/L119I/H156N/F161W/N190S/T194S/D203N, D18R/V40T/M56I/R108T/R138E/H156N, G53A/R108T/Q167T/A184S/T194S/N243P, I143R/Q167T/V198A/W228F, I82F/R108T/L119I/V150I/F161W/Q167T/T194S/D203N, L15I/D18R/R108T/R138E/I139A/F161W/A184S/N190S/D203N, M56I/I82F/R108T/I139A/F161W/T194S/D203N/N241P, M56I/S88T/R108T/N190S/L227R, N9A/S22A/G46S/M56I/R72P/F92Q/L119I/T221S/M225L, N9A/S22A/Q167T, N9A/V40T/L49G/I54V/R108T/V150I/D203N/T221S/M225L, Q5E/N9A/M56I/F92Q/R108T/L119I/Q167T/N253Y, Q5E/S22A/R72P/H77Q/F92Q, R108T/L119I/K147Q/F161W/A184S/D203N, S101F/T136A, S22A/A24S/G46S/V150I/Q167T, S22A/A97G/V150I/D203N/M225L/R236E, S22A/G46S/S101L/F161W/D203N/R236E, -continued S22A/L49G/M56I/V83T/S101L/R108T/L119I/A127M/T194S, S27T/I82L/P213N, S27T/T48S/I82L/F92Y/S252T, S27T/T48S/I82L/L90F/A135G/S140A/I143N/T145S/P213N, S27T/T48S/I82L/S140A/I143N/G149A, S88T/R108T/V150I/A184S/D203N/T221S/M225L/N243P, T16E/D18R/G53A/I54V/R72P/L119I/A127M/Q167T/V200L, T16E/D18R/M56I/A127M/R138E/T194S/V200L/M225L, T16E/D18R/M56I/K147Q/Q167T/A184S/D203N, T16E/D18R/M56I/N85D/S88T/R108T/F161W/Q167T, T16E/D18R/R108T/K147Q/Q167T/A184S/N190S/T194S, T16E/D18R/S22A/M56I/N85D/L119I/A184S, T16E/D18R/S22A/V40T/A97G/S101L/L119I/A127M/Q167T/D203N, T16E/D18R/S88T/R108T/W228F, T16E/D18R/V40T/M56I/I82F/R108T/L119I/F161W/L227R/Q258P, T16E/D18R/V40T/S88T/L119I/A127M/V150I/D203N, T16E/D18R/Y26T/S88T/S101L/H156N/V200L, T17A/I82L/F92Y/P213N, T17A/I82L/L90F/F92Y/A135G/S140A/I143N/G149A/Q167V, T17A/I82L/L90F/F92Y/Q167V, T17A/I82L/S140A/I143N/Q167V/P213N/S252T, T17A/Q167V, T17A/S27T, T17A/S27T/I82L, T17A/S27T/I82L/G149A/Q167V/P213N, T17A/S27T/I82L/L90F/F92Y/Q167V, T17A/S27T/I82L/P213N, T17A/S27T/I82L/P213N/S252T, T17A/S27T/I82L/S252T, T17A/S27T/I82L/T145S/G149A/P213N, T17A/S27T/L90F/A135G/S140A/Q167V/P213N/S252T, T17A/S27T/L90F/F92Y/A135G/Q167V/S252T, T17A/S27T/L90F/F92Y/P213N, T17A/S27T/T48S, T17A/S27T/T48S/A135G/Q167V/P213N, T17A/S27T/T48S/A135G/S140A, T17A/S27T/T48S/I82L, T17A/S27T/T48S/I82L/L90F/F92Y/Q167V/S252T, T17A/S27T/T48S/I82L/L90F/F92Y/S140A/T145S, T17A/S27T/T48S/I82L/L90F/F92Y/S140A/T145S/P213N, T17A/S27T/T48S/I82L/L90F/F92Y/S252T, T17A/S27T/T48S/I82L/L90F/P213N/S252T, T17A/S27T/T48S/I82L/L90F/Q167V, T17A/S27T/T48S/I82L/L90F/Q167V/P213N/S252T, T17A/S27T/T48S/I82L/P213N/S252T, T17A/S27T/T48S/L90F/F92Y, T17A/S27T/T48S/P213N, T17A/S27T/T48S/T145S/Q167V, T17A/T48S/I82L, T17A/T48S/I82L/F92Y/Q167V/S252T, T17A/T48S/I82L/L90F/A135G/S140A/Q167V, T17A/T48S/P213N, T17K/A125S and V177A/A216L.

In some embodiments, said variant Bhr-PETase comprises a set of amino acid substitutions selected from the group consisting of L90F/F92G/D158L/A174R/D203V, V23L/A24V/S32K/N87F/F92Y/A125S/T136A, P20T/L90Y/F92L/S101M/D158E/A174K/I222L, D18R/S32K/Y60H/L90F, P20T/F21W/A24V/L90Y/F92L/T109K/A125S/T136A, Y60H/S101A/A114K/A117Q/D203R/I222L, S32Q/F92G/S101Q/A114K/Q142W/D158I/D203R/I222L, T17G/L90F/F92L/T109R/A114K/D158E/D203V/I222L, R12K/S32K/F92L/T136A/D158E/A174R, L90F/F92G/T109K/A125S/A174K, S32K/L90F/F92L/T109K/A114K/Q142W, V23T/S32Q/N87I/L90F/F92Y/S101N/A114V/Q142W/A174R/D203R/I222L/V229I, S32Q/F92G/A114V/D203V, R12K/S32K/L90Y/F92L/T136A/A174K/D203V/I222L, R12K/A14K/V23T/L90Y/F92G/S101A/D203R, T17G/S32M/L90Y/F92Y/D203R/A216P, S32Q/F92L/A114V/A125S, P20T/F21W/S32M/L90Y/F92G/A114K/A125S/T136V/D158E/A174K/D203V/I222L, R12K/F21W/S32K/F92L/T109K/A125S/T136V/D158E/D203R, T17Q/L90Y/F92L/A174K/D203V/I222L, F21W/F92L/S101A/A117Q/D203R, T17A/S32M/Y60H/Q142L/D203V/I222L, R12K/Y60H/L90F/S101R/A114V/A117N/D158E, T17S/D18R/L90Y/F92G/A114V/A117Q/D203R, L90Y/F92L/S101A/S110R/A125S/Q142W/A174R/A216P, S32M/S110R/A125S/D158E, R12K/V23L/A24V/F92G/T136V/D203R, A24V/S32Q/F92L/T136V, S32K/L90Y/F92G/A114K/D203V, S32M/L90F/F92G/A114V/A117N/A125S/A174K/D203R, R12K/T17A/V23L/A24V/L90F/F92G/S101N/A125S/Q142W/D158I/D203R, P20T/F21W/Y60I/S101A/T109K/A174K, T17C/L90Y/F92L/S101N/T109L/S110R/A125S/A174K/D203R, T17Q/L90F/F92G/S101M/A117Q/T136A/D158I/A174R, V23L/L90F/F92G/A125S/D203V/I222L, T17C/L90Y/F92L/A125S/T136V/D158E/A174K, V23L/S32Q/Y60I/A117Q/T136A/A174K/V229C, V23T/L90F/F92Y/D203V, R12K/A24V/Y60H/A174R, T17G/P20T/Y60I/F92G/D203V, L90Y/F92L/S110R/A125S/D158E/D203V, T17Q/L90Y/F92L/T109L/T136A/D158E/A174R/D203V/V229C, R12K/V23T/A24V/S32Q/F92G/D158L/A174R/D203R, S32M/N87Y/L90F/F92G/A174K/D203V, T17S/V23L/S32Q/L90F/F92L/A114K/A117N/A125S/T136V/D158E/D203V/V229I, P20T/F21W/S32M/L90Y/F92G/T109L/S110R, A14K/S32M/L90Y/S101R/A114V/T136A/A216P, P20T/F21W/L90Y/F92G/A125S/A174K/V229I, -continued V23L/S32K/L90F/F92L/S101R/T109R/T136V/I222L, A24V/F92L/Q142L/A216P, F92G/A125S/T136A/D158E/A216P, N87R/F92G/A117N/D203V/A216P, R12K/A14K/F92G/S110R/A117N/A125S/A174R/D203R, S32Q/N87F/L90F/F92G/S101M/A114V/A117Q/D203V, T17Q/A24V/N87M/F92G/A114K/A117N/D158E/D203R/I222L, N2R/S32Q/L90F/F92G/Q142L/D203V, A14K/S32Q/L90F/F92G/A114K/A117N/A174R/D203V/A216P/I222L, R12K/P20T/D158E/D203R/I222L, N2R/A14K/T17A/L90F/F92G/S101H/A174R/D203V, T17G/A24V/L90F/F92G/Q142W, S32K/L90Y/F92Y/S101A, V23T/N87I/F92G/A125S/T136A/D158L/D203R, T17S/N87L/V229I, A24T/L90F/F92L/A125S/T136A/D203V, R12K/A14K/F92G/T109R/T136A/Q142L/D158E/A174K/D203R/I222L, A24V/S32Q/Y60A/T136A, D18R/S32Q/N87H/L90Y/F92G/S101K/Q142L/D158I/A174R, T17A/F21W/S32K/N87F/L90F/F92Y/S101Q/T136A/D203R, A24V/L90F/F92G/A114V/A117N/T136V/Q142L/D203V/V229C, T17Q/L90Y/F92G/S101N/T109L/S110R/T136V/Q142L/D203V/A216P, S32Q/L90Y/F92L/T109K/A125S/T136V, Y60H/N87K/A114K/A117Q/D158E/A174K/A216P, P20T/L90Y/T109K/T136A/D158I/D203R, T17L/Y60A/D203V, N2R/S32Q/L90Y/F92Y/T109K/D203V, T17H/A24V/S32Q/L90Y/F92L/S101H/A114K/D158I/A174R/D203V, N2R/S32M/F92Y/T109K/S110R/I222L, P20T/F92Y/S101K/A125S/D158E/D203R, R12K/A14K/P20T/F21W/S32M/F92L, R12K/A14K/V23T/A24V/L90F/F92L/S101W/T136A/D203V, T17L/S32K/F92L/T109L/A114V/T136V/D158L/R236H, P20T/F21W/S32Q/N87F/F92L/D158E/D203V, F21W/L90F/F92G/S101A/A114V/A125S/T136V/Q142L/D203V/A216P, P20T/F21W/S32K/F92G/A125S/V229I, V23T/A24V/L90Y/F92G/A125S/T136V/D203V, P20T/S32K/L90Y/F92G/S101N/T109L/S110R/A125S/A174K/D203R/A216P, V23L/L90F/F92L/T136A/D203R/I222L, R12K/A14K/A24V/N87L/L90Y/A125S/T136V/A216P, P20T/F21W/L90Y/A125S, N2R/L90Y/A114K/A117Q/D203V/V229I, F21W/S32K/L90Y/A125S/D158E/A216P/V229I, S27L/T136V, S27L/P8T/T17Q/F21W/S101A/T136V/Q142L, S27L/N2R/T17L, S27L/V23T/A24V/T136A/Q142W, S27L/F21W/T136V, S27L/T17Q/T109K/A114K/T136V/V229I, S27L/T17Q, S27L/T136V/I222L/V229C, S27L/T17A/A114V/A117N/T136A, S27L/Parent, S27L/N2R/T136A, S27L/N2R/T17A, S27L/T17C/S101A/T136V, S27L/P20T/T136A, S27L/T136V/Q142W/V229I, S27L/T109K/T136V/I222L/V229I, S27L/T17L/S101H/A117N/Q142L/I222L/V229I, S27L/S101Q/T109L/A117N/T136A/Q142L, S27L/T109K/S110R/S193N/S252T/R255M, S27L/S22R/Y26K/R236Q, S27L/L90F/F92L/S98E/S113Y/A114K/T136A/D158E/S181R/T206G/S212M/V219I, S27L/N9S/S22P/T48N/L90Y/F92G/T109K/S110R/T136A/Q189V/N211F/R236Q, S27L/T17A/Y26L/T48N/I82M/S101D/R236Q, S27L/Y26T/S101D/D158E/V219I/S252T, S27L/S13R/S98E/T136V/S181R/T206G/V229I/N231S, S27L/F21W/F92L/S98N/S193P/I222L, S27L/S1G/Y26K/L90Y/S113Y/A114V/T136A/Q189V/N204R/N211L/R236Q, S27L/S22K/I82L/L90Y/F92G/R108S/A117N/D158E/S193N, S27L/S1G/N9S/T48S/L90Y/S98T/S101A/S113N/A114K/L119M/S193N/T206G/S252T, S27L/N9E/R12K/S22P/V23L/T160R/D203R/I222L, S27L/N9E/R12K/S22P/V23T/T48S/S98E/R108S/T160S/Q189V/T206G/S212L/V229I, S27L/S1A/N2R/N9S/T48N/L90F/F92L/D203V/S223A, S27L/N9E/R12K/V23T/I82M/L90Y/F92L/T136V/N204K/N231S/R255M, S27L/S1G/N9S/S22V/I82F/L90Y/F92L/A117N/L119M/Q142L/T206G/S212L/S223A, S27L/N9S/Y60H/R108C/S193P/V219L, S27L/N9E/S22K/S32M/L90F/F92G/R108T/L119M/Q189V/I222L/S223A/R236Q, S27L/T17Q/F92G/S98N/Q142L/Q189L/R236C, S27L/N9E/R12K/Q142W/T160Q/T206G/S212M, S27L/Y26T/S113N/A114V/T136A/D158E/D203R/N211F/R236Q/S252T/R255M, S27L/S1A/T17H/S22V/L90Y/F92G/S98E/A114V/T136A, S27L/N9E/T48S/I82M/L90Y/F92L/N122A/A127S/T160S/A174R/T206G/S212L/R255M, S27L/N9S/S22P/V23L/L90Y/F92G/A125S/T160S/N204R/I222L/S223A/R236Q, S27L/N9E/S22P/T48S/L90Y/F92L/T109R/E173R/A174K/D203V/S223A, S27L/R12K/Y26K/T48N/I82L/L90F/A125S/N211I/A216P, S27L/N9S/R12K/F92Y/T109K/S110R/T160K/Q189L/S223A/S252T/R255M, S27L/S1A/N2R/N9E/R12K/S32K/N87F/R108T/N211I/V219K/R255M, S27L/L90F/F92G/N122A/T136A/T160V/E173R/D203R/S252T, S27L/L90Y/F92G/S98T/T109L/D158I/S193K/V219K/R236Q/S252T, S27L/N9E/R12K/T48N/L90F/S98L/R108Q/A117Q/T136A/T206G/S212F/V219I/V229I/R255L, S27L/S1A/S22V/N87K/R108K/N122E/D158E/S193P/V219I/R255M, S27L/F21W/Y26T/S34R/R108H/L119M/N211M/R236C/S252T, S27L/S1A/N9E/R12K/V23T/T48S/N87H/S101Q/Q189L/N211M/V219I/R236Q/R255M, S27L/N9S/T25Q/L90Y/S101D/T136A/Q142L/Q189L/R236Q, S27L/A14K/I82F/F92G/S98E/R108C/A117N/L119M/Q189V/T206G/I222L/S223A, S27L/T17C/Y26T/N87V/R108C/N122E/T136V/S193P/S252T/R255M, S27L/L90Y/F92G/T109L/N122S/R255M, S27L/R12K/L90Y/T160V/A174R/R236Q, S27L/N9E/R12K/T48N/L90Y/F92G/S98T/S113R/N122R/A127S/T136A/A174K/N204K/S212L, S27L/V23T/L90Y/F92G/S98E/T109L/A125S/T160V/A174K/S181C/S193K/T206G/S212M/R255M, S27L/A24V/F92G/S101D/A114V/A117N/A125S/T136V/D203R, -continued S27L/R12K/S32Q/S101Q, S27L/L90F/F92G/T136V/A174R/D203R, S27L/P20T/S32K/L90Y/D203V, S27L/N2R/A14K/T17S/L90Y/T109K/T136V/A216P, S27L/N2R/V23T/A24V/S32M/L90Y/F92G, S27L/A14K/L90Y/F92L/S101D/A117N/D158I/D203R, S27L/F21W/N87H/A114V/A117N/T136V, S27L/N2R/V23T/A24V/N87M/F92L/S101K/A125S/T136A, S27L/L90Y/F92L/S101N/T109R/S110R/Q142W, S27L/S32M/F92G/A216P, S27L/F21W/L90Y/F92L/A114K/A117N/T136A/D203V, S27L/N2R/V23T/S32M/N87M/F92L/T136A, S27L/R12K/L90F/F92G/S101A/D203V, S27L/A24V/L90F/F92G, S27L/R12K/F92L/S101A/A125S/T136A/D203R, S27L/R12K/V23L/L90F/F92L/A114K/T136A/D158E/D203V/I222L, S27L/L90F/F92G, S27L/A14K/P20T/S32Q/L90Y/A125S/D203V, S27L/T17L/L90F/F92G/A125S/A174R/D203V, S27L/N2R/N87K/A114K/A117Q/T136V/D203V, S27L/N2R/A114K/T136V/D203V, S27L/N2R/T17A/T136V/A216P, S27L/N2R/R12K/N87F/T136V/D158E/A174R, S27L/D203R, S27L/R12K/T17Q/T136V/D203V/A216P, S27L/N87F/T109L/Q142L, S27L/N2R/T17Q/A24V/A114K/A117Q/T136A/D158E/A174K/D203V/I222L, S27L/N2R/P20T/F21W/N87M/T109R/A117N/A125S/T136V/D203V/I222L, S27L/V23T/A24V/T136A/D158E/A174K/D203V/I222L, S27L/R12K/V23L/A114K/T136A/D158I/D203V/I222L, S27L/N87Y/T136V/D158E/D203V, S27L/T109K/S110R/D203R, S27L/N2R/T17L/A125S/T136A/D158E, S27L/A24V/D158E/A174K/A216P, S27L/T17G/V23L/N87L/A117Q/A125S/T136V/D158E/V229C, S27L/V23L/N87L/T109R/A114K/A117N/A125S/T136V/Q142L, S27L/N87Y/S101A/A114V/A117Q/T136V/A174K/A216P/I222L, S27L/R12K/T109R/Q142L, S27L/D203V, S27L/T17G/N87F/S101A/D203V, S27L/T17L/N87M/Q142L/D203V, S27L/N2R/R12K/S101D/A117N/T136A/D203V, S27L/R12K/P20T/F21W/A114K/Q142W/D203R, S27L/N2R/T17G/T109L/S110R/A114K/A117Q/T136V/Q142L/D203R, S27L/N2R, S27L/S32K/L90F/F92G/S101M/A114V/A117N/A125S/T136A/D158E/D203V, S27L/R12K/T17A/F21W/S32Q/Y60H/D203R, S27L/R12K/F92L/S110R/T136V/I222L, S27L/A14K/V23T/A24V/L90Y/F92G/A114V/A117Q/Q142L/A174R/I222L, S27L/F21W/S32Q/L90Y/S101D/T109K/A125S/T136A/A174K, S27L/V23T/L90Y/F92G/T136A/D203V/A216P, S27L/T17S/L90Y/F92G/A117N/T136A/D158L, S27L/A14K/V23L/A24V/F92L/Q142W/D203V, S27L/T17L/L90F/F92G/S101K/A174K, S27L/L90F/F92L/A125S/T136V/A174K/D203V/A216P/I222L, S27L/R12K/P20T/S32M/L90F/F92G/S101M/A114V/D203V, S27L/T17A/S32Q/L90F/F92L/T136V/Q142W/A174K/D203R, S27L/R12K/S32M/L90F/F92G/S101W/A114V/D158I/I222L, S27L/P20T/S32M/L90Y/F92L/A114V/A117N/I222L, S27L/T17C/L90Y/F92G/T136A/A174K/D203V, S27L/S32Q/N87Y/F92G/T109K/A114K/A117N/T136V/D203V/V229C, S27L/F21W/L90F/F92G/T136V/A174R, S27L/P20T/N87Y/T136A/D203V/I222L, S27L/A24V/L90Y/F92L/D158I/A174K/D203R/I222L, S27L/F21W/S32Q/L90Y/S110R/A114K/T136V/D203R/A216P/V229I, S27L/N87H/F92G/D203R, S27L/R12K/S32K/Y60A/A125S/T136V/D158L, S27L/V23T/A24V/S32Q/L90F/F92L/T136A, S27L/F92L/A114V/D158E/D203R, S27L/S32Q/L90Y/D203V/V229I, S27L/V23T/S32Q/Y60H/T109K/T136V/A216P/I222L, S27L/A14K/A24V/L90F/F92G/T109K/T136V/D158L/A174R/D203V/I222L/V229I, S27L/R12K/N87F/A174K, S27L/P20T/S32Q/Y60H/T109K/A114V/T136A/A174K, S27L/V23T/A24V/Y60A/A125S/A174R/A216P, S27L/F92Y/D158L/I222L, S27L/V23L/A24V/L90Y/F92G/D203V/I222L, S27L/V23T/A24V/S32Q/L90F/F92G/S101H/T136A/A174K/D203V/V229C, S27L/S32K/N87H/A125S, S27L/P20T/F21W/F92G/A114V, S27L/T17L/V23L/A24V/L90Y/F92L/A117N/T136V/L137M/Q142L, S27L/P20T/L90Y/D203R, S27L/S110R/Q142L/D158I/D203R/V229I, S27L/P20T/S32Q/L90F/F92L/T109K/S110R/A125S/D203V, S27L/V23T/A24V/L90F/F92G/D158E/D203R, S27L/F92G/T136A/A174R/D203V/V229C, S27L/P20T/L90Y/F92G/T109R/S110R/A125S/D203R, S27L/A14K/L90Y/F92L/D158L/A174R/D203V, S27L/F21W/S32Q/L90Y/F92G/T109L/S110R/A117N/D158I/A174K/D203V, S27L/R12K/A114K/A117N/D158E/D203V, S27L/T17S/N87H/T109R/A114K/A117N/T136V/Q142W/D203V, S27L/N2R/N87Y, S27L/T17S/V23T/A24V/S32Q/Y60H/N87K/T136A/D203R, S27L/P20T/F92Y/T109K/D158E/D203V, S27L/S32K/N87M/F92L/S101M/T109L/S110R/D203V, S27L/L90Y/F92G/T136A/D158E/D203V/A216P/V229I, S27L/A14K/S32M/F92L/A125S, S27L/L90Y/F92G/T136V/D158L/D203V, S27L/A24V/L90Y/F92G/S101A/T109L/S110R/A117Q/A174R/D203R, S27L/P20T/S101D/A114V/T136V/Q142W/D158E/D203R/A216P, S27L/N87Y/F92G/S101Q/A114K/A117N/T136A/D158L/D203R/A216P, S27L/V23T/A24V/N87Y/L90Y/F92L/S101D/T109R/A174K/D203R/A216P, S27L/N2R/P20T/F21W/L90F/F92Y, S27L/L90Y/F92G/D158I/D203V/V229C, S27L/S32Q/F92G/Q142W/I222L, S27L/N2R/R12K/S32M/N87Q/L90F/F92L/I222L, S27L/R12K/S32K/F92L/A114V/A117Q/T136A/D158E/A216P, S27L/L90Y/F92G, S27L/R12K/F21W/S32M/F92G/T136V/Q142L/D203R, S27L/R12K/A14K/L90Y/F92L/A125S/A174K, S27L/A24V/A114V/A117Q/T136V/D203V, S27L/R12K/T17Q/V23L/S32M/L90Y/F92G/S101D/T136V/I222L, -continued S27L/V23T/A24V/S32Q/F92L/S101N/T109L/S110R/D203R, S27L/P20T/Y60H/N87K/T136A/A174R/D203V, S27L/P20T/F21W/L90Y/F92L/T136A/A174R/D203V/V229C, S27L/T17G/F21W/S32K/L90F/F92G/A125S/T136A/A174K, S27L/T17G/N87Y/T136A/D203V/A216P, S27L/F21W/L90F/F92G/S101D/A117N/T136A/A174K/D203V, S27L/R12K/A14K/A24V/L90Y/D203V, S27L/N2R/L90F/F92G/S101M/Q142L/D158L, S27L/N2R/T17C/A24V/N87K/A174K/A216P, S27L/N87M/Q142L/I222L, S27L/F92L/S98T/R108C/A117Q/A127S/Q142L/Q189V/A216P/R236Q, S27L/S22K/F92L/R108H/A127S/T136A/N211I, S27L/F21W/T48S/L90Y/F92L/T109L/A127S/T136V/N204K/S223A, S27L/T17L/L90Y/F92L/S98M/A174K/D203V/N211M/S212L/S223A, S27L/N87K/S98M/N211M, S27L/N9E/S22P/L90Y/N204K, S27L/S32M/T48S/F92G/A127S/Q142W, S27L/T17S/S22K/L90F/F92L/D158E/D203V/V219I/S252T, S27L/L90F/F92L/A127S/D203V, S27L/T25F/L90Y/F92G/N204R/S223A/N231S/R236C, S27L/F21W/S22V/T48S/L90F/F92L, S27L/S1A/S98T/S113K/A114V/L119M/A127S/Q142W/S193K/V219K/S252T/R255L, S27L/A24V/I82L/L90F/F92G/T109L/L119M/A127S/E173R/N204K, S27L/T17C/Y60H/L90F/A127S/E173R/A174R/N204K, S27L/L90F/F92L/Q142W/D203V/S223A, S27L/P20Q/L90Y/Q142L/S223A, S27L/N9S/Y60A/A216P/R236Q/R255M, S27L/F92G/R108C/S110R/A117Q/T136A/N211M, S27L/S22P/Y60H/S98A/S113K/A114K/T136V/Q189L/S193H, S27L/V23L/S98A/Q142L/N211M, S27L/V23L/Y26L/L31M/T48S/F92G/A174R/N204K/S252T, S27L/S13R/A14K/Y26T/T136A/S181R/N211M/S212M, S27L/F21W/I82F/L90Y/F92G/A127S/N211M, S27L/P20T/Y60H/S98L/T136A/R255L, S27L/P20T/S34R/N87M/D158E/S252T, S27L/T25A/L90F/F92G/Q189L/S193P/V229I, S27L/V219L/I222L, S27L/N9E/T48S/L90F/F92L/S98N/R108H/S110R/S113Y/N211V/S212L/S252T, S27L/L90F/F92Y/S113R/V219I/R255L, S27L/F21W/S22K/T48S/F92G/T109R/A127S, S27L/S1G/A14K/P20T/S32K/T48S/L90Y/F92L/T109L/T160R/V219L/I222L/S252T/R255L, S27L/L90F/F92G/D158E/T160R/S193N/N204K/S223A, S27L/A14K/Y26T/F92L/Q142L/S212L, S27L/S22R/L90Y/F92G/V126I/A127S/A174K/N204K, S27L/P20T/T25A/L90F/F92L/A117N/L119M/S252T/R255L, S27L/T17A/A24V/T48S/L90F/F92G/T109R/A127S/T160K/D203R/S223A, S27L/F21W/T48S/T109L/A127S/V219I/R255L, S27L/A14K/S22P/T48S/L90F/F92L/T109L/A127S/Q142L/A174R/N204K/S223A, S27L/T136A/S212M/N231S, S27L/F21W/L90F/F92G/A127S/S223A, S27L/T48S/L90Y/F92L/R108S/S110R/A127S/T136V/E173R/S223A, S27L/T48S/F92G/S98E/Q142L/Q189V/S193P/N204R/S223A, S27L/T17S/L90F/F92Y/S101K/A127S/T136V/N204R/N211I/V229I/N231S, S27L/N9E/F21W/T48S/L90Y/F92L/T109R/N204K/R236Q, S27L/N9E/S22R/T48S/F92L/S101N/A127S/E173R/N204R, S27L/S22K/N87F/A117Q/S181C/N204K/N211M/V229I/N231S/R236Q, S27L/N9S/T48S/L90F/F92G/S101N/A127S/N204K/A216P/S252T/R255M, S27L/I82L/S193H/N211M/S212F/S223A, S27L/A14K/P20T/T48S/L90F/F92G/S98N/R108C/T136A/N204K/N211L/S212L/R236Q/S252T, S27L/S13R/T17L/T25Q/L90F/F92G/R108C/A127S/T160R/I222L/R255L, S27L/T48S/L90Y/F92G/T109L/S193N, S27L/S22V/T48S/L90Y/F92L/S98E/A127S/T136A/N204K/A216P/S223A, S27L/V23L/N87H/F92L/R108C/S110R/N122A/T160S/Q189L/S193P/N204K/S223A/R255L, S27L/F92G/A127S/A174R/S223A/V229I/N231S/R236C, S27L/S1G/L90Y/A127S/E173R/S223A, S27L/F92Y/S98N/Q142W, S27L/P20T/S32M/S34R/T48S/L90Y/F92L/R108K/A127S/Q142W/A174R/N204K/V219I/S252T, S27L/F92G/A127S/Q189V/S193N/S223A, S27L/S34R/F92G/S110R/D158L/D203V/R255M, S27L/N9E/F21W/T48S/F92G/T109L/A127S/R236C, S27L/S1A/S22P/T48S/L90Y/F92G/A127S/E173R/A174R/N204K/S223A, S27L/S22K/T48S/T160S/N204K, S27L/F21W/T48S/L90Y/F92G/S98V/R108C/A127S/N211L/S212M/N231S/R236C, S27L/V23L/A24V/A114K/T136A/I222L/V229I, S27L/P20T/S101H/T109R/A114V/T136A/Q142L/I222L/V229I, S27L/V23L/S101H/T109K/A114K/A117N/T136V/Q142L/I222L/V229I, S27L/T17L/F21W/S101H/T109R/A114V/T136A/Q142L/I222L/V229I, S27L/T17S/T136V/Q142L/I222L/V229C, S27L/T17C/S22P/T48S/L90F/F92G/A127S/A174R/P192A/S193H/N204K/S223A/V229I/N231S/R236Q/R255L, S27L/N9E/T48N/N87H/F92L/A174K/Q189L/S193K/N204R/V219I, S27L/A14K/V23L/Y26L/L90F/F92G/S98E/S113K/A114K/T136A/V229I/N231S, S27L/L90Y/F92L/S101D/A117N/Q142L/S193N, S27L/S22K/T25A/L90Y/Q142L/E173R/N204K/S223A, S27L/P20T/L90Y/T109L/A127S/A174K/V229C, S27L/S22V/L90Y/F92L/A117Q/R236C/R255L, S27L/V23L/A24G/Y26T/I82F/L90Y/F92G/R108H/T136A/D158L/T160K/D203V, S27L/A14K/S22K/F92G/A127S/N204K/V229I, S27L/S22V/L90F/F92G/A127S/A174R/A216P/R236C, S27L/V23L/Y60A/S98T/T109L/A127S/T136V/T160Q/N204K/S223A/R255L, -continued S27L/S13R/L90Y/S98L/T160V/Q189L/S193P/A216P/S252T/N253S/R255L, S27L/S22R/I82M/F92L/T109L/A127S/Q142W/Q189L/S223A, S27L/S1G/Y60A/L90F/F92L/N122E/T136A/N204K/S223A/N231S, S27L/S32K/F92G/S98L/R108Q/S110R/R255L, S27L/L90Y/F92G/L119M/A127S/A174R/S252T, S27L/L90F/S110R/S181R/N211F, S27L/A14K/S22P/Y60H/S110R/N122S/D158I/N204K/S223A/R255M, S27L/F92L/S98V/T109L/N122A/E173R/R255L, S27L/S22R/N87L/F92G/R236C, S27L/S32M/S34R/I82L/F92G/N204K/S223A, S27L/A24V/T25Q/Y60I/A127S/A174K/N204K/V219I/S223A/S252T/R255M, S27L/S98V/T136A/N211F, S27L/N9S/L90F/F92L/A127S/N204R/S212M, S27L/S22R/T48S/F92G/R108H/S110R/A127S/E173R/N204K/S223A/R236Q, S27L/A14K/L90Y/F92G/A127S, S27L/A14K/T48S/F92G/E173R/N204R/S223A/N231S, S27L/L90Y/T109R/S113N/V219L/I222L, S27L/N9S/T48S/L90Y/T136A/T206G/S223A, S27L/S22K/T48N/L90F/F92G/N204K/S223A/V229C/N231S, S27L/S22P/T48S/L90F/F92G/A127S/A174R/N204R/S223A, S27L/S1G/P20T/S32K/S34R/T48S/N87F/S98A/A127S/T136A, S27L/F21W/S22R/S98E/Q142L/T160V/S223A/S252T/R255L, S27L/P20T/T48S/F92Y/R108K/S110R/A127S/V219L/S223A/V229I/R236Q, S27L/Y26T/L90Y/F92L/A127S/V219L/S252T/R255L, S27L/N9S/F21W/T48S/F92L/A127S/D203V/S212F, S27L/F21W/Y60H/S98E/L119M/D158E/R236Q, S27L/F21W/S22R/L90F/F92L/N122S/Q142W/R236Q, S27L/F21W/T48S/L90F/F92G/T109K, S27L/L90Y/F92L/T109R/A127S/E173R/N204K/S223A, S27L/N9S/F21W/T48S/L90Y/F92G/A127S/N204K/V219I/R255M, S27L/N9E/I82F/L90Y/F92L/S95N/T109L/A127S/A174R/S223A, S27L/L90F/F92L/S98L/N204K/A216P, S27L/A24V/T48S/A117Q/N211M/S212M/S223A, S27L/L90Y/F92G/T109L/A127S/N204R/S223A, S27L/N2R/S32Q/N87K/A125S/V219L, S27L/S22P/T48S/L90F/F92L/S193N/V219L/S223A, S27L/T25Q/L119M/N211M/R236Q, S27L/L90Y/F92G/N122S/A127S/E173R/A216P/R236Q, S27L/P20T/S32K/L90F/F92G/N122E/D158E/T160S/Q189L/S223A/S252T, S27L/N9S/F21W/T48S/N87H/L90F/F92L/S113N/V229C, S27L/T25Q/I82L/L90F/F92G/S98L/S113R/A114V/T136A/S181R, S27L/P20T/R108Q/S110R/D203V/N211I, S27L/S1G/N2R/P20T/Y26T/S32M/T48S/L90Y/F92L/A127S/N204R/V219L, S27L/A14K/P20T/T48N/L90F/F92G/A117Q/A127S, S27L/N9S/T48N/L90Y/F92L/S98M/T109K/A127S/N204R/N211I/S212L/V219I, S27L/F21W/S22R/T48S/L90F/F92L/R108Q/A174K/N204K/S212F/S223A, S27L/S22R/Y60H/S98T/T136V/S193K/R236Q, S27L/S22K/Y26K/N87Y/L90Y/F92G/T109R/A127S/S252T/R255L, S27L/L90F/F92L/T109L, S27L/F21W/F92L/N204K/S252T/R255L, S27L/V23L/L90Y/F92G/A127S/S193K/N204R/V219I/R236C/R255L, S27L/F21W/L90Y/F92G/A114V/N122S/A127S/N204K/S223A/S252T, S27L/P20T/Y60A/T109L/Q189L/S212L, S27L/S22V/T48S/L90Y/F92G/N204K, S27L/S22V/S32K/T48S/I82F/F92G/A127S/N204K/S223A, S27L/A55L, S27L/A97V, S27L/F250L, S27L/T109G, S27L/G38D, S27L/A97S, S27L/A55V/A216T, S27L/P20D, S27L/A55V, S27L/T109Y, S27L/V165I, S27L/A184G, S27L/A97E, S27L/A184S, S27L/A97F, S27L/A97T, S27L/K197Y, S27L/A55I, S27L/A97P, S27L/A55M, S27L/P20E, S27L/A117L, S27L/T109L, S27L/K197T, S27L/T136S, S27L/A97L, S27L/T109A, S27L/P20I, S27L/L191V, S27L/A184C, S27L/A97Q, S27L/F250V, S27L/K197V, S27L/A117S, S27L/K197R, S27L/T109K, S27L/A55C, S27L/N2S/V177A, S27L/Q142D, S27L/G149C, S27L/F21Y, S27L/G149A, S27L/P164E, S27L/Y26C, S27L/T17N, S27L/S57M, S27L/D249I, S27L/T17S, S27L/P164T, S27L/Q142L, S27L/D249N, S27L/I185R, S27L/V83L, S27L/G149S, S27L/A24D, S27L/R251V, S27L/V83I, S27L/S110N, S27L/T17M, S27L/F161W, S27L/G46E, S27L/D249T, S27L/T17I, S27L/S57C, S27L/S57T, S27L/S57L, S27L/Q167T, S27L/S57E, S27L/T17K, S27L/G149N, S27L/Q142E, S27L/S57F, S27L/T17A, S27L/P164H, S27L/T17R, S27L/G149T, S27L/R251T, S27L/S101Y, S27L/S57V, S27L/A24T, S27L/I185E, S27L/G46N, S27L/P164N, S27L/P164S, S27L/Q167V, S27L/F161V, S27L/S57I, S27L/G149D S27L/Q167I, S27L/I185Q, S27L/N2L/T17I/T136S/P164H/D249M, S27L/P20E/F21Y/I139T/P164H/K197T/R251E, S27L/A114V/A117N/T136A/I222L/V229I, S27L/P20T/A24V/S101Q/T109R/A117Q/I222L/V229I, S27L/S110D/A184S/K197T, S27L/T136S/D249T, S27L/F21Y/A184S, S27L/N2F/P20E/S110D/A184S/L191V/R251V, S27L/T17G/V23T/A24V/T109L/A117Q/T136A/I222L/V229I, S27L/P20D/F21Y/A55T/F250L/R251V, S27L/T109R/A117N/I222L/V229C, S27L/F21Y/A55T/T109A/A184S, S27L/V23L/A24V/S101K/A117N/I222L/V229C, S27L/S110K/A117Y/P164R, S27L/I139T/Q142E/I169V, S27L/A24H/R251V, S27L/F21W/A114V/T136A/I222L/V229I, S27L/N2S/A55V/I185Q/R251E, S27L/N2F/S101Y/Q142L/G149T/Q167I/I169C/V229L, S27L/N2F/S101C/A117F/P164S, S27L/Q142H/I185S/R251A, S27L/F21W/T109R/A117N/T136V/I222L/V229I, S27L/G46R/T109K/T136S/D249T, S27L/N2E/G46N/A55V/I185Y/D249I, S27L/V83L/F250V/R251E, S27L/F21W, S27L/S57C/R251E, S27L/V23L/A114V/A117N/T136A/I222L/V229I, S27L/A24N, S27L/T17A/P20T/S101Q/T109K/S110R/T136A/I222L/V229C, S27L/P164T/V165I/R251E, S27L/F21Y/G46E/A117T/T136S/G149C/R251Q, S27L/G46N/I139T/Q142E/P164T/I185A/V229L/F250V, S27L/V23L/T136A/I222L/V229I, S27L/V23T/A24V/T109K/A114K/A117Q/T136A/I222L/V229C, S27L/F250L/R251Q, S27L/P20E/F21Y/S57T/P164N/A184C/V229C, S27L/P20T/V23T/A24V/I222L/V229I, S27L/V83L/A97S/A184C/D249S, S27L/P20T/S101H/A114V/A117N/I222L/V229I, -continued S27L/N2E/R251L, S27L/P20E/F21Y/S110D/A117S, S27L/T17A/V23T/A24V/T136A, S27L/P20D/S57E/S101C, S27L/N2S/V83L/A184S, S27L/T17S/S101N/T109K/A117N/T136V/Q142L/I222L/V229C, S27L/P20D/A55T/A117Y/K197R, S27L/P20T/I222L/V229C, S27L/T17I/A24D/S57I, S27L/N2F, S27L/T109K/A117N/T136V/I222L/V229C, S27L/N2L/A24T, S27L/N2F/P20I/F21Y/R251Q, S27L/N2F/G46E, S27L/T136V/Q142W/I222L/V229I, S27L/K197R/R251E, S27L/T17S/R251T, S27L/P20I/F21Y/A117F/I185G/D249N, S27L/T17L/S101M/T109K/S110R/A117Q/I222L/V229C, S27L/T17Q/T136A/I222L/V229C, S27L/V229I, S27L/T17A/F21W/S101Q/I222L/V229C, S27L/T17S/F21W/Q142L, S27L/T17L/T109L/S110R/A117Q/I222L/V229I, S27L/F21W/T136A, S27L/P20E/F21Y/G46E/V83L/A97Q, S27L/P20T/F21W/T136A/Q142L/I222L/V229I, S27L/T17G/F21W/A117N/I222L/V229I, S27L/F21W/T109K/S110R/T136A/V229I, S27L/T17C/T109K/A117N/T136A/I222L/V229I, S27L/P20T/T109L/S110R/A117N/I222L/V229I, S27L/A24N/P164S/K197V/R251T, S27L/V23L/A117Q, S27L/A55V/V83L/A117T, S27L/P20D/G46S/A55I/K197T, S27L/A117Y, S27L/F21W/S101M/I222L/V229C, S27L/N2L/T17N/S57C/S110D/A117L/P164N/I185G/V229L/R251T, S27L/N2E/G46S/V83L/T136S/A172T/V229C/D249N, S27L/P20T/T109R/A114K/A117Q/T136V/I222L/V229C, S27L/V23L/A24V/T136A/Q142W/I222L/V229I, S27L/N2L, S27L/T17A/F21W/T109R/S110R/I222L/V229I, S27L/T17C/A114K/A117N/T136V/I222L/V229I, S27L/V23L/I222L/V229C, S27L/S101N/A117Q/I222L, S27L/N2E/P20I/T109L/L191V/K197L/V229C, S27L/P20T/F21W/Q142W/I222L/V229C, S27L/N2L/G46E/T109K/F161V, S27L/T17S/V229I, S27L/T17Q/T136A/I222L/V229I, S27L/N2L/A172T, S27L/P20D/F21Y/F250V, S27L/N2L/A24H/A55C/V229L, S27L/N2L/P20E/F21Y/V229L, S27L/V23T/T109L/A114V/T136A/Q142L/I222L/V229C, S27L/P20T/F21W/I222L/V229C, S27L/T17H/F21W/T136V/Q142W/I222L/V229I, S27L/G46E/A55I/Q142E, S27L/N2F/R251Q, S27L/F21W/Q142L/I222L/V229C, S27L/I222L/V229I, S27L/P20T/S101M/A114V/A117N/Q142W/I222L/V229C, S27L/T17Q/A24V/S101W/T136A, S27L/N2S/P20D/A97C/A117F/F250L/R251E, S27L/S101M/A114V/A117Q/T136A, S27L/T163I, S27L/S101Q/Q142L/I222L/V229I, S27L/F21W/I222L/V229C, S27L/S101M/T136A/I222L/V229I, S27L/F21W/A24V, S27L/A24D/K197L, S27L/T17H/S110K, S27L/P20T/F21W/V229I, S27L/T17G/P20T/F21W/A117Q/I222L/V229C, S27L/F21W/A24V/A114V/A117Q/Q142W/I222L/V229C, S27L/P20T/A117Q/I222L/V229C, S27L/T17Q/V23T/A24V/I222L/V229I, S27L/N2F/D249N/F250L, S27L/V23T/Q142L/I222L/V229C, S27L/P20E/A24D/D249S/F250V, S27L/A24D/S110K, S27L/T109R/I222L/V229I, S27L/P20E/F21Y/K197T, S27L/T17A/V23L/S101M/T109K/S110R/A114V/A117Q/T136V/V229I, S27L/P20T/F21W/Q142W/I222L/V229I, S27L/F21W/I222L/V229I, S27L/P20T/V23T/A24V/T109L/S110R/I222L/V229I, S27L/A24D/L191F/R251Q, S27L/A24D/T136S/F250V, S27L/P20T/F21W/T109L/T136A/Q142W/I222L/V229C, S27L/N2E/I169L/F250L/R251Q, S27L/N2S/A24N/G46E/A55L/Q142D/V229C/R251L, S27L/N2E/P20E/F250V/R251L, S27L/N2F/P20E, S27L/A24V/V229C, S27L/P20D/F21Y/G46N/S110K/T163I/Q167V, S27L/P20T/T109K/A114K/Q142W/I222L/V229C, S27L/T17Q/S101D/T136A/I222L/V229I, S27L/F21W/T109R/A117N/T136V/Q142W/I222L/V229C, S27L/A24D/T109L/K197L, S27L/T17Q/Q142L/I222L/V229I, S27L/T17A/A24V/S101D/S110R/T136A, S27L/P20T/F21W/T109R/A117Q/T136V/Q142L/I222L/V229I, S27L/P20T/F21W/T109K/A117N/I222L/V229C, S27L/P20T/S101M/I222L/V229I, S27L/N2S/A24D/S101Y/P164E/V165I/I185E, S27L/T17N/A117S/V229L/R251A, S27L/S101W/A114V/T136V/V229C, S27L/P20D/G46N/A55C/S110N/T163I/A184S, S27L/A24H/G46E, S27L/T17H/S101Q/T136V/Q142L/V229C and S27L/V23T/A24V/I222L/V229C.

In another aspect, the present disclosure relates to a nucleic acid encoding the variant Bhr-PETase enzyme of any one of the preceding claims. In another aspect, the present disclosure relates to an expression vector comprising the nucleic acid. In another aspect, the present disclosure relates to a host cell comprising the expression vector. In some embodiments, the cell is bacteria, yeast or fungi.

In another aspect, the present disclosure relates to a method of making a variant Bhr-PETase enzyme comprising culturing the host cell described herein under conditions wherein said variant Bhr-PETase enzyme is produced, and recovering said variant Bhr-PETase enzyme.

In another aspect, the present disclosure relates to a method of pretreating PET, comprising a mechanical pretreatment, a thermo-mechanical pretreatment, and/or a chemical pretreatment of the PET prior to an enzymatic degradation of the PET. In some embodiments, the mechanical pretreatment comprises grinding of the PET into particles. In some embodiments, the thermo-mechanical pretreatment comprises extruding the PET at a temperature configured to amorphize and reduce crystallinity of the PET. In some embodiments, the chemical pretreatment comprises contacting the PET with an ionic liquid, strong acid, base, or solvent configured to reduce crystallinity or to change a surface structure of the PET.

In another aspect, the present disclosure relates to a method of degrading PET, comprising contacting the PET with the variant Bhr-PETase enzyme described herein. In some embodiments, the method further comprises pretreating the PET according to the method described herein. In some embodiments, the method degrades the PET in a mixed plastics composition. In some embodiments, the plastics composition comprises analog of PET, PET-like or PET substitute derived biologically or chemically. In some embodiments, the plastics composition comprises at least one selected from the group consisting of Polybutylene terephthalate (PBT), Polycabonate (PC), Polycaprolactone (PCL), Polyethylene Furanoate (PEF), and High Density Polyethylene (HDPE). In some embodiments, the method excludes sorting plastics to select PET from a mixture of plastics.

BRIEF DESCRIPTION OF THE DRAWINGS

FIG. 1 depicts the sequence of an exemplary wild type Bhr-PETase (also called G1P Bhr-PETase herein; SEQ ID NO:1).

FIGS. 2A-2I depicts the sequence alignment of the exemplary wild type Bhr-PETase (SEQ ID NO:1), wild type Lcc-PETase (SEQ ID NO:4), wild type Is-PETase (SEQ ID NO:6) and 20 exemplary homologs of Bhr-PETase. Figure also discloses SEQ ID NOS 8-34, respectively, in order of appearance.

FIG. 3 depicts % Sequence identity of the exemplary wild type Bhr-PETase (SEQ ID NO:1), wild type Lcc-PETase (SEQ ID NO:4), wild type Is-PETase (SEQ ID NO:6) and 20 exemplary homologs of Bhr-PETase w.r.t. wild type Bhr-PETase.

(FIG. 5 graph A) and at 72° C. (FIG. 5 graph B).

(FIG. 6 graph A) and at 72° C. (FIG. 6 graph B).

FIGS. 7A-D show the Bhr-PETase G1 variants with improved total activity and thermostability over Bhr-PETase G1P (wild type Bhr-PETase). A Bhr-PETase G1 variant with amino acid substitution S27L exhibited 1.80 fold improved total activity and 3.36 fold improved thermostability over Bhr-PETase G1P and therefore selected as Bhr-PETase G2P.

FIGS. 8A-B show the Bhr-PETase G1 variants with improved thermostability over Bhr-PETase G1P (wild type Bhr-PETase).

FIGS. 9A-AA show the Bhr-PETase G1 variants with improved total activity over Bhr-PETase G1P (wild type Bhr-PETase). FIGS. 9J-AA show the Bhr-PETase G2 variants with improved total activity over Bhr-PETase G2P (Bhr-PETase G1P with amino acid substitution S27L).

FIGS. 10A-B display particular variants of Bhr-PETase by position that demonstrate beneficial properties in total activity, and/or thermostability as displayed in FIGS. 7A-D, FIGS. 8A-B and FIGS. 9A-AA.

FIGS. 11A-B depict the wild type sequences of Bhr-PETase, Lcc-PETase, and Is-PETase, as well as starting nucleic acids and codon optimized sequences for expression in Bacteria, Yeast and Fungi.

DETAILED DESCRIPTION OF THE INVENTION

A. Introduction

The present invention is directed to enzymes that will hydrolyze polyethylene terephthalate (PET). PET is a polyester polymer created by the combination of two monomers: modified ethylene glycol and purified terephthalic acid. While plastics such as PET find literally thousands of uses in modem society, PET, is essentially non-degradable. As such, plastic pollution has contaminated the entire planet, which poses a number of significant issues for the planet and human health. PET can be recycled; however this still does not prevent major amounts of PET from being dumped into landfill and/or the ocean.

Plastics including PET are remarkably resistant to enzymatic degradation. There are two categories of PET hydrolases: (i) PET-modifying enzymes that limit the degradation only at the surface of PET without visible change by electron microscope observations and (ii) PET-degrading enzymes or PETases that can significantly degrade the inner block of PET (e.g., by at least 10%) with visible change by electron microscope observations. To date, a plethora of PET-modifying enzymes have been reported but they may not significantly degrade the body of PET and may not be applicable for biorecycling of PET. As is known in the art, there are a few enzyme types that show limited ability to degrade the inner block of PET. The first reported enzyme able to act on ester bonds of PET polymers was a cutinase from *Thermobifida fusca* in 2005. Subsequent work identified additional enzymes, including a PET-hydrolyzing enzyme from *Ideonella sakaiensis*, Is-PETase, in 2016 and a leaf branch compost cutinase (Lcc-PETase) in 2012. While these PETases show activity at ambient temperatures, these enzymes are not particularly thermostable and do not show robust PET degradation.

PET exists both as an amorphous and as a semi-crystalline material. Chain mobility may be increased in the amorphous phase around PET's glass transition temperature Tg (around 70° C.), which allows better access to ester linkages and hence faster degradation. The reaction temperature around Tg may be controlled to achieve efficient enzymatic PET degradation. In addition, the physical aging process of PET at around 70° C. may convert the mobile amorphous fraction to recalcitrant microstructures which hinders further enzymatic hydrolysis of PET. Therefore, a thermostable and thermoactive PETase is desirable to allow the degradation reaction to occur at around glass transition temperature and overcome the competing physical aging process.

Figure 4:
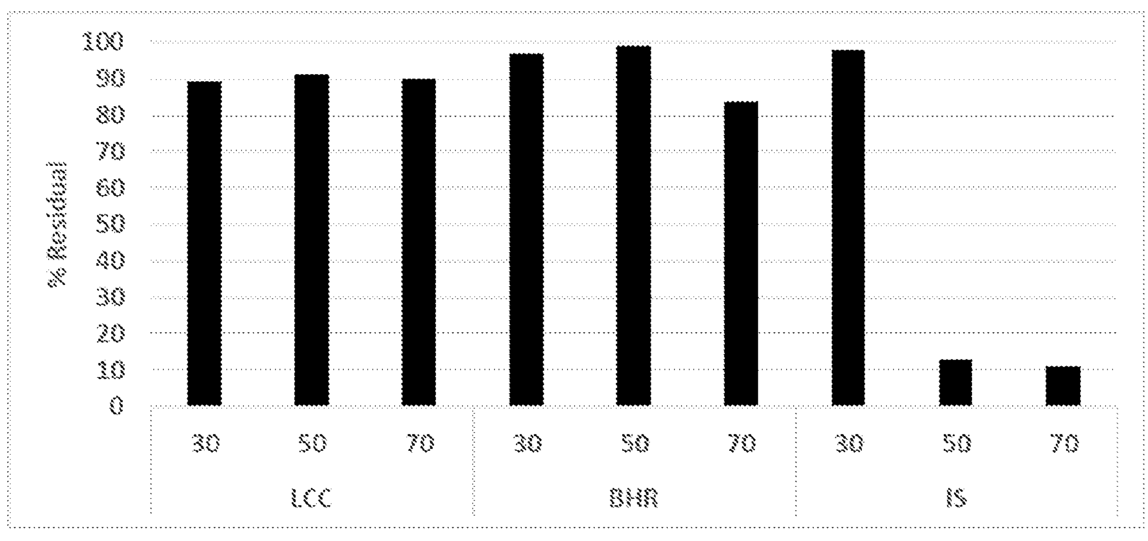
FIG. 4 depicts the comparison of thermostability between three wild type enzymes Lcc-PETase, Bhr-PETase and Is-PETase.
Figure 5:
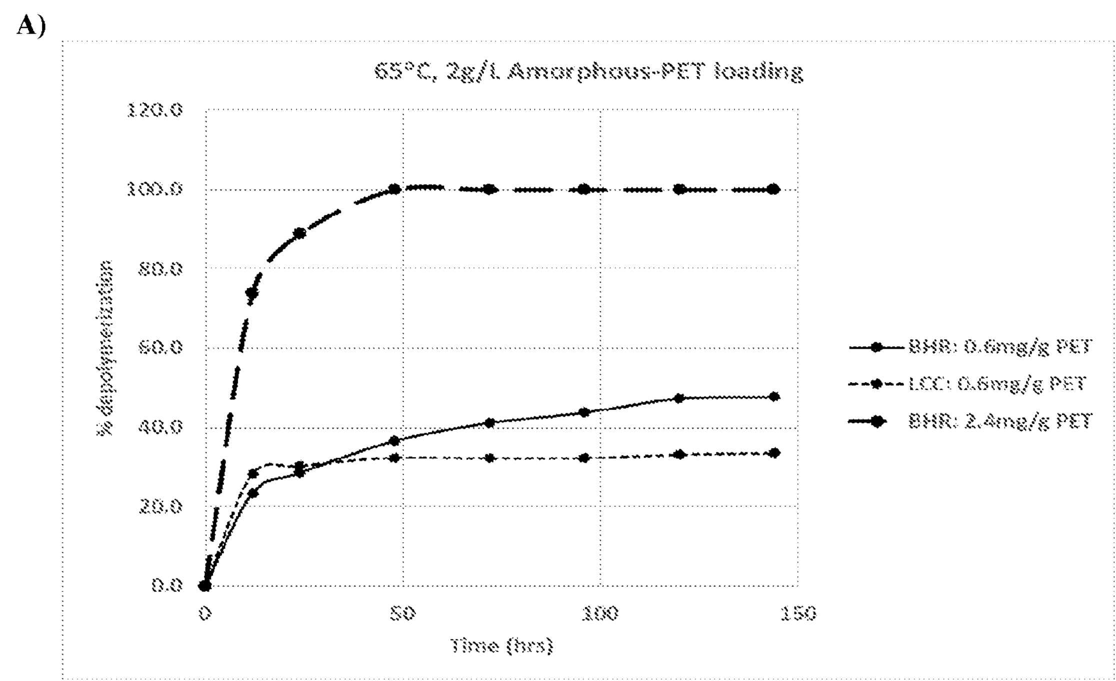
FIG. 5 depicts the comparison of Bhr-PETase and Lcc-PETase on amorphous PET at 65° C.
Figure 5:
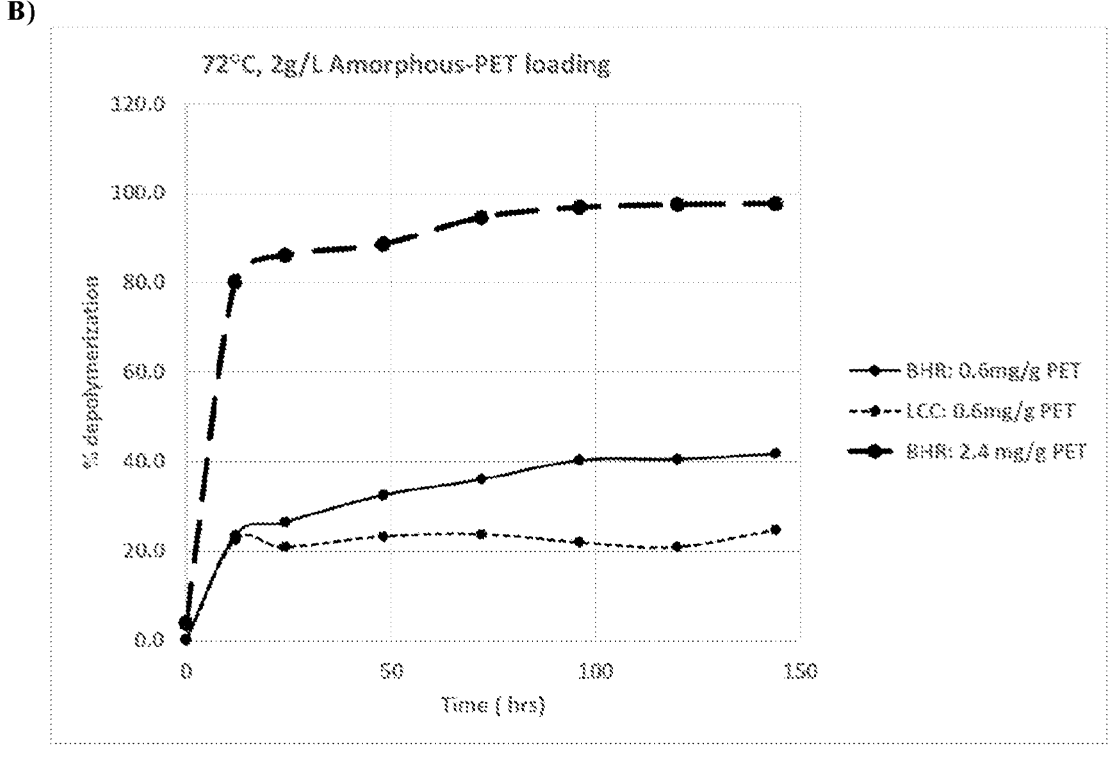
Figure 6:
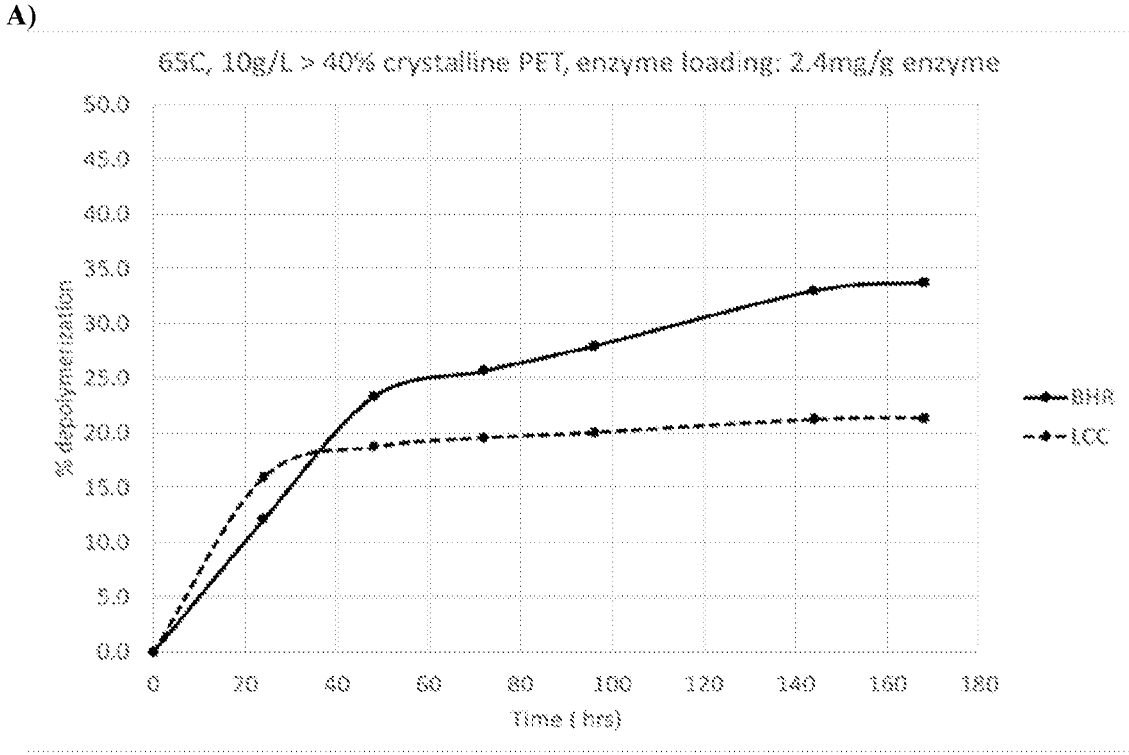
FIG. 6 depicts the comparison of Bhr-PETase and Lcc-PETase on >40% crystalline PET at 65° C.
Figure 6:
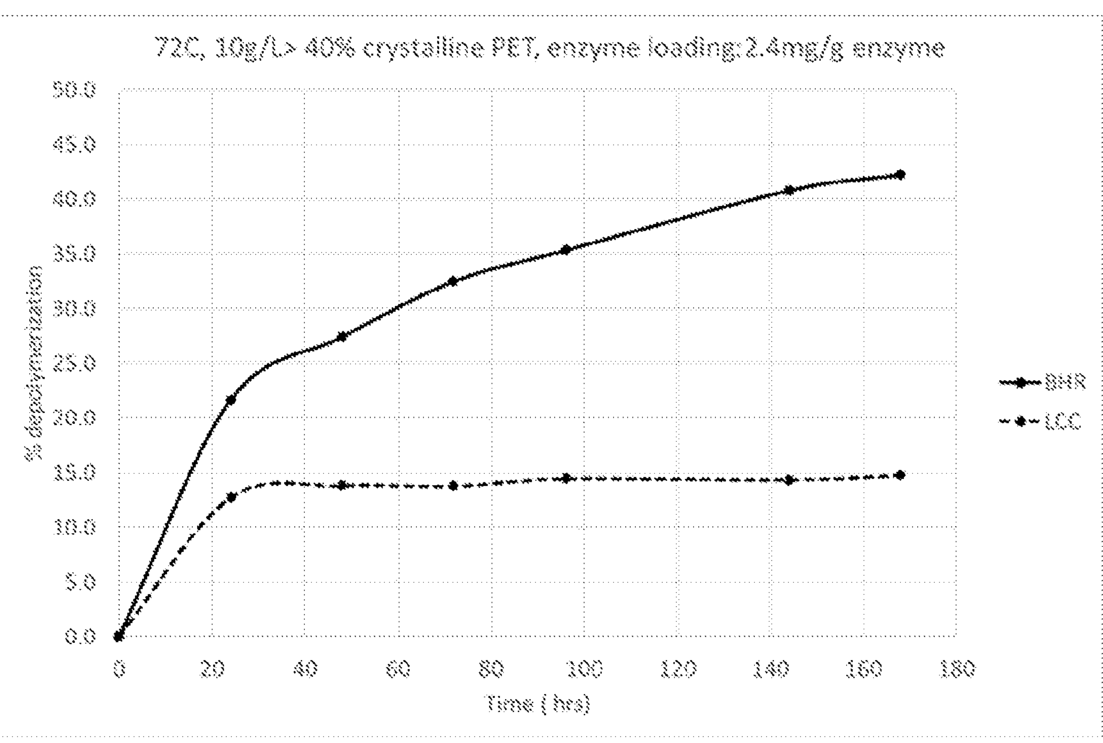

As shown in FIGS. 4, 5 and 6, although wild type Bhr-PETase is a close homolog of Lcc-PETase, sharing 94% sequence identity between the two enzymes, it is found to be more thermostable and thermoactive than Lcc-PETase, as well as Is-PETase. Thermostability and thermosactivity are key factors for efficient PET degradation. The present disclosure relates to variants of a PETase from the bacterium HR29 (Bhr-PETase) that have been engineered to exhibit even greater activity and thermostability. The outstanding thermostability and high PET hydrolyzing thermoactivity of Bhr-PETase variants render them great potentials for further analysis and industrial applications.

B. Definitions

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g. the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution S27L refers to a variant polypeptide, in this case a PETase, in which the serine (S) at position 27 is replaced with leucine L. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "amino acid insertion" or "insertion" as used herein is meant the addition of an amino acid sequence at a particular position in a parent polypeptide sequence. For example, −233E or 233E designates an insertion of glutamic acid after position 233 and before position 234. Additionally, −233ADE or A233ADE designates an insertion of AlaAspGlu after position 233 and before position 234.

By "amino acid deletion" or "deletion" as used herein is meant the removal of an amino acid sequence at a particular position in a parent polypeptide sequence. For example, F250− or F250 #, F250( ) or F250del designates a deletion of glutamic acid at position 250. Additionally, FRS250− or FRS250 #designates a deletion of the sequence PheArgSer that begins at position 250.

By "parent polypeptide" as used herein is meant a starting polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. In the present case, some embodiments utilize an exemplary wild-type Bhr-PETase (also called G1P Bhr-PETase; SEQ ID NO: 1; sequence shown in FIG. 1) as the parent polypeptide.

By "variant protein" or "protein variant", or "variant" as used herein is meant a protein that differs from that of a parent protein by virtue of at least one amino acid modification. Protein variant may refer to the protein itself, a composition comprising the protein, or the amino sequence that encodes it. Preferably, the protein variant has at least one amino acid modification compared to the parent protein, e.g. from about one to about seventy amino acid modifications, and preferably from about one to about five amino acid modifications compared to the parent. As described below, in some embodiments the parent polypeptide is a wild type sequence, for example the exemplary wild type Bhr-PETase designated "G1P" herein. As further discussed below, the protein variant sequence herein will preferably possess at least about 80, 81, 82, 83, 84, 84, 85, 86, 87, 88, 89, 90, 91, 92, 93, 94, 95, 96, 97, 98, 99 or 100% identity with a parent protein sequence, preferably at least about 90% identity, and preferably at least about 95-98-99% identity. Variant protein can refer to the variant protein itself, compositions comprising the protein variant, or the DNA sequence that encodes it. Thus, by "variant PETase" herein is meant a novel PETase that has at least one amino acid modification in the amino acid sequence as compared to a parent PETase enzyme. Unless otherwise noted or as will be obvious from the context, the variant PETases of the invention generally are compared to the wild type G1P sequence. Additionally, unless otherwise noted, the variant PETases of the invention are enzymatically active, that is, there is detectable PETase activity using the PETase assay described in Example 9.

As used herein, "protein" herein is meant at least two covalently attached amino acids, which includes proteins, polypeptides, oligopeptides and peptides. The peptidyl group generally comprise naturally occurring amino acids and peptide bonds. In addition, polypeptides may include synthetic derivatization of one or more side chains or termini, glycosylation, PEGylation, circular permutation, cyclization, linkers to other molecules, fusion to proteins or protein domains, and addition of peptide tags or labels.

By "residue" as used herein is meant a position in a protein and its associated amino acid identity. For example, Serine 27 (also referred to as Ser27 or S27) is a residue at position 27 in the G1P parental enzyme.

By "non-naturally occurring modification" as used herein is meant an amino acid modification that is not found in the parent (e.g. G1P) enzyme in nature.

By "amino acid" and "amino acid identity" as used herein is meant one of the 20 naturally occurring amino acids that are coded for by DNA and RNA.

By "position" as used herein is meant a location in the sequence of a protein. In general, the position number (which is more fully discussed below) is relative to the first amino acid of the mature PETase sequence, e.g. excluding the signal peptide.

By "PETase" herein is meant a protein with PETase activity. By "PETase activity" herein is meant that in the absence of MHTase, the enzyme catalyzes the hydrolysis of PET to mono(hydroxyethyl)terephthalate (MHET) as the major product. In the presence of MHTase, which is the case of Example 9, MHTase will further convert MHET to terephthalic acid (TPA) and ethylene glycol (EG) as the major products of the enzymatic reaction. Enzymes having detectable PETase activity in the assay outlined below and in Example 9 are considered PETases herein. The PETase activity may be measured as PETase total activity and/or PETase thermostability as described herein.

By "identity" in reference to two sequences herein is meant that the same amino acid is at the same position considering the alignment. The degree of identity between an amino acid sequence of the present invention ("invention sequence") and the parent amino acid sequence referred to in the claims (e.g. for G1P, SEQ ID NO:1) is calculated as the number of exact matches in an alignment of the two sequences, divided by the length of the "invention sequence," or the length of the SEQ ID NO:1, whichever is the shortest. The result is expressed in percent identity as calculated below.

For purposes of the present invention, the mature polypeptide disclosed in SEQ ID NO:1 is used to determine the corresponding amino acid residue in another PETase of the present invention. The amino acid sequence of another PETase is aligned with the mature polypeptide disclosed in SEQ ID NO:1, and based on the alignment, the amino acid position number corresponding to any amino acid residue in the mature polypeptide disclosed in SEQ ID NO:1 is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another PETase can be determined by an alignment of multiple polypeptide sequences using several computer programs including, but not limited to, MUSCLE (multiple sequence comparison by log-expectation; version 3.5 or later; Edgar, 2004, Nucleic Acids Research 32: 1792-1797), MAFFT (version 6.857 or later; Katoh and Kuma, 2002, Nucleic Acids Research 30: 3059-3066; Katoh et al., 2005, Nucleic Acids Research 33: 51 1-518; Katoh and Toh, 2007, Bioinformatics 23: 372-374; Katoh et al., 2009, Methods in Molecular Biology 537: 39-64; Katoh and Toh, 2010, Bioinformatics 26: 1899-1900), EMBOSS EMMA employing ClustalW (1.83 or later; Thompson et al., 1994, Nucleic Acids Research 22: 4673-4680), and EMBL-EBI employing Clustal Omega (Sievers and Higgins, 2014, Methods Mol Biol. 2014; 1079:105-16), using their respective default parameters.

When the other enzyme has diverged from the polypeptide of SEQ ID NO:1 such that traditional sequence-based comparison fails to detect their relationship (Lindahl and Elofsson, 2000, J. Mol. Biol. 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, Nucleic Acids Res. 25: 3389-3402). Even greater sensitivity can be achieved if the family or superfamily for the polypeptide has one or more representatives in the protein structure databases. Programs such as GenTHREADER (Jones, 1999, J. Mol. Biol. 287: 797-815; McGuffin and Jones, 2003, Bioinformatics 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, J. Mol. Biol. 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, Proteins 33: 88-96) or combinatorial extension (Shindyalov and Bourne, 1998, Protein Engineering 11: 739-747), and implementation of these algorithms can additionally be utilized to query structure databases with a structure of interest in order to discover possible structural homologs (e.g., Holm and Park, 2000, Bioinformatics 16: 566-567).

In describing the variants of the present invention, the nomenclature described below is adapted for ease of reference. The standardly accepted IUPAC single letter or three letter amino acid abbreviation is employed.

For an amino acid substitution, the following nomenclature is used herein: Original amino acid, position, substituted amino acid. Accordingly, the substitution of serine at position 27 with leucine is designated as "Ser27Leu" or "S27L". Multiple mutations are separated by forward slash marks ("/"), e.g., "A102V/T136M", representing substitutions at positions 102 and 136, respectively.

| Abbreviatio | 1 letter | Amino acid | Abbreviation | 1 letter | Amino acid name |
|---|---|---|---|---|---|
| Ala | A | Alanine | Leu | L | Leucine |
| Arg | R | Arginine | Lys | K | Lysine |
| Asn | N | Asparagine | Met | M | Methionine |
| Asp | D | Aspartic acid | Phe | F | Phenylalanine |
| Cys | C | Cysteine | Pro | P | Proline |
| Gln | Q | Glutamine | Ser | S | Serine |
| Glu | E | Glutamic acid | Thr | T | Threonine |
| Gly | G | Glycine | Trp | W | Tryptophan |
| His | H | Histidine | Tyr | Y | Tyrosine |
| Ile | I | Isoleucine | Val | V | Valine |

By "isolated" in the context of a PETase herein is meant that the polypeptide is devoid of other proteins. In a particular embodiment the PETase of the invention is isolated. The term "isolated" as used herein refers to a polypeptide which is at least 20% pure, preferably at least 40% pure, more preferably at least 60% pure, even more preferably at least 80% pure, most preferably at least 90% pure, and even most preferably at least 95 to 98% pure, as determined by SDS-PAGE. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

By "recombinant enzyme" herein is meant that the enzyme is produced by recombinant techniques and that nucleic acid encoding the enzyme of the invention is operably linked to at least one exogeneous (e.g. not native to the parent PETase) sequence, including, for examples, promoters, terminators, signal sequences, etc., as are more fully outlined below.

The term "nucleic acid construct" refers to a nucleic acid molecule, either single-stranded or double-stranded, which is isolated from a naturally occurring gene or is modified to contain segments of nucleic acids in a manner that would not otherwise exist in nature or which is synthetic, and which comprises one or more control sequences.

The term "operably linked" refers to a configuration in which a control sequence is placed at an appropriate position relative to the coding sequence of a polynucleotide such that the control sequence directs expression of the coding sequence.

As used herein, the term "about" means modifying, for example, lengths of nucleotide sequences, degrees of errors, dimensions, the quantity of an ingredient in a composition, concentrations, volumes, process temperature, process time, yields, flow rates, pressures, and like values, and ranges thereof, refers to variation in the numerical quantity that may occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of, for example, a composition, formulation, or cell culture with a particular initial concentration or mixture, and amounts that differ due to mixing or processing a composition or formulation with a particular initial concentration or mixture. Whether modified by the term "about" the claims appended hereto include equivalents to these quantities. The term "about" further may refer to a range of values that are similar to the stated reference value. In certain embodiments, the term "about" refers to a range of values that fall within 10, 9, 8, 7, 6, 5, 4, 3, 2, 1 percent or less of the stated reference value.

C. PETases of the Invention

Accordingly, the present invention provides variant PETases with improved enzymatic activity that can be used in a variety of applications, most notably in the degradation of plastics made from PET.

In general, the variant PETases of the invention have modified, improved biochemical properties as compared to the wild type Bhr-PETase, "G1P" (i.e. "Generation 1 Parent"), SEQ ID NO:1 herein, as shown in FIG. 1. The variant PETases of the invention can also have modified, improved biochemical properties as compared to the "G2P" (i.e. "Generation 2 Parent"), which has amino acid substitution S27L. The biochemical properties of the variant PETases that can be improved herein include, but are not limited to, thermostability, thermoactivity, specific activity, and production.

The variant Bhr-PETases of the invention have one or more improved properties as compared to G1P or G2P. By "improved" herein is meant a desirable change of at least one biochemical property. "Improved function" can be measured as a percentage increase or decrease of a particular activity, or as a "fold" change, with increases of desirable properties (e.g. activity or thermostability). That is, a variant Bhr-PETase may have a 10% increase in thermostability or a 10% increase in PETase activity, as compared to G1P or G2P. In general, percentage changes are used to describe changes in biochemical activity of less than 100%, and fold-changes are used to describe changes in biochemical activity of greater than 100% (as compared to the parental enzyme, in many cases G1P or G2P). In the present invention, percentage changes (usually increases) of biochemical activity of at least about 10%, 20%, 30%, 40%, 50%, 60%, 70%, 80%, 90%, 95%, 98% and 99% can be accomplished. In the present invention, a "fold increase" (or decrease) is measured as compared to the starting or parent enzyme. For example, as shown in the FIGS. 9A-AA, the variant T17A/S27T/T48S/I82L/L90F/Q167V/P213N/S252T has 1.6 fold increase in specific activity as compared to G1P: this is calculated by [(activity of variant)/(activity of parent)]. In many embodiments, the improvement is at least 1.1 fold, 1.2 fold, 1.3 fold, 1.4 fold, 1.5 fold, 1.6 fold, 1.7 fold, 1.8 fold, 1.9 fold, 2 fold, 3 fold, 4 fold, 5 fold, 6 fold, 7 fold, 8 fold, 9 fold, or 10 fold or higher.

In general, improvements are measured as compared to the G1P or G2P enzyme using a Bhr-PETase activity assay, under conditions that challenge the variant Bhr-PETase against the G1P or G2P enzyme.

1. Total Activity Increases

The present invention provides variant Bhr-PETases that have total activity equal to or greater than the total activity of G1P (the wild type Bhr-PETase of SEQ ID NO:1) or G2P (G1P with amino acid substitution S27L). The "total activity" herein may be determined by monitoring the production of TPA (terephthalic acid) during the PET depolymerization reaction at an elevated temperature such as 65° C., quantified using a colorimetric assay or HPLC as described in Example 9. Any improvement in total activity may be due to the improvement of thermoactivity, specific activity, and/or production of the variant PETase.

In many embodiments, the variant Bhr-PETases have improved total activity that is at least 1.1 fold, 1.2 fold, 1.3 fold, 1.4 fold, 1.5 fold, 1.6 fold, 1.7 fold, 1.8 fold, 1.9 fold, 2 fold, 3 fold, 4 fold, 5 fold, 6 fold, 7 fold, 8 fold, 9 fold, or 10 fold or higher.

In general, improvements are measured as compared to the G1P or G2P enzyme using a Bhr-PETase activity assay, under conditions that challenge the variant Bhr-PETase against the G1P or G2P enzyme.

(i) Thermoactivity Increases

In one aspect, the variant Bhr-PETases may have increased thermoactivity. The "thermoactivity" herein may be determined by monitoring the production of TPA (terephthalic acid), MHET (mono(hydroxyethyl)terephthalate) and BHET (bis(2-hydroxyl) terephthalate during the PET depolymerization reaction at an elevated temperature such as 65° C., quantified in mg of equivalent TPA generated per h per mg of enzyme ($mg_{TPAeq.}$ $h^{-1}$ $mg_{enzyme}^{-1}$). Herein "Equivalent TPA" is calculated by a sum of TPA, MHET converted to TPA, BHET converted to TPA, and any other measurable oligomers converted to TPA. Thus, PETases that have increased activity per milligram of enzyme as compared to G1P (the wild type Bhr-PETase of SEQ ID NO:1) or G2P (G1P with amino acid substitution S27L) may show an improved thermoactivity.

In many embodiments, the variant Bhr-PETases have improved thermoactivity that is at least 1.1 fold, 1.2 fold, 1.3 fold, 1.4 fold, 1.5 fold, 1.6 fold, 1.7 fold, 1.8 fold, 1.9 fold, 2 fold, 3 fold, 4 fold, 5 fold, 6 fold, 7 fold, 8 fold, 9 fold, or 10 fold or higher.

In general, improvements are measured as compared to the G1P or G2P enzyme using a Bhr-PETase activity assay, under conditions that challenge the variant Bhr-PETase against the G1P or G2P enzyme.

(ii) Specific Activity Increases

In another aspect, the variant Bhr-PETases may have increased specific activity. The "specific activity" herein may be determined by monitoring the production of TPA (terephthalic acid), MHET (mono(hydroxyethyl)terephthalate) and BHET (bis(2-hydroxyl) terephthalate during the PET depolymerization reaction at the optimal operating temperature of Bhr-PETases, quantified in mg of equivalent TPA generated per h per mg of enzyme ($mg_{TPAeq.}$ $h^{-1}$ $mg_{enzyme}^{-1}$). Thus, PETases that have increased activity per milligram of enzyme as compared to G1P (the wild type Bhr-PETase of SEQ ID NO: 1) or G2P (G1P with amino acid substitution S27L) may show an improved specific activity.

In many embodiments, the variant Bhr-PETases have improved specific activity that is at least 1.1 fold, 1.2 fold, 1.3 fold, 1.4 fold, 1.5 fold, 1.6 fold, 1.7 fold, 1.8 fold, 1.9 fold, 2 fold, 3 fold, 4 fold, 5 fold, 6 fold, 7 fold, 8 fold, 9 fold, or 10 fold or higher. In some embodiments, the variant Bhr-PETases have increased equivalent TPA generated per h per mg of enzyme that is at least 1.1 fold, 1.2 fold, 1.3 fold, 1.4 fold, 1.5 fold, 1.6 fold, 1.7 fold, 1.8 fold, 1.9 fold, 2 fold, 3 fold, 4 fold, 5 fold, 6 fold, 7 fold, 8 fold, 9 fold, or 10 fold or higher.

In general, improvements are measured as compared to the G1P or G2P enzyme, under conditions that challenge the variant Bhr-PETase against the G1P or G2P enzyme.

(iii) Production Increases

In one aspect, the variant Bhr-PETases may have increased production. The "production" herein may be determined by monitoring the protein titer of Bhr-PETase in g/L. Thus, PETases that have increased quantity per liter of enzyme supernatant as compared to G1P (the wild type Bhr-PETase of SEQ ID NO:1) or G2P (G1P with amino acid substitution S27L) may show an improved production.

In many embodiments, the variant Bhr-PETases have improved thermoactivity that is at least 1.1 fold, 1.2 fold, 1.3 fold, 1.4 fold, 1.5 fold, 1.6 fold, 1.7 fold, 1.8 fold, 1.9 fold, 2 fold, 3 fold, 4 fold, 5 fold, 6 fold, 7 fold, 8 fold, 9 fold, or 10 fold or higher.

In general, improvements are measured as compared to the G1P or G2P enzyme using a Bhr-PETase activity assay, under conditions that challenge the variant Bhr-PETase against the G1P or G2P enzyme.

2. Thermostability

Additionally, as will be appreciated by those in the art, it can be desirable to run PET degradation at around the glass transition temperature. Amorphous PET domains will increase the mobility at around the glass transition temperature (around 67-72° C.), making it more accessible for enzyme hydrolysis. At higher temperatures above the transition temperature, the PET substrate will re-crystalize over time, which is not favorable for PET degradation. Therefore, for example, about 65-72° C. may be considered an optimal temperature range for PET degradation.

Accordingly, in many embodiments, the variant Bhr-PETases have improved thermostability. "Thermostability" in this context means that the variant enzymes are more stable than G1P (the wild type Bhr-PETase of SEQ ID NO:1) or G2P (G1P with amino acid substitution S27L) under the same thermal challenge conditions, that is, the activity of the variant is higher than that of the G1P or G2P enzyme under identical conditions (generally using an assay as outlined herein and as shown in Example 9).

In one embodiment, the variant Bhr-PETases are more stable than the G1P or G2P enzyme when exposed to temperatures of about 65, 66, 67, 68, 69, 70, 71, 72, 73, 74, 75, 76, 77, 78, 79, 80, 81, 82, 83, 84 and/or 85° C. for a period of time, for example ranging from about 0.5, 1, 2, 3, 4, 5, or 6 hour to about 5, 6, 7, 8, 9, 10 hours or longer, depending on the ultimate conditions for the use of the variant Bhr-PETase. In some embodiments, the variant Bhr-PETases are more stable than the G1P or G2P enzyme when exposed to temperatures preferably from about 65° C. to 85° C. for at least about 0.5 hour, preferably from about 65° C. to 72° C. for at least about 1 hour, preferably at least 65° C. for at least about 1 hour, preferably at least 70° C. for at least about 1.5 hour.

Accordingly, in many embodiments, the variant Bhr-PETases are more thermostable than the G1P or G2P enzyme by at least 1.1 fold, 1.2 fold, 1.3 fold, 1.4 fold, 1.5 fold, 1.6 fold, 1.7 fold, 1.8 fold, 1.9 fold, 2 fold, 3 fold, 4 fold, 5 fold, 6 fold, 7 fold, 8 fold, 9 fold, or 10 fold or higher.

In general, improvements are measured as compared to the G1P or G2P enzyme using a Bhr-PETase activity assay, under conditions that measure the variant Bhr-PETase or the G1P or G2P enzyme activity with and without thermal treatment.

3. PETase Assays

There are several PETase activity assays that can be used to determine activity, as generally outlined in Examples 6 and 9 for PET film-based assay, as well as in Example 5 for BHET-based assay. PETase activity can also be monitored by pNPB (p-Nitrophenyl Butyrate) assay. In pNPB assay, surrogate substrate p-nitrophenylbutyrate may be hydrolyzed by PETase to p-nitrophenol and butyric acid. The release of p-nitrophenol directly correlates to PETase activity and can be determined spectrophotometrically at 405 nm, for example.

4. Bhr-PETases

The present invention provides a number of specific variant Bhr-PETases with improved activity and/or thermostability for use in the degradation of PET.

In some embodiments, the variant Bhr-PETase has one or more amino acid substitutions at a position (relative to G1P, SEQ ID NO:1) selected from the group consisting of 27, 1, 2, 5, 9, 12, 13, 14, 15, 16, 17, 18, 20, 21, 22, 23, 24, 25, 26, 30, 32, 33, 34, 40, 46, 48, 49, 53, 54, 55, 56, 57, 60, 62, 68, 70, 72, 74, 77, 82, 83, 85, 87, 88, 90, 92, 97, 98, 101, 102, 105, 108, 109, 110, 113, 114, 117, 119, 121, 122, 125, 127, 135, 136, 138, 139, 140, 142, 143, 145, 147, 149, 150, 153, 156, 157, 158, 160, 161, 162, 163, 164, 167, 170, 173, 174, 177, 179, 181, 182, 184, 185, 189, 190, 193, 194, 195, 198, 200, 203, 204, 206, 208, 209, 211, 212, 213, 216, 217, 218, 219, 221, 222, 223, 225, 227, 228, 229, 231, 236, 237, 241, 242, 243, 246, 249, 250, 251, 252, 253, 254, 255, 258, 8, 31, 38, 95, 126, 137, 165, 169, 172, 191, 192 and 197. In some embodiments, the variant Bhr-PETase has 1, 2, 3, 4, 5, 6, 7, 8, 9, 10 or more amino acid substitutions at a position (relative to G1P, SEQ ID NO:1) selected from the same group.

In some embodiments, the variant Bhr-PETase has one more amino acid substitutions selected from the group consisting of S27L, S27F, S27H, S27T, S27W, S1A, S1G, S1M, S1R, N2E, N2F, N2L, N2R, N2S, Q5E, N9A, N9E, N9S, R12K, S13L, S13R, A14K, A14S, L15I, T16E, T17A, T17C, T17G, T17H, T17I, T17K, T17L, T17M, T17N, T17Q, T17R, T17S, D18R, P20D, P20E, P20I, P20Q, P20T, F21W, F21Y, S22A, S22I, S22K, S22P, S22R, S22V, V23L, V23T, A24D, A24G, A24H, A24N, A24S, A24T, A24V, T25A, T25F, T25H, T25Q, T25R, T25V, Y26C, Y26K, Y26L, Y26T, R30K, S32K, S32M, S32Q, S32Y, V33G, V33Q, V33T, S34R, V40T, G46E, G46L, G46N, G46R, G46S, T48N, T48S, L49G, G53A, I54V, A55C, A55I, A55L, A55M, A55T, A55V, M56I, M56L, S57C, S57E, S57F, S57I, S57L, S57M, S57T, S57V, Y60A, Y60H, Y60I, A62T, A68F, L70M, R72P, L74W, H77Q, I82F, I82L, I82M, V83I, V83L, V83T, N85D, N87F, N87H, N87I, N87K, N87L, N87M, N87Q, N87R, N87V, N87W, N87Y, S88K, S88T, L90F, L90K, L90Y, F92G, F92I, F92K, F92L, F92N, F92Q, F92V, F92Y, A97C, A97E, A97F, A97G, A97L, A97P, A97Q, A97S, A97T, A97V, S98A, S98D, S98E, S98L, S98M, S98N, S98Q, S98T, S98V, S101A, S101C, S101D, S101F, S101H, S101K, S101L, S101M, S101N, S101Q, S101R, S101V, S101W, S101Y, A102V, N105D, R108C, R108E, R108H, R108K, R108N, R108P, R108Q, R108S, R108T, R108V, T109A, T109F, T109G, T109K, T109L, T109N, T109R, T109Y, SHOD, S110G, S110H, S110K, S110N, S110R, S113A, S113K, S113N, S113P, S113Q, S113R, S113T, S113Y, A114K, A114L, A114S, A114V, A117F, A117G, A117L, A117N, A117Q, A117S, A117T, A117Y, L119I, L119M, A121S, N122A, N122E, N122H, N122P, N122R, N122S, A125S, A127M, A127S, A127V, A135G, T136A, T136M, T136S, T136V, R138E, R138L, I139A, I139T, S140A, Q142D, Q142E, Q142H, Q142L, Q142W, I143N, I143R, T145S, K147F, K147G, K147N, K147Q, G149A, G149C, G149D, G149N, G149S, G149T, G149V, V150I, V150L, T153L, H156N, T157A, T157G, D158E, D158I, D158K, D158L, T160K, T160Q, T160R, T160S, T160V, F161V, F161W, N162E, N162H, N162P, N162R, T163I, T163S, P164E, P164H, P164N, P164R, P164S, P164T, Q167I, Q167T, Q167V, V170L, E173R, A174K, A174R, V177A, P179Q, S181A, S181C, S181R, Q182T, A184C, A184G, A184S, I185A, I185E, I185G, I185L, I185Q, I185R, I185S, I185Y, Q189I, Q189L, Q189V, N190S, S193E, S193F, S193H, S193K, S193N, S193P, S193T, S193V, T194G, T194S, T195F, V198A, V200L, D203N, D203R, D203V, N204A, N204K, N204R, N204S, T206G, T206K, T206L, T206P, T206R, F208G, F208L, F208R, F208T, A209V, N211F, N211I, N211L, N211M, N211V, S212F, S212L, S212M, P213N, P213R, A216L, A216P, A216S, A216T, A216V, I217S, S218A, V219F, V219I, V219K, V219L, V219R, T221S, I222L, S223A, S223C, M225L, L227R, W228F, V229C, V229I, V229L, N231L, N231Q, N231S, R236C, R236E, R236H, R236K, R236Q, Q237R, N241P, V242T, N243P, A246D, A246K, A246S, A246T, D249I, D249M, D249N, D249S, D249T, F250I, F250L, F250V, F250Y, R251A, R251E, R251I, R251K, R251L, R251Q, R251T, R251V, S252T, N253S, N253Y, N254R, R255E, R255G, R255L, R255M, R255S, R255V, R255W, R255Y, Q258P, P8T, L31M, G38D, S95N, V126I, L137M, V165I, I169C, I169L, I169V, A172T, L191F, L191V, P192A, K197L, K197R, K197T, K197V and K197Y. In some embodiments, the variant Bhr-PETase has 1, 2, 3, 4, 5, 6, 7, 8, 9, 10 or more amino acid substitutions selected from the same group.

In some embodiments, the variant Bhr-PETase has an amino acid substitution of the serine at position 27 of SEQ ID NO: 1. In some embodiments, the substitution is with any other of the 19 naturally occurring amino acids, namely threonine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is S27L. In some embodiments, the amino acid substitution is S27F. In some embodiments, the amino acid substitution is S27H. In some embodiments, the amino acid substitution is S27T. In some embodiments, the amino acid substitution is S27W.

In some embodiments, the variant Bhr-PETase has an amino acid substitution of the serine at position 1 of SEQ ID NO:1. In some embodiments, the substitution is with any other of the 19 naturally occurring amino acids, namely threonine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is SIA. In some embodiments, the amino acid substitution is S1G. In some embodiments, the amino acid substitution is S1M. In some embodiments, the amino acid substitution is S1R.

In some embodiments, the variant Bhr-PETase has an amino acid substitution of the asparagine at position 2 of SEQ ID NO:1. In some embodiments, the substitution is with any other of the 19 naturally occurring amino acids, namely serine, threonine, glutamine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is N2E. In some embodiments, the amino acid substitution is N2F. In some embodiments, the amino acid substitution is N2L. In some embodiments, the amino acid substitution is N2R. In some embodiments, the amino acid substitution is N2S.

In some embodiments, the variant Bhr-PETase has an amino acid substitution of the glutamine at position 5 of SEQ ID NO: 1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is Q5E.

In some embodiments, the variant Bhr-PETase has an amino acid substitution of the asparagine at position 9 of SEQ ID NO: 1. In some embodiments, the substitution is with any other of the 19 naturally occurring amino acids, namely serine, threonine, glutamine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is N9A. In some embodiments, the amino acid substitution is N9E. In some embodiments, the amino acid substitution is N9S.

In some embodiments, the variant Bhr-PETase has an amino acid substitution of the arginine at position 12 of SEQ ID NO:1. In some embodiments, the substitution is with any other of the 19 naturally occurring amino acids, namely serine, threonine, glutamine, asparagine, lysine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is R12K.

In some embodiments, the variant Bhr-PETase has an amino acid substitution of the serine at position 13 of SEQ ID NO: 1. In some embodiments, the substitution is with any other of the 19 naturally occurring amino acids, namely threonine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is S13L. In some embodiments, the amino acid substitution is S13R.

In some embodiments, the variant Bhr-PETase has an amino acid substitution of the alanine at position 14 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is A14K. In some embodiments, the amino acid substitution is A14S.

In some embodiments, the variant Bhr-PETase has an amino acid substitution of the leucine at position 15 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, methionine, phenylalanine, tryptophan, valine and tyrosine, with some embodiments not utilizing cysteine (due to possible disulfide formation) or proline (due to steric effects). In some embodiments, the amino acid substitution is L15I.

In some embodiments, the variant Bhr-PETase has an amino acid substitution of the threonine at position 16 of SEQ ID NO:1. In some embodiments, the substitution is with any other of the 19 naturally occurring amino acids, namely serine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is T16E.

In some embodiments, the variant Bhr-PETase has an amino acid substitution of the threonine at position 17 of SEQ ID NO:1. In some embodiments, the substitution is with any other of the 19 naturally occurring amino acids, namely serine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing proline (due to steric effects). In some embodiments, the amino acid substitution is T17A. In some embodiments, the amino acid substitution is T17C. In some embodiments, the amino acid substitution is T17G. In some embodiments, the amino acid substitution is T17H. In some embodiments, the amino acid substitution is T17I. In some embodiments, the amino acid substitution is T17K. In some embodiments, the amino acid substitution is T17L. In some embodiments, the amino acid substitution is T17M. In some embodiments, the amino acid substitution is T17N. In some embodiments, the amino acid substitution is T17Q. In some embodiments, the amino acid substitution is T17R. In some embodiments, the amino acid substitution is T17S.

In some embodiments, the variant Bhr-PETase has an amino acid substitution of the aspartic acid at position 18 of SEQ ID NO:1. In some embodiments, the substitution is with any other of the 19 naturally occurring amino acids, namely serine, threonine, glutamine, asparagine, lysine, arginine, histidine, glutamic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is D18R.

In some embodiments, the variant Bhr-PETase has an amino acid substitution of the proline at position 20 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, alanine, isoleucine, leucine, methionine, phenylalanine, tryptophan, valine and tyrosine, with some embodiments not utilizing cysteine (due to possible disulfide formation). In some embodiments, the amino acid substitution is P20D. In some embodiments, the amino acid substitution is P20E. In some embodiments, the amino acid substitution is P20I. In some embodiments, the amino acid substitution is P20Q. In some embodiments, the amino acid substitution is P20T.

In some embodiments, the variant Bhr-PETase has an amino acid substitution of the phenylalanine at position 21 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, tryptophan, valine and tyrosine, with some embodiments not utilizing cysteine (due to possible disulfide formation) or proline (due to steric effects). In some embodiments, the amino acid substitution is F21W. In some embodiments, the amino acid substitution is F21Y.

In some embodiments, the variant Bhr-PETase has an amino acid substitution of the serine at position 22 of SEQ ID NO: 1. In some embodiments, the substitution is with any other of the 19 naturally occurring amino acids, namely threonine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation). In some embodiments, the amino acid substitution is S22A. In some embodiments, the amino acid substitution is S22I. In some embodiments, the amino acid substitution is S22K. In some embodiments, the amino acid substitution is S22P. In some embodiments, the amino acid substitution is S22R. In some embodiments, the amino acid substitution is S22V.

In some embodiments, the variant Bhr-PETase has an amino acid substitution of the valine at position 23 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, phenylalanine, tryptophan and tyrosine, with some embodiments not utilizing cysteine (due to possible disulfide formation) or proline (due to steric effects). In some embodiments, the amino acid substitution is V23L. In some embodiments, the amino acid substitution is V23T.

In some embodiments, the variant Bhr-PETase has an amino acid substitution of the alanine at position 24 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is A24D. In some embodiments, the amino acid substitution is A24G. In some embodiments, the amino acid substitution is A24H. In some embodiments, the amino acid substitution is A24N. In some embodiments, the amino acid substitution is A24S. In some embodiments, the amino acid substitution is A24T. In some embodiments, the amino acid substitution is A24V.

In some embodiments, the variant Bhr-PETase has an amino acid substitution of the threonine at position 25 of SEQ ID NO:1. In some embodiments, the substitution is with any other of the 19 naturally occurring amino acids, namely serine, glutamine, asparagine, arginine, histidine, glutamic acid, aspartic acid, cysteine, glycine, proline, alanine, isoleucine, leucine, lysine, methionine, phenylalanine, tryptophan, valine and tyrosine, with some embodiments not utilizing cysteine (due to possible disulfide formation) or proline (due to steric effects). In some embodiments, the amino acid substitution is T25A. In some embodiments, the amino acid substitution is T25F. In some embodiments, the amino acid substitution is T25H. In some embodiments, the amino acid substitution is T25Q. In some embodiments, the amino acid substitution is T25R. In some embodiments, the amino acid substitution is T25V.

In some embodiments, the variant Bhr-PETase has an amino acid substitution of the tyrosine at position 26 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, phenylalanine, tryptophan and valine, with some embodiments not utilizing proline (due to steric effects). In some embodiments, the amino acid substitution is Y26C. In some embodiments, the amino acid substitution is Y26K. In some embodiments, the amino acid substitution is Y26L. In some embodiments, the amino acid substitution is Y26T.

In some embodiments, the variant Bhr-PETase has an amino acid substitution of the arginine at position 30 of SEQ ID NO:1. In some embodiments, the substitution is with any other of the 19 naturally occurring amino acids, namely serine, threonine, glutamine, asparagine, lysine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is R30K.

In some embodiments, the variant Bhr-PETase has an amino acid substitution of the serine at position 32 of SEQ ID NO:1. In some embodiments, the substitution is with any other of the 19 naturally occurring amino acids, namely threonine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is S32K. In some embodiments, the amino acid substitution is S32M. In some embodiments, the amino acid substitution is S32Q. In some embodiments, the amino acid substitution is S32Y.

In some embodiments, the variant Bhr-PETase has an amino acid substitution of the valine at position 33 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, phenylalanine, tryptophan and tyrosine, with some embodiments not utilizing cysteine (due to possible disulfide formation) or proline (due to steric effects). In some embodiments, the amino acid substitution is V33G. In some embodiments, the amino acid substitution is V33Q. In some embodiments, the amino acid substitution is V33T.

In some embodiments, the variant Bhr-PETase has an amino acid substitution of the serine at position 34 of SEQ ID NO: 1. In some embodiments, the substitution is with any other of the 19 naturally occurring amino acids, namely threonine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is S34R.

In some embodiments, the variant Bhr-PETase has an amino acid substitution of the valine at position 40 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, phenylalanine, tryptophan and tyrosine, with some embodiments not utilizing cysteine (due to possible disulfide formation) or proline (due to steric effects). In some embodiments, the amino acid substitution is V40T.

In some embodiments, the variant Bhr-PETase has an amino acid substitution of the glycine at position 46 of SEQ ID NO: 1. In some embodiments, the substitution is with any other of the 19 naturally occurring amino acids, namely serine, threonine, glutamine, asparagine, lysine, arginine, histidine, glutamic acid, aspartic acid, cysteine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is G46E. In some embodiments, the amino acid substitution is G46L. In some embodiments, the amino acid substitution is G46N. In some embodiments, the amino acid substitution is G46R. In some embodiments, the amino acid substitution is G46S.

In some embodiments, the variant Bhr-PETase has an amino acid substitution of the threonine at position 48 of SEQ ID NO: 1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is T48N. In some embodiments, the amino acid substitution is T48S.

In some embodiments, the variant Bhr-PETase has an amino acid substitution of the leucine at position 49 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, methionine, phenylalanine, tryptophan, valine and tyrosine, with some embodiments not utilizing cysteine (due to possible disulfide formation) or proline (due to steric effects). In some embodiments, the amino acid substitution is L49G.

In some embodiments, the variant Bhr-PETase has an amino acid substitution of the glycine at position 53 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is G53A.

In some embodiments, the variant Bhr-PETase has an amino acid substitution of the isoleucine at position 54 of SEQ ID NO: 1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, leucine, methionine, phenylalanine, tryptophan, valine and tyrosine, with some embodiments not utilizing cysteine (due to possible disulfide formation) or proline (due to steric effects). In some embodiments, the amino acid substitution is I54V.

In some embodiments, the variant Bhr-PETase has an amino acid substitution of the alanine at position 55 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, isoleucine, leucine, methionine, phenylalanine, tryptophan, valine and tyrosine, with some embodiments not utilizing proline (due to steric effects). In some embodiments, the amino acid substitution is A55C. In some embodiments, the amino acid substitution is A55I. In some embodiments, the amino acid substitution is A55L. In some embodiments, the amino acid substitution is A55M. In some embodiments, the amino acid substitution is A55T. In some embodiments, the amino acid substitution is A55V.

In some embodiments, the variant Bhr-PETase has an amino acid substitution of the methionine at position 56 of SEQ ID NO: 1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, phenylalanine, tryptophan, valine and tyrosine, with some embodiments not utilizing cysteine (due to possible disulfide formation) or proline (due to steric effects). In some embodiments, the amino acid substitution is M56I. In some embodiments, the amino acid substitution is M56L.

In some embodiments, the variant Bhr-PETase has an amino acid substitution of the serine at position 57 of SEQ ID NO: 1. In some embodiments, the substitution is with any other of the 19 naturally occurring amino acids, namely threonine, glutamine, asparagine, lysine, arginine, histidine, glutamic acid, aspartic acid, cysteine, glycine, proline, alanine, isoleucine, leucine, methionine, phenylalanine, tryptophan valine and tyrosine, with some embodiments not utilizing proline (due to steric effects). In some embodiments, the amino acid substitution is S57C. In some embodiments, the amino acid substitution is S57E. In some embodiments, the amino acid substitution is S57F. In some embodiments, the amino acid substitution is S57I. In some embodiments, the amino acid substitution is S57L. In some embodiments, the amino acid substitution is S57M. In some embodiments, the amino acid substitution is S57T. In some embodiments, the amino acid substitution is S57V.

In some embodiments, the variant Bhr-PETase has an amino acid substitution of the tyrosine at position 60 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, phenylalanine, tryptophan and valine, with some embodiments not utilizing cysteine (due to possible disulfide formation) or proline (due to steric effects). In some embodiments, the amino acid substitution is Y60A. In some embodiments, the amino acid substitution is Y60H. In some embodiments, the amino acid substitution is Y60I.

In some embodiments, the variant Bhr-PETase has an amino acid substitution of the alanine at position 62 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is A62T.

In some embodiments, the variant Bhr-PETase has an amino acid substitution of the alanine at position 68 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is A68F.

In some embodiments, the variant Bhr-PETase has an amino acid substitution of the leucine at position 70 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, methionine, phenylalanine, tryptophan, valine and tyrosine, with some embodiments not utilizing cysteine (due to possible disulfide formation) or proline (due to steric effects). In some embodiments, the amino acid substitution is L70M.

In some embodiments, the variant Bhr-PETase has an amino acid substitution of the arginine at position 72 of SEQ ID NO:1. In some embodiments, the substitution is with any other of the 19 naturally occurring amino acids, namely serine, threonine, glutamine, asparagine, lysine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation). In some embodiments, the amino acid substitution is R72P.

In some embodiments, the variant Bhr-PETase has an amino acid substitution of the leucine at position 74 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, methionine, phenylalanine, tryptophan, valine and tyrosine, with some embodiments not utilizing cysteine (due to possible disulfide formation) or proline (due to steric effects). In some embodiments, the amino acid substitution is L74W.

In some embodiments, the variant Bhr-PETase has an amino acid substitution of the histidine at position 77 of SEQ ID NO: 1. In some embodiments, the substitution is with any other of the 19 naturally occurring amino acids, namely serine, threonine, glutamine, asparagine, lysine, arginine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is H77Q.

In some embodiments, the variant Bhr-PETase has an amino acid substitution of the isoleucine at position 82 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is I82F. In some embodiments, the amino acid substitution is I82L. In some embodiments, the amino acid substitution is I82M.

In some embodiments, the variant Bhr-PETase has an amino acid substitution of the valine at position 83 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, phenylalanine, tryptophan and tyrosine, with some embodiments not utilizing cysteine (due to possible disulfide formation) or proline (due to steric effects). In some embodiments, the amino acid substitution is V83I. In some embodiments, the amino acid substitution is V83L. In some embodiments, the amino acid substitution is V83T.

In some embodiments, the variant Bhr-PETase has an amino acid substitution of the asparagine at position 85 of SEQ ID NO:1. In some embodiments, the substitution is with any other of the 19 naturally occurring amino acids, namely serine, threonine, glutamine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is N85D.

In some embodiments, the variant Bhr-PETase has an amino acid substitution of the asparagine at position 87 of SEQ ID NO:1. In some embodiments, the substitution is with any other of the 19 naturally occurring amino acids, namely serine, threonine, glutamine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is N87F. In some embodiments, the amino acid substitution is N87H. In some embodiments, the amino acid substitution is N87I. In some embodiments, the amino acid substitution is N87K. In some embodiments, the amino acid substitution is N87L. In some embodiments, the amino acid substitution is N87M. In some embodiments, the amino acid substitution is N87Q. In some embodiments, the amino acid substitution is N87R. In some embodiments, the amino acid substitution is N87V. In some embodiments, the amino acid substitution is N87W. In some embodiments, the amino acid substitution is N87Y.

In some embodiments, the variant Bhr-PETase has an amino acid substitution of the serine at position 88 of SEQ ID NO: 1. In some embodiments, the substitution is with any other of the 19 naturally occurring amino acids, namely threonine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is S88K. In some embodiments, the amino acid substitution is S88T.

In some embodiments, the variant Bhr-PETase has an amino acid substitution of the leucine at position 90 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, methionine, phenylalanine, tryptophan, valine and tyrosine, with some embodiments not utilizing cysteine (due to possible disulfide formation) or proline (due to steric effects). In some embodiments, the amino acid substitution is L90F. In some embodiments, the amino acid substitution is L90K. In some embodiments, the amino acid substitution is L90Y.

In some embodiments, the variant Bhr-PETase has an amino acid substitution of the phenylalanine at position 92 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, tryptophan, valine and tyrosine, with some embodiments not utilizing cysteine (due to possible disulfide formation) or proline (due to steric effects). In some embodiments, the amino acid substitution is F92G. In some embodiments, the amino acid substitution is F92I. In some embodiments, the amino acid substitution is F92K. In some embodiments, the amino acid substitution is F92L. In some embodiments, the amino acid substitution is F92N. In some embodiments, the amino acid substitution is F92Q. In some embodiments, the amino acid substitution is F92V. In some embodiments, the amino acid substitution is F92Y.

In some embodiments, the variant Bhr-PETase has an amino acid substitution of the alanine at position 97 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, isoleucine, leucine, methionine, phenylalanine, tryptophan, valine and tyrosine. In some embodiments, the amino acid substitution is A97C. In some embodiments, the amino acid substitution is A97E. In some embodiments, the amino acid substitution is A97F. In some embodiments, the amino acid substitution is A97G. In some embodiments, the amino acid substitution is A97L. In some embodiments, the amino acid substitution is A97P. In some embodiments, the amino acid substitution is A97Q. In some embodiments, the amino acid substitution is A97S. In some embodiments, the amino acid substitution is A97T. In some embodiments, the amino acid substitution is A97V.

In some embodiments, the variant Bhr-PETase has an amino acid substitution of the serine at position 98 of SEQ ID NO: 1. In some embodiments, the substitution is with any other of the 19 naturally occurring amino acids, namely threonine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is S98A. In some embodiments, the amino acid substitution is S98D. In some embodiments, the amino acid substitution is S98E. In some embodiments, the amino acid substitution is S98L. In some embodiments, the amino acid substitution is S98M. In some embodiments, the amino acid substitution is S98N. In some embodiments, the amino acid substitution is S98Q. In some embodiments, the amino acid substitution is S98T. In some embodiments, the amino acid substitution is S98V.

In some embodiments, the variant Bhr-PETase has an amino acid substitution of the serine at position 101 of SEQ ID NO:1. In some embodiments, the substitution is with any other of the 19 naturally occurring amino acids, namely threonine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing proline (due to steric effects). In some embodiments, the amino acid substitution is S101A. In some embodiments, the amino acid substitution is S101C. In some embodiments, the amino acid substitution is S101D. In some embodiments, the amino acid substitution is S101F. In some embodiments, the amino acid substitution is S101H. In some embodiments, the amino acid substitution is S101K. In some embodiments, the amino acid substitution is S101L. In some embodiments, the amino acid substitution is S101M. In some embodiments, the amino acid substitution is S101N. In some embodiments, the amino acid substitution is S101Q. In some embodiments, the amino acid substitution is S101R. In some embodiments, the amino acid substitution is S101V. In some embodiments, the amino acid substitution is S101W. In some embodiments, the amino acid substitution is S101Y.

In some embodiments, the variant Bhr-PETase has an amino acid substitution of the alanine at position 102 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is A102V.

In some embodiments, the variant Bhr-PETase has an amino acid substitution of the asparagine at position 105 of SEQ ID NO:1. In some embodiments, the substitution is with any other of the 19 naturally occurring amino acids, namely serine, threonine, glutamine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is N105D.

In some embodiments, the variant Bhr-PETase has an amino acid substitution of the arginine at position 108 of SEQ ID NO:1. In some embodiments, the substitution is with any other of the 19 naturally occurring amino acids, namely serine, threonine, glutamine, asparagine, lysine, histidine, glutamic acid, aspartic acid, cysteine, glycine, proline, alanine, isoleucine, leucine, methionine, phenylalanine, tryptophan, valine and tyrosine. In some embodiments, the amino acid substitution is R108C. In some embodiments, the amino acid substitution is R108E. In some embodiments, the amino acid substitution is R108H. In some embodiments, the amino acid substitution is R108K. In some embodiments, the amino acid substitution is R108N. In some embodiments, the amino acid substitution is R108P. In some embodiments, the amino acid substitution is R108Q. In some embodiments, the amino acid substitution is R108S. In some embodiments, the amino acid substitution is R108T. In some embodiments, the amino acid substitution is R108V.

In some embodiments, the variant Bhr-PETase has an amino acid substitution of the threonine at position 109 of SEQ ID NO:1. In some embodiments, the substitution is with any other of the 19 naturally occurring amino acids, namely serine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is T109A. In some embodiments, the amino acid substitution is T109F. In some embodiments, the amino acid substitution is T109G. In some embodiments, the amino acid substitution is T109K. In some embodiments, the amino acid substitution is T109L. In some embodiments, the amino acid substitution is T109N. In some embodiments, the amino acid substitution is T109R. In some embodiments, the amino acid substitution is T109Y.

In some embodiments, the variant Bhr-PETase has an amino acid substitution of the serine at position 110 of SEQ ID NO:1. In some embodiments, the substitution is with any other of the 19 naturally occurring amino acids, namely threonine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is S110D. In some embodiments, the amino acid substitution is S110G. In some embodiments, the amino acid substitution is S110H. In some embodiments, the amino acid substitution is S110K. In some embodiments, the amino acid substitution is S110N. In some embodiments, the amino acid substitution is S110R.

In some embodiments, the variant Bhr-PETase has an amino acid substitution of the serine at position 113 of SEQ ID NO:1. In some embodiments, the substitution is with any other of the 19 naturally occurring amino acids, namely threonine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation). In some embodiments, the amino acid substitution is S113A. In some embodiments, the amino acid substitution is S113K. In some embodiments, the amino acid substitution is S113N. In some embodiments, the amino acid substitution is S113P. In some embodiments, the amino acid substitution is S113Q. In some embodiments, the amino acid substitution is S113R, S113T. In some embodiments, the amino acid substitution is S113Y.

In some embodiments, the variant Bhr-PETase has an amino acid substitution of the alanine at position 114 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is A114K. In some embodiments, the amino acid substitution is A114L. In some embodiments, the amino acid substitution is A114S. In some embodiments, the amino acid substitution is A114V.

In some embodiments, the variant Bhr-PETase has an amino acid substitution of the alanine at position 117 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is A117F. In some embodiments, the amino acid substitution is A117G. In some embodiments, the amino acid substitution is A117L. In some embodiments, the amino acid substitution is A117N. In some embodiments, the amino acid substitution is A117Q. In some embodiments, the amino acid substitution is A117S. In some embodiments, the amino acid substitution is A117T. In some embodiments, the amino acid substitution is A117Y.

In some embodiments, the variant Bhr-PETase has an amino acid substitution of the leucine at position 119 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, methionine, phenylalanine, tryptophan, valine and tyrosine, with some embodiments not utilizing cysteine (due to possible disulfide formation) or proline (due to steric effects). In some embodiments, the amino acid substitution is L119I. In some embodiments, the amino acid substitution is L119M.

In some embodiments, the variant Bhr-PETase has an amino acid substitution of the alanine at position 121 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is A121S.

In some embodiments, the variant Bhr-PETase has an amino acid substitution of the asparagine at position 122 of SEQ ID NO:1. In some embodiments, the substitution is with any other of the 19 naturally occurring amino acids, namely serine, threonine, glutamine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation). In some embodiments, the amino acid substitution is N122A. In some embodiments, the amino acid substitution is N122E. In some embodiments, the amino acid substitution is N122H. In some embodiments, the amino acid substitution is N122P. In some embodiments, the amino acid substitution is N122R. In some embodiments, the amino acid substitution is N122S.

In some embodiments, the variant Bhr-PETase has an amino acid substitution of the alanine at position 125 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is A125S.

In some embodiments, the variant Bhr-PETase has an amino acid substitution of the alanine at position 127 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is A127M. In some embodiments, the amino acid substitution is A127S. In some embodiments, the amino acid substitution is A127V.

In some embodiments, the variant Bhr-PETase has an amino acid substitution of the alanine at position 135 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is A135G.

In some embodiments, the variant Bhr-PETase has an amino acid substitution of the threonine at position 136 of SEQ ID NO:1. In some embodiments, the substitution is with any other of the 19 naturally occurring amino acids, namely serine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is T136A. In some embodiments, the amino acid substitution is T136M. In some embodiments, the amino acid substitution is T136S. In some embodiments, the amino acid substitution is T136V.

In some embodiments, the variant Bhr-PETase has an amino acid substitution of the arginine at position 138 of SEQ ID NO: 1. In some embodiments, the substitution is with any other of the 19 naturally occurring amino acids, namely serine, threonine, glutamine, asparagine, lysine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is R138E. In some embodiments, the amino acid substitution is R138L.

In some embodiments, the variant Bhr-PETase has an amino acid substitution of the isoleucine at position 139 of SEQ ID NO: 1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, leucine, methionine, phenylalanine, tryptophan, valine and tyrosine, with some embodiments not utilizing cysteine (due to possible disulfide formation) or proline (due to steric effects). In some embodiments, the amino acid substitution is I139A. In some embodiments, the amino acid substitution is I139T.

In some embodiments, the variant Bhr-PETase has an amino acid substitution of the serine at position 140 of SEQ ID NO:1. In some embodiments, the substitution is with any other of the 19 naturally occurring amino acids, namely threonine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is S140A.

In some embodiments, the variant Bhr-PETase has an amino acid substitution of the glutamine at position 142 of SEQ ID NO: 1. In some embodiments, the substitution is with any other of the 19 naturally occurring amino acids, namely serine, threonine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is Q142D. In some embodiments, the amino acid substitution is Q142E. In some embodiments, the amino acid substitution is Q142H. In some embodiments, the amino acid substitution is Q142L. In some embodiments, the amino acid substitution is Q142W.

In some embodiments, the variant Bhr-PETase has an amino acid substitution of the isoleucine at position 143 of SEQ ID NO: 1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, leucine, methionine, phenylalanine, tryptophan, valine and tyrosine, with some embodiments not utilizing cysteine (due to possible disulfide formation) or proline (due to steric effects). In some embodiments, the amino acid substitution is I143N. In some embodiments, the amino acid substitution is I143R.

In some embodiments, the variant Bhr-PETase has an amino acid substitution of the threonine at position 145 of SEQ ID NO:1. In some embodiments, the substitution is with any other of the 19 naturally occurring amino acids, namely serine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is T145S.

In some embodiments, the variant Bhr-PETase has an amino acid substitution of the lysine at position 147 of SEQ ID NO:1. In some embodiments, the substitution is with any other of the 19 naturally occurring amino acids, namely serine, threonine, glutamine, asparagine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is K147F. In some embodiments, the amino acid substitution is K147G. In some embodiments, the amino acid substitution is K147N. In some embodiments, the amino acid substitution is K147Q.

In some embodiments, the variant Bhr-PETase has an amino acid substitution of the glycine at position 149 of SEQ ID NO: 1. In some embodiments, the substitution is with any other of the 19 naturally occurring amino acids, namely serine, threonine, glutamine, asparagine, lysine, arginine, histidine, glutamic acid, aspartic acid, cysteine, proline, alanine, isoleucine, leucine, methionine, phenylalanine, tryptophan, valine and tyrosine, with some embodiments not utilizing proline (due to steric effects). In some embodiments, the amino acid substitution is G149A. In some embodiments, the amino acid substitution is G149C. In some embodiments, the amino acid substitution is G149D. In some embodiments, the amino acid substitution is G149N. In some embodiments, the amino acid substitution is G149S. In some embodiments, the amino acid substitution is G149T. In some embodiments, the amino acid substitution is G149V.

In some embodiments, the variant Bhr-PETase has an amino acid substitution of the valine at position 150 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, phenylalanine, tryptophan and tyrosine, with some embodiments not utilizing cysteine (due to possible disulfide formation) or proline (due to steric effects). In some embodiments, the amino acid substitution is V150I. In some embodiments, the amino acid substitution is V150L.

In some embodiments, the variant Bhr-PETase has an amino acid substitution of the threonine at position 153 of SEQ ID NO:1. In some embodiments, the substitution is with any other of the 19 naturally occurring amino acids, namely serine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is T153L.

In some embodiments, the variant Bhr-PETase has an amino acid substitution of the histidine at position 156 of SEQ ID NO:1. In some embodiments, the substitution is with any other of the 19 naturally occurring amino acids, namely serine, threonine, glutamine, asparagine, lysine, arginine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is H156N.

In some embodiments, the variant Bhr-PETase has an amino acid substitution of the threonine at position 157 of SEQ ID NO:1. In some embodiments, the substitution is with any other of the 19 naturally occurring amino acids, namely serine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is T157A. In some embodiments, the amino acid substitution is T157G.

In some embodiments, the variant Bhr-PETase has an amino acid substitution of the aspartic acid at position 158 of SEQ ID NO:1. In some embodiments, the substitution is with any other of the 19 naturally occurring amino acids, namely serine, threonine, glutamine, asparagine, lysine, arginine, histidine, glutamic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is D158E. In some embodiments, the amino acid substitution is D158I. In some embodiments, the amino acid substitution is D158K. In some embodiments, the amino acid substitution is D158L.

In some embodiments, the variant Bhr-PETase has an amino acid substitution of the threonine at position 160 of SEQ ID NO:1. In some embodiments, the substitution is with any other of the 19 naturally occurring amino acids, namely serine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is T160K. In some embodiments, the amino acid substitution is T160Q. In some embodiments, the amino acid substitution is T160R. In some embodiments, the amino acid substitution is T160S. In some embodiments, the amino acid substitution is T160V.

In some embodiments, the variant Bhr-PETase has an amino acid substitution of the phenylalanine at position 161 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, tryptophan, valine and tyrosine, with some embodiments not utilizing cysteine (due to possible disulfide formation) or proline (due to steric effects). In some embodiments, the amino acid substitution is F161V. In some embodiments, the amino acid substitution is F161W.

In some embodiments, the variant Bhr-PETase has an amino acid substitution of the asparagine at position 162 of SEQ ID NO:1. In some embodiments, the substitution is with any other of the 19 naturally occurring amino acids, namely serine, threonine, glutamine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation). In some embodiments, the amino acid substitution is N162E. In some embodiments, the amino acid substitution is N162H. In some embodiments, the amino acid substitution is N162P. In some embodiments, the amino acid substitution is N162R.

In some embodiments, the variant Bhr-PETase has an amino acid substitution of the threonine at position 163 of SEQ ID NO:1. In some embodiments, the substitution is with any other of the 19 naturally occurring amino acids, namely serine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is T163I. In some embodiments, the amino acid substitution is T163S.

In some embodiments, the variant Bhr-PETase has an amino acid substitution of the proline at position 164 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, alanine, isoleucine, leucine, methionine, phenylalanine, tryptophan, valine and tyrosine, with some embodiments not utilizing cysteine (due to possible disulfide formation). In some embodiments, the amino acid substitution is P164E. In some embodiments, the amino acid substitution is P164H. In some embodiments, the amino acid substitution is P164N. In some embodiments, the amino acid substitution is P164R. In some embodiments, the amino acid substitution is P164S. In some embodiments, the amino acid substitution is P164T.

In some embodiments, the variant Bhr-PETase has an amino acid substitution of the glutamine at position 167 of SEQ ID NO: 1. In some embodiments, the substitution is with any other of the 19 naturally occurring amino acids, namely serine, threonine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is Q167I. In some embodiments, the amino acid substitution is Q167T. In some embodiments, the amino acid substitution is Q167V.

In some embodiments, the variant Bhr-PETase has an amino acid substitution of the valine at position 170 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, phenylalanine, tryptophan and tyrosine, with some embodiments not utilizing cysteine (due to possible disulfide formation) or proline (due to steric effects). In some embodiments, the amino acid substitution is V170L.

In some embodiments, the variant Bhr-PETase has an amino acid substitution of the glutamic acid at position 173 of SEQ ID NO:1. In some embodiments, the substitution is with any other of the 19 naturally occurring amino acids, namely serine, threonine, glutamine, asparagine, lysine, arginine, histidine, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is E173R.

In some embodiments, the variant Bhr-PETase has an amino acid substitution of the alanine at position 174 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is A174K. In some embodiments, the amino acid substitution is A174R.

In some embodiments, the variant Bhr-PETase has an amino acid substitution of the valine at position 177 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, phenylalanine, tryptophan and tyrosine, with some embodiments not utilizing cysteine (due to possible disulfide formation) or proline (due to steric effects). In some embodiments, the amino acid substitution is V177A.

In some embodiments, the variant Bhr-PETase has an amino acid substitution of the proline at position 179 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, alanine, isoleucine, leucine, methionine, phenylalanine, tryptophan, valine and tyrosine, with some embodiments not utilizing cysteine (due to possible disulfide formation). In some embodiments, the amino acid substitution is P179Q.

In some embodiments, the variant Bhr-PETase has an amino acid substitution of the serine at position 181 of SEQ ID NO:1. In some embodiments, the substitution is with any other of the 19 naturally occurring amino acids, namely threonine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing proline (due to steric effects). In some embodiments, the amino acid substitution is S181A. In some embodiments, the amino acid substitution is S181C. In some embodiments, the amino acid substitution is S181R.

In some embodiments, the variant Bhr-PETase has an amino acid substitution of the glutamine at position 182 of SEQ ID NO: 1. In some embodiments, the substitution is with any other of the 19 naturally occurring amino acids, namely serine, threonine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is Q182T.

In some embodiments, the variant Bhr-PETase has an amino acid substitution of the alanine at position 184 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, isoleucine, leucine, methionine, phenylalanine, tryptophan, valine and tyrosine, with some embodiments not utilizing proline (due to steric effects). In some embodiments, the amino acid substitution is A184C. In some embodiments, the amino acid substitution is A184G. In some embodiments, the amino acid substitution is A184S.

In some embodiments, the variant Bhr-PETase has an amino acid substitution of the isoleucine at position 185 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, leucine, methionine, phenylalanine, tryptophan, valine and tyrosine, with some embodiments not utilizing cysteine (due to possible disulfide formation) or proline (due to steric effects). In some embodiments, the amino acid substitution is I185A. In some embodiments, the amino acid substitution is I185E. In some embodiments, the amino acid substitution is I185G. In some embodiments, the amino acid substitution is I185L. In some embodiments, the amino acid substitution is I185Q. In some embodiments, the amino acid substitution is I185R. In some embodiments, the amino acid substitution is I185S. In some embodiments, the amino acid substitution is I185Y.

In some embodiments, the variant Bhr-PETase has an amino acid substitution of the glutamine at position 189 of SEQ ID NO: 1. In some embodiments, the substitution is with any other of the 19 naturally occurring amino acids, namely serine, threonine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is Q189I. In some embodiments, the amino acid substitution is Q189L. In some embodiments, the amino acid substitution is Q189V.

In some embodiments, the variant Bhr-PETase has an amino acid substitution of the asparagine at position 190 of SEQ ID NO:1. In some embodiments, the substitution is with any other of the 19 naturally occurring amino acids, namely serine, threonine, glutamine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is N190S.

In some embodiments, the variant Bhr-PETase has an amino acid substitution of the serine at position 193 of SEQ ID NO:1. In some embodiments, the substitution is with any other of the 19 naturally occurring amino acids, namely threonine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation). In some embodiments, the amino acid substitution is S193E. In some embodiments, the amino acid substitution is S193F. In some embodiments, the amino acid substitution is S193H. In some embodiments, the amino acid substitution is S193K. In some embodiments, the amino acid substitution is S193N. In some embodiments, the amino acid substitution is S193P. In some embodiments, the amino acid substitution is S193T. In some embodiments, the amino acid substitution is S193V.

In some embodiments, the variant Bhr-PETase has an amino acid substitution of the threonine at position 194 of SEQ ID NO:1. In some embodiments, the substitution is with any other of the 19 naturally occurring amino acids, namely serine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is T194G. In some embodiments, the amino acid substitution is T194S.

In some embodiments, the variant Bhr-PETase has an amino acid substitution of the threonine at position 195 of SEQ ID NO:1. In some embodiments, the substitution is with any other of the 19 naturally occurring amino acids, namely serine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is T195F.

In some embodiments, the variant Bhr-PETase has an amino acid substitution of the valine at position 198 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, phenylalanine, tryptophan and tyrosine, with some embodiments not utilizing cysteine (due to possible disulfide formation) or proline (due to steric effects). In some embodiments, the amino acid substitution is V198A.

In some embodiments, the variant Bhr-PETase has an amino acid substitution of the valine at position 200 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, phenylalanine, tryptophan and tyrosine, with some embodiments not utilizing cysteine (due to possible disulfide formation) or proline (due to steric effects). In some embodiments, the amino acid substitution is V200L.

In some embodiments, the variant Bhr-PETase has an amino acid substitution of the aspartic acid at position 203 of SEQ ID NO:1. In some embodiments, the substitution is with any other of the 19 naturally occurring amino acids, namely serine, threonine, glutamine, asparagine, lysine, arginine, histidine, glutamic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is D203N. In some embodiments, the amino acid substitution is D203R. In some embodiments, the amino acid substitution is D203V.

In some embodiments, the variant Bhr-PETase has an amino acid substitution of the asparagine at position 204 of SEQ ID NO:1. In some embodiments, the substitution is with any other of the 19 naturally occurring amino acids, namely serine, threonine, glutamine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is N204A. In some embodiments, the amino acid substitution is N204K. In some embodiments, the amino acid substitution is N204R. In some embodiments, the amino acid substitution is N204S.

In some embodiments, the variant Bhr-PETase has an amino acid substitution of the threonine at position 206 of SEQ ID NO:1. In some embodiments, the substitution is with any other of the 19 naturally occurring amino acids, namely serine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation). In some embodiments, the amino acid substitution is T206G. In some embodiments, the amino acid substitution is T206K. In some embodiments, the amino acid substitution is T206L. In some embodiments, the amino acid substitution is T206P. In some embodiments, the amino acid substitution is T206R.

In some embodiments, the variant Bhr-PETase has an amino acid substitution of the phenylalanine at position 208 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, tryptophan, valine and tyrosine, with some embodiments not utilizing cysteine (due to possible disulfide formation) or proline (due to steric effects). In some embodiments, the amino acid substitution is F208G. In some embodiments, the amino acid substitution is F208L. In some embodiments, the amino acid substitution is F208R. In some embodiments, the amino acid substitution is F208T.

In some embodiments, the variant Bhr-PETase has an amino acid substitution of the alanine at position 209 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is A209V.

In some embodiments, the variant Bhr-PETase has an amino acid substitution of the asparagine at position 211 of SEQ ID NO:1. In some embodiments, the substitution is with any other of the 19 naturally occurring amino acids, namely serine, threonine, glutamine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is N211F. In some embodiments, the amino acid substitution is N211I. In some embodiments, the amino acid substitution is N211L. In some embodiments, the amino acid substitution is N211M. In some embodiments, the amino acid substitution is N211V.

In some embodiments, the variant Bhr-PETase has an amino acid substitution of the serine at position 212 of SEQ ID NO:1. In some embodiments, the substitution is with any other of the 19 naturally occurring amino acids, namely threonine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is S212F. In some embodiments, the amino acid substitution is S212L. In some embodiments, the amino acid substitution is S212M.

In some embodiments, the variant Bhr-PETase has an amino acid substitution of the proline at position 213 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, alanine, isoleucine, leucine, methionine, phenylalanine, tryptophan, valine and tyrosine, with some embodiments not utilizing cysteine (due to possible disulfide formation). In some embodiments, the amino acid substitution is P213N. In some embodiments, the amino acid substitution is P213R.

In some embodiments, the variant Bhr-PETase has an amino acid substitution of the alanine at position 216 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, isoleucine, leucine, methionine, phenylalanine, tryptophan, valine and tyrosine, with some embodiments not utilizing cysteine (due to possible disulfide formation). In some embodiments, the amino acid substitution is A216L. In some embodiments, the amino acid substitution is A216P. In some embodiments, the amino acid substitution is A216S. In some embodiments, the amino acid substitution is A216T. In some embodiments, the amino acid substitution is A216V.

In some embodiments, the variant Bhr-PETase has an amino acid substitution of the isoleucine at position 217 of SEQ ID NO: 1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, leucine, methionine, phenylalanine, tryptophan, valine and tyrosine, with some embodiments not utilizing cysteine (due to possible disulfide formation) or proline (due to steric effects). In some embodiments, the amino acid substitution is I217S.

In some embodiments, the variant Bhr-PETase has an amino acid substitution of the serine at position 218 of SEQ ID NO:1. In some embodiments, the substitution is with any other of the 19 naturally occurring amino acids, namely threonine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is S218A.

In some embodiments, the variant Bhr-PETase has an amino acid substitution of the valine at position 219 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, phenylalanine, tryptophan and tyrosine, with some embodiments not utilizing cysteine (due to possible disulfide formation) or proline (due to steric effects). In some embodiments, the amino acid substitution is V219F. In some embodiments, the amino acid substitution is V219I. In some embodiments, the amino acid substitution is V219K. In some embodiments, the amino acid substitution is V219L. In some embodiments, the amino acid substitution is V219R.

In some embodiments, the variant Bhr-PETase has an amino acid substitution of the threonine at position 221 of SEQ ID NO:1. In some embodiments, the substitution is with any other of the 19 naturally occurring amino acids, namely serine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is T221S.

In some embodiments, the variant Bhr-PETase has an amino acid substitution of the isoleucine at position 222 of SEQ ID NO: 1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, leucine, methionine, phenylalanine, tryptophan, valine and tyrosine, with some embodiments not utilizing cysteine (due to possible disulfide formation) or proline (due to steric effects). In some embodiments, the amino acid substitution is I222L.

In some embodiments, the variant Bhr-PETase has an amino acid substitution of the serine at position 223 of SEQ ID NO:1. In some embodiments, the substitution is with any other of the 19 naturally occurring amino acids, namely threonine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing proline (due to steric effects). In some embodiments, the amino acid substitution is S223A. In some embodiments, the amino acid substitution is S223C.

In some embodiments, the variant Bhr-PETase has an amino acid substitution of the methionine at position 225 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, phenylalanine, tryptophan, valine and tyrosine, with some embodiments not utilizing cysteine (due to possible disulfide formation) or proline (due to steric effects). In some embodiments, the amino acid substitution is M225L.

In some embodiments, the variant Bhr-PETase has an amino acid substitution of the leucine at position 227 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, methionine, phenylalanine, tryptophan, valine and tyrosine, with some embodiments not utilizing cysteine (due to possible disulfide formation) or proline (due to steric effects). In some embodiments, the amino acid substitution is L227R.

In some embodiments, the variant Bhr-PETase has an amino acid substitution of the tryptophan at position 228 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, phenylalanine, valine and tyrosine, with some embodiments not utilizing cysteine (due to possible disulfide formation) or proline (due to steric effects). In some embodiments, the amino acid substitution is W228F.

In some embodiments, the variant Bhr-PETase has an amino acid substitution of the valine at position 229 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, phenylalanine, tryptophan and tyrosine, with some embodiments not utilizing proline (due to steric effects). In some embodiments, the amino acid substitution is V229C. In some embodiments, the amino acid substitution is V229I. In some embodiments, the amino acid substitution is V229L.

In some embodiments, the variant Bhr-PETase has an amino acid substitution of the asparagine at position 231 of SEQ ID NO:1. In some embodiments, the substitution is with any other of the 19 naturally occurring amino acids, namely serine, threonine, glutamine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is N231L. In some embodiments, the amino acid substitution is N231Q. In some embodiments, the amino acid substitution is N231S.

In some embodiments, the variant Bhr-PETase has an amino acid substitution of the arginine at position 236 of SEQ ID NO:1. In some embodiments, the substitution is with any other of the 19 naturally occurring amino acids, namely serine, threonine, glutamine, asparagine, lysine, histidine, glutamic acid, aspartic acid, cysteine, glycine, proline, alanine, isoleucine, leucine, methionine, phenylalanine, tryptophan, valine and tyrosine, with some embodiments not utilizing proline (due to steric effects). In some embodiments, the amino acid substitution is R236C. In some embodiments, the amino acid substitution is R236E. In some embodiments, the amino acid substitution is R236H. In some embodiments, the amino acid substitution is R236K. In some embodiments, the amino acid substitution is R236Q.

In some embodiments, the variant Bhr-PETase has an amino acid substitution of the glutamine at position 237 of SEQ ID NO: 1. In some embodiments, the substitution is with any other of the 19 naturally occurring amino acids, namely serine, threonine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is Q237R.

In some embodiments, the variant Bhr-PETase has an amino acid substitution of the asparagine at position 241 of SEQ ID NO:1. In some embodiments, the substitution is with any other of the 19 naturally occurring amino acids, namely serine, threonine, glutamine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation). In some embodiments, the amino acid substitution is N241P.

In some embodiments, the variant Bhr-PETase has an amino acid substitution of the valine at position 242 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, phenylalanine, tryptophan and tyrosine, with some embodiments not utilizing cysteine (due to possible disulfide formation) or proline (due to steric effects). In some embodiments, the amino acid substitution is V242T.

In some embodiments, the variant Bhr-PETase has an amino acid substitution of the asparagine at position 243 of SEQ ID NO:1. In some embodiments, the substitution is with any other of the 19 naturally occurring amino acids, namely serine, threonine, glutamine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation). In some embodiments, the amino acid substitution is N243P.

In some embodiments, the variant Bhr-PETase has an amino acid substitution of the alanine at position 246 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is A246D. In some embodiments, the amino acid substitution is A246K. In some embodiments, the amino acid substitution is A246S. In some embodiments, the amino acid substitution is A246T.

In some embodiments, the variant Bhr-PETase has an amino acid substitution of the aspartic acid at position 249 of SEQ ID NO:1. In some embodiments, the substitution is with any other of the 19 naturally occurring amino acids, namely serine, threonine, glutamine, asparagine, lysine, arginine, histidine, glutamic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is D249I. In some embodiments, the amino acid substitution is D249M. In some embodiments, the amino acid substitution is D249N. In some embodiments, the amino acid substitution is D249S. In some embodiments, the amino acid substitution is D249T.

In some embodiments, the variant Bhr-PETase has an amino acid substitution of the phenylalanine at position 250 of SEQ ID NO:1. In some embodiments, the substitution is with any other of the 19 naturally occurring amino acids, namely serine, threonine, glutamine, asparagine, lysine, arginine, histidine, glutamic acid, aspartic acid, cysteine, glycine, proline, alanine, isoleucine, leucine, methionine, tryptophan, valine and tyrosine, with some embodiments not utilizing cysteine (due to possible disulfide formation) or proline (due to steric effects). In some embodiments, the amino acid substitution is F250I. In some embodiments, the amino acid substitution is F250L. In some embodiments, the amino acid substitution is F250V. In some embodiments, the amino acid substitution is F250Y.

In some embodiments, the variant Bhr-PETase has an amino acid substitution of the arginine at position 251 of SEQ ID NO:1. In some embodiments, the substitution is with any other of the 19 naturally occurring amino acids, namely serine, threonine, glutamine, asparagine, lysine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is R251A. In some embodiments, the amino acid substitution is R251E. In some embodiments, the amino acid substitution is R251I. In some embodiments, the amino acid substitution is R251K. In some embodiments, the amino acid substitution is R251L. In some embodiments, the amino acid substitution is R251Q. In some embodiments, the amino acid substitution is R251T. In some embodiments, the amino acid substitution is R251V.

In some embodiments, the variant Bhr-PETase has an amino acid substitution of the serine at position 252 of SEQ ID NO:1. In some embodiments, the substitution is with any other of the 19 naturally occurring amino acids, namely threonine, glutamine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is S252T.

In some embodiments, the variant Bhr-PETase has an amino acid substitution of the asparagine at position 253 of SEQ ID NO:1. In some embodiments, the substitution is with any other of the 19 naturally occurring amino acids, namely serine, threonine, glutamine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is N253S. In some embodiments, the amino acid substitution is N253Y.

In some embodiments, the variant Bhr-PETase has an amino acid substitution of the asparagine at position 254 of SEQ ID NO:1. In some embodiments, the substitution is with any other of the 19 naturally occurring amino acids, namely serine, threonine, glutamine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is N254R.

In some embodiments, the variant Bhr-PETase has an amino acid substitution of the arginine at position 255 of SEQ ID NO: 1. In some embodiments, the substitution is with any other of the 19 naturally occurring amino acids, namely serine, threonine, glutamine, asparagine, lysine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is R255E. In some embodiments, the amino acid substitution is R255G. In some embodiments, the amino acid substitution is R255L. In some embodiments, the amino acid substitution is R255M. In some embodiments, the amino acid substitution is R255S. In some embodiments, the amino acid substitution is R255V. In some embodiments, the amino acid substitution is R255W. In some embodiments, the amino acid substitution is R255Y.

In some embodiments, the variant Bhr-PETase has an amino acid substitution of the glutamine at position 258 of SEQ ID NO: 1. In some embodiments, the substitution is with any other of the 19 naturally occurring amino acids, namely serine, threonine, asparagine, lysine, arginine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation). In some embodiments, the amino acid substitution is Q258P.

In some embodiments, the variant Bhr-PETase has an amino acid substitution of the arginine at position 8 of SEQ ID NO:1. In some embodiments, the substitution is with any other of the 19 naturally occurring amino acids, namely serine, threonine, glutamine, asparagine, lysine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation). In some embodiments, the amino acid substitution is P8T.

In some embodiments, the variant Bhr-PETase has an amino acid substitution of the arginine at position 31 of SEQ ID NO:1. In some embodiments, the substitution is with any other of the 19 naturally occurring amino acids, namely serine, threonine, glutamine, asparagine, lysine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is L31M.

In some embodiments, the variant Bhr-PETase has an amino acid substitution of the arginine at position 38 of SEQ ID NO:1. In some embodiments, the substitution is with any other of the 19 naturally occurring amino acids, namely serine, threonine, glutamine, asparagine, lysine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is G38D.

In some embodiments, the variant Bhr-PETase has an amino acid substitution of the arginine at position 95 of SEQ ID NO: 1. In some embodiments, the substitution is with any other of the 19 naturally occurring amino acids, namely serine, threonine, glutamine, asparagine, lysine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is S95N.

In some embodiments, the variant Bhr-PETase has an amino acid substitution of the arginine at position 126 of SEQ ID NO: 1. In some embodiments, the substitution is with any other of the 19 naturally occurring amino acids, namely serine, threonine, glutamine, asparagine, lysine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is V126I.

In some embodiments, the variant Bhr-PETase has an amino acid substitution of the arginine at position 137 of SEQ ID NO:1. In some embodiments, the substitution is with any other of the 19 naturally occurring amino acids, namely serine, threonine, glutamine, asparagine, lysine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is L137M.

In some embodiments, the variant Bhr-PETase has an amino acid substitution of the arginine at position 165 of SEQ ID NO:1. In some embodiments, the substitution is with any other of the 19 naturally occurring amino acids, namely serine, threonine, glutamine, asparagine, lysine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is V165I.

In some embodiments, the variant Bhr-PETase has an amino acid substitution of the arginine at position 169 of SEQ ID NO: 1. In some embodiments, the substitution is with any other of the 19 naturally occurring amino acids, namely serine, threonine, glutamine, asparagine, lysine, histidine, glutamic acid, aspartic acid, cysteine, glycine, proline, alanine, isoleucine, leucine, methionine, phenylalanine, tryptophan, valine and tyrosine, with some embodiments not utilizing proline (due to steric effects). In some embodiments, the amino acid substitution is I169C. In some embodiments, the amino acid substitution is I169L. In some embodiments, the amino acid substitution is I169V.

In some embodiments, the variant Bhr-PETase has an amino acid substitution of the arginine at position 172 of SEQ ID NO: 1. In some embodiments, the substitution is with any other of the 19 naturally occurring amino acids, namely serine, threonine, glutamine, asparagine, lysine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is A172T.

In some embodiments, the variant Bhr-PETase has an amino acid substitution of the arginine at position 191 of SEQ ID NO: 1. In some embodiments, the substitution is with any other of the 19 naturally occurring amino acids, namely serine, threonine, glutamine, asparagine, lysine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is L191F. In some embodiments, the amino acid substitution is L191V.

In some embodiments, the variant Bhr-PETase has an amino acid substitution of the arginine at position 192 of SEQ ID NO: 1. In some embodiments, the substitution is with any other of the 19 naturally occurring amino acids, namely serine, threonine, glutamine, asparagine, lysine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation). In some embodiments, the amino acid substitution is P192A.

In some embodiments, the variant Bhr-PETase has an amino acid substitution of the arginine at position 197 of SEQ ID NO: 1. In some embodiments, the substitution is with any other of the 19 naturally occurring amino acids, namely serine, threonine, glutamine, asparagine, lysine, histidine, glutamic acid, aspartic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid substitution is K197L. In some embodiments, the amino acid substitution is K197R. In some embodiments, the amino acid substitution is K197T. In some embodiments, the amino acid substitution is K197V. In some embodiments, the amino acid substitution is K197Y.

In some embodiments, the variant Bhr-PETase enzyme has one or more amino acid substitutions at 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 of the positions of SEQ ID NO: 1 as described above.

D. Nucleic Acids of the Invention

The present invention additional provides nucleic acids encoding the variant Bhr-PETases of the invention. As will be appreciated by those in the art, due to the degeneracy of the genetic code, an extremely large number of nucleic acids may be made, all of which encode the variant Bhr-PETases of the present invention. Thus, having identified a particular amino acid sequence, those skilled in the art could make any number of different nucleic acids, by simply modifying the sequence of one or more codons in a way which does not change the amino acid sequence of the protein. Thus, providing the amino acid sequence allows the generation of a very large number of different nucleic acid sequences encoding the proteins.

In some embodiments, specific variant Bhr-PETases are encoded by specific nucleic acid sequences, as are listed in SEQ ID NOs 2 and 3. In some embodiments, specific variant Bhr-PETases are encoded by a nucleic acid sequence having at least about 80, 81, 82, 83, 84, 85, 85, 86, 87, 88, 89, 90, 91, 92, 93, 94, 95, 96, 97, 98, 99 or 100% identity to SEQ ID NOs 2 and 3.

As is known in the art, the nucleic acids encoding the components of the invention can be incorporated into expression vectors as is known in the art, and depending on the host cells used to produce the heterodimeric antibodies of the invention. Generally the nucleic acids are operably linked to any number of regulatory elements (promoters, origin of replication, selectable markers, ribosomal binding sites, inducers, etc.). The expression vectors can be extra-chromosomal or integrating vectors.

The nucleic acids and/or expression vectors of the invention are then transformed into any number of different types of host cells as is well known in the art, including mammalian, bacterial, yeast, insect and/or fungal cells, with bacteria, yeast and fungi finding use in many embodiments.

1. Preparation of Variants

The nucleic acids encoding the variant Bhr-PETases of the invention can be prepared using any mutagenesis procedure known in the art, such as site-directed mutagenesis and synthetic gene construction as are well known in the art.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips. A preferred technique is GenScript®.

2. Regulatory Sequences

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Promoters for bacteria, yeast and fungi are well known in the art. Exemplary operons for expression in lactic acid bacteria include *S. thermophilus* lactose operons or L. lactic lac ABCDFEGX operons, which have been successfully used to induce foreign gene expression in hosts (e.g., Simons et al., 1993, J. Bact. 175: 5186-5175; see Mollet et al., 1993, J. Bact. 175: 4315-4324). Non-limiting additional examples of constitutive promoters for bacteria include lac promoter, trp promoter, tac promoter, T7 promoter, erm promoter, tip promoter, nit promoter, and Sp6 promoter. Exemplary promoters for yeasts include, but not limited to, AOX1 promoter, ADH promoter, PH05 promoter, gal10 promoter, PKG promoter and GAP promoter. Other useful promoters for yeast host cells are described by Romanos et al., 1992, Yeast 8: 423-488. Moreover, examples of useful promoters for fungi vectors include, but not limit to, *Aspergillus niger* GLA promoter, *Aspergillus nidulans* GPD promoter, those derived from *Aspergillus nidulans* glycolytic genes, such as the adh3 promoter (McKnight et al., EMBO J. 4:2093-2099, 1985).

3. Codon Optimization

While the wild-type coding sequence of Bhr-PETase is shown in SEQ ID NO:1, those of skill in the art will recognize that for heterologous expression, codon optimization can be done to increase expression in any particular host organism. Codon optimization can be employed with any of the variant Bhr-PETase polypeptides of the present invention, in order to optimize expression in the host cell employed. Such methods are well known in the art and described in, for example, WO 2007/142954. In heterologous expression systems, optimization steps can improve the ability of the host to produce the desired variant Bhr-PETase polypeptides. Protein expression is governed by a host of factors including those that affect transcription, mRNA processing, and stability and initiation of translation. The polynucleotide optimization steps can include steps to improve the ability of the host to produce the foreign protein as well as steps to assist the researcher in efficiently designing expression constructs. Optimization strategies can include, for example, the modification of translation initiation regions, alteration of mRNA structural elements, and the use of different codon biases. The following paragraphs discuss potential problems that may result in reduced heterologous protein expression, and techniques that may overcome these problems.

In some embodiments, reduced heterologous protein expression results from a rare codon-induced translational pause. A rare codon-induced translational pause includes the presence of codons in the polynucleotide of interest that are rarely used in the host organism can have a negative effect on protein translation due to their scarcity in the available tRNA pool. One method of improving optimal translation in the host organism includes performing includes performing codon optimization which can result in rare host codons being modified in the synthetic polynucleotide sequence.

In some embodiments, reduced heterologous protein expression results from by alternate translational initiation. Alternate translational initiation can include a synthetic polynucleotide sequence inadvertently containing motifs capable of functioning as a ribosome binding site (RBS). These sites can result in initiating translation of a truncated protein from a gene-internal site. One method of reducing the possibility of producing a truncated protein, which can be difficult to remove during purification, includes modifying putative internal RBS sequences from an optimized polynucleotide sequence.

In some embodiments, reduced heterologous protein expression occurs through repeat-induced polymerase slippage. Repeat-induced polymerase slippage involves nucleotide sequence repeats that have been shown to cause slippage or stuttering of DNA polymerase which can result in frameshift mutations. Such repeats can also cause slippage of RNA polymerase. In an organism with a high G+C content bias, there can be a higher degree of repeats composed of G or C nucleotide repeats. Therefore, one method of reducing the possibility of inducing RNA polymerase slippage includes altering extended repeats of G or C nucleotides.

In some embodiments, reduced heterologous protein expression occurs through interfering secondary structures. Secondary structures can sequester the RBS sequence or initiation codon and have been correlated to a reduction in protein expression. Stemloop structures can also be involved in transcriptional pausing and attenuation. An optimized polynucleotide sequence can contain minimal secondary structures in the RBS and gene coding regions of the nucleotide sequence to allow for improved transcription and translation.

In some embodiments, restriction sites can affect heterologous protein expression. By modifying restriction sites that could interfere with subsequent sub-cloning of transcription units into host expression vectors a polynucleotide sequence can be optimized.

Optimizing a DNA sequence can negatively or positively affect gene expression or protein production. For example, modifying a less-common codon with a more common codon may affect the half-life of the mRNA or alter its structure by introducing a secondary structure that interferes with translation of the message. It may therefore be necessary, in certain instances, to alter the optimized message.

All or a portion of a gene can be optimized. In some embodiments, the desired modulation of expression is achieved by optimizing essentially the entire gene. In other embodiments, the desired modulation will be achieved by optimizing part but not all of the gene.

The codon usage of any coding sequence can be adjusted to achieve a desired property, for example high levels of expression in a specific cell type. The starting point for such an optimization may be a coding sequence with 100% common codons, or a coding sequence which contains a mixture of common and non-common codons.

Two or more candidate sequences that differ in their codon usage can be generated and tested to determine if they possess the desired property. Candidate sequences can be evaluated by using a computer to search for the presence of regulatory elements, such as silencers or enhancers, and to search for the presence of regions of coding sequence which could be converted into such regulatory elements by an alteration in codon usage. Additional criteria can include enrichment for particular nucleotides, e.g., A, C, G or U, codon bias for a particular amino acid, or the presence or absence of particular mRNA secondary or tertiary structure. Adjustment to the candidate sequence can be made based on a number of such criteria.

Promising candidate sequences are constructed and then evaluated experimentally. Multiple candidates may be evaluated independently of each other, or the process can be iterative, either by using the most promising candidate as a new starting point, or by combining regions of two or more candidates to produce a novel hybrid. Further rounds of modification and evaluation can be included.

Modifying the codon usage of a candidate sequence can result in the creation or destruction of either a positive or negative element. In general, a positive element refers to any element whose alteration or removal from the candidate sequence could result in a decrease in expression of the therapeutic protein, or whose creation could result in an increase in expression of a therapeutic protein. For example, a positive element can include an enhancer, a promoter, a downstream promoter element, a DNA binding site for a positive regulator (e.g., a transcriptional activator), or a sequence responsible for imparting or modifying an mRNA secondary or tertiary structure. A negative element refers to any element whose alteration or removal from the candidate sequence could result in an increase in expression of the therapeutic protein, or whose creation would result in a decrease in expression of the therapeutic protein. A negative element includes a silencer, a DNA binding site for a negative regulator (e.g., a transcriptional repressor), a transcriptional pause site, or a sequence that is responsible for imparting or modifying an mRNA secondary or tertiary structure. In general, a negative element arises more frequently than a positive element. Thus, any change in codon usage that results in an increase in protein expression is more likely to have arisen from the destruction of a negative element rather than the creation of a positive element. In addition, alteration of the candidate sequence is more likely to destroy a positive element than create a positive element. In some embodiments, a candidate sequence is chosen and modified so as to increase the production of a therapeutic protein. The candidate sequence can be modified, e.g., by sequentially altering the codons or by randomly altering the codons in the candidate sequence. A modified candidate sequence is then evaluated by determining the level of expression of the resulting therapeutic protein or by evaluating another parameter, e.g., a parameter correlated to the level of expression. A candidate sequence which produces an increased level of a therapeutic protein as compared to an unaltered candidate sequence is chosen.

In some embodiments, one or a group of codons can be modified, e.g., without reference to protein or message structure and tested. Alternatively, one or more codons can be chosen on a message-level property, e.g., location in a region of predetermined, e.g., high or low GC content, location in a region having a structure such as an enhancer or silencer, location in a region that can be modified to introduce a structure such as an enhancer or silencer, location in a region having, or predicted to have, secondary or tertiary structure, e.g., intra-chain pairing, inter-chain pairing, location in a region lacking, or predicted to lack, secondary or tertiary structure, e.g., intra-chain or inter-chain pairing. A particular modified region is chosen if it produces the desired result.

Methods which systematically generate candidate sequences are useful. For example, one or a group, e.g., a contiguous block of codons, at various positions of a synthetic nucleic acid sequence can be modified with common codons (or with non common codons, if for example, the starting sequence has been optimized) and the resulting sequence evaluated. Candidates can be generated by optimizing (or de-optimizing) a given "window" of codons in the sequence to generate a first candidate, and then moving the window to a new position in the sequence, and optimizing (or de-optimizing) the codons in the new position under the window to provide a second candidate. Candidates can be evaluated by determining the level of expression they provide, or by evaluating another parameter, e.g., a parameter correlated to the level of expression. Some parameters can be evaluated by inspection or computationally, e.g., the possession or lack thereof of high or low GC content; a sequence element such as an enhancer or silencer; secondary or tertiary structure, e.g., intra-chain or inter-chain paring.

In some embodiments, the optimized nucleic acid sequence can express the variant Bhr-PETase polypeptide of the invention, at a level which is at least about 110%, 150%, 200%, 500%, 1,000%, 5,000% or even 10,000% of that expressed by nucleic acid sequence that has not been optimized.

Staring with the amino acid sequence of a variant Bhr-PETase, a candidate DNA sequence can be designed. During the design of the synthetic DNA sequence, the frequency of codon usage can be compared to the codon usage of the host expression organism and rare host codons can be modified in the synthetic sequence. Additionally, the synthetic candidate DNA sequence can be modified in order to remove undesirable enzyme restriction sites and add or alter any desired signal sequences, linkers or untranslated regions. The synthetic DNA sequence can be analyzed for the presence of secondary structure that may interfere with the translation process, such as G/C repeats and stem-loop structures. Before the candidate DNA sequence is synthesized, the optimized sequence design can be checked to verify that the sequence correctly encodes the desired amino acid sequence. Finally, the candidate DNA sequence can be synthesized using DNA synthesis techniques, such as those known in the art.

In some embodiments, the general codon usage in a host organism, such as any of those described herein, can be utilized to optimize the expression of the heterologous polynucleotide sequence in the host organism. The percentage and distribution of codons that rarely would be considered as preferred for a particular amino acid in the host expression system can be evaluated. Values of 5% and 10% usage can be used as cutoff values for the determination of rare codons.

4. Host Cells and Production Strains

In one aspect, the present disclosure relates to an expression vector comprising the nucleic acid encoding the variant Bhr-PETase described herein. In another aspect, the present disclosure also relates to a host cell comprising the expression vector. In some embodiments, the host cell is bacteria. In some embodiments, the host cell is yeast. In some embodiments, the host cell is fungi. In some embodiments, the host cell may be bacteria, including but not limited to *E. coli, Bacillus*. In some embodiments, the host cell may be yeast, including but not limited to *Saccharomyces cerevisiae, Pichia*. In some embodiments, the host cell may be fungi, including but not limited to *A. niger, T. reseei*, or *Myceliophthora thermophila*.

The expression vector may be any of integration vectors which are to be integrated into genome or autonomously replicating plasmids in the selected host. In one embodiment, the vector can be stably maintained in the introduced cell, with the variant Bhr-PETase gene supported thereon in a fit state for expression. The expression vector may be selected to be suitable for the specific host cells to which the vector is introduced. Specific examples available for use include but not limit to pBR322, pACYC184, pUC18, pKK223-2, pHSG398 (Takara Bio Inc.), pTrcHis (Invitrogen Corporation) and pET11a (Stratagene Corporation) in the case where *Escherichia coli* is used as a host; pBBR122 (Mobiotech) and pBHR1 (Mobiotech) for the other gram-negative bacteria; pHW1520 (Mobiotech) and pHY300PLK (Takara Bio Inc.) for *Bacillus*; pSH19 (Herai et al., Proc. Natl. Acad. Sci., 101, 14031-14035, 2004), pIJ702 (John Innes Centre), pIJ943 (John Innes Centre), pIJ8600 (John Innes Centre), pIJ602 (John Innes Centre), 1, pTip-vectors (Nakashima et al., Appli. Environ. Microbiol., 70, 5557-5568, 2004), pTYM19 (Onaka et al., J. Antibiot., 56, 950-956, 2003) for actinomycetes; pPICZα and pPIC9 (Thermo Fisher Scientific) for *Pichia*, and pAO815 (Invitrogen Corporation), pAUR101 (Takara Bio Inc.), pAUR123 (Takara Bio Inc.) and pAUR316 (Takara Bio Inc.) for fungi.

In another aspect, the present disclosure also relates to a method of expressing the variant Bhr-PETase in the host cell. In another aspect, the present disclosure also relates to a method of making the variant Bhr-PETase comprising culturing the host cell under conditions wherein said variant Bhr-PETase is produced, and recovering said variant Bhr-PETase.

The culture of a transformed organism may be performed in the medium which can be a nutritive medium of the transformed host cell without affecting the transformation of the variant Bhr-PETase. Such a medium comprises an appropriate carbon source, nitrogen source, inorganic salt, natural organic nutrient and the like. As a carbon source, glucose, fructose, glycerol, sorbitol, organic acids can be used individually or in combination. The concentration of the carbon source is not particularly limited and may be 1 to 10%. As a nitrogen source, ammonium, urea, ammonium sulfate, ammonium nitrate, ammonium acetate and the like can be used individually or in combination of two or more members thereof. As an inorganic salt, salts such as monopotassium phosphate, dipotassium phosphate, magnesium sulfate, manganese sulfate and ferrous sulfate can be used. In addition, as an organic nutrient source having growth-promoting effects of the bacteria to be used, peptone, meat extract, yeast extract, corn steep liquor and casamino acids can be used and furthermore, a small amount vitamins and nucleic acids may be contained in the medium.

5. PETase Formulations and Uses

As will be appreciated by those in the art, the formulation of the variant Bhr-PETases of the invention depends on its end use and the associated conditions. Suitable formulations for the variant Bhr-PETases of the invention include liquid formulations, dried formulations (including spray dried formulations), powdered formulations, granular formulations, and pelleted formulations. Bhr-PETases can also be formulated as "embedded in PET particles" for natural degradation.

In some embodiments, the enzyme composition (i.e., polypeptide compositions) of the present invention can be in any form suitable for use, such as, for example, a crude fermentation broth with or without cells removed, a cell lysate with or without cellular debris, a semi-purified or purified enzyme composition, or a host cell, as a source of the enzymes.

In some embodiments, the enzyme composition may be a dry powder or granulate, a non-dusting granulate, a liquid, a stabilized liquid, or a stabilized protected enzyme. Liquid enzyme compositions may, for instance, be stabilized by adding stabilizers such as a sugar, a sugar alcohol or another polyol, and/or lactic acid or another organic acid according to established processes.

In some embodiments, the dosage of the polypeptide composition of the invention and other conditions under which the composition is used may be determined on the basis of methods known in the art.

The above compositions are suitable for use in PET biodegradation, PET biocycling, PET upcycling, and/or PET surface modification processes.

In some embodiments, the above compositions are used to degrade pretreated PET. PET pretreatment may be performed before the enzymatic degradation step. Commonly used PET pretreatment can be broadly classified into a) mechanical pretreatment, b) thermo-mechanical pretreatment, and c) chemical pretreatment. The mechanical process may involve grinding of the PET film into particles less than about 500 μm post sieving. This process could be combined with immersing the PET film into liquid nitrogen mainly for ease of the process of grinding. The advantage of this type of mechanical pretreatment may be enzyme accessibility due to reduced particle size. In the thermo-mechanical degradation, the main-chain scission reactions may affect the stability of the cyclic oligomers. In the thermo-mechanical pretreatment, highly crystalline PET flakes may be amorphized at very high temperatures (>260° C.) using extruder equipped with melt pump and later micronized to particle size of less than 500 μm. An example of a commercial method of pretreating PET is by using an extrusion cast process, namely molten polymer cast onto chilled rolls of PET to solidify. The thermo-mechanical pretreatment may lower the crystallinity as well as particle size of the industrial grade PET allowing accessibility of the enzymes to depolymerize it. In case of chemical pretreatment, ionic liquid, strong acid, base, solvents etc. can be used to reduce crystallinity or to change the surface structure of the PET to facilitate access of the enzymes to further depolymerize it to its monomers.

The two significant stumbling blocks in recycling plastics irrespective of using chemical or biological method may be material variability and the costs associated with identifying and separating waste plastics into recognizable grade ranges. Different types and grades of plastics differ in densities and molecular weights. The advantage of knowing the properties of a particular plastic that is in the recycling process would make it easier to determine its value and durability when put into valuable second use applications. But, the process of sorting is a major hindrance from the standpoint of resource utilization, time management, and cost effectiveness. Hence, when looking at biological mitigations to overcoming the roadblocks associated with differential plastic sorting, depolymerization of mixed plastics using robust enzymes that has broad substrate specificity becomes the utmost priority. Mixed plastic is a term that covers all non-bottle plastic packaging sourced from the domestic waste stream, and it includes rigid and flexible plastic items of various polymer types and colours that are typically found in the household waste bin. The mixed plastic refers to a mixture of different plastics. Various polymer types may refer to PET and/or analog of PET, PET-like or PET substitute derived biologically or chemically. Examples of analog of PET, PET-like or PET substitute include but are not limited to Polybutylene terephthalate (PBT), Polycabonate (PC), Polycaprolactone (PCL), Polyethylene Furanoate (PEF) and High Density Polyethylene (HDPE). Bhr-PETase alone or in conjunction with other accessory enzyme (s) can revolutionize the biological method of depolymerization of mixed plastics. The process of enzymatic depolymerization of mixed plastics as opposed to chemical methodologies may be environmentally safer and capable of retaining the market value of the second use applications. Such biological treatments can also be combined with mild chemical or thermomechanical pretreatment to achieve higher depolymerization efficiencies.

After PET pretreatment and enzymatic degradation, products may be recycled and generate other valuable chemicals. In one embodiment, TPA (terephthalic acid) is purified using an industry relevant process, and the process also may produce sodium sulphate, a chemical commonly used in the detergent, paper, and glass industries. In another embodiment, recycled TPA is used as the starting material to synthesize virgin PET. PET synthesized from recycled TPA may demonstrate similar properties, such as average molecular weight and intrinsic viscosity, as PET synthesized using petrochemical TPA. In one embodiment, bottles blown from recycled PET exhibits similar mechanical property and better lightness value than regular PET bottles.

In some embodiments, the present invention provides a method of preparing enzyme cocktail comprising the variant Bhr-PETase as described herein with other PET degrading accessory enzymes and downstream MHETase to produce a PET degrading enzyme cocktail for the efficient turn-over of pretreated PET.

EXAMPLES

Example 1: PET Hydrolase Gene Selection, Synthesis and Cloning

Multiple novel PET hydrolases were selected based on bioinformatics analysis and were synthesized by GeneWiz (https://www.genewiz.com/en/). The synthesized genes were cloned into the pET28b (+) vector (Millipore Inc., Catalog #69865). Three hydrolases (Lcc-PETase, Bhr-PETase, Is-PETase) were selected for further purification and characterization.

Example 2: Preparation of PET Hydrolases Produced by *Escherichia coli* in 250 ml Shake Flask The BL21(DE3) Chemically Competent *E. coli*, (ThermoFisher Scientific, USA: Catalogue #C600003) containing recombinant hydrolase-encoding genes from single colonies were inoculated into individual culture tubes containing 5 mL lysogeny broth (LB broth) with 1% glucose and 50 μg/mL of Kanamycin. The cultures were grown overnight at 30° C., 200 rpm and 85% humidity. 1 mL of overnight culture was transferred into shake flasks containing 50 mL of terrific broth (TB broth) with 50 μg/mL Kanamycin. The flasks were then incubated for 2-2.5 hrs at 37° C., 250 rpm and 85% humidity. Pre-induction OD was measured at 2-2.5 hrs and if OD600 reached around 0.6-0.8, induction with IPTG (Isopropyl β-D-1-thiogalactopyranoside) was carried out to obtain final concentration of 0.5 mM IPTG in flasks. The flasks were then incubated for 18-24 hrs at 30° C., 250 rpm and 85% humidity all except Is-PETase which was grown at 16° C. The supernatants and lysates were transferred to 50 mL centrifuge tubes and stored at −20° C. prior to activity assay. A total of three candidates (Lcc-PETase, Bhr-PETase, Is-PETase) were grown based on the procedure herein.

Example 3: Ni-Column Purification of the His-tag PET Hydrolases Produced from Shake Flasks Each sample was concentrated to 15-20 ml before using Thermo Scientific HisPur™ Ni-NTA Spin Columns (catalog number 88226). The three PET hydrolases (Lcc-PETase, Bhr-PETase, Is-PETase) were purified from the cell culture. The protocol was followed as per manufacturer's guidelines. Multiple elution was done in 250 mM Imidazole and based on protein band intensity from the eluents in various fractions (measured using gel quantification), a stock solution of combined fractions was used for the desalting step.

Example 4: Desalting of Purified PET Hydrolases Produced from Shake Flasks

Using one time use Thermo Scientific Zeba™ Spin Desalting Columns, 7K MWCO (catalog number 89892), imidazole and NaCl were removed from Ni Purified enzyme. Desalting protocol was followed according to manufacturer's guidelines. Desalted enzyme was then quantified to determine protein concentration (g/L).

Example 5: Thermostability Testing of *Escherichia coli* Produced PET Hydrolases Using BHET (Bis(2-Hydroxyethyl)terephthalate) as a Substrate Normalized PET hydrolase proteins of each candidate were subjected to a 1.5 hr challenge at either 30° C., 50° C., or 70° C. Enzymes kept on ice for the same time served as unchallenged condition. Post challenge, into Costar Deep wells plate, 250 μL of 10 mM BHET (Bis(2-Hydroxyethyl) terephthalate), 62.5u μL of unchallenged and challenged enzyme, and 170 μL of 0.1M sodium phosphate buffer, pH 8 was added. The plates were incubated at 50° C. for 2 hours. After 2 hours, the samples were centrifuged at 4,000 rpm for 2 minutes. The supernatants were analyzed using High Performance Liquid Chromatography (HPLC) to determine the amount of TPA produced in our reactions. Zorbax Eclipase Plus C18 (Rapid Resolution HD 2.1×50 mm 1.8-Micron) column with part number 959757-902 was used along with guard column part number 82175-901. Flow rate of 0.6 mL/minute with column temperature of 35° C. was set up for running in HPLC. The gradient method was used to detect Terephthalic Acid (TPA) with mobile phase 1 consist of water with 0.1% trifluoroacetic acid and mobile phase 2 consist of Acetonitrile with 0.10% trifluoroacetic acid. % residual of each PET hydrolase was calculated by the following formula: (MHET+TPA produced at challenged condition)/(MHET+TPA produced at unchallenged condition)*100.

The thermostability results of the three candidates (Lcc-PETase, Bhr-PETase, Is-PETase) are shown in FIG. 4. Under the current experimental condition, Is-PETase is the most unstable candidate that looses 90% activity at 50° C. Bhr-PETase and Lcc-PETase retain ≥80% residual activity at all temperature tested.

Example 6: Large Scale PET Film Assay to Evaluate *Escherichia coli Produced PET Hydrolases*

These experiments were carried out in 250 ml glass bottles. Two types of PET substrate were used in these experiments. A) Amorphous PET film was obtained from Goodfellow (Catalog #ES301445) with 0.25 mm thickness. PET film was cut using paper trimmer into 1×30 cm strips, and then cut again to approximately 1×0.25 cm strips. Strips of PET film were grinded into fine powder with mechanical grinder. B) Highly crystalline PET powder >40% crystallinity was obtained from Goodfellow (Catalog #ES306031/1). 2-10 g/L PET powder loading was done in 0.1M sodium phosphate buffer, pH 8.0 to a final volume of 50 mls. Various doses of normalized proteins of the three candidates were used for evaluation at either 65° C. or 72° C. with 200 rpm shaking. The reactions were continued for anywhere between 6-144 hrs. At various timepoints the bottles were sampled, and the reactions were analyzed using High Performance Liquid Chromatography (HPLC) to determine the amount of TPA produced in our reactions. Zorbax Eclipase Plus C18 (Rapid Resolution HD 2.1×50 mm 1.8-Micron) column with part number 959757-902 was used along with guard column part number 82175-901. Flow rate of 0.6 mL/minute with column temperature of 35° C. was set up for running in HPLC. The gradient method was used to detect Terephthalic Acid (TPA) with mobile phase 1 consist of water with 0.1% trifluoroacetic acid and mobile phase 2 consist of Acetonitrile with 0.1% trifluoroacetic acid.

Results for PET assay are summarized in FIGS. 5 and 6. Both in amorphous and >40% crystalline PET, Bhr-PETase outperforms Lcc-PETase. Results further suggests that Lcc-PETase is less thermostable compared to Bhr-PETase irrespective of substrate type. In comparison to Bhr-PETase which can depolymerize >90% amorphous PET at both 65° C. and 72° C. at an enzyme loading of 2.4 mg/g PET (FIG. 5), depolymerization activity of Lcc-PETase at higher doses is significantly lower (data not shown). FIG. 6 further suggests that Bhr-PETase cannot fully degrade highly crystalline PET and might require additional pretreatment or accessory enzymes to do so.

Overall, Bhr-PETase was identified as the best performing PET hydrolases among all that have been evaluated. Therefore, Bhr-PETase was selected as a target for further improvement.

Example 7: Design and Construction of Bhr-PETase Collections

To further improve the activity and thermostability of Bhr-PETase, multiple G1 variant collections were designed based on sequence and structure analysis. The design includes one to multiple specific mutations per variant. The G1 variant collections were subsequently constructed on Bhr-PETase G1P (wild type Bhr-PETase, Generation 1 Parent) using standard site-directed mutagenesis methods and subsequently cloned into the pET28b (+) vector (Millipore Inc., Catalog #69865) for production in *Escherichia coli.*

To further improve the activity and thermostability of Bhr-PETase, multiple G2 variant collections were designed based on sequence and structure analysis. The design includes one to multiple specific mutations per variant. The G2 variant collections were constructed on Bhr-PETase G2P (Generation 2 Parent, i.e. G1P with amino acid substitution S27L) using standard site-directed mutagenesis methods and subsequently cloned into a relevant vector for production in a desired host.

Example 8: HTP Growth: Preparation of Bhr-PETase G1P, G1 Variants, G2P and G2 Variants in Microtiter Plates The BL21(DE3) Chemically Competent *E. coli*, (ThermoFisher Scientific, USA: Catalogue #C600003) containing recombinant Bhr-PETase encoding genes from single colonies were inoculated into individual wells of 96 well plates containing 180 μl lysogeny broth (LB broth) with 1% glucose and 50 μg/mL of Kanamycin. The cultures were grown overnight at 30° C., 200 rpm and 85% humidity. 20 μL of overnight culture was transferred from each well into 96 wells plate containing 380 μL of terrific broth (TB broth) with 50 μg/mL Kanamycin. The plates were then incubated for 2-2.5 hrs at 37° C., 250 rpm and 85% humidity. Pre-induction OD was measured at 2-2.5 hrs and if OD600 reached around 0.6-0.8, induction with IPTG (Isopropyl β-D-1-thiogalactopyranoside) was carried out to obtain final concentration of 0.5 mM IPTG in wells. The plates were then incubated for 18-24 hrs at 30° C., 250 rpm and 85% humidity. The supernatants were transferred to round bottom plates and stored at −20° C. prior to activity assay.

The host containing recombinant Bhr-PETase encoding genes from single colonies were inoculated into individual wells of 24 or 96 well plates containing relevant medium. The cultures were then grown overnight at 30° C., 200 rpm and 85% humidity. Overnight culture was subcultured into 24 or 96 wells plate containing relevant medium. The plates were then incubated at 30° C., 200 rpm and 85% humidity. Culture was induced at every 24 hours with respective inducer for up to 120 hours. The supernatants were transferred to round bottom plates at desired harvesting time and stored at −20° C. prior to activity assay.

Example 9: HTP PET Film Assay to Evaluate Bhr-PETase G1P, G1 Variants, G2P and G2 Variants Activity/Thermostability For total activity testing, amorphous PET film was obtained from Goodfellow (Catalog #ES301445) with 0.25 mm thickness. PET film was cut using paper trimmer into 1×30 cm strips, and then cut again to approximately 1×0.25 cm strips. Strips of PET film were grinded into fine powder with mechanical grinder. PET powder was loaded into 96-well plates using resin loader. Approximately 8-9 mg of PET powder were dispensed in each of the 96 costar deep well. Into costar deep well containing PET powder, 1.4 mL of 0.1M sodium phosphate buffer was added, pH 8.0. 100 μL of enzyme was dispensed into costar deep wells, the plates were sealed, and then incubated at 65° C. for 72 hours. After 72 hours, plates were centrifuged at 4,000 rpm for 2 minutes. Into costar round bottom plates, 180 μL of above reaction was transferred and 20 μL of in-house prepared Is-MHETase was added. The plates were incubated at 50° C. for 30 minutes. After 30 minutes, the plates were centrifuged at 4,000 rpm for 2 minutes. Reaction mixture was diluted to linear assay detection using sodium phosphate buffer, pH 7.2 in Costar Deep with addition of 50 μL of 10 mM EDTA, and 50 μL of 10 mM $FeSO_4$. Incubate the reaction in dark for 10 minutes and centrifuge plates at 4,000 rpm for 2 minutes before transferring 200 μL of reaction into black clear-bottom fluorometric plate. Endpoint reading was measured after 10 minutes with 328 nm for excitation and 421 emission for TPA (Terephthalic Acid) activity.

For thermostability testing, 150 μL of enzyme was transferred into PCR plates. The plates were incubated at 86° C. for 3 hours. After 3 hours, 100 μL of enzyme was transferred into costar deep well plates containing 1.4 mL of 0.1M sodium phosphate buffer, pH 8.0, and 8-9 mg/well of grinded PET powder. Plates were at 65° C. for 72 hours. After 72 hours, plates were centrifuged at 4,000 rpm for 2 minutes. Into costar round bottom plates, 180 μL of above reaction was transferred and 20 μL of Is-MHETase was added. The plates were incubated at 50° C. for 30 minutes. After 30 minutes, the plates were centrifuged at 4,000 rpm for 2 minutes. The reactions were analyzed using High Performance Liquid Chromatography (HPLC) to determine the amount of TPA produced in our reactions. Zorbax Eclipase Plus C18 (Rapid Resolution HD 2.1×50 mm 1.8-Micron) column with part number 959757-902 was used along with guard column part number 82175-901. Flow rate of 0.6 mL/minute with column temperature of 35° C. is set up for running in HPLC. The gradient method was used to detect Terephthalic Acid (TPA) with mobile phase 1 consist of water with 0.1% trifluoroacetic acid and mobile phase 2 consist of Acetonitrile with 0.1% trifluoroacetic acid.

The results are summarized in FIGS. 7, 8 and 9. All G1 variants showed improved total activity and/or thermostability than Bhr-PETase G1P (wild type Bhr-PETase). A Bhr-PETase G1 variant with amino acid substitution S27L exhibited 1.80 fold improved total activity and 3.36 fold improved thermostability over Bhr-PETase G1P and therefore selected as Bhr-PETase G2P. All G2 variants showed further improved total activity than Bhr-PETase G2P.

The invention claimed is:

1. A composition comprising a variant bacterium HR29 polyethylene terephthalate hydrolase (Bhr-PETase) as compared to SEQ ID NO:1, wherein said variant has PETase activity greater than SEQ ID NO:1, and said variant Bhr-PETase comprises a set of amino acid substitutions selected from the group consisting of P20T/L90Y/F92L/S101M/D158E/A174K/I222L, P20T/F21W/A24V/L90Y/F92L/T109K/A125S/T136A, R12K/S32K/L90Y/F92L/T136A/A174K/D203V/I222L, R12K/A14K/V23T/L90Y/F92G/S101A/D203R, T17G/S32M/L90Y/F92Y/D203R/A216P, P20T/F21W/S32M/L90Y/F92G/A114K/A125S/T136V/D158E/A174K/D203V/I222L, T17Q/L90Y/F92L/A174K/D203V/I222L, T17S/D18R/L90Y/F92G/A114V/A117Q/D203R, L90Y/F92L/S101A/S110R/A125S/Q142W/A174R/A216P, S32K/L90Y/F92G/A114K/D203V, -continued T17C/L90Y/F92L/S101N/T109L/S110R/A125S/A174K/D203R, T17C/L90Y/F92L/A125S/T136V/D158E/A174K, L90Y/F92L/S110R/A125S/D158E/D203V, T17Q/L90Y/F92L/T109L/T136A/D158E/A174R/D203V/V229C, P20T/F21W/S32M/L90Y/F92G/T109L/S110R, A14K/S32M/L90Y/S101R/A114V/T136A/A216P, P20T/F21W/L90Y/F92G/A125S/A174K/V229I, S32K/L90Y/F92Y/S101A, D18R/S32Q/N87H/L90Y/F92G/S101K/Q142L/D158I/A174R, T17Q/L90Y/F92G/S101N/T109L/S110R/T136V/Q142L/D203V/A216P, S32Q/L90Y/F92L/T109K/A125S/T136V, P20T/L90Y/T109K/T136A/D158I/D203R, N2R/S32Q/L90Y/F92Y/T109K/D203V, T17H/A24V/S32Q/L90Y/F92L/S101H/A114K/D158I/A174R/D203V, V23T/A24V/L90Y/F92G/A125S/T136V/D203V, P20T/S32K/L90Y/F92G/S101N/T109L/S110R/A125S/A174K/D203R/A216P, R12K/A14K/A24V/N87L/L90Y/A125S/T136V/A216P, P20T/F21W/L90Y/A125S, N2R/L90Y/A114K/A117Q/D203V/V229I, F21W/S32K/L90Y/A125S/D158E/A216P/V229I, S27L/T136V, S27L/P8T/T17Q/F21W/S101A/T136V/Q142L, S27L/N2R/T17L, S27L/V23T/A24V/T136A/Q142W, S27L/F21W/T136V, S27L/T17Q/T109K/A114K/T136V/V229I, S27L/T17Q, S27L/T136V/I222L/V229C, S27L/T17A/A114V/A117N/T136A, S27L/N2R/T136A, S27L/N2R/T17A, S27L/T17C/S101A/T136V, S27L/P20T/T136A, S27L/T136V/Q142W/V229I, S27L/T109K/T136V/I222L/V229I, S27L/T17L/S101H/A117N/Q142L/I222L/V229I, S27L/S101Q/T109L/A117N/T136A/Q142L, S27L/T109K/S110R/S193N/S252T/R255M, S27L/S22R/Y26K/R236Q, S27L/L90F/F92L/S98E/S113Y/A114K/T136A/D158E/S181R/T206G/S212M/V219I, S27L/N9S/S22P/T48N/L90Y/F92G/T109K/S110R/T136A/Q189V/N211F/R236Q, S27L/T17A/Y26L/T48N/I82M/S101D/R236Q, S27L/Y26T/S101D/D158E/V219I/S252T, S27L/S13R/S98E/T136V/S181R/T206G/V229I/N231S, S27L/F21W/F92L/S98N/S193P/I222L, S27L/S1G/Y26K/L90Y/S113Y/A114V/T136A/Q189V/N204R/N211L/R236Q, S27L/S22K/I82L/L90Y/F92G/R108S/A117N/D158E/S193N, S27L/S1G/N9S/T48S/L90Y/S98T/S101A/S113N/A114K/L119M/S193N/T206G/S252T, S27L/N9E/R12K/S22P/V23L/T160R/D203R/I222L, S27L/N9E/R12K/S22P/V23T/T48S/S98E/R108S/T160S/Q189V/T206G/S212L/V229I, S27L/S1A/N2R/N9S/T48N/L90F/F92L/D203V/S223A, S27L/N9E/R12K/V23T/I82M/L90Y/F92L/T136V/N204K/N231S/R255M, S27L/S1G/N9S/S22V/I82F/L90Y/F92L/A117N/L119M/Q142L/T206G/S212L/S223A, S27L/N9S/Y60H/R108C/S193P/V219L, S27L/N9E/S22K/S32M/L90F/F92G/R108T/L119M/Q189V/I222L/S223A/R236Q, S27L/T17Q/F92G/S98N/Q142L/Q189L/R236C, S27L/N9E/R12K/Q142W/T160Q/T206G/S212M, S27L/Y26T/S113N/A114V/T136A/D158E/D203R/N211F/R236Q/S252T/R255M, S27L/S1A/T17H/S22V/L90Y/F92G/S98E/A114V/T136A, S27L/N9E/T48S/I82M/L90Y/F92L/N122A/A127S/T160S/A174R/T206G/S212L/R255M, S27L/N9S/S22P/V23L/L90Y/F92G/A125S/T160S/N204R/I222L/S223A/R236Q, S27L/N9E/S22P/T48S/L90Y/F92L/T109R/E173R/A174K/D203V/S223A, S27L/R12K/Y26K/T48N/I82L/L90F/A125S/N211I/A216P, S27L/N9S/R12K/F92Y/T109K/S110R/T160K/Q189L/S223A/S252T/R255M, S27L/S1A/N2R/N9E/R12K/S32K/N87F/R108T/N211I/V219K/R255M, S27L/L90F/F92G/N122A/T136A/T160V/E173R/D203R/S252T, S27L/L90Y/F92G/S98T/T109L/D158I/S193K/V219K/R236Q/S252T, S27L/N9E/R12K/T48N/L90F/S98L/R108Q/A117Q/T136A/T206G/S212F/V219I/V229I/R255L, S27L/S1A/S22V/N87K/R108K/N122E/D158E/S193P/V219I/R255M, S27L/F21W/Y26T/S34R/R108H/L119M/N211M/R236C/S252T, S27L/S1A/N9E/R12K/V23T/T48S/N87H/S101Q/Q189L/N211M/V219/R236Q/R255M, S27L/N9S/T25Q/L90Y/S101D/T136A/Q142L/Q189L/R236Q, S27L/A14K/I82F/F92G/S98E/R108C/A117N/L119M/Q189V/T206G/I222L/S223A, S27L/T17C/Y26T/N87V/R108C/N122E/T136V/S193P/S252T/R255M, S27L/L90Y/F92G/T109L/N122S/R255M, S27L/R12K/L90Y/T160V/A174R/R236Q, S27L/N9E/R12K/T48N/L90Y/F92G/S98T/S113R/N122R/A127S/T136A/A174K/N204K/S212L, S27L/V23T/L90Y/F92G/S98E/T109L/A125S/T160V/A174K/S181C/S193K/T206G/S212M/R255M, S27L/A24V/F92G/S101D/A114V/A117N/A125S/T136V/D203R, S27L/R12K/S32Q/S101Q, S27L/L90F/F92G/T136V/A174R/D203R, S27L/P20T/S32K/L90Y/D203V, S27L/N2R/A14K/T17S/L90Y/T109K/T136V/A216P, S27L/N2R/V23T/A24V/S32M/L90Y/F92G, S27L/A14K/L90Y/F92L/S101D/A117N/D158I/D203R, S27L/F21W/N87H/A114V/A117N/T136V, S27L/N2R/V23T/A24V/N87M/F92L/S101K/A125S/T136A, S27L/L90Y/F92L/S101N/T109R/S110R/Q142W, S27L/S32M/F92G/A216P, S27L/F21W/L90Y/F92L/A114K/A117N/T136A/D203V, S27L/N2R/V23T/S32M/N87M/F92L/T136A, S27L/R12K/L90F/F92G/S101A/D203V, S27L/A24V/L90F/F92G, S27L/R12K/F92L/S101A/A125S/T136A/D203R, S27L/R12K/V23L/L90F/F92L/A114K/T136A/D158E/D203V/I222L, S27L/L90F/F92G, S27L/A14K/P20T/S32Q/L90Y/A125S/D203V, S27L/T17L/L90F/F92G/A125S/A174R/D203V, S27L/N2R/N87K/A114K/A117Q/T136V/D203V, S27L/N2R/A114K/T136V/D203V, S27L/N2R/T17A/T136V/A216P, S27L/N2R/R12K/N87F/T136V/D158E/A174R, S27L/D203R, S27L/R12K/T17Q/T136V/D203V/A216P, S27L/N87F/T109L/Q142L, S27L/N2R/T17Q/A24V/A114K/A117Q/T136A/D158E/A174K/D203V/I222L, S27L/N2R/P20T/F21W/N87M/T109R/A117N/A125S/T136V/D203V/I222L, S27L/V23T/A24V/T136A/D158E/A174K/D203V/I222L, S27L/R12K/V23L/A114K/T136A/D158/D203V/I222L, S27L/N87Y/T136V/D158E/D203V, S27L/T109K/S110R/D203R, S27L/N2R/T17L/A125S/T136A/D158E, S27L/A24V/D158E/A174K/A216P, S27L/T17G/V23L/N87L/A117Q/A125S/T136V/D158E/V229C, S27L/V23L/N87L/T109R/A114K/A117N/A125S/T136V/Q142L, S27L/N87Y/S101A/A114V/A117Q/T136V/A174K/A216P/I222L, S27L/R12K/T109R/Q142L, S27L/D203V, S27L/T17G/N87F/S101A/D203V, S27L/T17L/N87M/Q142L/D203V, S27L/N2R/R12K/S101D/A117N/T136A/D203V, S27L/R12K/P20T/F21W/A114K/Q142W/D203R, S27L/N2R/T17G/T109L/S110R/A114K/A117Q/T136V/Q142L/D203R, S27L/N2R, S27L/S32K/L90F/F92G/S101M/A114V/A117N/A125S/T136A/D158E/D203V, S27L/R12K/T17A/F21W/S32Q/Y60H/D203R, S27L/R12K/F92L/S110R/T136V/I222L, S27L/A14K/V23T/A24V/L90Y/F92G/A114V/A117Q/Q142L/A174R/I222L, S27L/F21W/S32Q/L90Y/S101D/T109K/A125S/T136A/A174K, S27L/V23T/L90Y/F92G/T136A/D203V/A216P, S27L/T17S/L90Y/F92G/A117N/T136A/D158L, S27L/A14K/V23L/A24V/F92L/Q142W/D203V, S27L/T17L/L90F/F92G/S101K/A174K, S27L/L90F/F92L/A125S/T136V/A174K/D203V/A216P/I222L, S27L/R12K/P20T/S32M/L90F/F92G/S101M/A114V/D203V, S27L/T17A/S32Q/L90F/F92L/T136V/Q142W/A174K/D203R, S27L/R12K/S32M/L90F/F92G/S101W/A114V/D158I/I222L, S27L/P20T/S32M/L90Y/F92L/A114V/A117N/I222L, S27L/T17C/L90Y/F92G/T136A/A174K/D203V, S27L/S32Q/N87Y/F92G/T109K/A114K/A117N/T136V/D203V/V229C, S27L/F21W/L90F/F92G/T136V/A174R, S27L/P20T/N87Y/T136A/D203V/I222L, S27L/A24V/L90Y/F92L/D158I/A174K/D203R/I222L, S27L/F21W/S32Q/L90Y/S110R/A114K/T136V/D203R/A216P/V229I, S27L/N87H/F92G/D203R, S27L/R12K/S32K/Y60A/A125S/T136V/D158L, S27L/V23T/A24V/S32Q/L90F/F92L/T136A, S27L/F92L/A114V/D158E/D203R, S27L/S32Q/L90Y/D203V/V229I, S27L/V23T/S32Q/Y60H/T109K/T136V/A216P/I222L, S27L/A14K/A24V/L90F/F92G/T109K/T136V/D158L/A174R/D203V/I222L/V229I, S27L/R12K/N87F/A174K, S27L/P20T/S32Q/Y60H/T109K/A114V/T136A/A174K, S27L/V23T/A24V/Y60A/A125S/A174R/A216P, S27L/F92Y/D158L/I222L, S27L/V23L/A24V/L90Y/F92G/D203V/I222L, S27L/V23T/A24V/S32Q/L90F/F92G/S101H/T136A/A174K/D203V/V229C, S27L/S32K/N87H/A125S, S27L/P20T/F21W/F92G/A114V, S27L/T17L/V23L/A24V/L90Y/F92L/A117N/T136V/L137M/Q142L, S27L/P20T/L90Y/D203R, S27L/S110R/Q142L/D158I/D203R/V229I, S27L/P20T/S32Q/L90F/F92L/T109K/S110R/A125S/D203V, S27L/V23T/A24V/L90F/F92G/D158E/D203R, S27L/F92G/T136A/A174R/D203V/V229C, S27L/P20T/L90Y/F92G/T109R/S110R/A125S/D203R, S27L/A14K/L90Y/F92L/D158L/A174R/D203V, S27L/F21W/S32Q/L90Y/F92G/T109L/S110R/A117N/D158I/A174K/D203V, S27L/R12K/A114K/A117N/D158E/D203V, S27L/T17S/N87H/T109R/A114K/A117N/T136V/Q142W/D203V, S27L/N2R/N87Y, S27L/T17S/V23T/A24V/S32Q/Y60H/N87K/T136A/D203R, S27L/P20T/F92Y/T109K/D158E/D203V, S27L/S32K/N87M/F92L/S101M/T109L/S110R/D203V, S27L/L90Y/F92G/T136A/D158E/D203V/A216P/V229I, S27L/A14K/S32M/F92L/A125S, S27L/L90Y/F92G/T136V/D158L/D203V, S27L/A24V/L90Y/F92G/S101A/T109L/S110R/A117Q/A174R/D203R, S27L/P20T/S101D/A114V/T136V/Q142W/D158E/D203R/A216P, S27L/N87Y/F92G/S101Q/A114K/A117N/T136A/D158L/D203R/A216P, S27L/V23T/A24V/N87Y/L90Y/F92L/S101D/T109R/A174K/D203R/A216P, S27L/N2R/P20T/F21W/L90F/F92Y, S27L/L90Y/F92G/D158I/D203V/V229C, S27L/S32Q/F92G/Q142W/I222L, S27L/N2R/R12K/S32M/N87Q/L90F/F92L/I222L, S27L/R12K/S32K/F92L/A114V/A117Q/T136A/D158E/A216P, S27L/L90Y/F92G, S27L/R12K/F21W/S32M/F92G/T136V/Q142L/D203R, S27L/R12K/A14K/L90Y/F92L/A125S/A174K, S27L/A24V/A114V/A117Q/T136V/D203V, S27L/R12K/T17Q/V23L/S32M/L90Y/F92G/S101D/T136V/I222L, S27L/V23T/A24V/S32Q/F92L/S101N/T109L/S110R/D203R, S27L/P20T/Y60H/N87K/T136A/A174R/D203V, S27L/P20T/F21W/L90Y/F92L/T136A/A174R/D203V/V229C, S27L/T17G/F21W/S32K/L90F/F92G/A125S/T136A/A174K, S27L/T17G/N87Y/T136A/D203V/A216P, S27L/F21W/L90F/F92G/S101D/A117N/T136A/A174K/D203V, S27L/R12K/A14K/A24V/L90Y/D203V, S27L/N2R/L90F/F92G/S101M/Q142L/D158L, S27L/N2R/T17C/A24V/N87K/A174K/A216P, S27L/N87M/Q142L/I222L, S27L/F92L/S98T/R108C/A117Q/A127S/Q142L/Q189V/A216P/R236Q, S27L/S22K/F92L/R108H/A127S/T136A/N211I, S27L/F21W/T48S/L90Y/F92L/T109L/A127S/T136V/N204K/S223A, S27L/T17L/L90Y/F92L/S98M/A174K/D203V/N211M/S212L/S223A, S27L/N87K/S98M/N211M, S27L/N9E/S22P/L90Y/N204K, S27L/S32M/T48S/F92G/A127S/Q142W, S27L/T17S/S22K/L90F/F92L/D158E/D203V/V219/S252T, S27L/L90F/F92L/A127S/D203V, S27L/T25F/L90Y/F92G/N204R/S223A/N231S/R236C, S27L/F21W/S22V/T48S/L90F/F92L, S27L/S1A/S98T/S113K/A114V/L119M/A127S/Q142W/S193K/V219K/S252T/R255L, S27L/A24V/I82L/L90F/F92G/T109L/L119M/A127S/E173R/N204K, S27L/T17C/Y60H/L90F/A127S/E173R/A174R/N204K, S27L/L90F/F92L/Q142W/D203V/S223A, S27L/P20Q/L90Y/Q142L/S223A, S27L/N9S/Y60A/A216P/R236Q/R255M, S27L/F92G/R108C/S110R/A117Q/T136A/N211M, S27L/S22P/Y60H/S98A/S113K/A114K/T136V/Q189L/S193H, S27L/V23L/S98A/Q142L/N211M, S27L/V23L/Y26L/L31M/T48S/F92G/A174R/N204K/S252T, S27L/S13R/A14K/Y26T/T136A/S181R/N211M/S212M, S27L/F21W/I82F/L90Y/F92G/A127S/N211M, S27L/P20T/Y60H/S98L/T136A/R255L, S27L/P20T/S34R/N87M/D158E/S252T, S27L/T25A/L90F/F92G/Q189L/S193P/V229I, S27L/V219L/I222L, S27L/N9E/T48S/L90F/F92L/S98N/R108H/S110R/S113Y/N211V/S212L/S252T, S27L/L90F/F92Y/S113R/V219I/R255L, S27L/F21W/S22K/T48S/F92G/T109R/A127S, S27L/S1G/A14K/P20T/S32K/T48S/L90Y/F92L/T109L/T160R/V219L/I222L/S252T/R255L, S27L/L90F/F92G/D158E/T160R/S193N/N204K/S223A, S27L/A14K/Y26T/F92L/Q142L/S212L, S27L/S22R/L90Y/F92G/V126I/A127S/A174K/N204K, S27L/P20T/T25A/L90F/F92L/A117N/L119M/S252T/R255L, S27L/T17A/A24V/T48S/L90F/F92G/T109R/A127S/T160K/D203R/S223A, S27L/F21W/T48S/T109L/A127S/V219I/R255L, S27L/A14K/S22P/T48S/L90F/F92L/T109L/A127S/Q142L/A174R/N204K/S223A, S27L/T136A/S212M/N231S, S27L/F21W/L90F/F92G/A127S/S223A, S27L/T48S/L90Y/F92L/R108S/S110R/A127S/T136V/E173R/S223A, S27L/T48S/F92G/S98E/Q142L/Q189V/S193P/N204R/S223A, S27L/T17S/L90F/F92Y/S101K/A127S/T136V/N204R/N211I/V229I/N231S, S27L/N9E/F21W/T48S/L90Y/F92L/T109R/N204K/R236Q, S27L/N9E/S22R/T48S/F92L/S101N/A127S/E173R/N204R, S27L/S22K/N87F/A117Q/S181C/N204K/N211M/V229I/N231S/R236Q, S27L/N9S/T48S/L90F/F92G/S101N/A127S/N204K/A216P/S252T/R255M, S27L/I82L/S193H/N211M/S212F/S223A, S27L/A14K/P20T/T48S/L90F/F92G/S98N/R108C/T136A/N204K/N211L/S212L/R236Q/S252T, S27L/S13R/T17L/T25Q/L90F/F92G/R108C/A127S/T160R/I222L/R255L, S27L/T48S/L90Y/F92G/T109L/S193N, S27L/S22V/T48S/L90Y/F92L/S98E/A127S/T136A/N204K/A216P/S223A, S27L/V23L/N87H/F92L/R108C/S110R/N122A/T160S/Q189L/S193P/N204K/S223A/R255L, S27L/F92G/A127S/A174R/S223A/V229I/N231S/R236C, S27L/S1G/L90Y/A127S/E173R/S223A, S27L/F92Y/S98N/Q142W, S27L/P20T/S32M/S34R/T48S/L90Y/F92L/R108K/A127S/Q142W/A174R/N204K/V219I/S252T, S27L/F92G/A127S/Q189V/S193N/S223A, S27L/S34R/F92G/S110R/D158L/D203V/R255M, S27L/N9E/F21W/T48S/F92G/T109L/A127S/R236C, S27L/S1A/S22P/T48S/L90Y/F92G/A127S/E173R/A174R/N204K/S223A, S27L/S22K/T48S/T160S/N204K, S27L/F21W/T48S/L90Y/F92G/S98V/R108C/A127S/N211L/S212M/N231S/R236C, S27L/V23L/A24V/A114K/T136A/I222L/V229I, S27L/P20T/S101H/T109R/A114V/T136A/Q142L/I222L/V229I, S27L/V23L/S101H/T109K/A114K/A117N/T136V/Q142L/I222L/V229I, S27L/T17L/F21W/S101H/T109R/A114V/T136A/Q142L/I222L/V229I, S27L/T17S/T136V/Q142L/I222L/V229C, S27L/T17C/S22P/T48S/L90F/F92G/A127S/A174R/P192A/S193H/N204K/S223A/V229I/N231S/R236Q/R255L, S27L/N9E/T48N/N87H/F92L/A174K/Q189L/S193K/N204R/V219I, S27L/A14K/V23L/Y26L/L90F/F92G/S98E/S113K/A114K/T136A/V229I/N231S, S27L/L90Y/F92L/S101D/A117N/Q142L/S193N, S27L/S22K/T25A/L90Y/Q142L/E173R/N204K/S223A, S27L/P20T/L90Y/T109L/A127S/A174K/V229C, S27L/S22V/L90Y/F92L/A117Q/R236C/R255L, S27L/V23L/A24G/Y26T/I82F/L90Y/F92G/R108H/T136A/D158L/T160K/D203V, S27L/A14K/S22K/F92G/A127S/N204K/V229I, S27L/S22V/L90F/F92G/A127S/A174R/A216P/R236C, S27L/V23L/Y60A/S98T/T109L/A127S/T136V/T160Q/N204K/S223A/R255L, S27L/S13R/L90Y/S98L/T160V/Q189L/S193P/A216P/S252T/N253S/R255L, S27L/S22R/I82M/F92L/T109L/A127S/Q142W/Q189L/S223A, S27L/S1G/Y60A/L90F/F92L/N122E/T136A/N204K/S223A/N231S, S27L/S32K/F92G/S98L/R108Q/S110R/R255L, S27L/L90Y/F92G/L119M/A127S/A174R/S252T, S27L/L90F/S110R/S181R/N211F, S27L/A14K/S22P/Y60H/S110R/N122S/D158I/N204K/S223A/R255M, S27L/F92L/S98V/T109L/N122A/E173R/R255L, S27L/S22R/N87L/F92G/R236C, S27L/S32M/S34R/I82L/F92G/N204K/S223A, S27L/A24V/T25Q/Y60I/A127S/A174K/N204K/V219I/S223A/S252T/R255M, S27L/S98V/T136A/N211F, S27L/N9S/L90F/F92L/A127S/N204R/S212M, S27L/S22R/T48S/F92G/R108H/S110R/A127S/E173R/N204K/S223A/R236Q, S27L/A14K/L90Y/F92G/A127S, S27L/A14K/T48S/F92G/E173R/N204R/S223A/N231S, S27L/L90Y/T109R/S113N/V219L/I222L, S27L/N9S/T48S/L90Y/T136A/T206G/S223A, S27L/S22K/T48N/L90F/F92G/N204K/S223A/V229C/N231S, S27L/S22P/T48S/L90F/F92G/A127S/A174R/N204R/S223A, S27L/S1G/P20T/S32K/S34R/T48S/N87F/S98A/A127S/T136A, S27L/F21W/S22R/S98E/Q142L/T160V/S223A/S252T/R255L, S27L/P20T/T48S/F92Y/R108K/S110R/A127S/V219L/S223A/V229I/R236Q, S27L/Y26T/L90Y/F92L/A127S/V219L/S252T/R255L, S27L/N9S/F21W/T48S/F92L/A127S/D203V/S212F, S27L/F21W/Y60H/S98E/L119M/D158E/R236Q, S27L/F21W/S22R/L90F/F92L/N122S/Q142W/R236Q, S27L/F21W/T48S/L90F/F92G/T109K, S27L/L90Y/F92L/T109R/A127S/E173R/N204K/S223A, S27L/N9S/F21W/T48S/L90Y/F92G/A127S/N204K/V219I/R255M, S27L/N9E/I82F/L90Y/F92L/S95N/T109L/A127S/A174R/S223A, S27L/L90F/F92L/S98L/N204K/A216P, S27L/A24V/T48S/A117Q/N211M/S212M/S223A, S27L/L90Y/F92G/T109L/A127S/N204R/S223A, S27L/N2R/S32Q/N87K/A125S/V219L, S27L/S22P/T48S/L90F/F92L/S193N/V219L/S223A, S27L/T25Q/L119M/N211M/R236Q, S27L/L90Y/F92G/N122S/A127S/E173R/A216P/R236Q, S27L/P20T/S32K/L90F/F92G/N122E/D158E/T160S/Q189L/S223A/S252T, S27L/N9S/F21W/T48S/N87H/L90F/F92L/S113N/V229C, S27L/T25Q/I82L/L90F/F92G/S98L/S113R/A114V/T136A/S181R, S27L/P20T/R108Q/S110R/D203V/N211I, S27L/S1G/N2R/P20T/Y26T/S32M/T48S/L90Y/F92L/A127S/N204R/V219L, S27L/A14K/P20T/T48N/L90F/F92G/A117Q/A127S, S27L/N9S/T48N/L90Y/F92L/S98M/T109K/A127S/N204R/N211I/S212L/V219I, S27L/F21W/S22R/T48S/L90F/F92L/R108Q/A174K/N204K/S212F/S223A, S27L/S22R/Y60H/S98T/T136V/S193K/R236Q, S27L/S22K/Y26K/N87Y/L90Y/F92G/T109R/A127S/S252T/R255L, S27L/L90F/F92L/T109L, S27L/F21W/F92L/N204K/S252T/R255L, S27L/V23L/L90Y/F92G/A127S/S193K/N204R/V219I/R236C/R255L, S27L/F21W/L90Y/F92G/A114V/N122S/A127S/N204K/S223A/S252T, S27L/P20T/Y60A/T109L/Q189L/S212L, S27L/S22V/T48S/L90Y/F92G/N204K, S27L/S22V/S32K/T48S/I82F/F92G/A127S/N204K/S223A, S27L/A55L, S27L/A97V, S27L/F250L, S27L/T109G, S27L/G38D, S27L/A97S, S27L/A55V/A216T, S27L/P20D, S27L/A55V, S27L/T109Y, S27L/V165I, S27L/A184G, S27L/A97E, S27L/A184S, S27L/A97F, S27L/A97T, S27L/K197Y, S27L/A55I, S27L/A97P, S27L/A55M, S27L/P20E, S27L/A117L, S27L/T109L, S27L/K197T, S27L/T136S, S27L/A97L, S27L/T109A, S27L/P20I, S27L/L191V, S27L/A184C, S27L/A97Q, S27L/F250V, S27L/K197V, S27L/A117S, S27L/K197R, S27L/T109K, S27L/A55C, S27L/N2S/V177A, S27L/Q142D, S27L/G149C, S27L/F21Y, S27L/G149A, S27L/P164E, S27L/Y26C, S27L/T17N, S27L/S57M, S27L/D249I, S27L/T17S, S27L/P164T, S27L/Q142L, S27L/D249N, S27L/I185R, S27L/V83L, S27L/G149S, S27L/A24D, S27L/R251V, S27L/V83I, S27L/S110N, S27L/T17M, S27L/F161W, S27L/G46E, S27L/D249T, S27L/T17, S27L/S57C, S27L/S57T, S27L/S57L, S27L/Q167T, S27L/S57E, S27L/T17K, S27L/G149N, S27L/Q142E, S27L/S57F, S27L/T17A, S27L/P164H, S27L/T17R, S27L/G149T, S27L/R251T, S27L/S101Y, S27L/S57V, S27L/A24T, S27L/I185E, S27L/G46N, S27L/P164N, S27L/P164S, S27L/Q167V, S27L/F161V, S27L/S57I, S27L/G149D S27L/Q167I, S27L/I185Q, S27L/N2L/T17I/T136S/P164H/D249M, S27L/P20E/F21Y/I139T/P164H/K197T/R251E, S27L/A114V/A117N/T136A/I222L/V229I, S27L/P20T/A24V/S101Q/T109R/A117Q/I222L/V229I, S27L/S110D/A184S/K197T, S27L/T136S/D249T, S27L/F21Y/A184S, S27L/N2F/P20E/S110D/A184S/L191V/R251V, S27L/T17G/V23T/A24V/T109L/A117Q/T136A/I222L/V229I, S27L/P20D/F21Y/A55T/F250L/R251V, S27L/T109R/A117N/I222L/V229C, S27L/F21Y/A55T/T109A/A184S, S27L/V23L/A24V/S101K/A117N/I222L/V229C, S27L/S110K/A117Y/P164R, S27L/I139T/Q142E/I169V, S27L/A24H/R251V, S27L/F21W/A114V/T136A/I222L/V229I, S27L/N2S/A55V/I185Q/R251E, S27L/N2F/S101Y/Q142L/G149T/Q167I/I169C/V229L, S27L/N2F/S101C/A117F/P164S, S27L/Q142H/I185S/R251A, S27L/F21W/T109R/A117N/T136V/I222L/V229I, S27L/G46R/T109K/T136S/D249T, S27L/N2E/G46N/A55V/I185Y/D249I, S27L/V83L/F250V/R251E, S27L/F21W, S27L/S57C/R251E, S27L/V23L/A114V/A117N/T136A/I222L/V229I, S27L/A24N, S27L/T17A/P20T/S101Q/T109K/S110R/T136A/I222L/V229C, S27L/P164T/V165I/R251E, S27L/F21Y/G46E/A117T/T136S/G149C/R251Q, S27L/G46N/I139T/Q142E/P164T/I185A/V229L/F250V, S27L/V23L/T136A/I222L/V229I, S27L/V23T/A24V/T109K/A114K/A117Q/T136A/I222L/V229C, S27L/F250L/R251Q, S27L/P20E/F21Y/S57T/P164N/A184C/V229C, S27L/P20T/V23T/A24V/I222L/V229I, S27L/V83L/A97S/A184C/D249S, S27L/P20T/S101H/A114V/A117N/I222L/V229I, S27L/N2E/R251L, S27L/P20E/F21Y/S110D/A117S, S27L/T17A/V23T/A24V/T136A, S27L/P20D/S57E/S101C, S27L/N2S/V83L/A184S, S27L/T17S/S101N/T109K/A117N/T136V/Q142L/I222L/V229C, S27L/P20D/A55T/A117Y/K197R, S27L/P20T/I222L/V229C, S27L/T17I/A24D/S57I, S27L/N2F, S27L/T109K/A117N/T136V/I222L/V229C, S27L/N2L/A24T, S27L/N2F/P20I/F21Y/R251Q, S27L/N2F/G46E, S27L/T136V/Q142W/I222L/V229I, S27L/K197R/R251E, S27L/T17S/R251T, S27L/P20I/F21Y/A117F/I185G/D249N, S27L/T17L/S101M/T109K/S110R/A117Q/I222L/V229C, S27L/T17Q/T136A/I222L/V229C, S27L/V229I, S27L/T17A/F21W/S101Q/I222L/V229C, S27L/T17S/F21W/Q142L, S27L/T17L/T109L/S110R/A117Q/I222L/V229I, S27L/F21W/T136A, S27L/P20E/F21Y/G46E/V83L/A97Q, S27L/P20T/F21W/T136A/Q142L/I222L/V229I, S27L/T17G/F21W/A117N/I222L/V229I, S27L/F21W/T109K/S110R/T136A/V229I, S27L/T17C/T109K/A117N/T136A/I222L/V229I, S27L/P20T/T109L/S110R/A117N/I222L/V229I, S27L/A24N/P164S/K197V/R251T, S27L/V23L/A117Q, S27L/A55V/V83L/A117T, S27L/P20D/G46S/A55I/K197T, S27L/A117Y, S27L/F21W/S101M/I222L/V229C, S27L/N2L/T17N/S57C/S110D/A117L/P164N/I185G/V229L/R251T, S27L/N2E/G46S/V83L/T136S/A172T/V229C/D249N, S27L/P20T/T109R/A114K/A117Q/T136V/I222L/V229C, S27L/V23L/A24V/T136A/Q142W/I222L/V229I, S27L/N2L, S27L/T17A/F21W/T109R/S110R/I222L/V229I, S27L/T17C/A114K/A117N/T136V/I222L/V229I, S27L/V23L/I222L/V229C, S27L/S101N/A117Q/I222L, S27L/N2E/P20I/T109L/L191V/K197L/V229C, S27L/P20T/F21W/Q142W/I222L/V229C, S27L/N2L/G46E/T109K/F161V, S27L/T17S/V229I, S27L/T17Q/T136A/I222L/V229I, -continued S27L/N2L/A172T, S27L/P20D/F21Y/F250V, S27L/N2L/A24H/A55C/V229L, S27L/N2L/P20E/F21Y/V229L, S27L/V23T/T109L/A114V/T136A/Q142L/I222L/V229C, S27L/P20T/F21W/I222L/V229C, S27L/T17H/F21W/T136V/Q142W/I222L/V229I, S27L/G46E/A55I/Q142E, S27L/N2F/R251Q, S27L/F21W/Q142L/I222L/V229C, S27L/I222L/V229I, S27L/P20T/S101M/A114V/A117N/Q142W/I222L/V229C, S27L/T17Q/A24V/S101W/T136A, S27L/N2S/P20D/A97C/A117F/F250L/R251E, S27L/S101M/A114V/A117Q/T136A, S27L/T163I, S27L/S101Q/Q142L/I222L/V229I, S27L/F21W/I222L/V229C, S27L/S101M/T136A/I222L/V229I, S27L/F21W/A24V, S27L/A24D/K197L, S27L/T17H/S110K, S27L/P20T/F21W/V229I, S27L/T17G/P20T/F21W/A117Q/I222L/V229C, S27L/F21W/A24V/A114V/A117Q/Q142W/I222L/V229C, S27L/P20T/A117Q/I222L/V229C, S27L/T17Q/V23T/A24V/I222L/V229I, S27L/N2F/D249N/F250L, S27L/V23T/Q142L/I222L/V229C, S27L/P20E/A24D/D249S/F250V, S27L/A24D/S110K, S27L/T109R/I222L/V229I, S27L/P20E/F21Y/K197T, S27L/T17A/V23L/S101M/T109K/S110R/A114V/A117Q/T136V/V229I, S27L/P20T/F21W/Q142W/I222L/V229I, S27L/F21W/I222L/V229I, S27L/P20T/V23T/A24V/T109L/S110R/I222L/V229I, S27L/A24D/L191F/R251Q, S27L/A24D/T136S/F250V, S27L/P20T/F21W/T109L/T136A/Q142W/I222L/V229C, S27L/N2E/I169L/F250L/R251Q, S27L/N2S/A24N/G46E/A55L/Q142D/V229C/R251L, S27L/N2E/P20E/F250V/R251L, S27L/N2F/P20E, S27L/A24V/V229C, S27L/P20D/F21Y/G46N/S110K/T163I/Q167V, S27L/P20T/T109K/A114K/Q142W/I222L/V229C, S27L/T17Q/S101D/T136A/I222L/V229I, S27L/F21W/T109R/A117N/T136V/Q142W/I222L/V229C, S27L/A24D/T109L/K197L, S27L/T17Q/Q142L/I222L/V229I, S27L/T17A/A24V/S101D/S110R/T136A, S27L/P20T/F21W/T109R/A117Q/T136V/Q142L/I222L/V229I, S27L/P20T/F21W/T109K/A117N/I222L/V229C, S27L/P20T/S101M/I222L/V229I, S27L/N2S/A24D/S101Y/P164E/V165I/I185E, S27L/T17N/A117S/V229L/R251A, S27L/S101W/A114V/T136V/V229C, S27L/P20D/G46N/A55C/S110N/T163I/A184S, S27L/A24H/G46E, S27L/T17H/S101Q/T136V/Q142L/V229C and S27L/V23T/A24V/I222L/V229C.

2. A nucleic acid encoding the variant Bhr-PETase enzyme of claim 1.

3. An expression vector comprising the nucleic acid of claim 2.

4. A host cell comprising the expression vector of claim 3.

5. The host cell according to claim 4, wherein the cell comprises at least one selected from the group consisting of bacteria, yeast and fungi.

6. A method of making a variant Bhr-PETase enzyme comprising culturing the host cell of claim 4 under conditions wherein said variant Bhr-PETase enzyme is produced, and recovering said variant Bhr-PETase enzyme.

7. A method of degrading polyethylene terephthalate (PET), comprising contacting the PET with the variant Bhr-PETase enzyme of claim 1.

8. The method according to claim 7, further comprising pretreating the PET, comprising at least one selected from the group consisting of a mechanical pretreatment, a thermo-mechanical pretreatment, and a chemical pretreatment of the PET prior to an enzymatic degradation of the PET, wherein the mechanical pretreatment comprises grinding of the PET into particles, the thermo-mechanical pretreatment comprises extruding the PET at a temperature configured to amorphize and reduce crystallinity of the PET, and the chemical pretreatment comprises contacting the PET with an ionic liquid, strong acid, base, or solvent configured to reduce crystallinity or to change a surface structure of the PET.

9. The method according to claim 7, wherein the method degrades the PET in a mixed plastics composition.

10. The method according to claim 9, wherein the plastics composition comprises at least one selected from the group consisting of Polybutylene terephthalate (PBT), Polycabonate (PC), Polycaprolactone (PCL), Polyethylene Furanoate (PEF), and High Density Polyethylene (HDPE).

11. The method according to claim 7, wherein the method excludes sorting plastics to select the PET from the mixture of plastics.

* * * * *